United States Patent
Tanaka et al.

(10) Patent No.: US 10,023,799 B2
(45) Date of Patent: *Jul. 17, 2018

(54) LIQUID CRYSTAL COMPOUND, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Hiroyuki Tanaka, Chiba (JP); Hiroshi Endou, Chiba (JP)

(73) Assignees: JNC CORPORATION, Tokyo (JP); JNC PETROCHEMICAL CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/769,444

(22) PCT Filed: Jan. 27, 2014

(86) PCT No.: PCT/JP2014/051700
§ 371 (c)(1),
(2) Date: Aug. 20, 2015

(87) PCT Pub. No.: WO2014/129268
PCT Pub. Date: Aug. 28, 2014

(65) Prior Publication Data
US 2015/0376504 A1    Dec. 31, 2015

(30) Foreign Application Priority Data
Feb. 20, 2013 (JP) ................ 2013-031144

(51) Int. Cl.
G02F 1/1333 (2006.01)
C09K 19/34 (2006.01)
(Continued)

(52) U.S. Cl.
CPC ........ *C09K 19/3402* (2013.01); *C07C 43/225* (2013.01); *C07C 43/29* (2013.01); *C07C 255/50* (2013.01); *C07D 213/16* (2013.01); *C07D 213/30* (2013.01); *C07D 239/26* (2013.01); *C07D 309/06* (2013.01); *C07D 319/06* (2013.01); *C07D 319/08* (2013.01); *C07D 493/08* (2013.01); *C09K 19/20* (2013.01); *C09K 19/3066* (2013.01); *C09K 19/3068* (2013.01);
(Continued)

(58) Field of Classification Search
CPC C09K 19/3402; C09K 19/20; C09K 19/3066; C09K 19/3098; C09K 19/3068; C09K 2019/0407; C09K 2019/0466; C09K 2019/3422; C09K 2019/3077; C09K 2019/308; C09K 2019/3083; C07D 309/06; C07D 493/08; C07D 239/26; C07D 319/06; C07D 319/08; C07D 213/30; C07D 213/16; C07C 43/225; C07C 43/29; C07C 255/50
USPC .............. 252/299.01, 299.6, 299.61; 428/1.1
See application file for complete search history.

(56) References Cited

U.S. PATENT DOCUMENTS 6,548,126 B1    4/2003  Sasada et al.
7,846,514 B2 *  12/2010 Shimada ................ C09K 19/10
                                                              252/299.61
(Continued)

FOREIGN PATENT DOCUMENTS

CN    101616883    12/2009
CN    101712874     5/2010
(Continued)

OTHER PUBLICATIONS

"International Search Report (Form PCT/ISA/210)", dated Apr. 15, 2014, with English translation thereof, pp. 1-6, in which six of the listed references (JP2008-88164A, WO2012/020643A1, WO2008/090780A1, CN101712874, JP2007-2132A and JP2002-201474A) were cited.
(Continued)

*Primary Examiner* — Geraldina Visconti
(74) *Attorney, Agent, or Firm* — JCIPRNET

(57) ABSTRACT

To provide a liquid crystal compound satisfying at least one of physical properties such as high stability to light, a high clearing point, a low minimum temperature of a liquid crystal phase, small viscosity, suitable optical anisotropy, large dielectric anisotropy, a large dielectric constant in a minor axis direction, a suitable elastic constant and excellent compatibility; a liquid crystal composition containing the compound; and a liquid crystal display device including the composition. The compound is represented by formula (1):

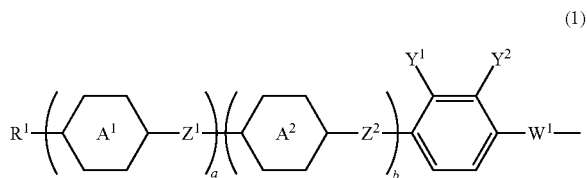

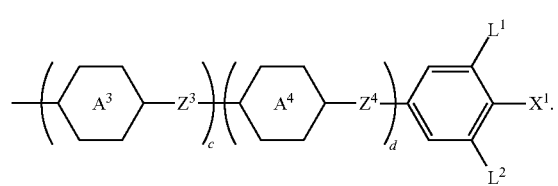

14 Claims, No Drawings

(51) Int. Cl.
| | |
|---|---|
| C07D 309/06 | (2006.01) |
| C07C 43/225 | (2006.01) |
| C07C 43/29 | (2006.01) |
| C07D 239/26 | (2006.01) |
| C07D 493/08 | (2006.01) |
| C09K 19/20 | (2006.01) |
| C09K 19/30 | (2006.01) |
| C07D 319/06 | (2006.01) |
| C07D 213/30 | (2006.01) |
| C07C 255/50 | (2006.01) |
| C07D 213/16 | (2006.01) |
| C07D 319/08 | (2006.01) |
| C09K 19/04 | (2006.01) |

(52) U.S. Cl.
CPC .. *C09K 19/3098* (2013.01); *C09K 2019/0407* (2013.01); *C09K 2019/0466* (2013.01); *C09K 2019/308* (2013.01); *C09K 2019/3077* (2013.01); *C09K 2019/3083* (2013.01); *C09K 2019/3422* (2013.01)

(56) References Cited

U.S. PATENT DOCUMENTS

| | | | | |
|---|---|---|---|---|
| 8,580,142 | B2* | 11/2013 | Shimada | C09K 19/20 252/299.01 |
| 9,512,360 | B2* | 12/2016 | Saito | C09K 19/3402 |
| 2012/0286199 | A1 | 11/2012 | Satou et al. | |
| 2015/0376502 | A1* | 12/2015 | Tanaka | C07D 309/06 252/299.61 |
| 2016/0032187 | A1* | 2/2016 | Tanaka | C09K 19/3458 252/299.61 |
| 2016/0177180 | A1* | 6/2016 | Saito | C09K 19/20 252/299.61 |
| 2016/0208169 | A1* | 7/2016 | Saito | C09K 19/20 |

FOREIGN PATENT DOCUMENTS

| | | |
|---|---|---|
| DE | 4006921 | 9/1990 |
| EP | 1785467 | 5/2007 |
| EP | 1897928 | 3/2008 |
| EP | 2199270 | 6/2010 |
| JP | H10-204016 | 8/1998 |
| JP | H10251186 | 9/1998 |
| JP | 2001-139511 | 5/2001 |
| JP | 2002-80452 | 3/2002 |
| JP | 2002-201474 | 7/2002 |
| JP | 2002-327175 | 11/2002 |
| JP | 2007-2132 | 1/2007 |
| JP | 2008-88164 | 4/2008 |
| WO | 96/011897 | 4/1996 |
| WO | 2008/090780 | 7/2008 |
| WO | 2012/020643 | 2/2012 |

OTHER PUBLICATIONS

"Search Report of Europe Counterpart Application", dated Nov. 8, 2016, p. 1-p. 14.
"Office Action of China Counterpart Application" with English translation thereof, dated Jan. 16, 2017, p. 1-p. 11.
"Office Action of China Counterpart Application" with English translation, dated Jun. 17, 2016, p. 1-p. 14.
"Office Action of China Counterpart Application," with English translation thereof, dated Jul. 31, 2017, p. 1-p. 17.
"Office Action of Taiwan Counterpart Application," with English translation thereof, dated Nov. 13, 2017, p. 1-p. 16.

\* cited by examiner

LIQUID CRYSTAL COMPOUND, LIQUID CRYSTAL COMPOSITION AND LIQUID CRYSTAL DISPLAY DEVICE

CROSS-REFERENCE TO RELATED APPLICATION

This application is a 371 application of an international PCT application serial no. PCT/JP2014/051700, filed on Jan. 27, 2014, which claims the priority benefit of Japan application no. 2013-031144, filed on Feb. 20, 2013. The entirety of each of the abovementioned patent applications is hereby incorporated by reference herein and made a part of this specification.

TECHNICAL FIELD

The invention relates to a liquid crystal compound, a liquid crystal composition and a liquid crystal display device. More specifically, the invention relates to a compound having difluoromethyleneoxy, a liquid crystal composition containing the compound and having a nematic phase, and a liquid crystal display device including the composition.

BACKGROUND ART

A liquid crystal display device has been widely utilized for a display of a personal computer, a television or the like. The device utilizes optical anisotropy, dielectric anisotropy and so forth of a liquid crystal compound. As an operating mode of the liquid crystal display device, such a mode is known as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode.

In such a liquid crystal display device, a liquid crystal composition having suitable physical properties is used. In order to further improve characteristics of the liquid crystal display device, the liquid crystal compound contained in the composition preferably has physical properties described in (1) to (8) below.

(1) High stability to heat, light and so forth,
(2) a high clearing point,
(3) low minimum temperature of a liquid crystal phase,
(4) small viscosity ($\eta$),
(5) suitable optical anisotropy ($\Delta n$),
(6) large dielectric anisotropy ($\Delta \varepsilon$),
(7) a suitable elastic constant (K),
(8) excellent compatibility with other liquid crystal compounds, and
(9) a large dielectric constant in a minor axis direction ($\varepsilon \perp$).

An effect of the physical properties of the liquid crystal compound on the characteristics of the device is as described below. A compound having the high stability to heat, light and so forth as described in (1) increases a voltage holding ratio of the device. Therefore, a service life of the device becomes long. A compound having the high clearing point as described in (2) extends a temperature range in which the device can be used. A compound having the low minimum temperature of the liquid crystal phase such as the nematic phase and a smectic phase, as described in (3), in particular, a compound having the low minimum temperature of the nematic phase, also extends the temperature range in which the device can be used. A compound having the small viscosity as described in (4) shortens a response time of the device.

A compound having the suitable optical anisotropy as described in (5) improves contrast of the device. According to a design of the device, a compound having a large optical anisotropy or a small optical anisotropy, more specifically, a compound having the suitable optical anisotropy, is required. When the response time is shortened by decreasing a cell gap of the device, a compound having the large optical anisotropy is suitable. A compound having the large dielectric anisotropy as described in (6) decreases a threshold voltage of the device. Thus, an electric power consumption of the device is decreased. On the other hand, a compound having a small dielectric anisotropy shortens the response time of the device by decreasing viscosity of the composition.

With regard to (7), a compound having a large elastic constant decreases the response time of the device. A compound having a small elastic constant decreases the threshold voltage of the device. Therefore, the suitable elastic constant is required according to characteristics to be desirably improved. A compound having the excellent compatibility with other liquid crystal compounds as described in (8) is preferred. The reason is that physical properties of the composition are adjusted by mixing liquid crystal compounds having different physical properties.

Further, an improvement of a transmittance in the liquid crystal composition has been strongly required in connection with a demand for achieving a low power consumption and a high definition in the liquid crystal display device in recent years. Above all, the transmittance in the liquid crystal composition used for an FFS mode liquid crystal display device is known to be correlated with the dielectric constant in the minor axis direction ($\varepsilon \perp$) of the liquid crystal composition, and therefore a liquid crystal compound having the large dielectric constant in the minor axis direction as described in (9) is preferred.

A variety of liquid crystal compounds each having a $CF_2O$ bonding group have so far been prepared as the liquid crystal compound having the large dielectric anisotropy, and some of the compounds have been practically used. However, in the above compounds, the dielectric constant in the minor axis direction is far from sufficiently large. Under such circumstances, desire has been expressed for development of a compound having excellent physical properties and a suitable balance regarding the physical properties (1) to (9) above, above all, a compound having both the large dielectric anisotropy ($\Delta \varepsilon$) and the large dielectric constant in the minor axis direction.

CITATION LIST

Patent Literature

Patent literature No. 1: WO 96/011897 A.
Patent literature No. 2: JP H10-204016 A.
Patent literature No. 3: DE 4006921 A.
Patent literature No. 4: JP 2001-139511 A.
Patent literature No. 5: JP 2002-80452 A.
Patent literature No. 6: JP 2002-327175 A.

SUMMARY OF INVENTION

Technical Problem

A first object of the invention is to provide a liquid crystal compound satisfying at least one of physical properties such as a high stability to light, a high clearing point, a low minimum temperature of a liquid crystal phase, a small viscosity, a suitable optical anisotropy, a large dielectric anisotropy, a large dielectric constant in a minor axis direction, a suitable elastic constant and an excellent compatibility with other liquid crystal compounds, and in particular, to provide a compound having both the large dielectric anisotropy and the large dielectric constant in the minor axis direction. A second object is to provide a liquid crystal composition containing the compound and satisfying at least one of physical properties such as a high maximum temperature of a nematic phase, a low minimum temperature of the nematic phase, a small viscosity, a suitable optical anisotropy, a large dielectric anisotropy, a large dielectric constant in a minor axis direction and a suitable elastic constant. The object is to provide a liquid crystal composition having a suitable balance regarding at least two of the physical properties. A third object is to provide a liquid crystal display device including the composition and having a wide temperature range in which the device can be used, a short response time, a large voltage holding ratio, a low threshold voltage, a large contrast ratio and a long service life.

Solution to Problem

The invention concerns a compound represented by formula (1), a liquid crystal composition containing the compound, and a liquid crystal display device including the composition:

$Z^1$, $Z^2$, $Z^3$ and $Z^4$ are independently a single bond, —(CH$_2$)$_2$—, —CH═CH—, —C≡C—, —COO—, —OCO—, —CF$_2$O—, —CH$_2$O—, —OCH$_2$— or —CF═CF—,
a, b, c and d are independently 0 or 1, and a sum of a, b, c and d is 1, 2 or 3; and
at least one of $Z^1$ when a is 1, $Z^2$ when b is 1, $Z^3$ when c is 1, and $Z^4$ when d is 1 is —CF$_2$O—.

Advantageous Effects of Invention

A first advantage of the invention is to provide a liquid crystal compound satisfying at least one of physical properties such as a high stability to light, a high clearing point, a low minimum temperature of a liquid crystal phase, a small viscosity, a suitable optical anisotropy, a large dielectric anisotropy, a suitable elastic constant, an excellent compatibility with other liquid crystal compounds and a large dielectric constant in a minor axis direction. In particular, the advantage is to provide a compound having both the large dielectric anisotropy and the large dielectric constant in the minor axis direction. A second advantage is to provide a liquid crystal composition containing the compound and satisfying at least one of physical properties such as a high maximum temperature of a nematic phase, a low minimum temperature of the nematic phase, a small viscosity, a suitable optical anisotropy, a large dielectric anisotropy, a large dielectric constant in a minor axis direction and a suitable elastic constant. A third advantage is to provide a liquid crystal display device including the composition and

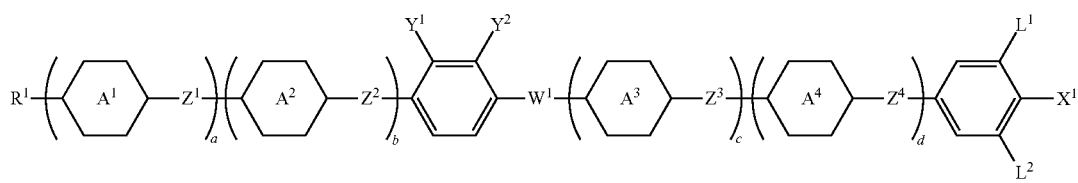

(1)

wherein, in formula (1),
$R^1$ is alkyl having 1 to 15 carbons, in the alkyl, at least one of —CH$_2$— may be replaced by —O— or —S—, at least one of —(CH$_2$)$_2$— may be replaced by —CH═CH—, and in the groups, at least one of hydrogen may be replaced by halogen;
ring $A^1$, ring $A^2$, ring $A^3$ and ring $A^4$ are independently 1,4-cyclohexylene, 1,4-cyclohexenylene, 1,4-phenylene, 2-fluoro-1,4-phenylene, 2,6-difluoro-1,4-phenylene, 2-chloro-1,4-phenylene, 2,6-dichloro-1,4-phenylene, 2-chloro-6-fluoro-1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl or pyridine-2,5-diyl;
$X^1$ is halogen, —C≡N, —N═C═S, alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine;
$L^1$ and $L^2$ are independently hydrogen or fluorine;
$Y^1$ and $Y^2$ are independently fluorine or chlorine;
$W^1$ is a single bond, —(CH$_2$)$_2$—, —CH═CH—, —C≡C—, —COO—, —OCO—, —CH$_2$O—, —OCH$_2$— or —CF═CF—;

having a wide temperature range in which the device can be used, a short response time, a large voltage holding ratio, a low threshold voltage, a large contrast ratio and a long service life.

DESCRIPTION OF EMBODIMENTS

Usage of terms herein is as described below. A liquid crystal compound is a generic term for a compound having a liquid crystal phase such as a nematic phase and a smectic phase, and also a compound having no liquid crystal phase but being added for adjusting physical properties such as a maximum temperature, a minimum temperature, viscosity and dielectric anisotropy. The compounds have a six-membered ring, such as 1,4-cyclohexylene and 1,4-phenylene, and rod like molecular structure. A liquid crystal composition is prepared by mixing such liquid crystal compounds. A ratio (content) of the liquid crystal compound is expressed in terms of weight percent (% by weight) based on the weight of the liquid crystal composition. An additive such as a polymerizable compound, a polymerization initiator, an optically active compound, an antioxidant, an ultraviolet light absorber, a light stabilizer, a heat stabilizer, an antifoaming agent and a dye is added to the composition, when necessary. A ratio (amount of addition) of the additive is expressed in terms of weight percent (% by weight) based on the weight of the liquid crystal composition in a manner similar to the ratio of the liquid crystal compounds. Weight parts per million (ppm) may be occasionally used. A liquid crystal display device is a generic term for a liquid crystal display panel and a liquid crystal display module. The liquid crystal compound, the liquid crystal composition and the liquid crystal display device may be occasionally abbreviated as "compound," "composition" and "device," respectively. A clearing point is a transition temperature between the liquid crystal phase and an isotropic phase in the liquid crystal compound. A lower limit of a temperature range of the liquid crystal phase is a transition temperature between a solid and the liquid crystal phase (a smectic phase, a nematic phase or the like) in the liquid crystal compound. A higher limit of the temperature range of the nematic phase is a transition temperature between the nematic phase and the isotropic phase in the liquid crystal composition, and may be occasionally abbreviated as "maximum temperature." A lower limit of the temperature range of the nematic phase may be occasionally abbreviated as "minimum temperature."

A compound represented by formula (1) may be occasionally abbreviated as "compound (1)." The abbreviation may also apply occasionally to a compound represented by formula (2) or the like. In formulas (1) to (15), a symbol such as $A^1$, $B^1$, $C^1$ or the like surrounded by a hexagonal shape corresponds to ring $A^1$, ring $B^1$, ring $C^1$ or the like, respectively. A symbol of terminal group $R^{11}$ is used for a plurality of compounds. In the compounds, two groups represented by two of arbitrary $R^{11}$ may be identical or different. For example, in one case, $R^{11}$ of compound (2) is ethyl and $R^{11}$ of compound (3) is ethyl. In another case, $R^{11}$ of compound (2) is ethyl and $R^{11}$ of compound (3) is propyl. A same rule further applies to a symbol of any other terminal group, ring or the like. In formula (5), when i is 2, two of ring $C^1$ exists. In the compound, two groups represented by two of ring $C^1$ may be identical or different. A same rule also applies to arbitrary two when i is larger than 2. A same rule further applies to a symbol of any other ring, a bonding group or the like.

An expression "at least one of "A" may be replaced by "B"" means that a position of "A" when the number of "A" is 1 is arbitrary, and that the positions can be selected without limitation when the number of "A" is 2 or more. An expression "at least one of A may be replaced by B, C or D" means inclusion of a case where arbitrary A is replaced by B, a case where arbitrary A is replaced by C, and a case where arbitrary A is replaced by D, and also a case where a plurality of A are replaced by at least two of B, C or D. For example, alkyl in which at least one of —$CH_2$— may be replaced by —O— or —CH=CH— includes alkyl, alkenyl, alkoxy, alkoxyalkyl, alkoxyalkenyl and alkenyloxyalkyl. In addition, a case where replacement of two successive —$CH_2$— by —O— results in forming —O—O— is not preferred. In the alkyl or the like, a case where replacement of —$CH_2$— of a methyl part (—$CH_2$—H) by —O— results in forming —O—H is not preferred, either.

Then, 2-fluoro-1,4-phenylene means two divalent groups described below. In a chemical formula thereof, fluorine may be leftward (L) or rightward (R). A same rule also applies to an asymmetrical divalent ring such as tetrahydropyran-2,5-diyl.

(L)

(R)

The invention includes the content described in items 1 to 14 below.

Item 1. A compound represented by formula (1):

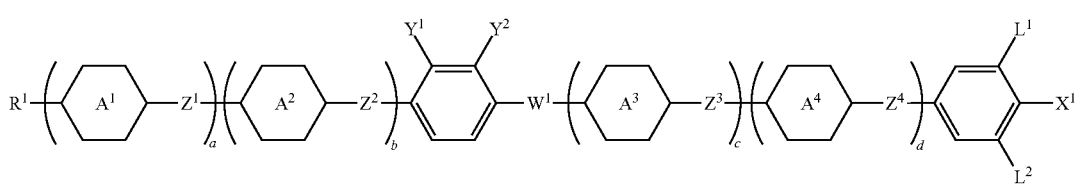

(1)

wherein, in formula (1),
$R^1$ is alkyl having 1 to 15 carbons, in the alkyl, at least one of —$CH_2$— may be replaced by —O— or —S—, at least one of —$(CH_2)_2$— may be replaced by —CH=CH—, and in the groups, at least one of hydrogen may be replaced by halogen;

ring $A^1$, ring $A^2$, ring $A^3$ and ring $A^4$ are independently 1,4-cyclohexylene, 1,4-cyclohexenylene, 1,4-phenylene, 2-fluoro-1,4-phenylene, 2,6-difluoro-1,4-phenylene, 2-chloro-1,4-phenylene, 2,6-dichloro-1,4-phenylene, 2-chloro-6-fluoro-1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl or pyridine-2,5-diyl;

$X^1$ is halogen, —C≡N, —N=C=S, alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine;

$L^1$ and $L^2$ are independently hydrogen or fluorine;
$Y^1$ and $Y^2$ are independently fluorine or chlorine;
$W^1$ is a single bond, —$(CH_2)_2$—, —CH=CH—, —C≡C—, —COO—, —OCO—, —$CH_2$O—, —O$CH_2$— or —CF=CF—;

$Z^1$, $Z^2$, $Z^3$ and $Z^4$ are independently a single bond, —$(CH_2)_2$—, —CH=CH—, —C≡C—, —COO—, —OCO—, —$CF_2$O—, —$CH_2$O—, —O$CH_2$— or —CF=CF—;

a, b, c and d are independently 0 or 1, a sum of a, b, c and d is 1, 2 or 3; and at least one of $Z^1$ when a is 1, $Z^2$ when b is 1, $Z^3$ when c is 1, and $Z^4$ when d is 1 is —$CF_2O$—.

Item 2. The compound according to item 1, wherein, in formula (1) described in item 1, $R^1$ is alkyl having 1 to 15 carbons, alkenyl having 2 to 15 carbons, alkoxy having 1 to 14 carbons or alkenyloxy having 2 to 14 carbons; and $X^1$ is fluorine, chlorine, —C≡N, —N=C=S, —$CH_2F$, —$CHF_2$, —$CF_3$, —$(CH_2)_2$—F, —$CH_2CF_3$, —$CF_2CF_3$, —$(CH_2)_3$—F, —$(CH_2)_2$—$CF_3$, —$(CF_2)_3$—F, —$(CH_2)_4$—F, —$(CH_2)_3$—$CF_3$, —$(CF_2)_4$—F, —$(CF_2)_5$—F, —$(CF_2)_6$—F, —$(CF_2)_7$—F, —$OCH_2F$, —$OCHF_2$, —$OCF_3$, —O—$(CH_2)_2$—F, —$OCH_2CF_3$, —$OCF_2CF_3$, —O—$(CH_2)_3$—F, —O—$(CH_2)_2$—$CF_3$, —O—$(CF_2)_3$—F, —O—$(CH_2)_4$—F, —O—$(CH_2)_3$—$CF_3$, —O—$(CF_2)_4$—F, —O—$(CF_2)_5$—F, —O—$(CF_2)_6$—F, —CH=CHF, —CH=$CF_2$, —CF=CHF, —CF=$CF_2$, —CH=$CHCH_2F$, —CH=$CHCF_3$, —CF=$CHCF_3$, —CF=$CFCF_3$, —$(CH_2)_2$—CH=$CF_2$, —$(CH_2)_2$—CF=$CF_2$, —$(CH_2)_2$—CH=$CHCF_3$, —$(CH_2)_2$—CF=$CHCF_3$ or —$(CH_2)_2$—CF=$CFCF_3$.

Item 3. The compound according to item 1, wherein, in formula (1) described in item 1, $R^1$ is alkyl having 1 to 10 carbons, alkenyl having 2 to 10 carbons, alkoxy having 1 to 9 carbons or alkenyloxy having 2 to 9 carbons; and $X^1$ is fluorine, chlorine, —C≡N, —$CF_3$, —$CHF_2$, —$OCF_3$, —$OCHF_2$, —CH=$CHCF_3$, —CF=$CHCF_3$ or —CF=$CFCF_3$.

Item 4. The compound according to item 1, represented by any one of formulas (1-1) to (1-7):

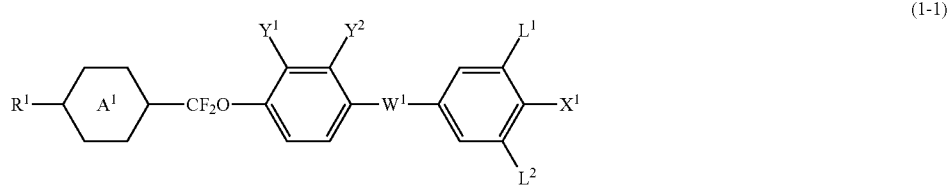
(1-1)

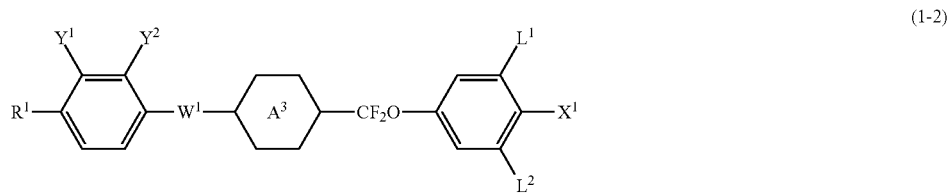
(1-2)

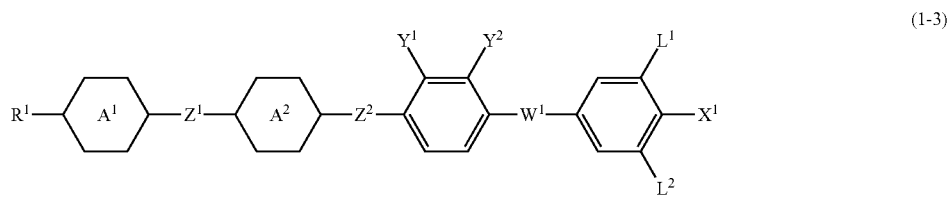
(1-3)

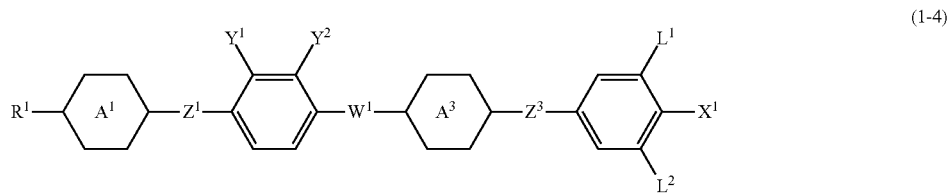
(1-4)

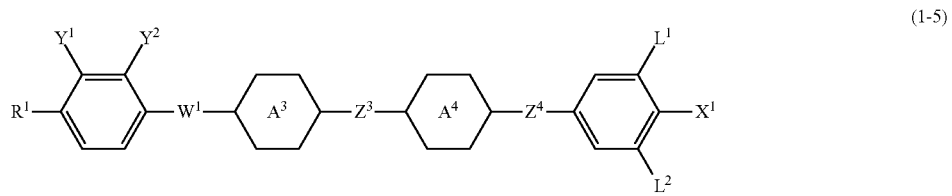
(1-5)

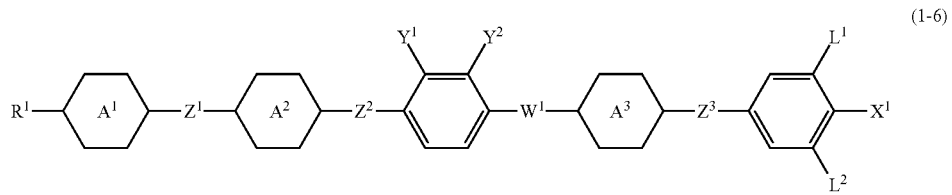
(1-6)

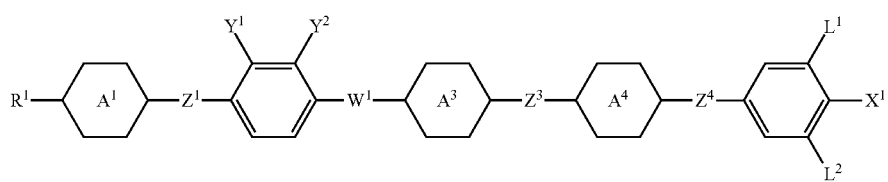
(1-7)

wherein, in formulas (1-1) to (1-7), $R^1$ is alkyl having 1 to 10 carbons, alkenyl having 2 to 10 carbons or alkoxy having 1 to 9 carbons;

ring $A^1$, ring $A^2$, ring $A^3$ and ring $A^4$ are independently 1,4-cyclohexylene, 1,4-cyclohexenylene, 1,4-phenylene, 2-fluoro-1,4-phenylene, 2,6-difluoro-1,4-phenylene, tetrahydropyran-2,5-diyl, or 1,3-dioxane-2,5-diyl;

$Z^1$, $Z^2$, $Z^3$ and $Z^4$ are independently a single bond, —(CH$_2$)$_2$—, —COO—, —CF$_2$O—, —CH$_2$O— or —OCH$_2$—;

$W^1$ is a single bond, —(CH$_2$)$_2$— or —OCH$_2$—;

$X^1$ is fluorine, —CF$_3$ or —OCF$_3$;

$L^1$ and $L^2$ are independently hydrogen or fluorine;

$Y^1$ and $Y^2$ are independently fluorine or chlorine;

in formula (1-3), any one of $Z^1$ and $Z^2$ is —CF$_2$O—;

in formula (1-4), any one of $Z^1$ and $Z^3$ is —CF$_2$O—;

in formula (1-5), any one of $Z^3$ and $Z^4$ is —CF$_2$O—;

in formula (1-6), any one of $Z^1$, $Z^2$ and $Z^3$ is —CF$_2$O—; and in formula (1-7), any one of $Z^1$, $Z^3$ and $Z^4$ is —CF$_2$O—.

Item 5. The compound according to item 1, represented by any one of formulas (1-8) to (1-12):

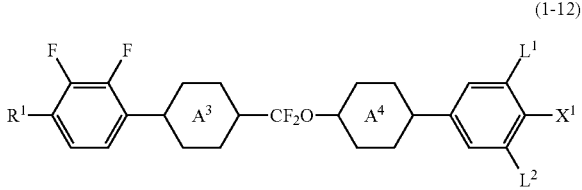
(1-12)

wherein, in formulas (1-8) to (1-12), $R^1$ is alkyl having 1 to 10 carbons, alkenyl having 2 to 10 carbons or alkoxy having 1 to 9 carbons;

ring $A^1$, ring $A^2$, ring $A^3$ and ring $A^4$ are independently 1,4-cyclohexylene, 1,4-cyclohexenylene, 1,4-phenylene, 2-fluoro-1,4-phenylene, 2,6-difluoro-1,4-phenylene, tetrahydropyran-2,5-diyl or 1,3-dioxane-2,5-diyl;

$X^1$ is fluorine, —CF$_3$ or —OCF$_3$; and $L^1$ and $L^2$ are independently hydrogen or fluorine.

Item 6. The compound according to item 1, represented by any one of formulas (1-13) to (1-22):

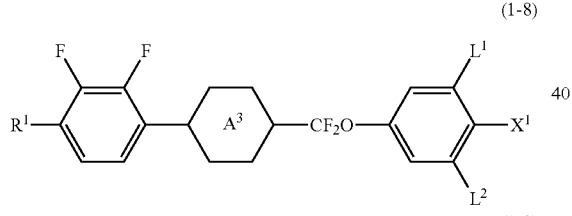
(1-8)

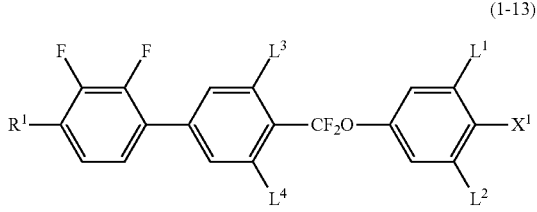
(1-13)

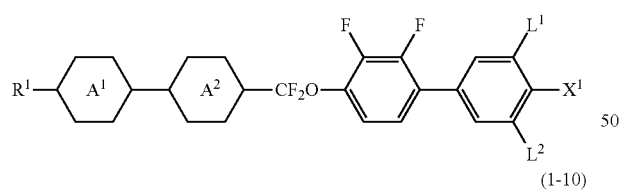
(1-9)

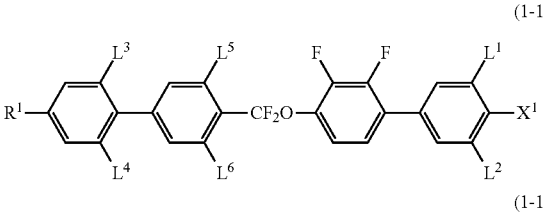
(1-14)

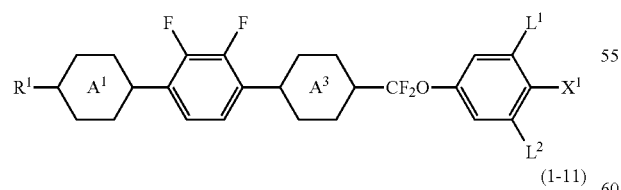
(1-10)

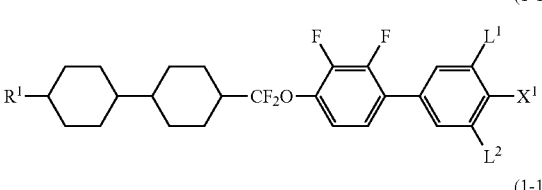
(1-15)

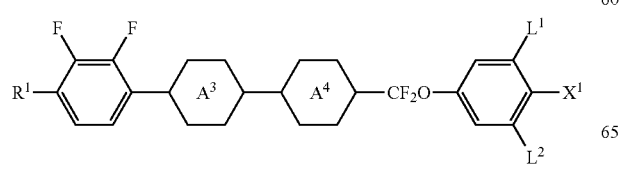
(1-11)

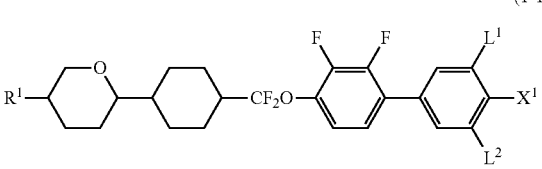
(1-16)

-continued (1-17)
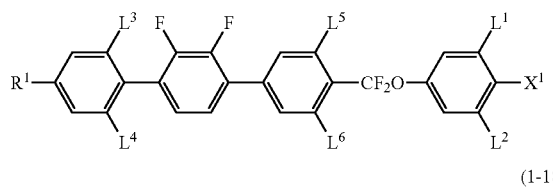

(1-18)
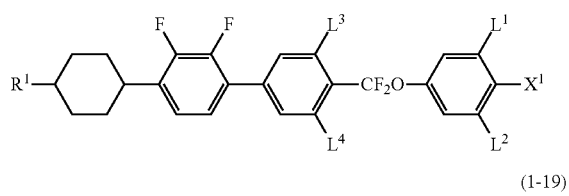

(1-19)
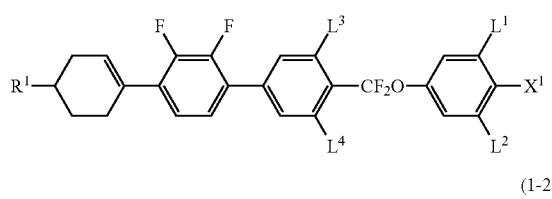

(1-20)
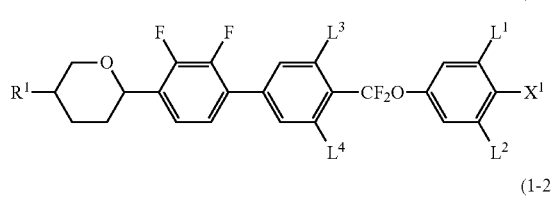

(1-21)
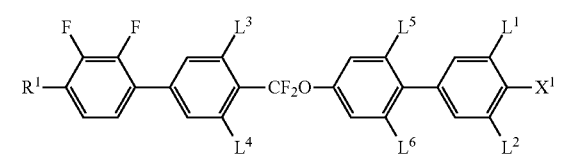

(1-22)

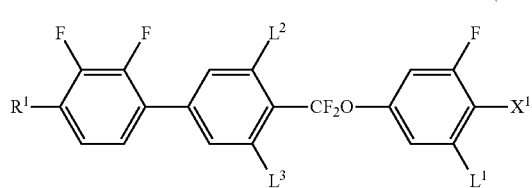

wherein, in formulas (1-13) to (1-22), $R^1$ is alkyl having 1 to 10 carbons, alkenyl having 2 to 10 carbons or alkoxy having 1 to 9 carbons; $X^1$ is fluorine, —$CF_3$ or —$OCF_3$; and $L^1$, $L^2$, $L^3$, $L^4$, $L^5$ and $L^6$ are independently hydrogen or fluorine.

Item 7. The compound according to item 1, represented by any one of formulas (1-23) to (1-25):

(1-23)
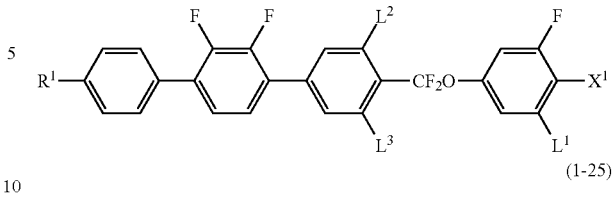

-continued (1-24)
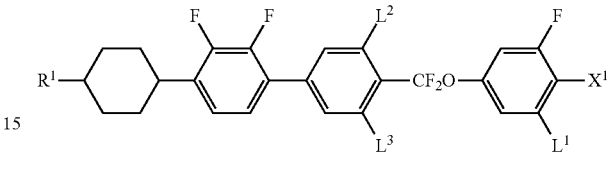

(1-25)
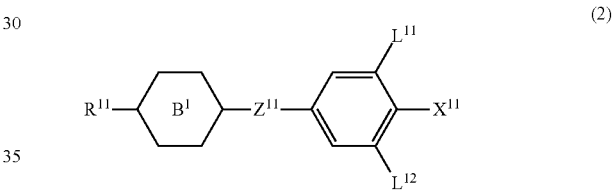

wherein, in formulas (1-23) to (1-25), $R^1$ is alkyl having 1 to 10 carbons, alkenyl having 2 to 10 carbons or alkoxy having 1 to 9 carbons; $X^1$ is fluorine, —$CF_3$ or —$OCF_3$; and $L^1$, $L^2$ and $L^3$ are independently hydrogen or fluorine.

Item 8. A liquid crystal composition, containing at least one compound according to any one of items 1 to 7.

Item 9. The liquid crystal composition according to item 8, further containing at least one compound selected from the group of compounds represented by formulas (2) to (4):

(2)
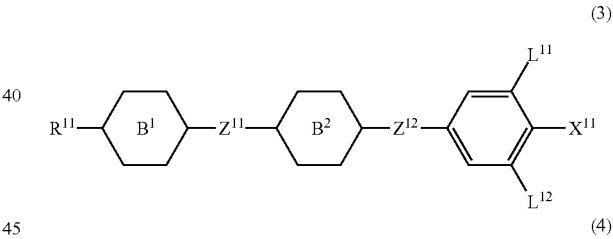

(3)

(4)
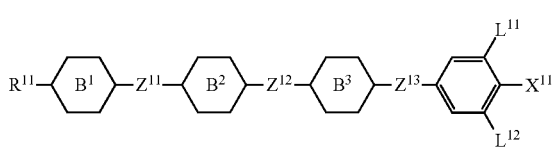

wherein, in formulas (2) to (4), $R^{11}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $B^1$, ring $B^2$ and ring $B^3$ are independently 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl or pyrimidine-2,5-diyl;

$Z^{11}$, $Z^{12}$ and $Z^{13}$ are independently a single bond, —$CH_2CH_2$—, —CH═CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

Item 10. The liquid crystal composition according to item 8 or 9, further containing at least one compound selected from the group of compounds represented by formula (5):

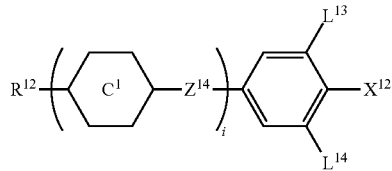
(5)

wherein, in formula (5), $R^{12}$ is alkyl having 1 to 10 carbons or alkenyl having 2 to 10 carbons, and in the alkyl and the alkenyl, at least one of hydrogen may be replaced by fluorine, and at least one of —CH$_2$— may be replaced by —O—;

$X^{12}$ is —C≡N or —C≡C—C≡N;

ring $C^1$ is 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl or pyrimidine-2,5-diyl;

$Z^{14}$ is a single bond, —CH$_2$CH$_2$—, —C≡C—, —COO—, —CF$_2$O—, —OCF$_2$— or —CH$_2$O—;

$L^{13}$ and $L^{14}$ are independently hydrogen or fluorine; and i is 1, 2, 3 or 4.

Item 11. The liquid crystal composition according to any one of items 8 to 10, further containing at least one compound selected from the group of compounds represented by formulas (6) to (12):

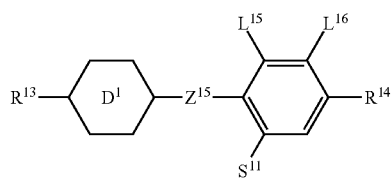
(6)

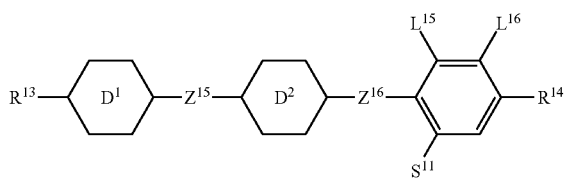
(7)

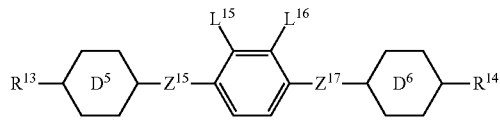
(8)

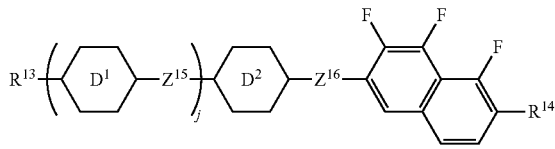
(9)

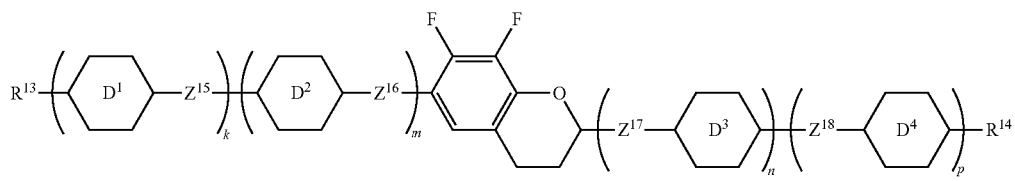
(10)

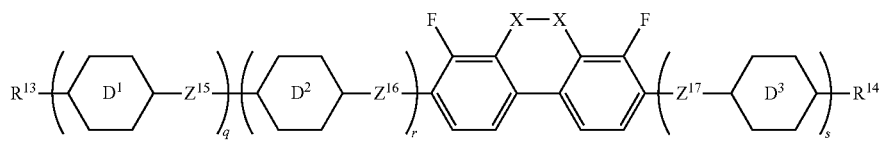
(11)

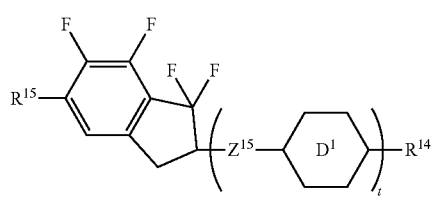
(12)

wherein, in formulas (6) to (12), $R^{13}$ and $R^{14}$ are independently alkyl having 1 to 10 carbons or alkenyl having 2 to 10 carbons, and in the alkyl and the alkenyl, at least one of —$CH_2$— may be replaced by —O—;

$R^{15}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$S^{11}$ is hydrogen or methyl;

X is —$CF_2$—, —O— or —CHF—;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

Item 12. The liquid crystal composition according to any one of items 8 to 11, further containing at least one compound selected from the group of compounds represented by formulas (13) to (15):

$Z^{19}$, $Z^{20}$ and $Z^{21}$ are independently a single bond, —$CH_2CH_2$—, —CH═CH—, —C≡C— or —COO—.

Item 13. The liquid crystal composition according to items 8 to 12, further containing at least one of a polymerizable compound, an optically active compound, an antioxidant, an ultraviolet light absorbent, a light stabilizer, a heat stabilizer and a defoaming agent.

Item 14. A liquid crystal display device, including the liquid crystal composition according to any one of items 8 to 13.

The compound, the liquid crystal composition and the liquid crystal display device of the invention are described in the order.

1-1. Compound (1)

Compound (1) of the invention has, as a ring, 1,4-phenylene in which hydrogen in 2-position and in 3-position are replaced by halogen, and as a bonding group, difluoromethyleneoxy, and therefore has a feature of having both a large dielectric anisotropy and a large dielectric constant in a minor axis direction. A preferred example of compound (1) of the invention is described. Preferred examples of a terminal group, a ring structure, a bonding group and a substituent in compound (1) are also applied to a subordinate formula of formula (1) for compound (1):

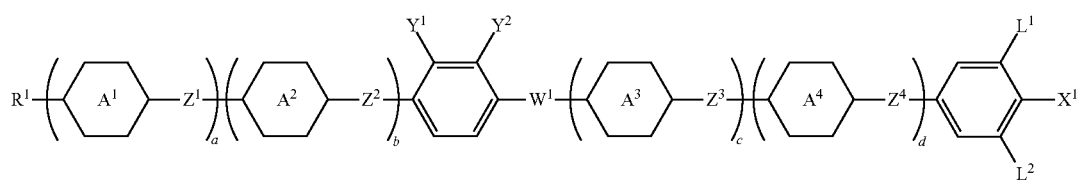

(1)

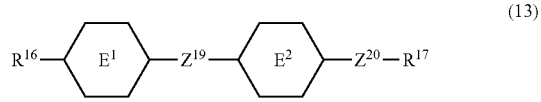

(13)

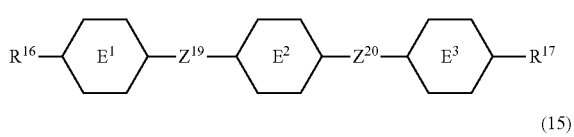

(14)

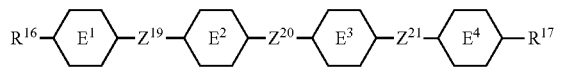

(15)

wherein, in formulas (13) to (15), $R^{16}$ and $R^{17}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and wherein, in formula (1), $R^1$ is alkyl having 1 to 15 carbons, in the alkyl, at least one of —$CH_2$— may be replaced by —O— or —S—, at least one of —$(CH_2)_2$— may be replaced by —CH═CH—, and in the groups, at least one of hydrogen may be replaced by halogen.

Examples of such a terminal group $R^1$ include alkyl, alkoxy, alkoxyalkyl, alkoxyalkoxy, alkylthio, alkylthioalkyl, alkenyl, alkenyloxy, alkenyloxyalkyl, alkoxyalkenyl and alkenylthio. In the groups, at least one of hydrogen may be replaced by halogen. Preferred halogen is fluorine and chlorine. Further preferred halogen is fluorine. The groups have a straight chain or a branched chain, and contains no cyclic group such as cyclohexyl. In the groups, the straight chain is preferred to the branched chain.

A preferred configuration of —CH═CH— in alkenyl depends on a position of a double bond. A trans configuration is preferred in alkenyl having the double bond in an odd-numbered position, such as —CH═CHCH$_3$, —CH═CHC$_2$H$_5$, —CH═CHC$_3$H$_7$, —CH═CHC$_4$H$_9$, —C$_2$H$_4$CH═CHCH$_3$ and —C$_2$H$_4$CH═CHC$_2$H$_5$. A cis configuration is preferred in alkenyl having the double bond in an even-numbered position, such as —CH$_2$CH═CHCH$_3$, —CH$_2$CH═CHC$_2$H$_5$ and —CH$_2$CH═CHC$_3$H$_7$. An alkenyl compound having a preferred configuration has a high clearing point or a wide temperature range of the liquid crystal phase. Detailed description is found in Mol. Cryst. Liq. Cryst., 1985, 131, 109 and Mol. Cryst. Liq. Cryst., 1985, 131, and 327.

Examples of alkyl include —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —C$_{13}$H$_{27}$, —C$_{14}$H$_{29}$ and —C$_{15}$H$_{31}$.

Examples of alkoxy include —OCH$_3$, —OC$_2$H$_5$, —OC$_3$H$_7$, —OC$_4$H$_9$, —OC$_5$H$_{11}$, —OC$_6$H$_{13}$, —OC$_7$H$_{15}$, —OC$_8$H$_{17}$, —OC$_9$H$_{19}$, —OC$_{10}$H$_{21}$, —OC$_{11}$H$_{23}$, —OC$_{12}$H$_{25}$, —OC$_{13}$H$_{27}$ and —OC$_{14}$H$_{29}$.

Examples of alkoxyalkyl include —CH$_2$OCH$_3$, —CH$_2$OC$_2$H$_5$, —CH$_2$OC$_3$H$_7$, —(CH$_2$)$_2$—OCH$_3$, —(CH$_2$)$_2$—OC$_2$H$_5$, —(CH$_2$)$_2$—OC$_3$H$_7$, —(CH$_2$)$_3$—OCH$_3$, —(CH$_2$)$_4$—OCH$_3$ and —(CH$_2$)$_5$—OCH$_3$.

Examples of alkenyl include —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$ and —(CH$_2$)$_3$—CH=CH$_2$.

Examples of alkenyloxy include —OCH$_2$CH=CH$_2$, —OCH$_2$CH=CHCH$_3$ and —OCH$_2$CH=CHC$_2$H$_5$.

Examples of alkyl in which at least one of hydrogen is replaced by halogen include —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F, —(CF$_2$)$_5$—F, —CH$_2$Cl, —CHCl$_2$, —CCl$_3$, —(CH$_2$)$_2$—Cl, —CCl$_2$CH$_2$Cl, —CCl$_2$CHCl$_2$, —CH$_2$CCl$_3$, —CCl$_2$CCl$_3$, —(CH$_2$)$_3$—Cl, —(CCl$_2$)$_3$—Cl, —CCl$_2$CHClCCl$_3$, —CHClCCl$_2$CCl$_3$, —(CH$_2$)$_4$—Cl, —(CCl$_2$)$_4$—Cl, —(CH$_2$)$_5$—Cl and —(CCl$_2$)$_5$—Cl.

Examples of alkoxy in which at least one of hydrogen is replaced by halogen include —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, —O—(CF$_2$)$_5$—F, —OCH$_2$Cl, —OCHCl$_2$, —OCCl$_3$, —O—(CH$_2$)$_2$—Cl, —OCCl$_2$CH$_2$Cl, —OCCl$_2$CHCl$_2$, —OCH$_2$CCl$_3$, —O—(CH$_2$)$_3$—Cl, —O—(CCl$_2$)$_3$—Cl, —OCCl$_2$CHClCCl$_3$, —OCHClCCl$_2$CCl$_3$, —O—(CH$_2$)$_4$—Cl, —O—(CCl$_2$)$_4$—Cl, —O—(CH$_2$)$_5$—Cl and —O—(CCl$_2$)$_5$—Cl.

Examples of alkenyl in which at least one of hydrogen is replaced by halogen include —CH=CHF, —CH=CF$_2$, —CF=CHF, —CH=CHCH$_2$F, —CH=CHCF$_3$, —(CH$_2$)$_2$—CH=CF$_2$, —CH$_2$CH=CHCF$_3$, —CH=CHCF$_2$CF$_3$, —CH=CHCl, —CH=CCl$_2$, —CCl=CHCl, —CH=CHCH$_2$Cl, —CH=CHCCl$_3$, —(CH$_2$)$_2$—CH=CCl$_2$, —CH$_2$CH=CHCCl$_3$ and —CH=CHCCl$_2$CCl$_3$.

Preferred examples of R$^1$ include alkyl having 1 to 15 carbons, alkenyl having 2 to 15 carbons and alkoxy having 2 to 15 carbons. Further preferred examples of R$^1$ include alkyl having 1 to 10 carbons and alkenyl having 2 to 10 carbons. Most preferred examples of R$^1$ include —CH$_3$, —C$_2$H$_5$, —C$_3$H$_7$, —C$_4$H$_9$, —C$_5$H$_{11}$, —C$_6$H$_{13}$, —C$_7$H$_{15}$, —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$ and —(CH$_2$)$_3$—CH=CH$_2$.

In formula (1), ring A$^1$, ring A$^2$, ring A$^3$ and ring A$^4$ are independently 1,4-cyclohexylene, 1,4-cyclohexenylene, 1,4-phenylene, 2-fluoro-1,4-phenylene, 2,6-difluoro-1,4-phenylene, 2-chloro-1,4-phenylene, 2,6-dichloro-1,4-phenylene, 2-chloro-6-fluoro-1,4-phenylene, tetrahydropyran-2, 5-diyl, 1,3-dioxane-2,5-diyl, 2,6,7-trioxabicyclo[2.2.2]octane-1,4-diyl, pyrimidine-2,5-diyl or pyridine-2,5-diyl.

Preferred examples of ring A$^1$, ring A$^2$, ring A$^3$ or ring A$^4$ include 1,4-cyclohexylene, 1,4-cyclohexenylene, 1,4-phenylene, 2-fluoro-1,4-phenylene, 2,6-difluoro-1,4-phenylene, tetrahydropyran-2,5-diyl, 1,3-dioxane-2,5-diyl and 2,6,7-trioxabicyclo[2.2.2]octane-1,4-diyl. Cis and trans configurations exist in 1,4-cyclohexylene. From a viewpoint of a high maximum temperature, the trans configuration is preferred.

Then, 2-fluoro-1,4-phenylene groups (A-1 and A-2) are left-right asymmetrical. In a chemical formula thereof, a case where fluorine is located on a side of a right-terminal group (rightward: A-1) and a case where fluorine is located on a side of a left-terminal group (leftward: A-2) exist. Preferred 2-fluoro-1,4-phenylene is (rightward: A-1) in order to increase the dielectric anisotropy. A same rule also applies to 2,6-difluoro-1,4-phenylene (A-3 and A-4), 2-chloro-1,4-phenylene (A-5 and A-6), 2,6-dichloro-1,4-phenylene (A-7 and A-8) and 2-chloro-6-fluoro-1,4-phenylene (A-9 and A-10).

Tetrahydropyran-2,5-diyl groups (A-11 and A-12) are left-right asymmetrical. A case where —O— is located on a side of a right-terminal group (rightward: A-11) and a case where —O— is located on a side of a left-terminal group (leftward: A-12) exist. From a viewpoint of the large dielectric anisotropy, a rightward (A-11) configuration is preferred, and from a viewpoint of a large dielectric constant in a minor axis direction, a leftward (A-12) configuration is preferred. In 1,3-dioxane-2,5-diyl (A-13 and A-14), 2,6,7-trioxabicyclo[2.2.2]octane-1,4-diyl (A-15 and A-16), pyrimidine-2,5-diyl (A-17 and A-18) and pyridine-2,5-diyl (A-19 and A-20), rightward (A-13, A-15, A-17 and A-19) configurations are preferred in order to increase the dielectric anisotropy.

(A-1)

(A-2)

(A-3)

(A-4)

(A-5)

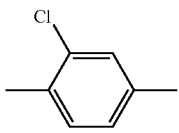 (A-6)

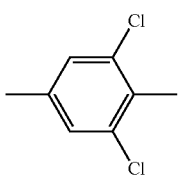 (A-7)

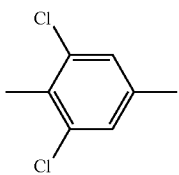 (A-8)

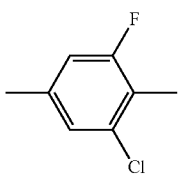 (A-9)

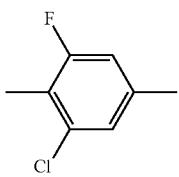 (A-10)

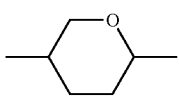 (A-11)

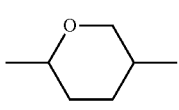 (A-12)

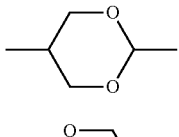 (A-13)

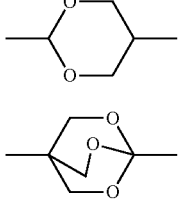 (A-14)

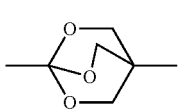 (A-15)

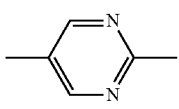 (A-16)

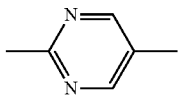 (A-17)

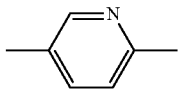 (A-18)

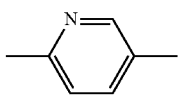 (A-19)

(A-20)

Further preferred examples of ring $A^1$, ring $A^2$, ring $A^3$ and ring $A^4$ include 1,4-cyclohexylene and 1,4-phenylene.

In formula (1), bonding group $W^1$ is a single bond, —(CH$_2$)$_2$—, —CH=CH—, —C≡C—, —COO—, —OCO—, —CH$_2$O—, —OCH$_2$— or —CF=CF—. Preferred examples of $W^1$ include a single bond, —(CH$_2$)$_2$—, —COO—, —CH$_2$O— and —OCH$_2$—. Further preferred examples of $W^1$ include a single bond.

In formula (1), bonding groups $Z^1$, $Z^2$, $Z^3$ and $Z^4$ are independently a single bond, —(CH$_2$)$_2$—, —CH=CH—, —C≡C—, —COO—, —OCO—, —CF$_2$O—, —CH$_2$O—, —OCH$_2$— or —CF=CF—, and at least one of $Z^1$ when a is 1, $Z^2$ when b is 1, $Z^3$ when c is 1, and $Z^4$ when d is 1 is —CF$_2$O—.

Preferred examples of $Z^1$, $Z^2$, $Z^3$ and $Z^4$ include a single bond, —(CH$_2$)$_2$—, —COO—, —CF$_2$O—, —CH$_2$O— and —OCH$_2$—. Further preferred examples of $Z^1$, $Z^2$, $Z^3$ and $Z^4$ include a single bond and —CF$_2$O—.

In formula (1), terminal group $X^1$ is halogen, —C≡N, —N=C=S, alkyl having 1 to 10 carbons in which at least one of hydrogen is replaced by fluorine, alkenyl having 2 to 10 carbons in which at least one of hydrogen is replaced by fluorine, alkoxy having 1 to 9 carbons in which at least one of hydrogen is replaced by fluorine, or alkenyloxy having 2 to 9 carbons in which at least one of hydrogen is replaced by fluorine.

Examples of alkyl in which at least one of hydrogen is replaced by fluorine include —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_2$—CF$_3$, —CF$_2$CHFCF$_3$, —CHFCF$_2$CF$_3$, —(CH$_2$)$_4$—F, —(CF$_2$)$_3$—CF$_3$, —(CH$_2$)$_5$—F and —(CF$_2$)$_4$—CF$_3$.

Examples of alkoxy in which at least one of hydrogen is replaced by fluorine include —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_2$—CF$_3$, —OCF$_2$CHFCF$_3$, —OCHFCF$_2$CF$_3$, —O—(CH$_2$)$_4$—F, —O—(CF$_2$)$_3$—CF$_3$, —O—(CH$_2$)$_5$—F and —O—(CF$_2$)$_4$—CF$_3$.

Examples of alkenyl in which at least one of hydrogen is replaced by fluorine include —CH=CHF, —CH=CF$_2$, —CF=CHF, —CF=CF$_2$, —CH=CHCH$_2$F, —CH=CHCF$_3$, —CF=CHCF$_3$, —CF=CFCF$_3$, —(CH$_2$)$_2$—CH=CF$_2$, —(CH$_2$)$_2$—CF=CF$_2$, —(CH$_2$)$_2$—CH=CHCF$_3$, —(CH$_2$)$_2$—CF=CHCF$_3$ and —(CH$_2$)$_2$—CF=CFCF$_3$.

Preferred examples of $X^1$ include fluorine, chlorine, —C≡N, —N=C=S, —CH$_2$F, —CHF$_2$, —CF$_3$, —(CH$_2$)$_2$—F, —CH$_2$CF$_3$, —CF$_2$CF$_3$, —(CH$_2$)$_3$—F, —(CH$_2$)$_2$—CF$_3$, —(CF$_2$)$_3$—F, —(CH$_2$)$_4$—F, —(CH$_2$)$_3$—CF$_3$, —(CF$_2$)$_4$—F, —(CF$_2$)$_5$—F, —(CF$_2$)$_6$—F, —(CF$_2$)$_7$—

F, —OCH$_2$F, —OCHF$_2$, —OCF$_3$, —O—(CH$_2$)$_2$—F, —OCH$_2$CF$_3$, —OCF$_2$CF$_3$, —O—(CH$_2$)$_3$—F, —O—(CH$_2$)$_2$—CF$_3$, —O—(CF$_2$)$_3$—F, —O—(CH$_2$)$_4$—F, —O—(CH$_2$)$_3$—CF$_3$, —O—(CF$_2$)$_4$—F, —O—(CF$_2$)$_5$—F, —O—(CF$_2$)$_6$—F, —CH=CHF, —CH=CF$_2$, —CF=CHF, —CF=CF$_2$, —CH=CHCH$_2$F, —CH=CHCF$_3$, —CF=CHCF$_3$, —CF=CFCF$_3$, —(CH$_2$)$_2$—CH=CF$_2$, —(CH$_2$)$_2$—CF=CF$_2$, —(CH$_2$)$_2$—CH=CHCF$_3$, —(CH$_2$)$_2$—CF=CHCF$_3$ and —(CH$_2$)$_2$—CF=CFCF$_3$.

Further preferred examples of $X^1$ include fluorine, chlorine, —C≡N, —CHF$_2$, —CF$_3$, —OCHF$_2$, —OCF$_3$, —CH=CHCF$_3$, —CF=CHCF$_3$ and —CF=CFCF$_3$. Most preferred examples of $X^1$ include fluorine, —CF$_3$ and —OCF$_3$.

In formula (1), $L^1$ and $L^2$ are independently hydrogen or fluorine. Preferred combinations of $L^1$ and $L^2$ include a combination in which both $L^1$ and $L^2$ are fluorine, and a combination in which one is hydrogen and the other is fluorine. Further preferred combinations of $L^1$ and $L^2$ include a combination in which both $L^1$ and $L^2$ are fluorine. When $X^1$ is alkyl having 1 to 10 carbons in which one of hydrogen is replaced by fluorine, alkenyl having 2 to 10 carbons in which one of hydrogen is replaced by fluorine, alkoxy having 1 to 9 carbons in which one of hydrogen is replaced by fluorine, or alkenyloxy having 2 to 9 carbons in which one of hydrogen is replaced by fluorine, $L^1$ is fluorine.

In formula (1), $Y^1$ and $Y^2$ are independently fluorine or chlorine. Preferred combinations of $Y^1$ and $Y^2$ include a combination in which both $Y^1$ and $Y^2$ are fluorine, and a combination in which one is fluorine and the other is chlorine. Further preferred combinations of $Y^1$ and $Y^2$ include a combination in which both $Y^1$ and $Y^2$ are fluorine.

In formula (1), a, b, c and d are independently 0 or 1, and a sum of a, b, c and d is 1, 2 or 3. Preferred combinations of a, b, c and d include combinations: (a=1, b=c=d=0), (c=1, a=b=d=0), (a=b=1, c=d=0), (a=c=1, b=d=0) and (c=d=1, a=b=0). Further preferred combinations of a, b, c and d include combinations: (c=1, a=b=d=0), (a=b=1, c=d=0), (a=c=1, b=d=0) and (c=d=1, a=b=0).

1-2. Physical Properties of Compound (1)

In compound (1), physical properties such as a clearing point, optical anisotropy and dielectric anisotropy can be arbitrarily adjusted by suitably selecting kinds of $R^1$, ring $A^1$ to ring $A^4$, $W^1$, $Z^1$ to $Z^4$, $X^1$, $L^1$, $L^2$, $Y^1$ and $Y^2$, a position of —CF$_2$O—, and a combination of a, b, c and d. Compound (1) may contain an isotope such as $^2$H (deuterium) and $^{13}$C in an amount larger than an amount of natural abundance because no significant difference is in the physical properties of the compound. A main effect of kinds of $R^1$ or the like on the physical properties of compound (1) is described below.

When left-terminal group $R^1$ has a straight chain, the temperature range of the liquid crystal phase is wide and the viscosity is small. When $R^1$ has a branched chain, compatibility with other liquid crystal compounds is good. A compound in which $R^1$ is optically active is useful as a chiral dopant. A reverse twisted domain to be generated in the liquid crystal display device can be prevented by adding the compound to the composition. A compound in which $R^1$ is not optically active is useful as a component of the composition. When $R^1$ is alkenyl, the preferred configuration depends on the position of the double bond. An alkenyl compound having the preferred configuration has the small viscosity, the high maximum temperature or the wide temperature range of the liquid crystal phase. When $R^1$ is alkoxy, the alkenyl compound has the high maximum temperature.

When all of ring $A^1$ to ring $A^4$ are 1,4-cyclohexylene, the clearing point is high and the viscosity is small. When at least one of ring $A^1$ to ring $A^4$ is 1,4-phenylene, 2-fluoro-1,4-phenylene, 2,6-difluoro-1,4-phenylene, 2-chloro-1,4-phenylene, 2,6-dichloro-1,4-phenylene or 2-chloro-6-fluoro-1,4-phenylene, the optical anisotropy is comparatively large and an orientational order parameter is comparatively large. When all of ring $A^1$ to ring $A^4$ are 1,4-phenylene, 2-fluoro-1,4-phenylene, 2,6-difluoro-1,4-phenylene, 2-chloro-1,4-phenylene, 2,6-dichloro-1,4-phenylene, 2-chloro-6-fluoro-1,4-phenylene, pyrimidine-2,5-diyl, pyridine-2,5-diyl or a combination thereof, the optical anisotropy is particularly large. When at least one of ring $A^1$ to ring $A^4$ is 2-fluoro-1,4-phenylene, 2-chloro-1,4-phenylene, 2,6-difluoro-1,4-phenylene, 2,6-dichloro-1,4-phenylene, 2-chloro-6-fluoro-1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl or pyridine-2,5-diyl, the dielectric anisotropy is large. When at least one of ring $A^1$ to ring $A^4$ is tetrahydropyran-2,5-diyl or 1,3-dioxane-2,5-diyl, the dielectric constant in the minor axis direction is large.

When bonding group $W^1$ is a single bond, —CH$_2$CH$_2$— or —CH=CH—, the viscosity is small. When $W^1$ is —CH=CH—, —CH$_2$O— or —OCH$_2$—, the temperature range of the liquid crystal phase is wide, and elastic constant (K) is large. When $W^1$ is a single bond, —CH=CH—, —C≡C—, —COO—, —OCO— or —CF=CF—, the clearing point is high. When $W^1$ is —CH=CH—, —C≡C— or —CF=CF—, the optical anisotropy is large. When $W^1$ is —COO—, the dielectric anisotropy is large. When $W^1$ is —OCH$_2$—, the dielectric constant in the minor axis direction is large. When $W^1$ is a single bond, —CH$_2$CH$_2$—, —CH$_2$O— or —OCH$_2$—, chemical stability is high.

When bonding groups $Z^1$ to $Z^4$ are a single bond, —CH$_2$CH$_2$—, —CH=CH— or —CF$_2$O—, the viscosity is small. When $Z^1$ to $Z^4$ are —CH=CH—, —CH$_2$O— or —OCH$_2$—, the temperature range of the liquid crystal phase is wide, and an elastic constant (K) is large. When $Z^1$ to $Z^4$ are a single bond, —CH=CH—, —C≡C—, —COO—, —OCO— or —CF=CF—, the clearing point is high. When $Z^1$ to $Z^4$ are —CH=CH—, —C≡C— or —CF=CF—, the optical anisotropy is large. When $Z^1$ to $Z^4$ are —CF$_2$O— or —COO—, the dielectric anisotropy is large. When $Z^1$ to $Z^4$ are —CH$_2$CH$_2$—, —CH$_2$O— or —OCH$_2$—, the dielectric constant in the minor axis direction is large. When $Z^1$ to $Z^4$ are a single bond, —CH$_2$CH$_2$—, —CH$_2$O— or —OCH$_2$—, the chemical stability is high.

When $X^1$ is fluorine, chlorine, —C≡N, —N=C=S, —CF$_3$, —CF=CHF, —CH=CHCF$_3$, —CF=CHCF$_3$ or —CF=CFCF$_3$, the dielectric anisotropy is particularly large. When $X^1$ is —C≡N, —N=C=S, —CH=CHF, —CH=CF$_2$, —CF=CHF, —CF=CF$_2$, —CH=CHCH$_2$F, —CH=CHCF$_3$, —CF=CHCF$_3$ or —CF=CFCF$_3$, the clearing point is high and the optical anisotropy is large. When $X^1$ is fluorine, chlorine, —OCH$_2$F, —OCHF$_2$ or —OCF$_3$, the compatibility with other liquid crystal compounds is good. When $X^1$ is fluorine, —CF$_3$, —CF$_2$CF$_3$, —(CF$_2$)$_3$—F, —(CF$_2$)$_4$—F, —(CF$_2$)$_5$—F, —(CF$_2$)$_6$—F, —(CF$_2$)$_7$—F, —OCF$_3$, —OCF$_2$CF$_3$, —O—(CF$_2$)$_3$—F, —O—(CF$_2$)$_4$—F, —O—(CF$_2$)$_5$—F or —O—(CF$_2$)$_6$—F, the chemical stability is high.

When both $L^1$ and $L^2$ are hydrogen, the clearing point is high. When any one of $L^1$ and $L^2$ is fluorine, the dielectric anisotropy is comparatively large, the dielectric constant in the minor axis direction is large, and the compatibility with other liquid crystal compounds is good. When both $L^1$ and $L^2$ are fluorine, the dielectric anisotropy is particularly large.

When both $Y^1$ and $Y^2$ are fluorine, or when $Y^1$ is fluorine and $Y^2$ is chlorine, the clearing point is high. When both $Y^1$ and $Y^2$ are fluorine, the viscosity is small, and the chemical stability is high.

When the combination of a, b, c and d is (a=1, b=c=d=0), and $Z^1$ is —$CF_2O$—, or when the combination is (c=1, a=b=d=0), and $Z^3$ is —$CF_2O$—, the compatibility with other liquid crystal compounds is good, the dielectric anisotropy is large, and the dielectric constant in the minor axis direction is particularly large. When the combination is (a=c=1, b=d=0), and $Z^3$ is —$CF_2O$—, or when the combination is (c=d=1, a=b=0), and $Z^4$ is —$CF_2O$—, the clearing point is high, the dielectric anisotropy is large, and the dielectric constant in the minor axis direction is large. When the combination is (a=b=1, c=d=0), and $Z^2$ is —$CF_2O$—, or when the combination is (c=d=1, a=b=0), and $Z^3$ is —$CF_2O$—, the dielectric anisotropy is large, and the compatibility with other liquid crystal compounds is good. When the combination is (a=b=c=1, d=0), and $Z^2$ is —$CF_2O$—, or when the combination is (a=b=c=1, d=0), and $Z^3$ is —$CF_2O$—, or when the combination is (a=c=d=1, b=0), and $Z^3$ is —$CF_2O$—, the clearing point is particularly high, and the dielectric anisotropy is large.

As described above, a compound having objective physical properties can be obtained by suitably selecting kinds of the ring structure, the terminal group, the bonding group or the like. Accordingly, compound (1) is useful as a component of a liquid crystal composition used for a liquid crystal display device having such a mode as PC, TN, STN, ECB, OCB, IPS, FFS or VA.

1-3. Preferred Compound

Preferred examples of compound (1) include compounds represented by formulas (1-1) to (1-7):

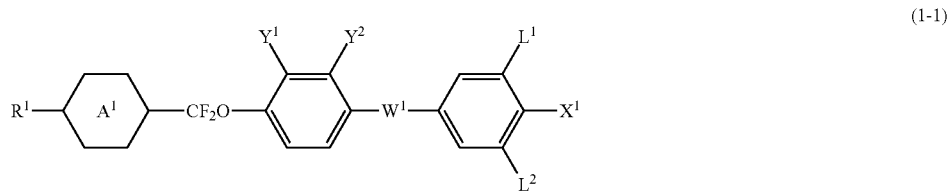

(1-1)

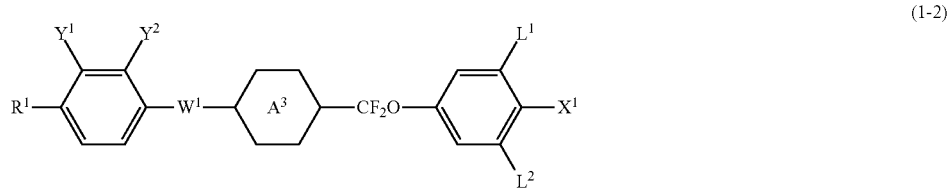

(1-2)

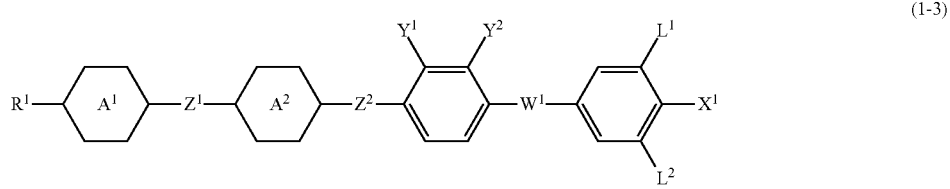

(1-3)

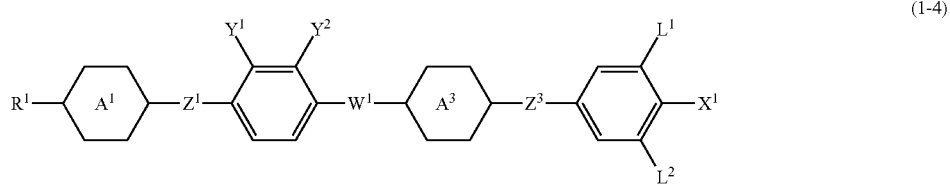

(1-4)

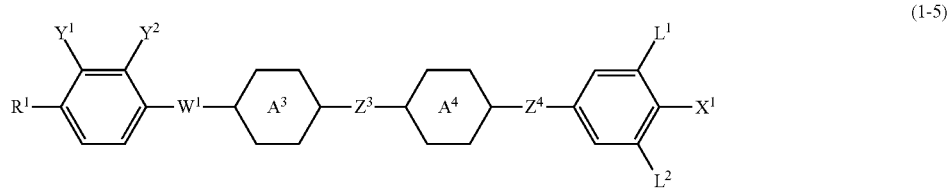

(1-5)

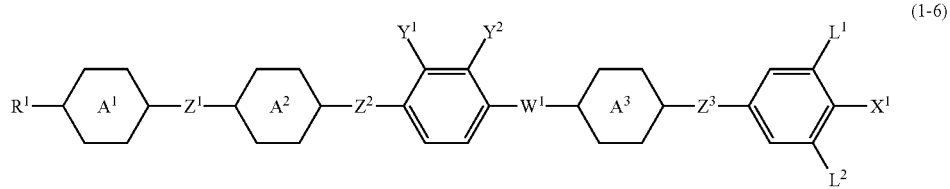

(1-6)

(1-7)

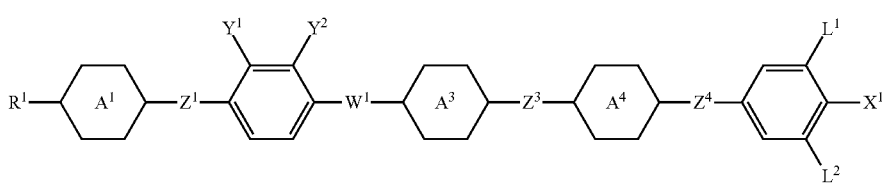

wherein, in formulas (1-1) to (1-7),
$R^1$ is alkyl having 1 to 10 carbons, alkenyl having 2 to 10 carbons or alkoxy having 1 to 9 carbons;
ring $A^1$, ring $A^2$, ring $A^3$ and ring $A^4$ are independently 1,4-cyclohexylene, 1,4-cyclohexenylene, 1,4-phenylene, 2-fluoro-1,4-phenylene, 2,6-difluoro-1,4-phenylene, tetrahydropyran-2,5-diyl or 1,3-dioxane-2,5-diyl;
$Z^1$, $Z^2$, $Z^3$ and $Z^4$ are independently a single bond, —$(CH_2)_2$—, —COO—, —$CF_2O$—, —$CH_2O$— or —$OCH_2$—;
$W^1$ is a single bond, —$(CH_2)_2$— or —$OCH_2$—;
$X^1$ is fluorine, —$CF_3$ or —$OCF_3$;
$L^1$ and $L^2$ are independently hydrogen or fluorine;
$Y^1$ and $Y^2$ are independently fluorine or chlorine;
in formula (1-3), any one of $Z^1$ and $Z^2$ is —$CF_2O$—;
in formula (1-4), any one of $Z^1$ and $Z^3$ is —$CF_2O$—;
in formula (1-5), any one of $Z^3$ and $Z^4$ is —$CF_2O$—;
in formula (1-6), any one of $Z^1$, $Z^2$ and $Z^3$ is —$CF_2O$—; and
in formula (1-7), any one of $Z^1$, $Z^3$ and $Z^4$ is —$CF_2O$—.

Preferred examples of compound (1) include compounds represented by formulas (1-8) to (1-12):

(1-8)

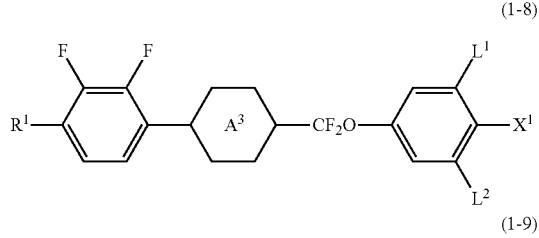

(1-9)

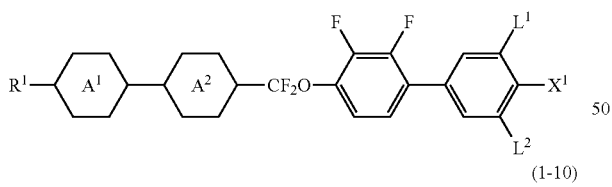

(1-10)

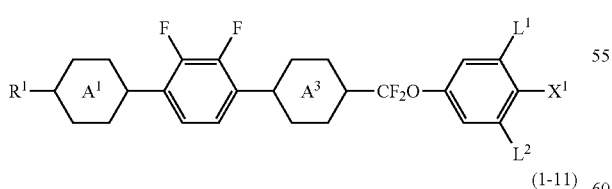

(1-11)

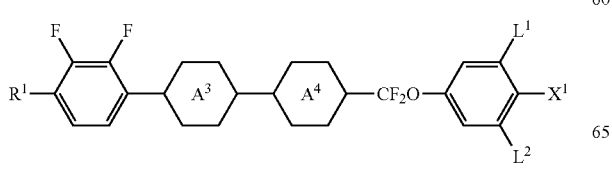

(1-12)

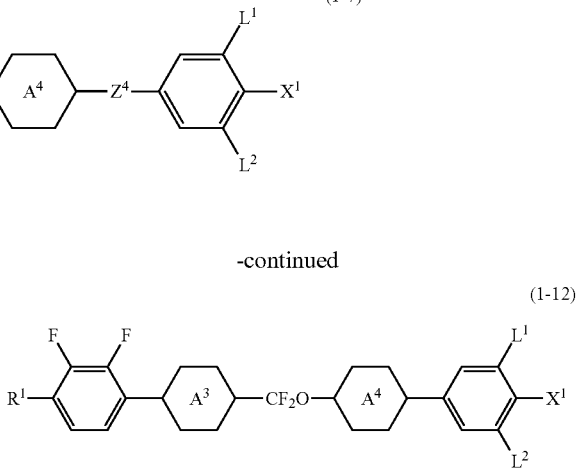

wherein, in formulas (1-8) to (1-12),
$R^1$ is alkyl having 1 to 10 carbons, alkenyl having 2 to 10 carbons or alkoxy having 1 to 9 carbons;
ring $A^1$, ring $A^2$, ring $A^3$ and ring $A^4$ are independently 1,4-cyclohexylene, 1,4-cyclohexenylene, 1,4-phenylene, 2-fluoro-1,4-phenylene, 2,6-difluoro-1,4-phenylene, tetrahydropyran-2,5-diyl or 1,3-dioxane-2,5-diyl;
$X^1$ is fluorine, —$CF_3$ or —$OCF_3$; and
$L^1$ and $L^2$ are independently hydrogen or fluorine.

Further preferred examples of compound (1) include compounds represented by formulas (1-13) to (1-22):

(1-13)

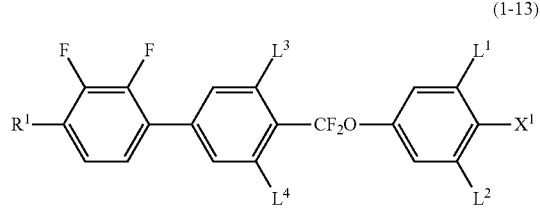

(1-14)

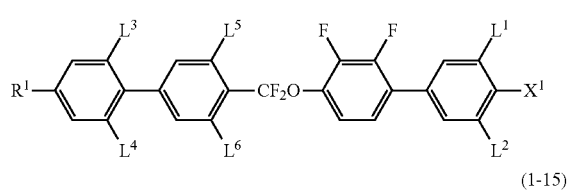

(1-15)

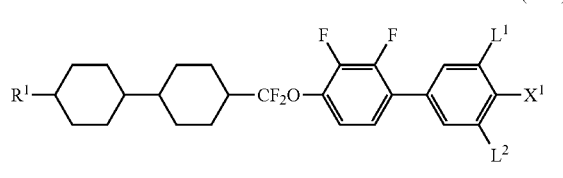

(1-16)

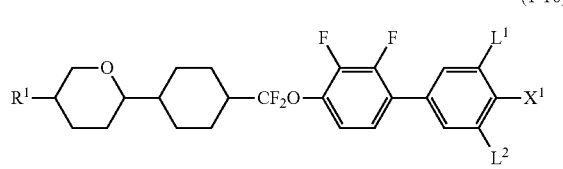

(1-17)
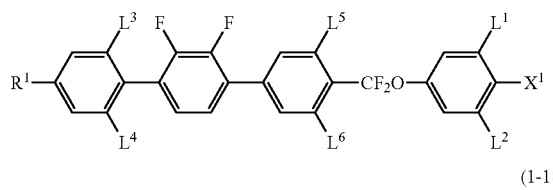

(1-18)
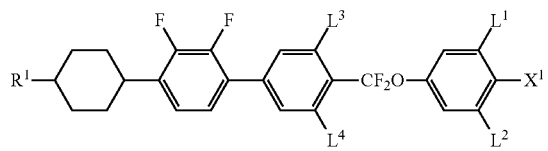

(1-19)
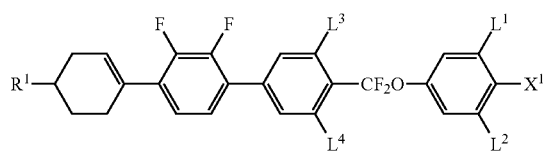

(1-20)
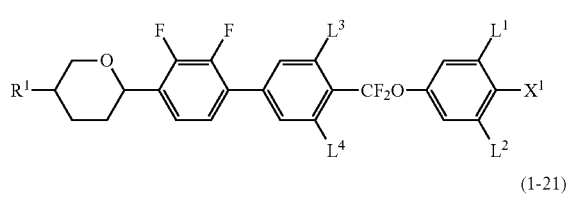

(1-21)
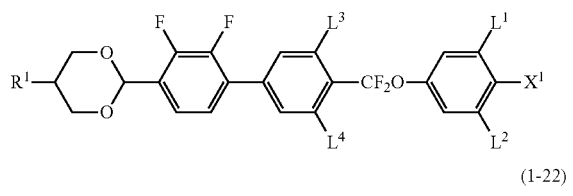

(1-22)
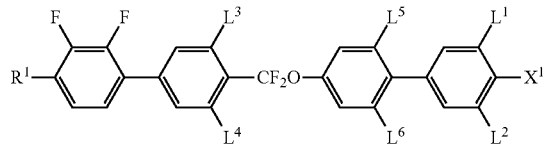

wherein, in formulas (1-13) to (1-22), $R^1$ is alkyl having 1 to 10 carbons, alkenyl having 2 to 10 carbons or alkoxy having 1 to 9 carbons; $X^1$ is fluorine, —$CF_3$ or —$OCF_3$; and $L^1$, $L^2$, $L^3$, $L^4$, $L^5$ and $L^6$ are independently hydrogen or fluorine.

Most preferred examples of compound (1) include compounds represented by formulas (1-23) to (1-25):

(1-23)
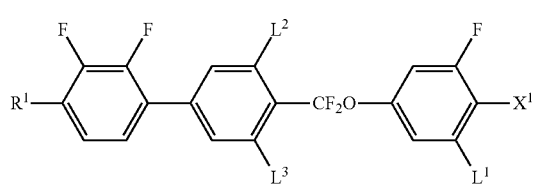

(1-24)
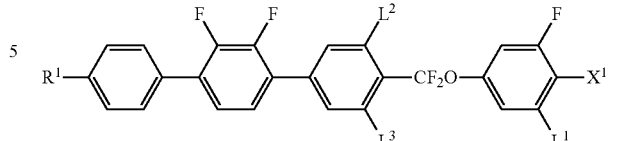

(1-25)
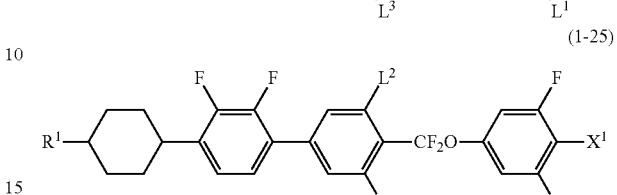

wherein, in formulas (1-23) to (1-25), $R^1$ is alkyl having 1 to 10 carbons, alkenyl having 2 to 10 carbons or alkoxy having 1 to 9 carbons; $X^1$ is fluorine, —$CF_3$ or —$OCF_3$; and $L^1$, $L^2$ and $L^3$ are independently hydrogen or fluorine.

1-4. Synthesis of Compound (1)

A method for preparing compound (1) is described. Compound (1) can be prepared by suitably combining methods in synthetic organic chemistry. Methods for introducing an objective terminal group, ring and bonding group into a starting material are described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.).

1-4-1. Formation of a Bonding Group

An example of a method for forming a bonding group in compound (1) is as described in a scheme below. In the scheme, $MSG^1$ (or $MSG^2$) is a monovalent organic group having at least one ring. The monovalent organic groups represented by a plurality of $MSG^1$ (or $MSG^2$) may be identical or different. Compounds (1A) to (1G) correspond to compound (1) or an intermediate of compound (1).

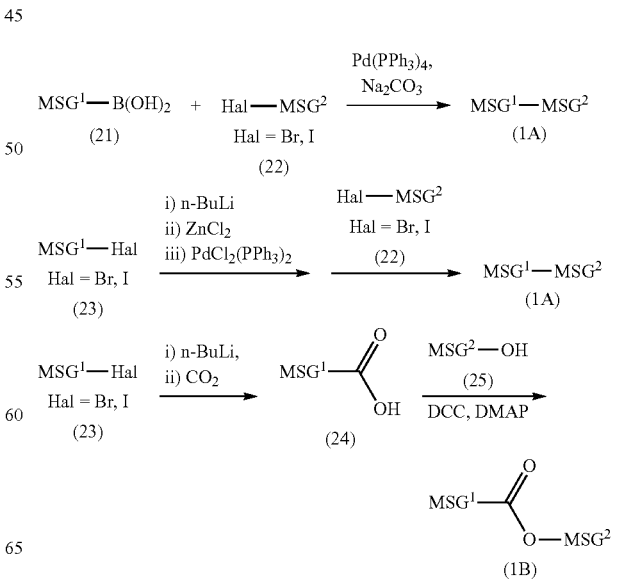

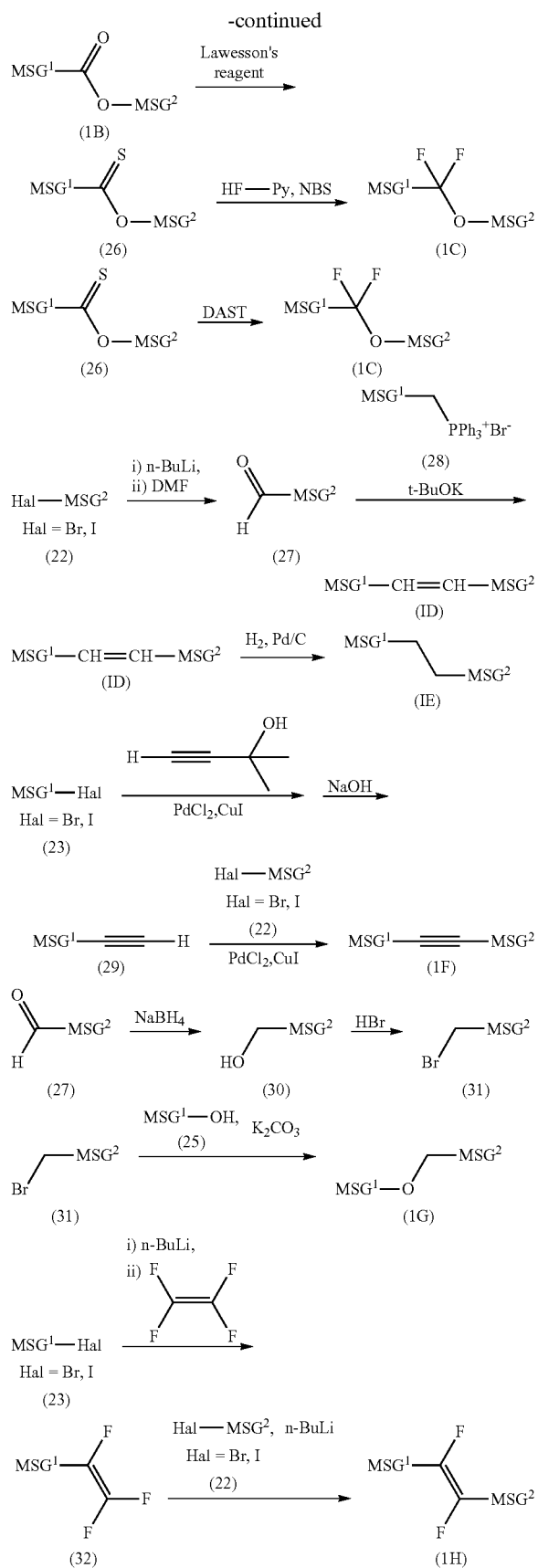

(I) Formation of a Single Bond

Compound (1A) is prepared by allowing aryl boronic acid (21) to react with compound (22) in the presence of carbonate and a catalyst such as tetrakis(triphenylphosphine) palladium. Compound (1A) is also prepared by allowing compound (23) to react with n-butyllithium and subsequently with zinc chloride, and further with compound (22) in the presence of a catalyst such as dichlorobis(triphenylphosphine)palladium.

(II) Formation of —COO— and —OCO—

Carboxylic acid (24) is obtained by allowing compound (23) to react with n-butyllithium and subsequently with carbon dioxide. Compound (1B) having —COO— is prepared by dehydrating, in the presence of 1,3-dicyclohexyl-carbodiimide (DCC) and 4-dimethylaminopyridine (DMAP), the carboxylic acid (24) and phenol (25) derived from compound (21). A compound having —OCO— is also prepared according to the method.

(III) Formation of —CF$_2$O—

Compound (26) is obtained by thionating compound (1B) with a Lawesson's reagent. Compound (1C) having —CF$_2$O— is prepared by fluorinating compound (26) with a hydrogen fluoride-pyridine complex and N-bromosuccinimide (NBS). Refer to M. Kuroboshi et al., Chem. Lett., 1992, 827. Compound (1C) is also prepared by fluorinating compound (26) with (diethylamino) sulfur trifluoride (DAST). Refer to W. H. Bunnelle et al., J. Org. Chem. 1990, 55, 768.

(IV) Formation of —CH═CH—

Aldehyde (27) is obtained by allowing compound (22) to react with n-butyllithium and subsequently with N,N-dimethylformamide (DMF). Compound (1D) is prepared by reacting aldehyde (27), with phosphorus ylide which is allowed to react with phosphonium salt (28) and potassium tert-butoxide. A cis isomer is generated depending on reaction conditions, and thus the cis isomer is isomerized into a trans isomer by a publicly known method, when necessary.

(V) Formation of —CH$_2$CH$_2$—

Compound (1E) is prepared by hydrogenating compound (1D) in the presence of a catalyst such as palladium on carbon.

(VI) Formation of —C≡C—

Compound (29) is obtained by allowing compound (23) to react with 2-methyl-3-butyn-2-ol in the presence of a catalyst including dichloropalladium and copper iodide, and then deprotecting the resulting product under basic conditions. Compound (1F) is prepared by allowing compound (29) to react with compound (22) in the presence of a catalyst including dichlorobis(triphenylphosphine)palladium and copper halide.

(VII) Formation of —CH$_2$O— and —OCH$_2$—

Compound (30) is obtained by reducing compound (27) with sodium borohydride. Compound (31) is obtained by brominating the resulting product with hydrobromic acid. Compound (1G) is prepared by allowing compound (25) to react with compound (31) in the presence of potassium carbonate. A compound having —OCH$_2$— is also prepared according to the method.

(VIII) Formation of —CF═CF—

Compound (32) is obtained by treating compound (23) with n-butyllithium and then allowing the treated product to react with tetrafluoroethylene. Compound (1H) is prepared by treating compound (22) with n-butyllithium and then allowing the resulting treated material to react with compound (32).

1-4-2. Formation of Ring A$^1$ and Ring A$^2$

With regard to rings such as 1,4-cyclohexylene, 1,4-cyclohexenylene, 1,4-phenylene, 2-fluoro-1,4-phenylene, 2,6-difluoro-1,4-phenylene, 2-chloro-1,4-phenylene, 2,6-dichloro-1,4-phenylene, 2-chloro-6-fluoro-1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl and pyridine-2,5-diyl, a starting material is commercially available or a synthetic process is well known.

1-4-3. Synthesis Examples

An example of a method for preparing compound (1) is as described below. In the compounds, $R^1$, ring $A^1$ to ring $A^4$, $W^1$, $Z^1$ to $Z^4$, $X^1$, $L^1$, $L^2$, $Y^1$, $Y^2$, a, b, c and d are defined in a manner identical with the definitions in item 1 described above.

In formula (1), compound (1-41) in which c=1 and $Z^3$ is —$CF_2O$— can be prepared by the method described below. Compound (43) is obtained by dehydrating, in the presence of DCC and DMAP, compound (41) prepared by a publicly known method and compound (42) prepared by a publicly known method. Next, compound (44) is obtained by thionating compound (43) with a Lawesson's reagent. Next, compound (1-41) can be derived from compound (44) by fluorinating compound (44) using a fluorinating reagent such as a hydrogen fluoride-pyridine complex and NBS, or DAST. In addition, a compound in which a=1 and $Z^1$ is —$CF_2O$—, a compound in which b=1 and $Z^2$ is —$CF_2O$—, and a compound in which d=1 and $Z^4$ is —$CF_2O$— can be prepared in a similar manner.

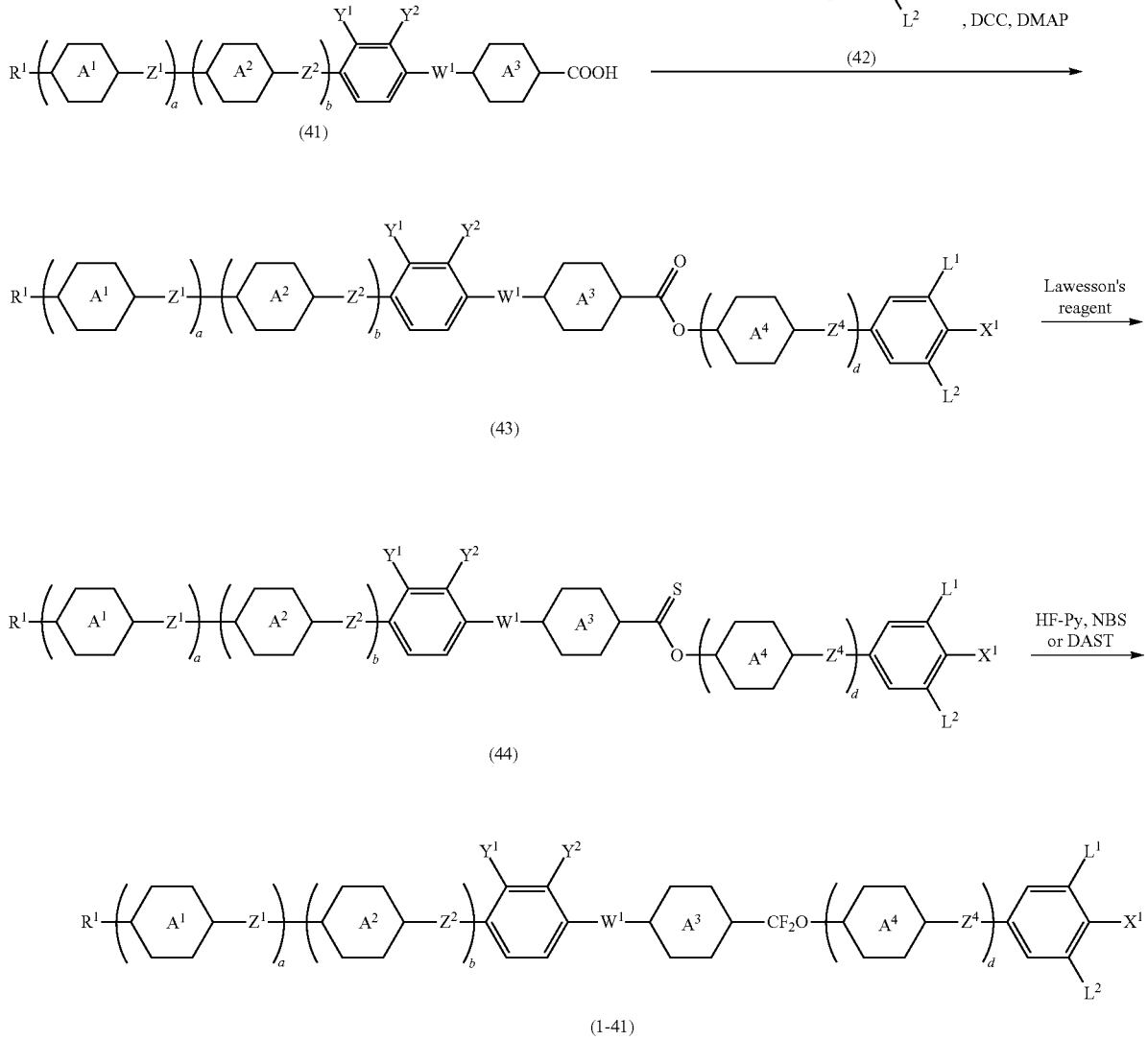

In formula (1), compound (1-41) in which c=1 and $Z^3$ is —$CF_2O$— can also be prepared by the method described below. Compound (45) is obtained by acting propanedithiol and trifluoromethanesulfonic acid on compound (41) prepared by a publicly known method. Next, compound (1-41) can be derived from compound (42) prepared by a publicly known method and compound (45) by allowing compound (42) to react with compound (45) using triethylamine, a hydrogen fluoride-triethylamine complex and bromine. In addition, a compound in which a=1 and $Z^1$ is —$CF_2O$—, a compound in which b=1 and $Z^2$ is —$CF_2O$—, and a compound in which d=1 and $Z^4$ is —$CF_2O$— can also be prepared in a similar manner.

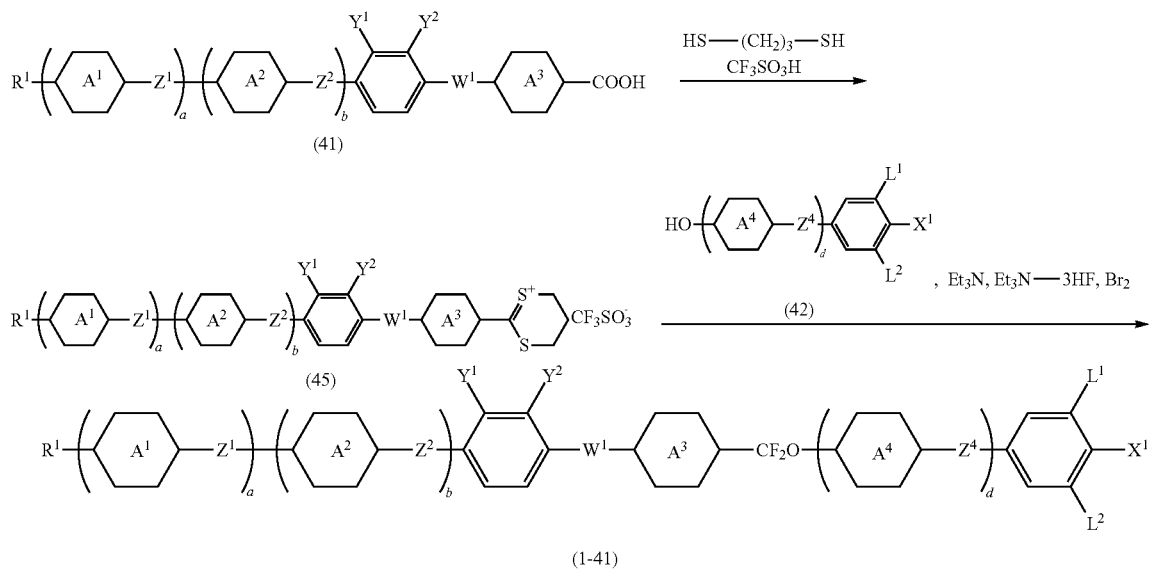

In formula (1), compound (1-42) in which c=1, $Z^3$ is —$CF_2O$—, ring $A^3$ is 1,4-phenylene and $W^1$ is a single bond can also be prepared by the method described below. Compound (47) is obtained by allowing compound (46) prepared according to the method described in JP 2011-98942 A to react with compound (42) prepared by a publicly known method in the presence of a base such as potassium carbonate. Next, compound (1-42) can be derived from compound (48) prepared by a publicly known method and compound (47) by allowing to compound (48) to react with compound (47) in the presence of a palladium catalyst such as tetrakis (triphenylphosphine)palladium and a base such as potassium carbonate. In addition, a compound in which a=1, $Z^1$ is —$CF_2O$—, ring $A^1$ is 1,4-phenylene and $W^1$ is a single bond, a compound in which b=1, $Z^2$ is —$CF_2O$—, ring $A^2$ is 1,4-phenylene and $W^1$ is a single bond, and a compound in which d=1, $Z^4$ is —$CF_2O$—, ring $A^4$ is 1,4-phenylene and $W^1$ is a single bond can also be prepared in a similar manner.

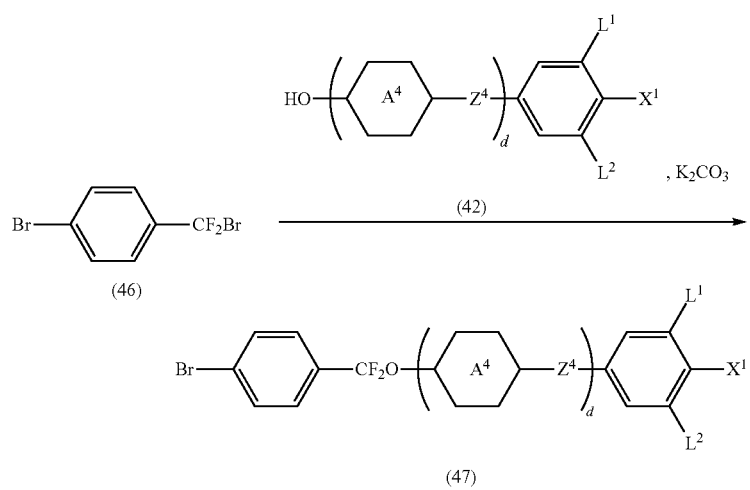

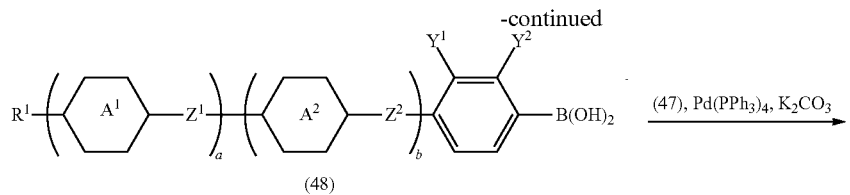

(48)

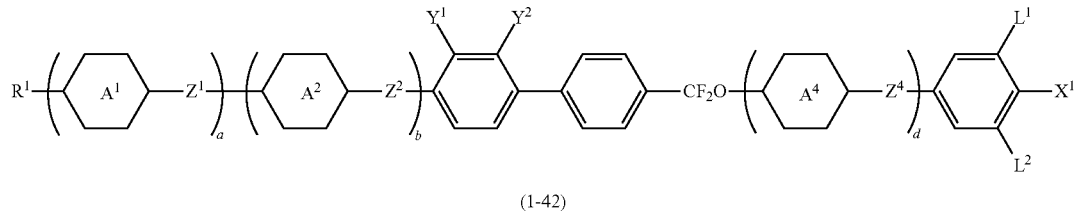

(1-42)

In formula (1), compound (1-43) in which c=1, $Z^3$ is —CF$_2$O— and ring $A^3$ is 2,6-difluoro-1,4-phenylene can also be prepared by the method described below. Compound (50) is obtained by acting n-butyllithium and dibromodifluoromethane on compound (49) prepared by a publicly known method. Next, compound (1-43) can be derived from compound (42) and compound (50) by allowing compound (42) to react with compound (50) in the presence of a base such as potassium carbonate. In addition, a compound in which a=1, $Z^1$ is —CF$_2$O— and ring $A^1$ is 2,6-difluoro-1,4-phenylene, a compound in which b=1, $Z^2$ is —CF$_2$O— and ring $A^2$ is 2,6-difluoro-1,4-phenylene, and a compound in which d=1, $Z^4$ is —CF$_2$O— and ring $A^4$ is 2,6-difluoro-1,4-phenylene can also be prepared in a similar manner.

In formula (1), compound (1-44) in which c=1, $Z^3$ is —CF$_2$O— and ring $A^3$ is 1,4-cyclohexenylene, or compound (1-45) in which c=1, $Z^3$ is —CF$_2$O—, and ring $A^3$ is 1,4-cyclohexenylene can also be prepared according to the method described below. Compound (52) is obtained by acting trisdiethylaminophosphine and dibromodifluoromethane on compound (51) prepared by a publicly known method. Next, compound (53) is obtained by acting bromine on the resulting product. Next, compound (1-44) can be obtained by allowing compound (42) to react with compound (53) in the presence of a base such as potassium carbonate. Next, compound (1-45) can be derived from compound (1-44) by catalytically hydrogenating compound (1-44) using a catalyst such as palladium on carbon. In

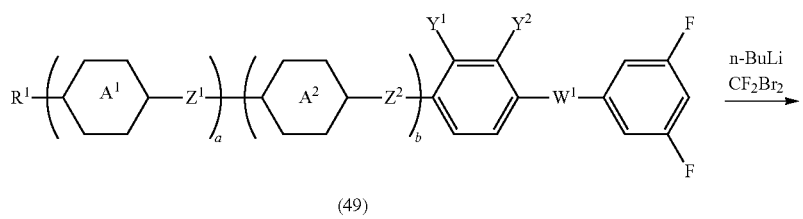

(49)

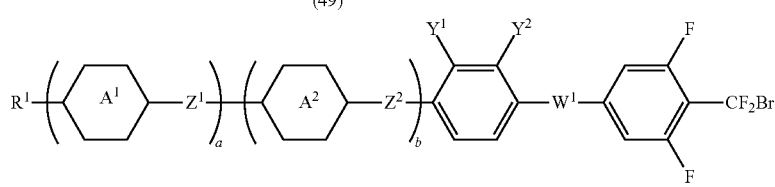

(50)

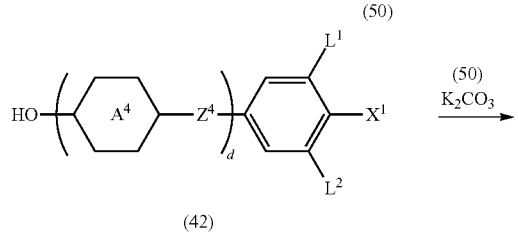

(42)

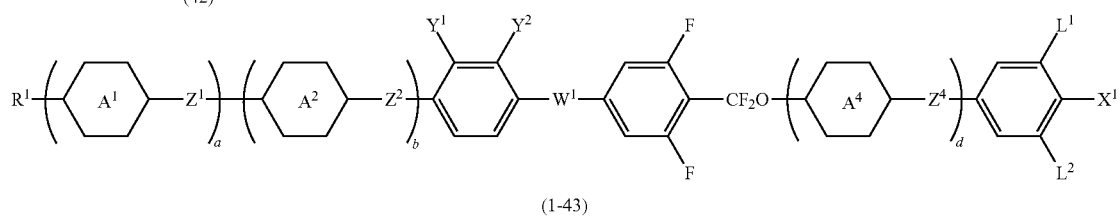

(1-43)

addition, a compound in which a=1, $Z^1$ is —$CF_2O$— and ring $A^1$ is 1,4-cyclohexenylene, or a compound in which a=1, $Z^1$ is —$CF_2O$— and ring $A^1$ is 1,4-cyclohexylene, a compound in which b=1, $Z^2$ is —$CF_2O$— and ring $A^2$ is 1,4-cyclohexenylene, or b=1, $Z^2$ is —$CF_2O$— and ring $A^2$ is 1,4-cyclohexylene, and a compound in which d=1, $Z^4$ is —$CF_2O$— and ring $A^4$ is 1,4-cyclohexenylene, or d=1, $Z^4$ is —$CF_2O$— and ring $A^4$ is 1,4-cyclohexylene can also be prepared in a similar manner.

anisotropy, a preferred content of compound (1) is in the range of 5 to 60% by weight. In a composition having a negative dielectric anisotropy, a preferred content of compound (1) is 30% by weight or less. Composition (1) may also contain compound (1) and various kinds of liquid crystal compounds that are not described herein.

A preferred composition contains a compound selected from components B, C, D and E shown below. When composition (1) is prepared, the component can also be

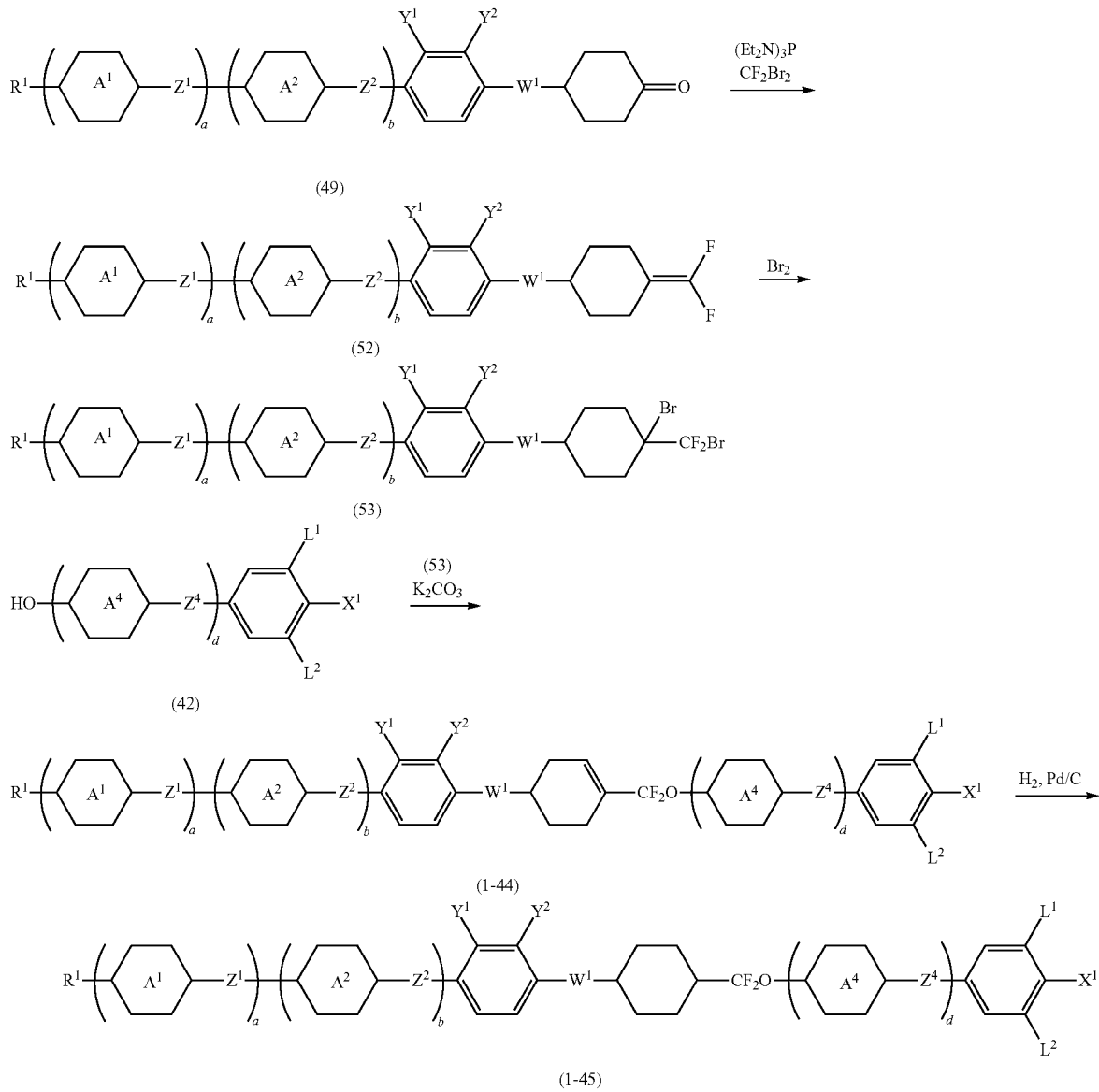

2. Composition (1)

Liquid crystal composition (1) of the invention is described. Composition (1) contains at least one compound (1) as component A. Composition (1) may contain two or more compounds (1). A component in the liquid crystal compound may be compound (1) only. In order to develop excellent physical properties, composition (1) preferably contains at least one compound (1) in the range of 1 to 99% by weight. In a composition having a positive dielectric selected by taking the dielectric anisotropy of compound (1) into consideration, for example. When a composition having the positive dielectric anisotropy is prepared for a mode such as TFT, IPS and FFS, a main component includes components A, B and E. When a composition having the positive dielectric anisotropy is prepared for a mode such as STN and TN, a main component includes components A, C and E. When a composition having the negative dielectric anisotropy is prepared for a mode such as VA and PSA, a main component includes components D and E, and component A is added for the purpose of adjusting a voltage-transmittance curve of the device. A composition prepared by suitably selecting the components has a high maximum temperature, a low minimum temperature, a small viscosity, a suitable optical anisotropy, a large dielectric anisotropy and a suitable elastic constant.

Component B includes compounds (2) to (4). Component C includes compound (5). Component D includes compounds (6) to (12). Component E includes compounds (13) to (15). The components are described in the order.

Component B is a compound having a halogen-containing group or a fluorine-containing group at a right terminal. Specific preferred examples of component B include compounds (2-1) to (2-16), compounds (3-1) to (3-113) and compounds (4-1) to (4-57). In the compounds, $R^{11}$ and $X^{11}$ are defined in a manner identical with the definitions in item 9 described above.

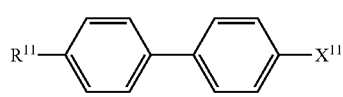
(2-1)

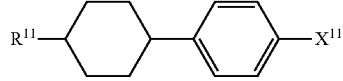
(2-2)

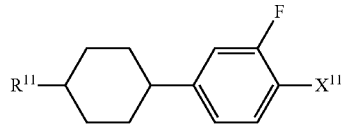
(2-3)

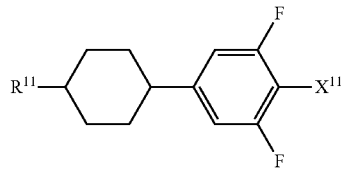
(2-4)

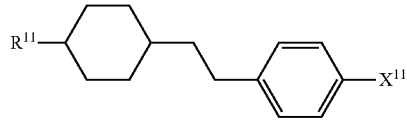
(2-5)

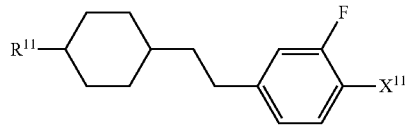
(2-6)

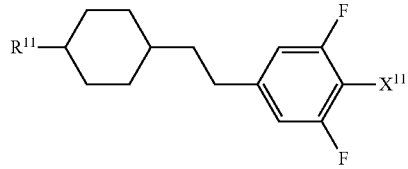
(2-7)

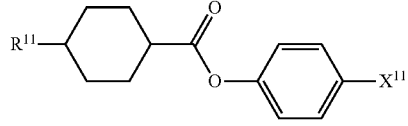
(2-8)

-continued

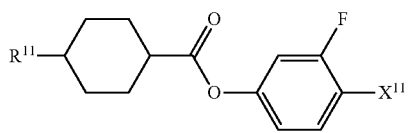
(2-9)

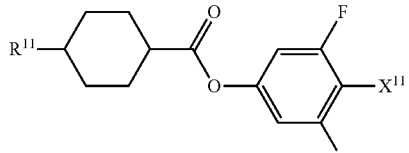
(2-10)

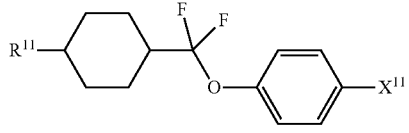
(2-11)

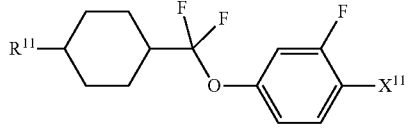
(2-12)

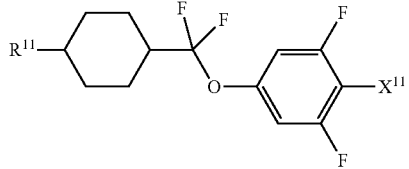
(2-13)

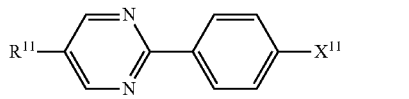
(2-14)

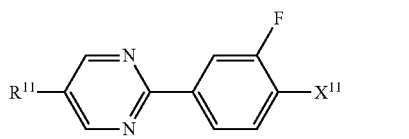
(2-15)

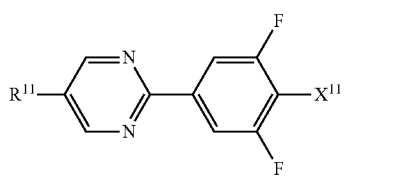
(2-16)

(3-1)

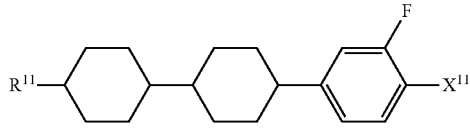
(3-2)

(3-3)
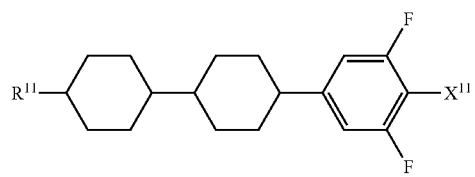
(3-4)
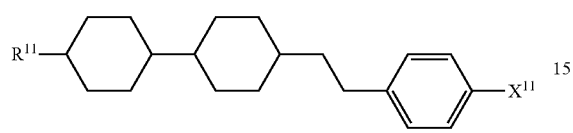
(3-5)
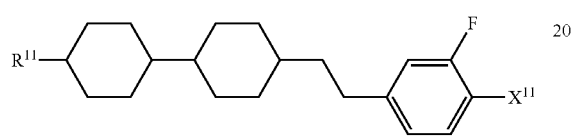
(3-6)
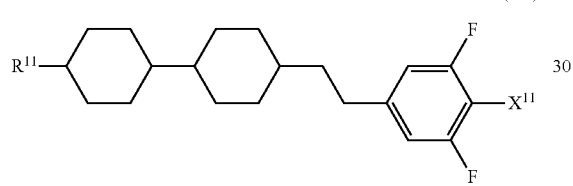
(3-7)
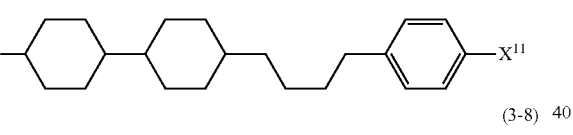
(3-8)
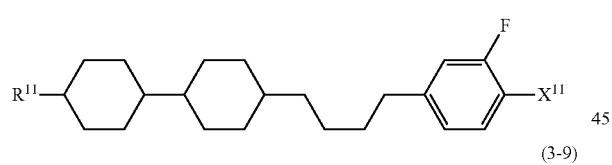
(3-9)
(3-10)
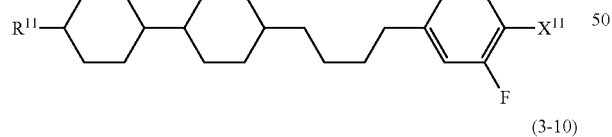
(3-11)
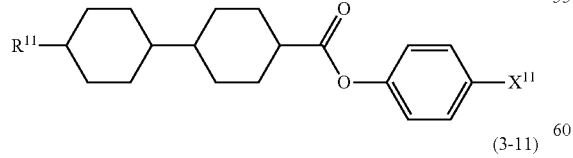
(3-12)
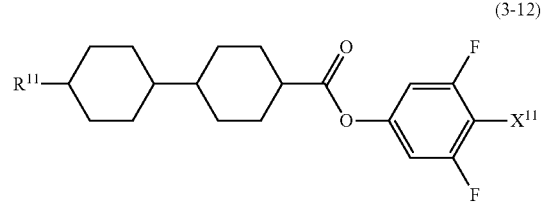
(3-13)
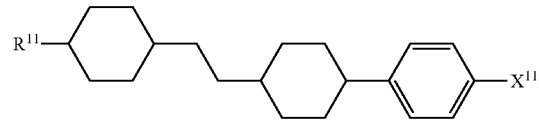
(3-14)
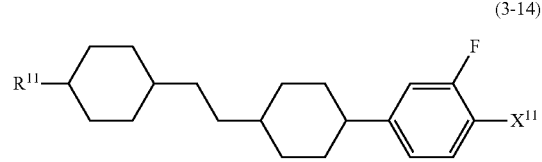
(3-15)
(3-16)
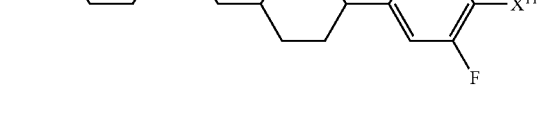
(3-17)
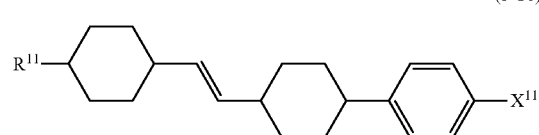
(3-18)
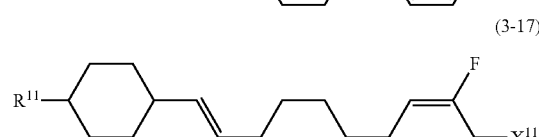
(3-19)
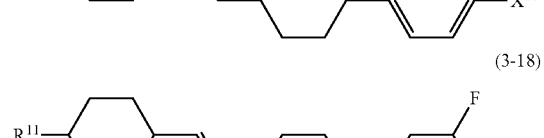
(3-20)
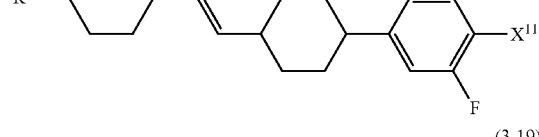
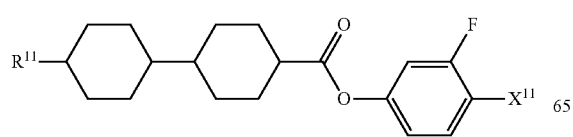
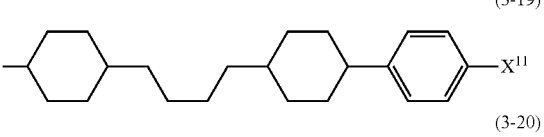

(3-21) 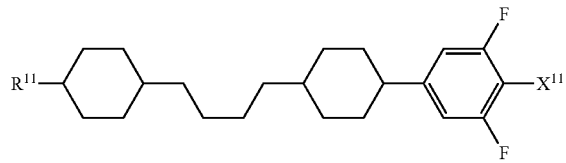
(3-22) 
(3-23) 
(3-24) 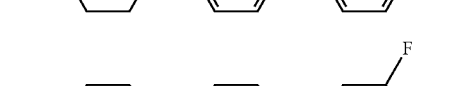
(3-25) 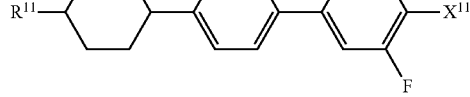
(3-26) 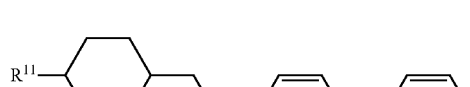
(3-27) 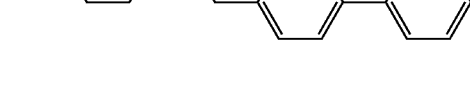
(3-28) 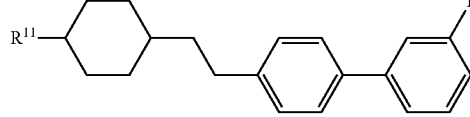
(3-29) 
(3-30) 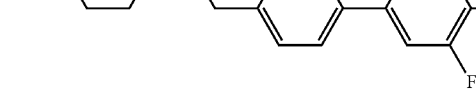
(3-31) 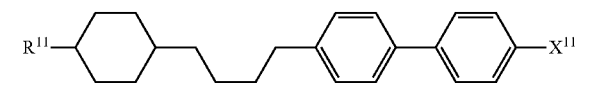
(3-32) 
(3-33) 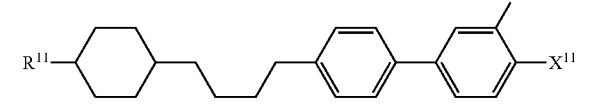
(3-34) 
(3-35) 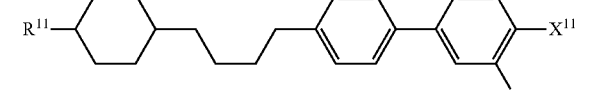
(3-36) 
(3-37) 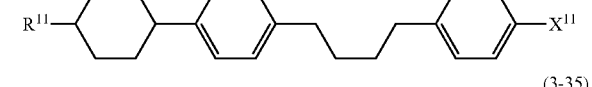
(3-38) 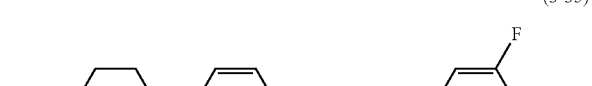
(3-39) 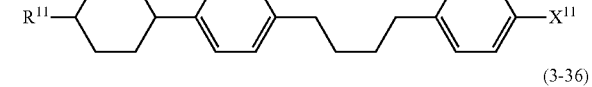
(3-40) 

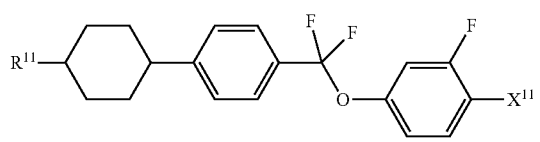
(3-41)
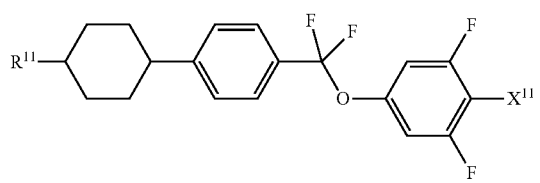
(3-42)
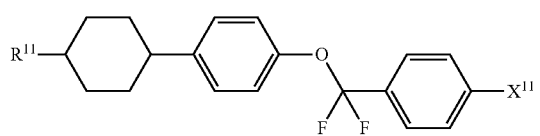
(3-43)
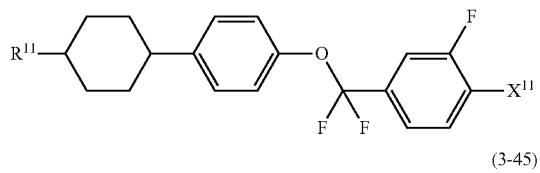
(3-44)
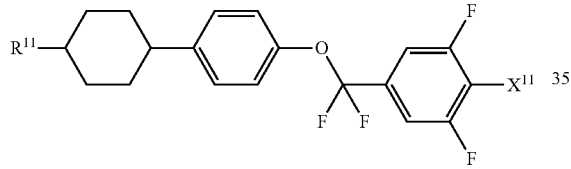
(3-45)
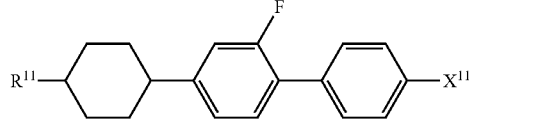
(3-46)
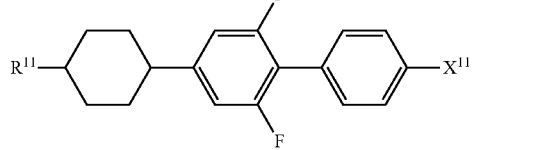
(3-47)
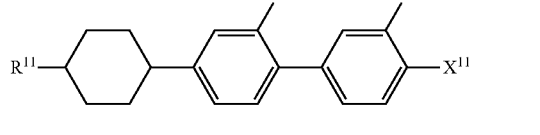
(3-48)
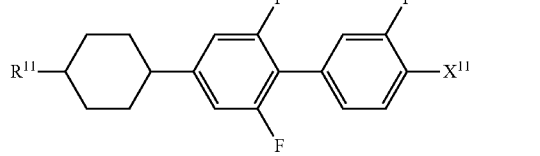
(3-49)
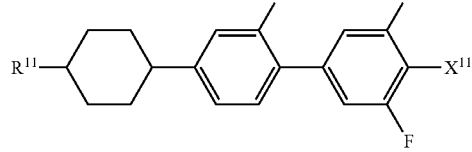
(3-50)
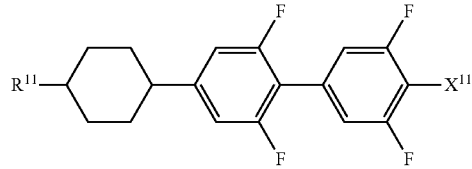
(3-51)
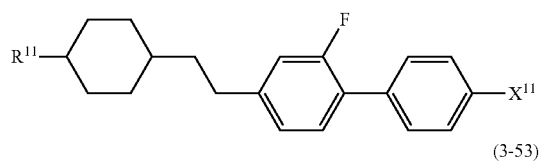
(3-52)
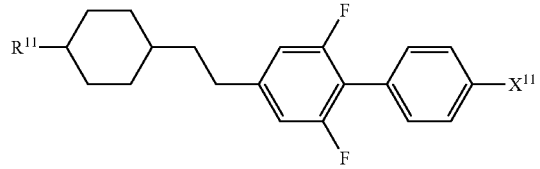
(3-53)
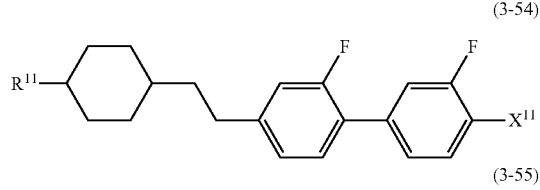
(3-54)
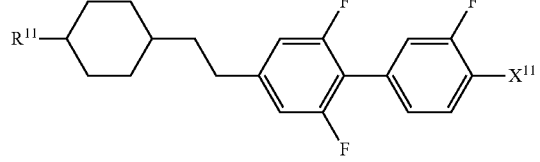
(3-55)
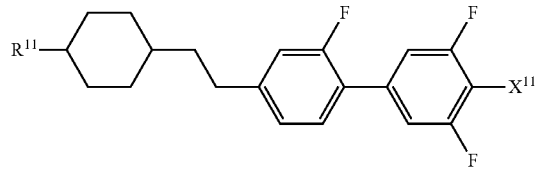
(3-56)
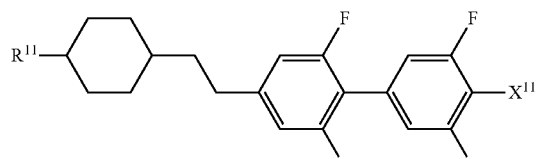
(3-57)

(3-58)
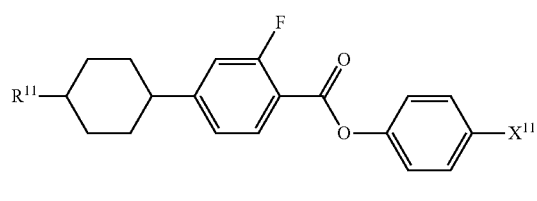
(3-59)
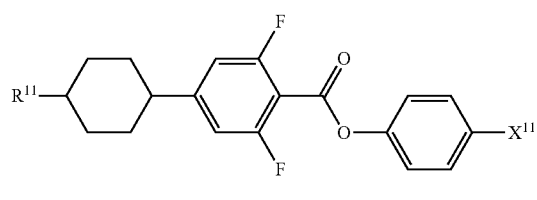
(3-60)
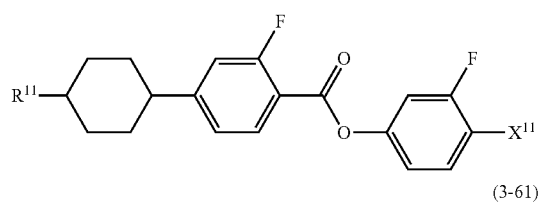
(3-61)
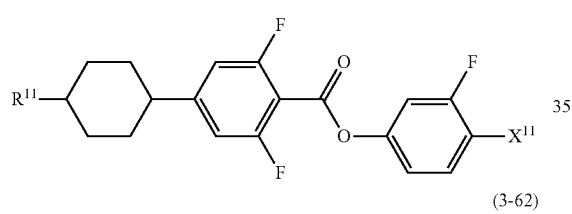
(3-62)
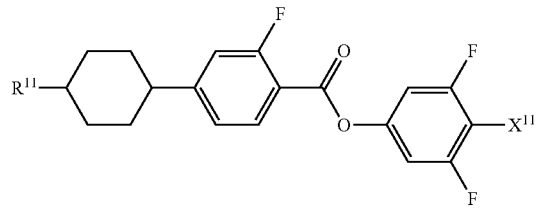
(3-63)
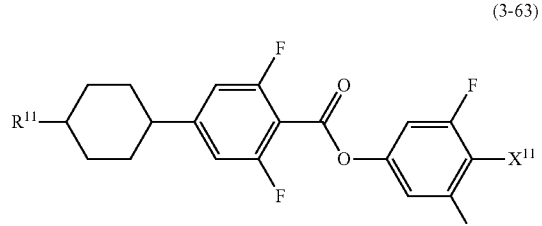
(3-64)
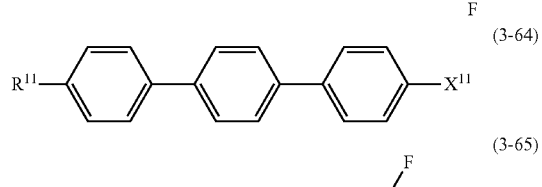
(3-65)
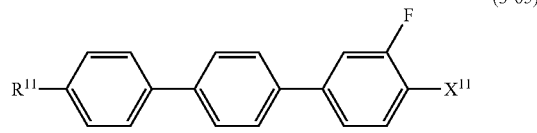
(3-66)
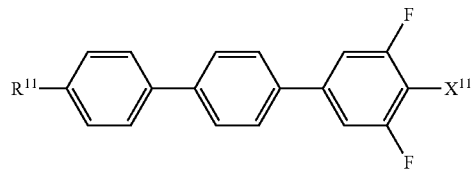
(3-67)
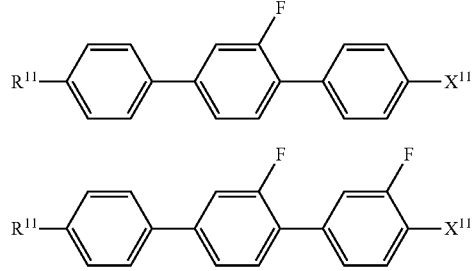
(3-68)
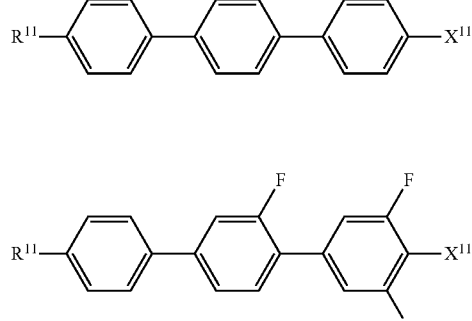
(3-69)
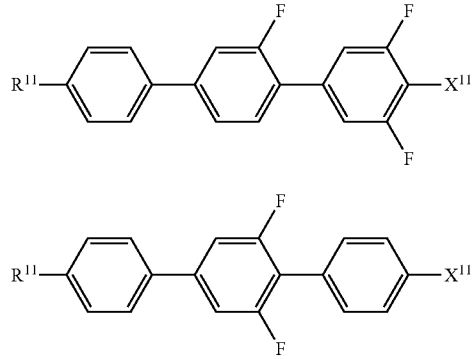
(3-70)
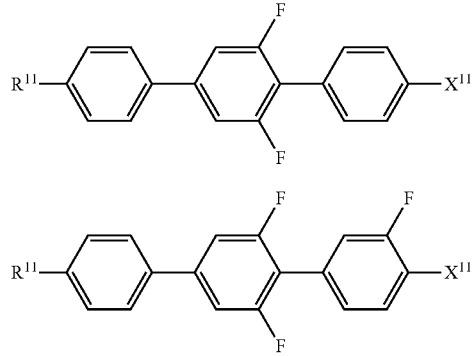
(3-71)
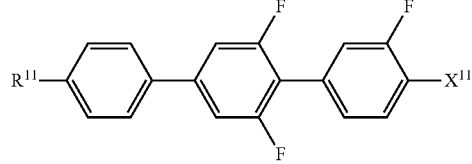
(3-72)
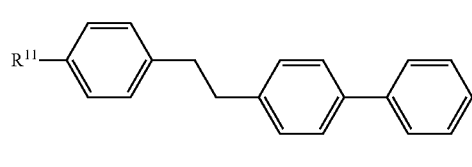
(3-73)
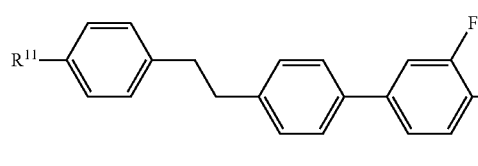
(3-74)
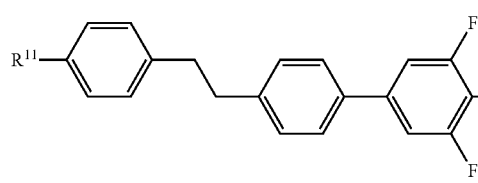

(3-75) 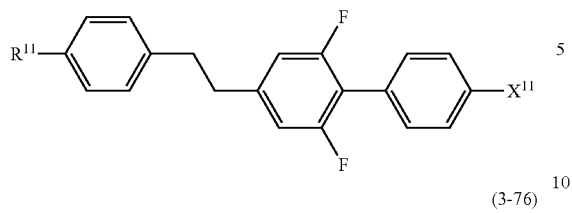
(3-76) 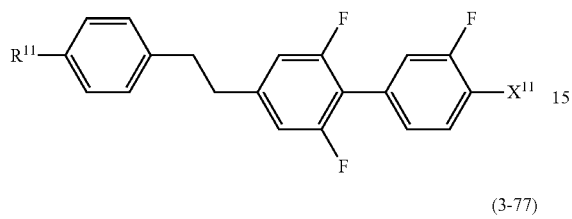
(3-77) 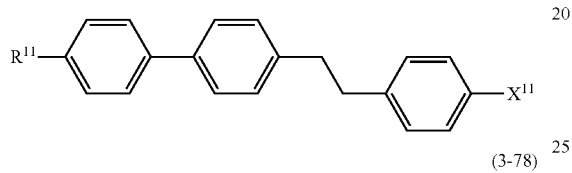
(3-78) 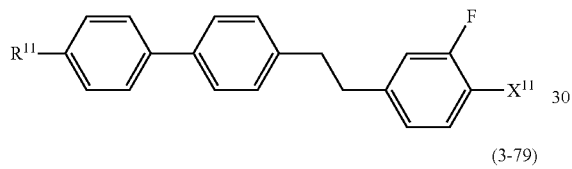
(3-79) 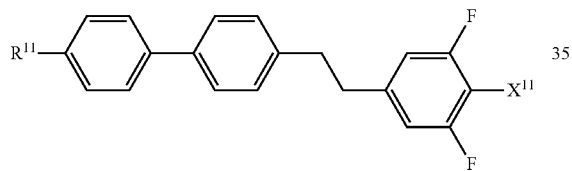
(3-80) 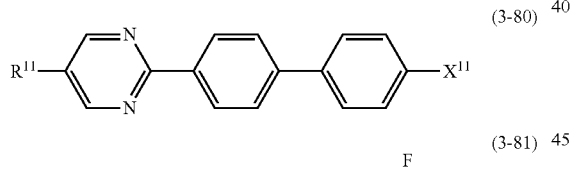
(3-81) 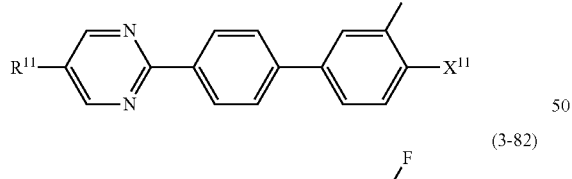
(3-82) 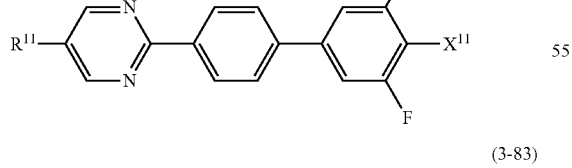
(3-83) 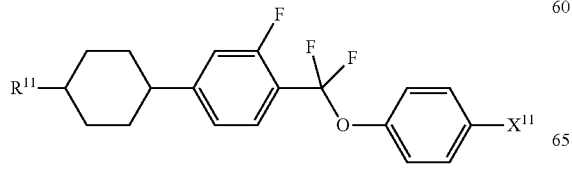
(3-84) 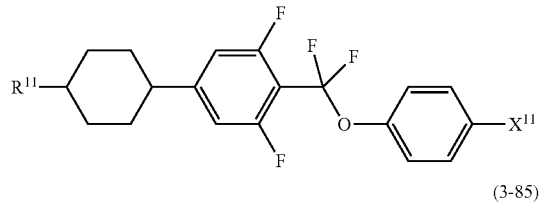
(3-85) 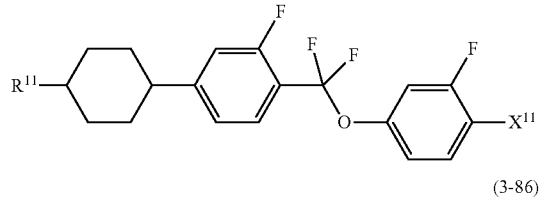
(3-86) 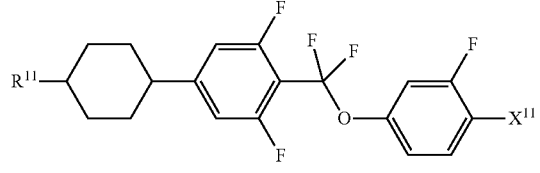
(3-87) 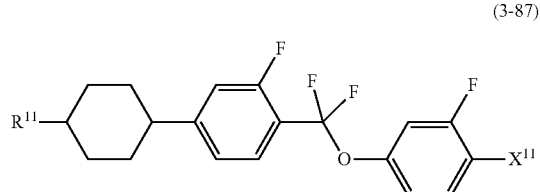
(3-88) 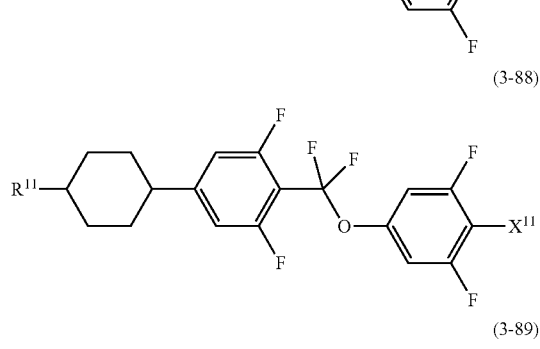
(3-89) 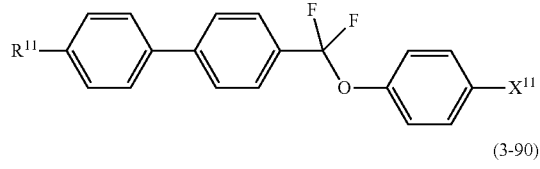
(3-90) 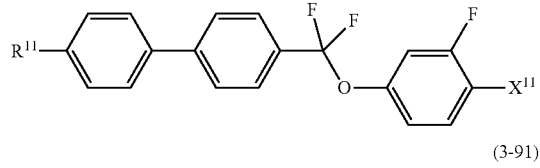
(3-91) 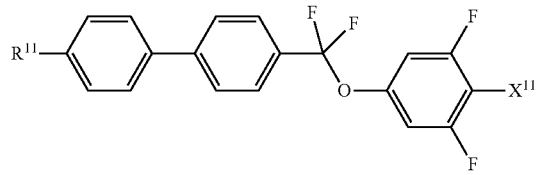

(3-92)
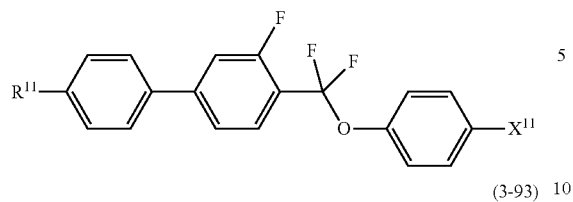
(3-93)
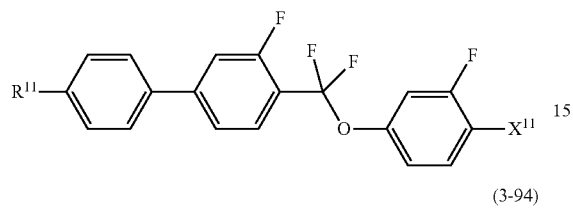
(3-94)
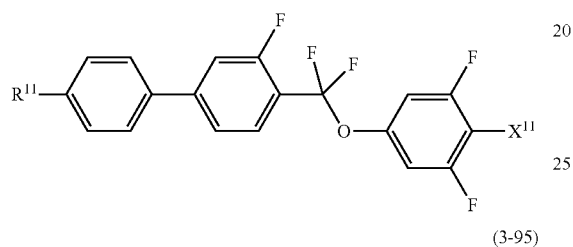
(3-95)
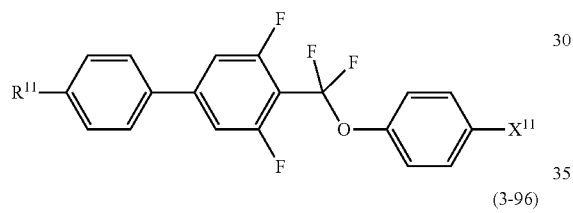
(3-96)
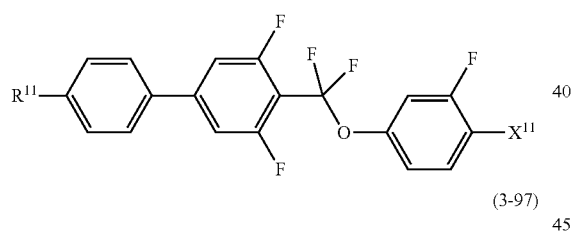
(3-97)
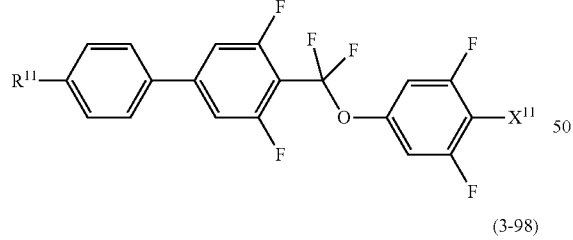
(3-98)
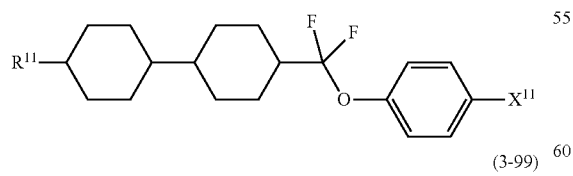
(3-99)
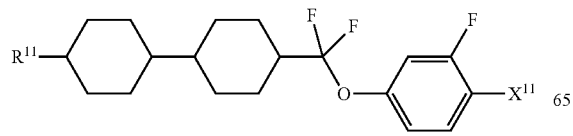
(3-100)
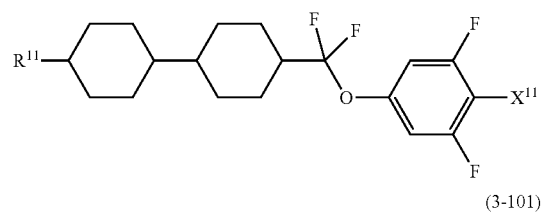
(3-101)
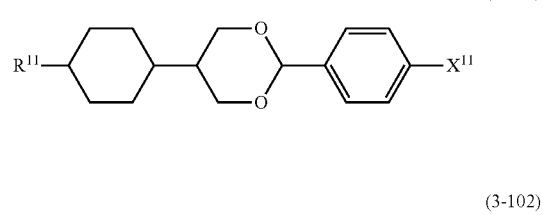
(3-102)
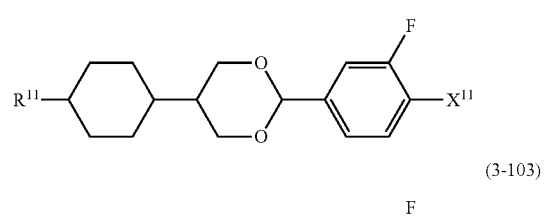
(3-103)
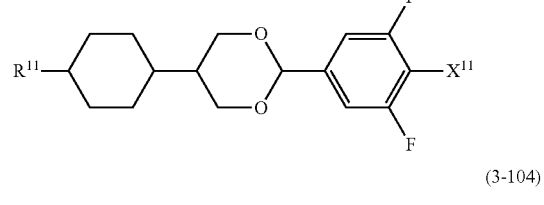
(3-104)
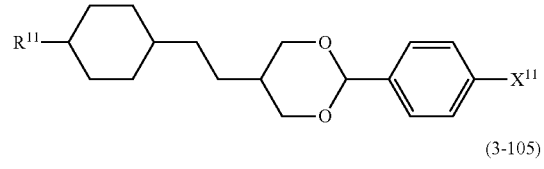
(3-105)
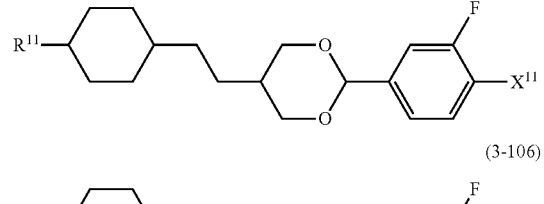
(3-106)
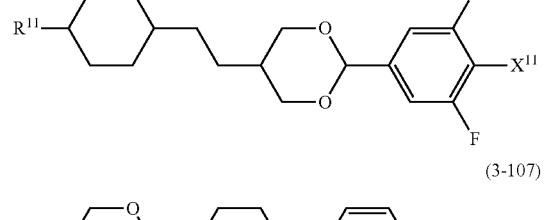
(3-107)
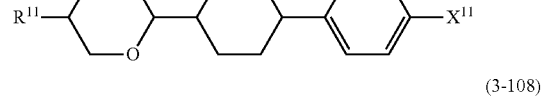
(3-108)
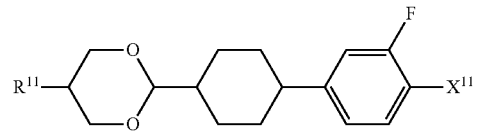

(3-109)
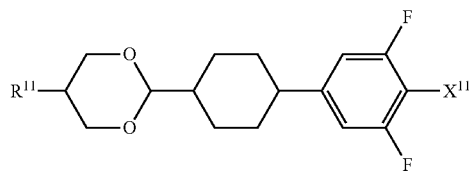
(3-110)
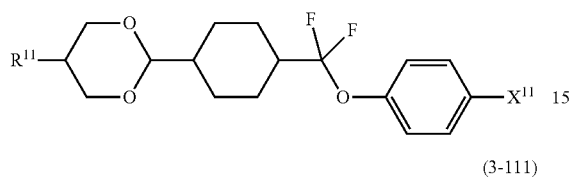
(3-111)
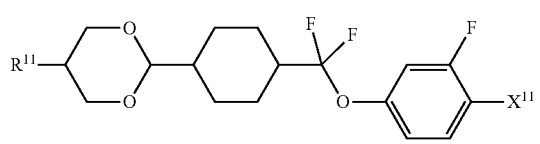
(3-112)
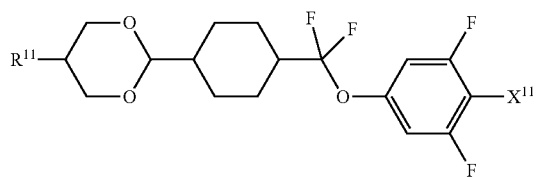
(3-113)
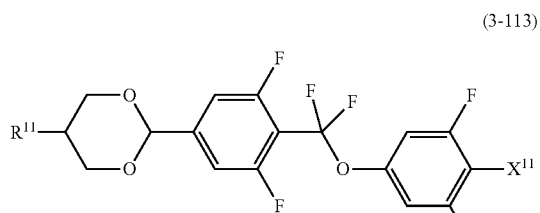
(4-1)
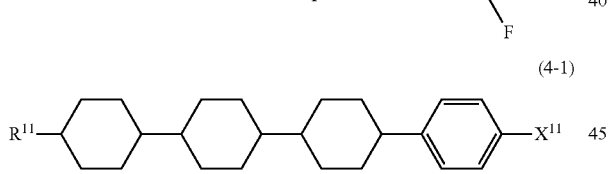
(4-2)
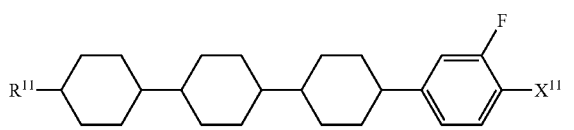
(4-3)
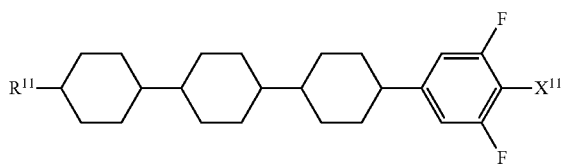
(4-4)
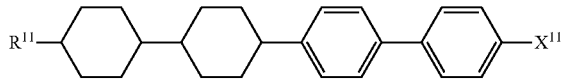
(4-5)
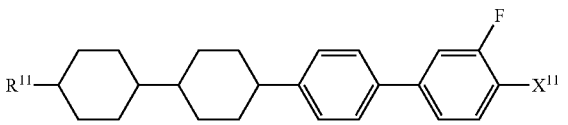
(4-6)
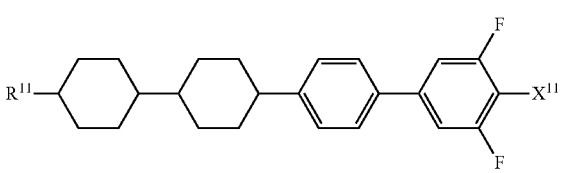
(4-7)
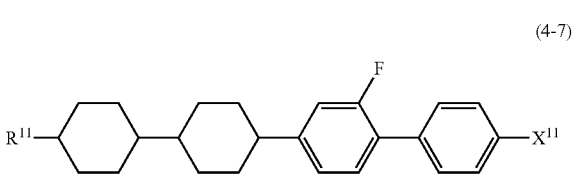
(4-8)
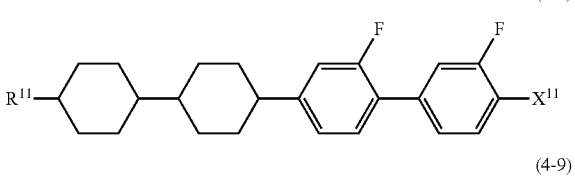
(4-9)
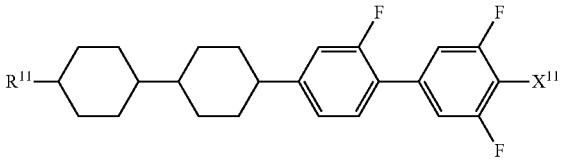
(4-10)
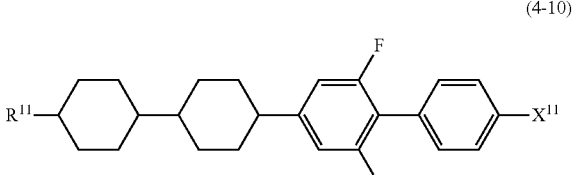
(4-11)
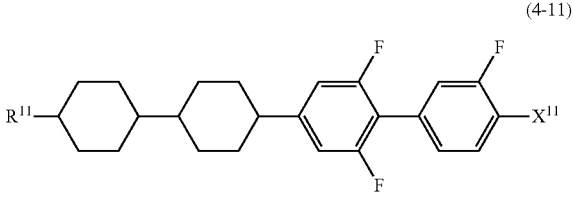
(4-12)
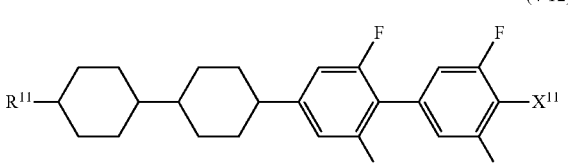
(4-13)
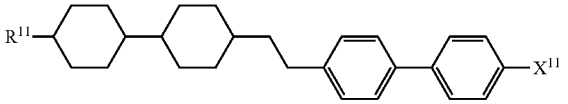

(4-14)
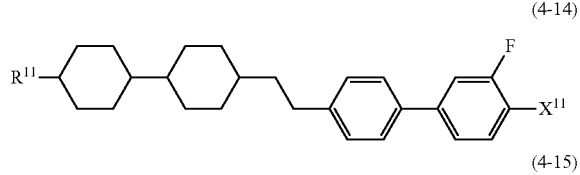
(4-15)
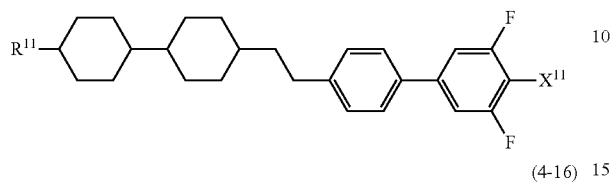
(4-16)
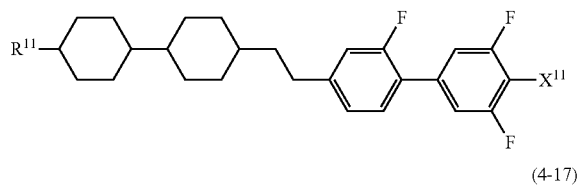
(4-17)
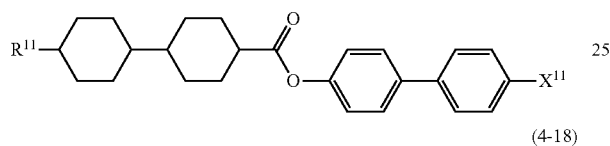
(4-18)
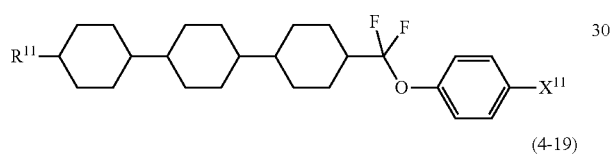
(4-19)
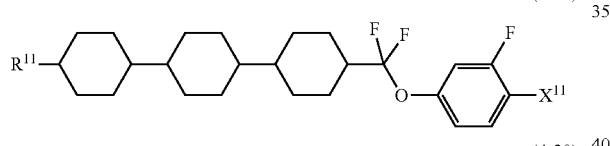
(4-20)
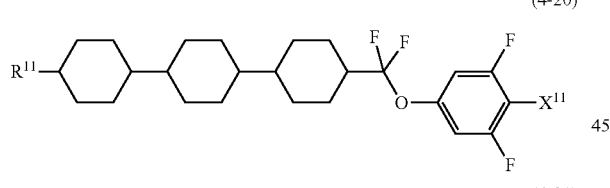
(4-21)
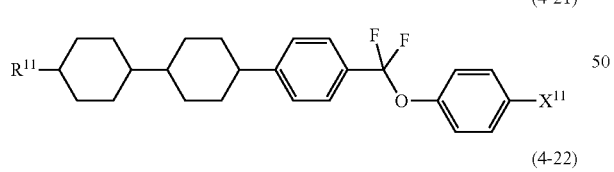
(4-22)
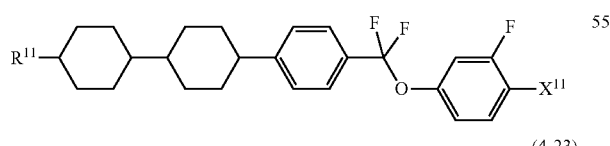
(4-23)
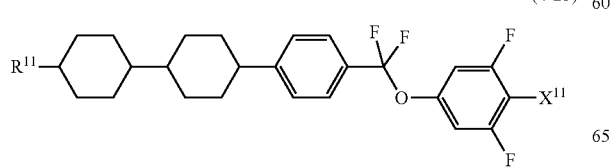
(4-24)
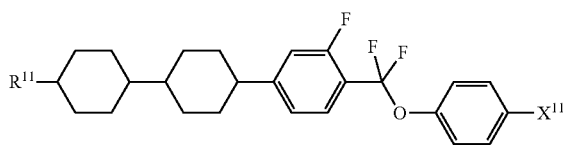
(4-25)
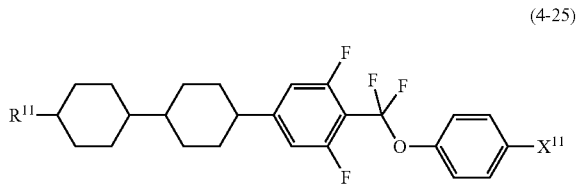
(4-26)
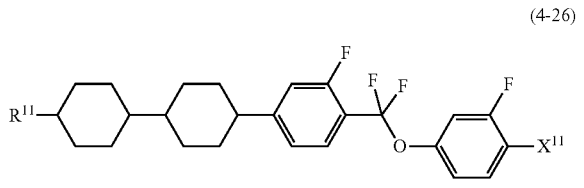
(4-27)
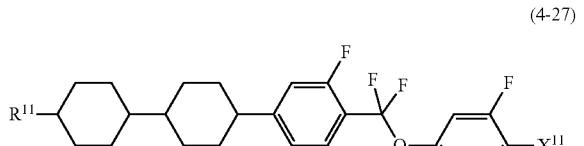
(4-28)
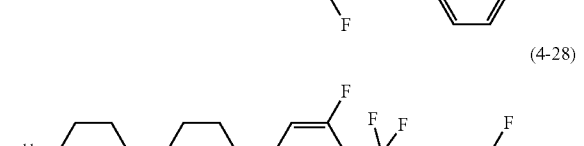
(4-29)
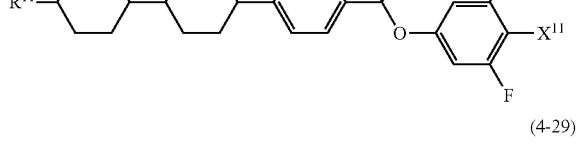
(4-30)
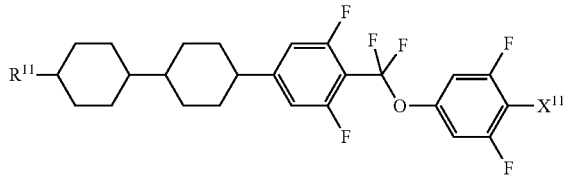
(4-31)
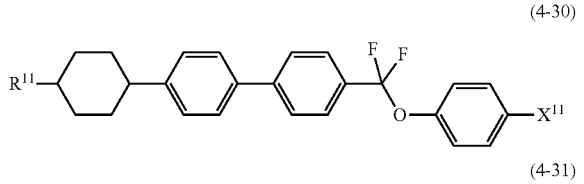
(4-32)
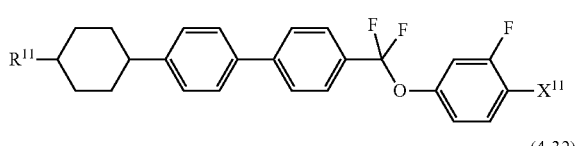
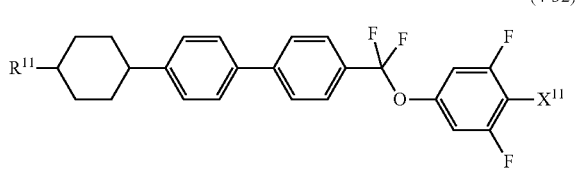

(4-33)
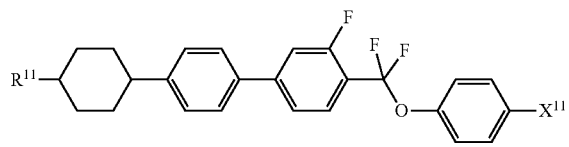
(4-34)
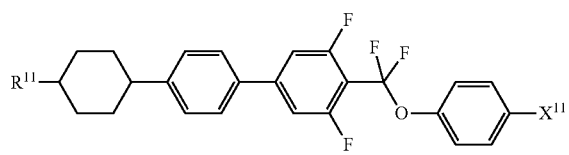
(4-35)
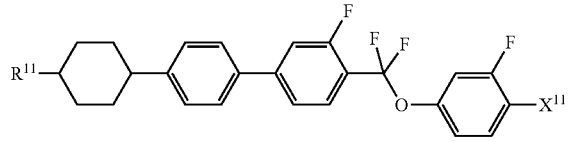
(4-36)
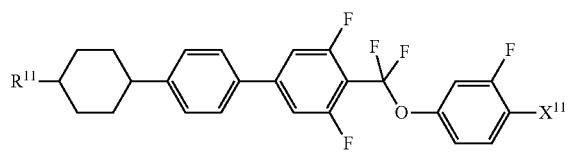
(4-37)
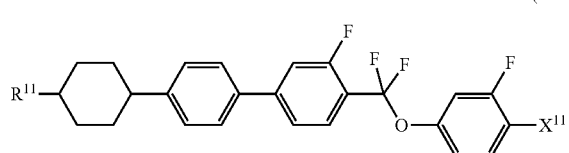
(4-38)
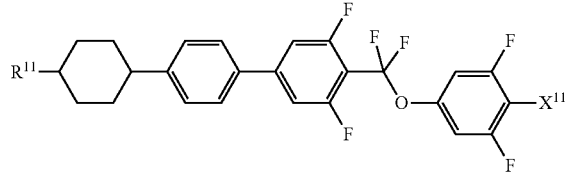
(4-39)
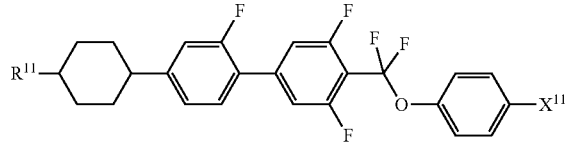
(4-40)
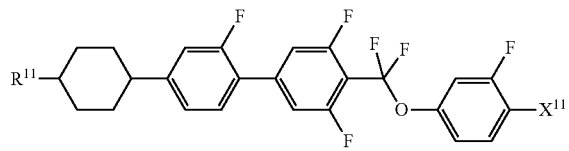
(4-41)
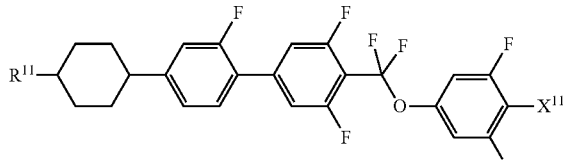
(4-42)
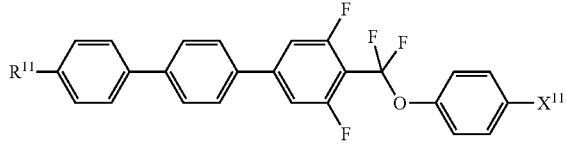
(4-43)
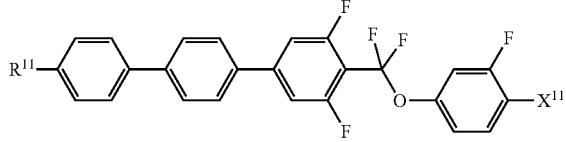
(4-44)
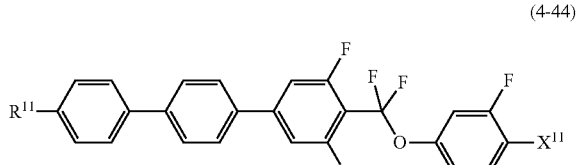
(4-45)
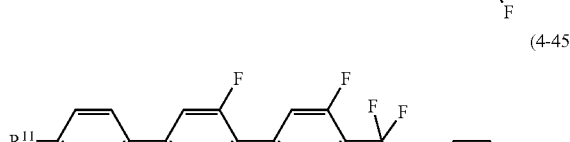
(4-46)
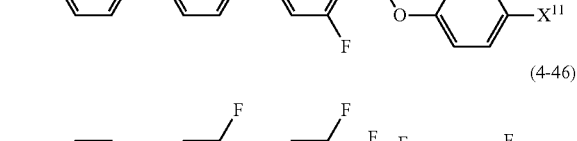
(4-47)
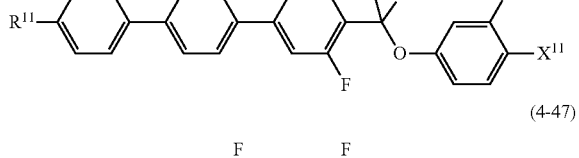
(4-48)
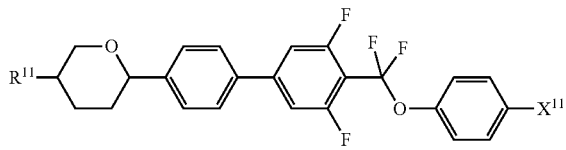

(4-49)
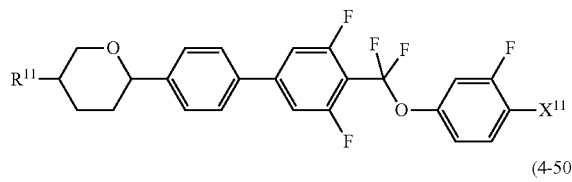

(4-50)
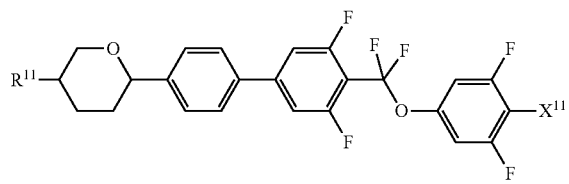

(4-51)
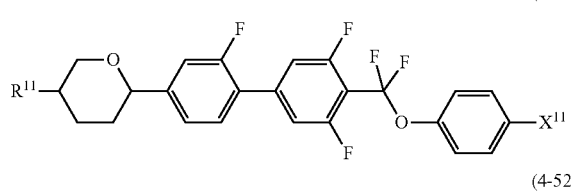

(4-52)
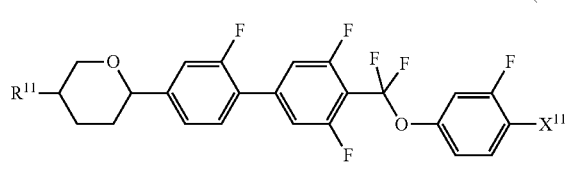

(4-53)
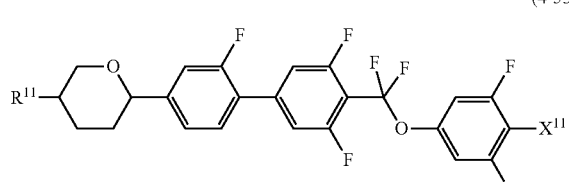

(4-54)
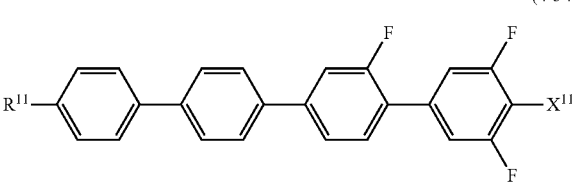

(4-55)
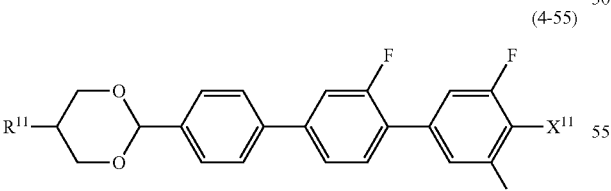

(4-56)
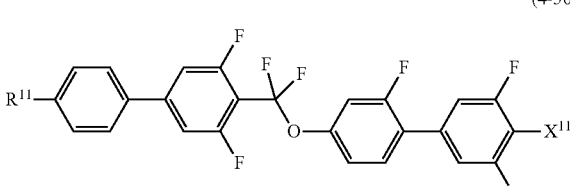

(4-57)
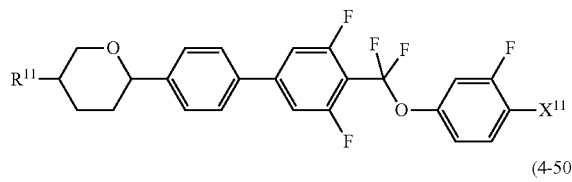

Component B has the positive dielectric anisotropy and superb stability to heat, light and so forth, and thus is used for preparing a composition for a mode such as TFT, IPS and FFS. A content of component B is suitably in the range of 1 to 99% by weight, preferably 10 to 97% by weight, and further preferably 40 to 95% by weight, based on the weight of the composition. The viscosity of the composition can be adjusted by further adding compounds (13) to (15) (component E).

Component C is compound (5) in which a right-terminal group is —C≡N or —C≡C—C≡N. Preferred examples of component C include compounds (5-1) to (5-64). In the compounds (component C), $R^{12}$ and $X^{12}$ are defined in a manner identical with the definitions in item 10 described above.

(5-1)
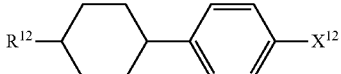

(5-2)

(5-3)
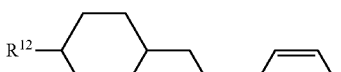

(5-4)

(5-5)
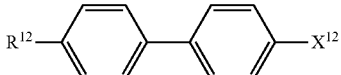

(5-6)

(5-7)

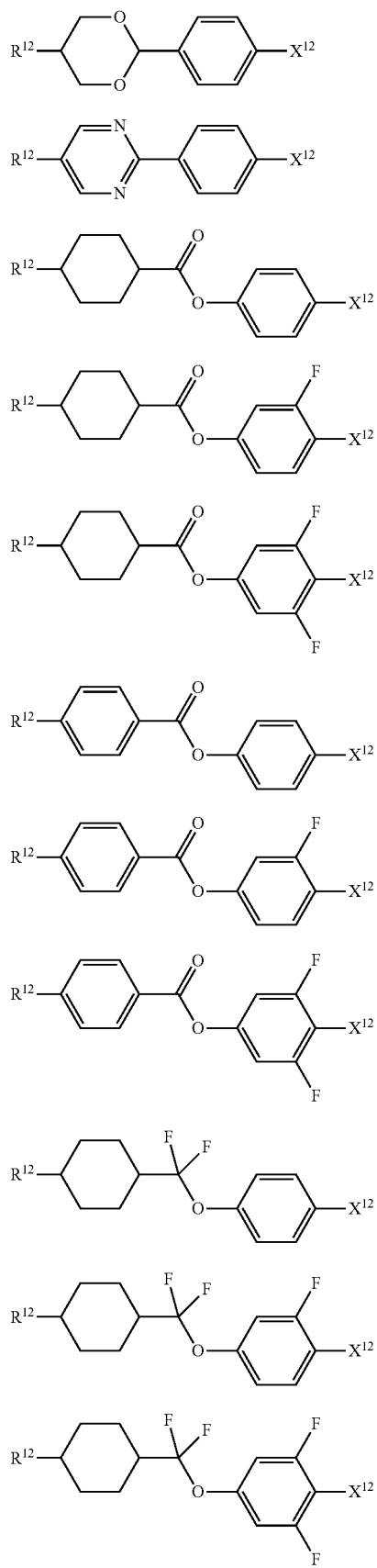
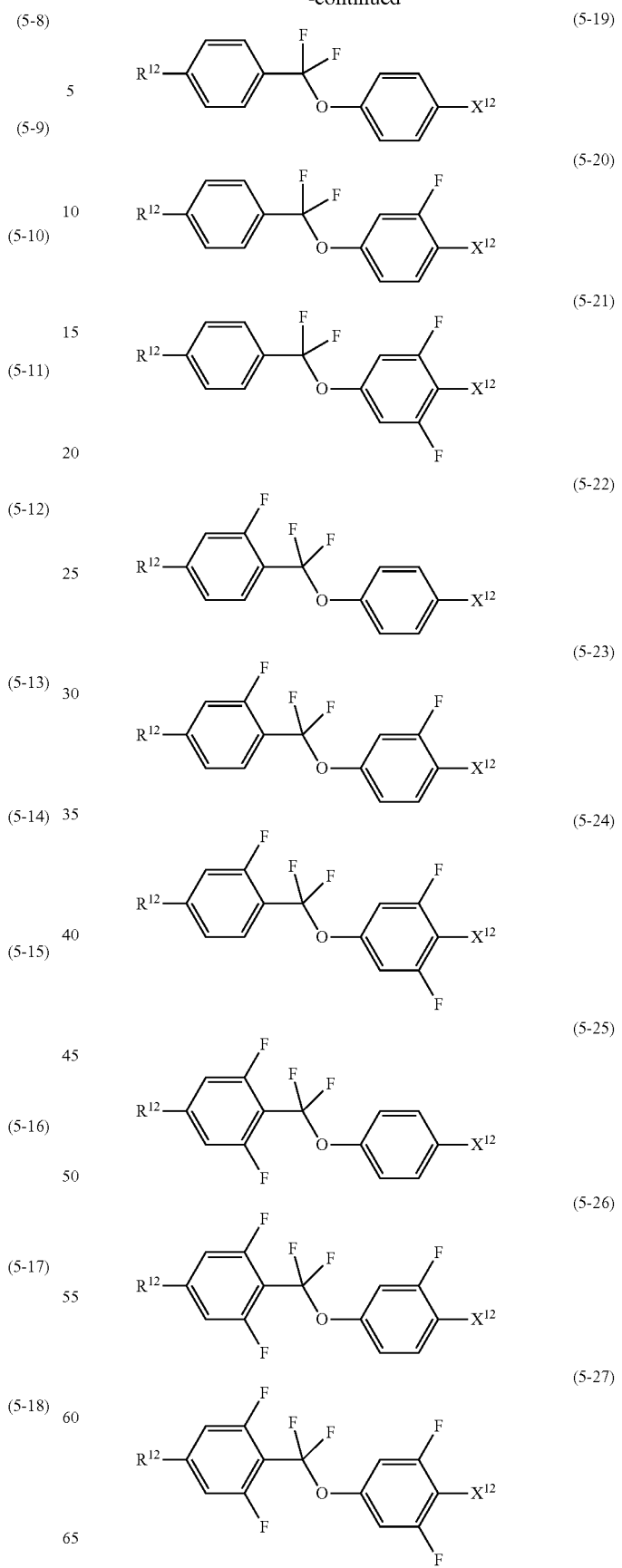

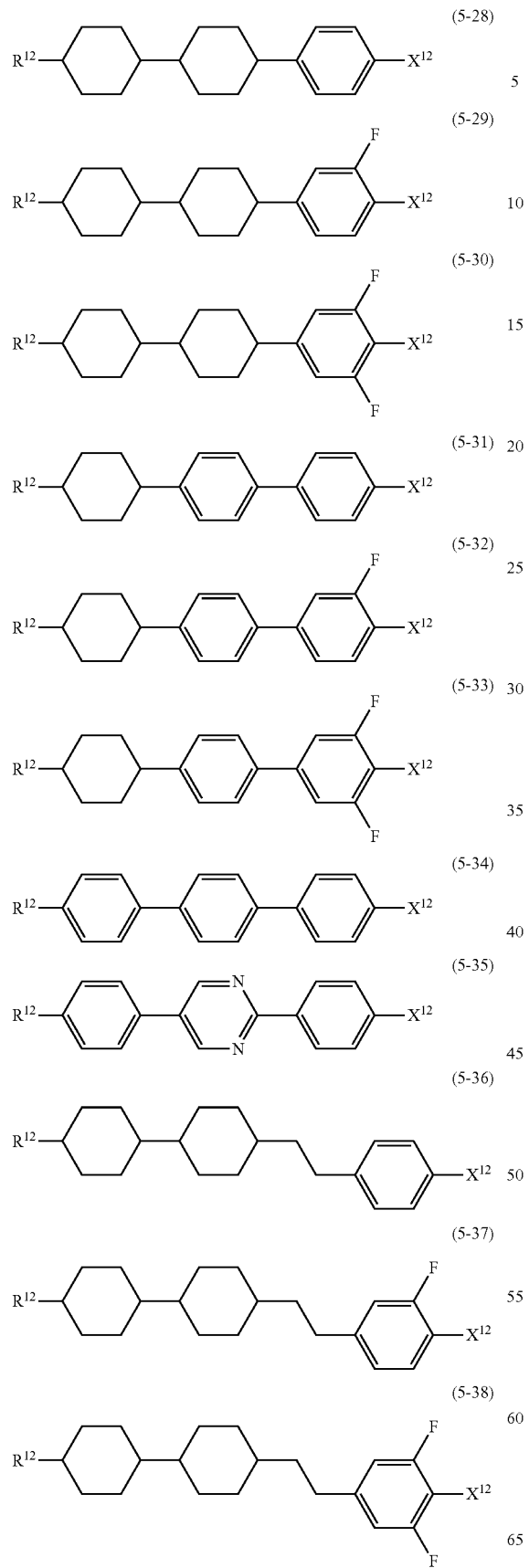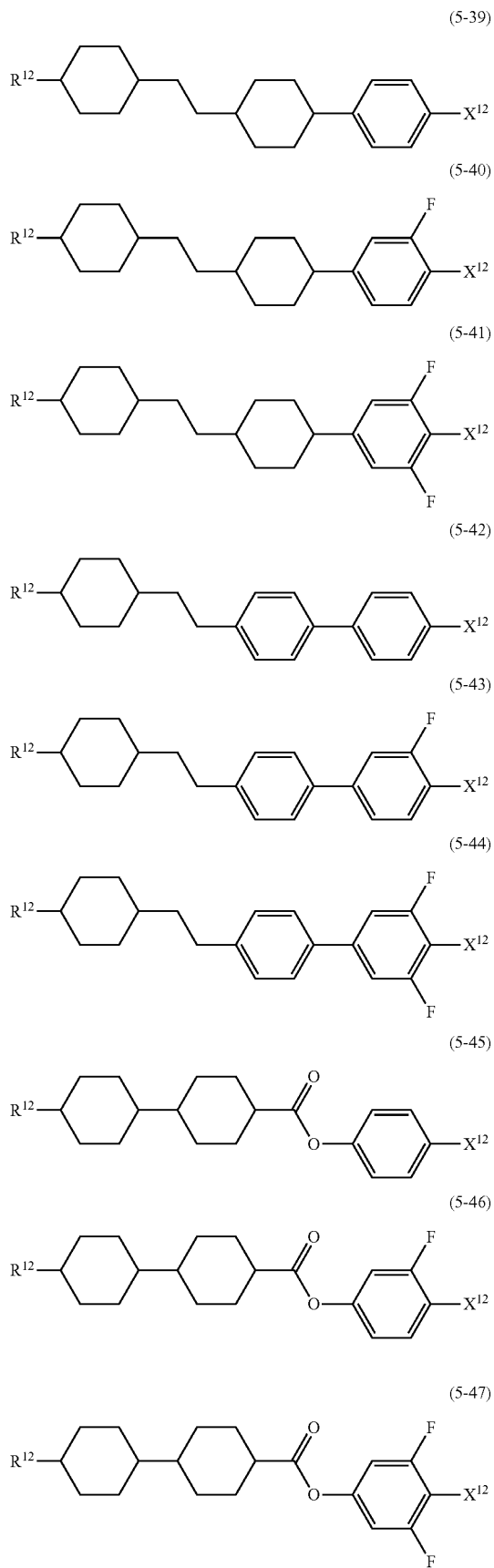

(5-48)
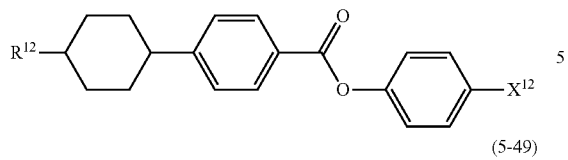

(5-49)
(5-50)
(5-51)
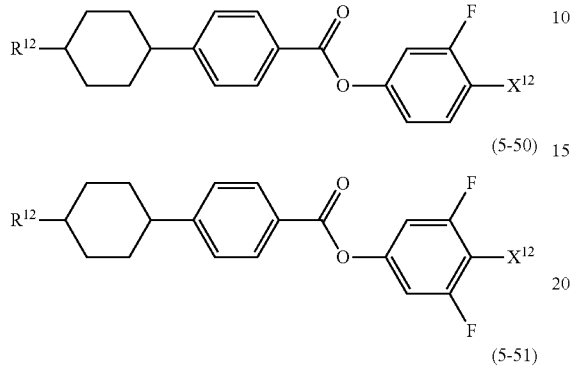

(5-52)
(5-53)
(5-54)
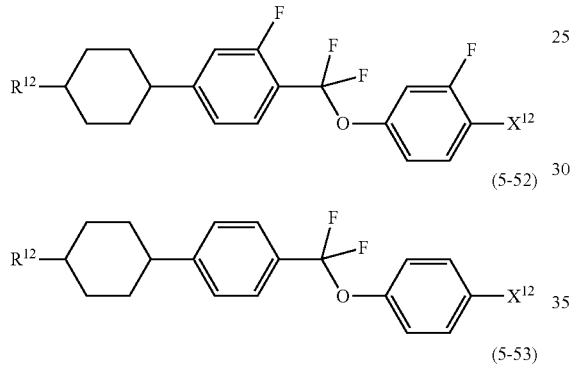

(5-55)
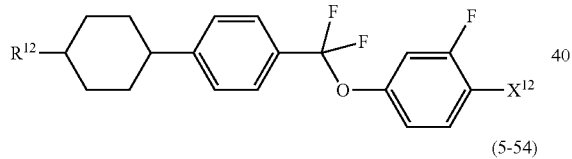

(5-56)
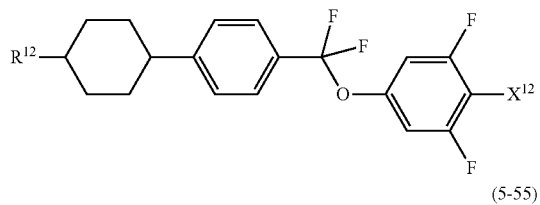

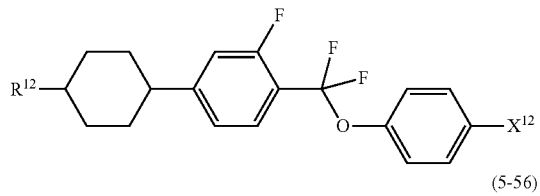

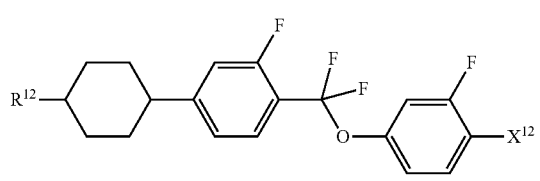

(5-57)
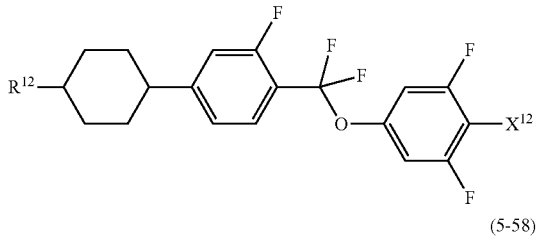

(5-58)
(5-59)
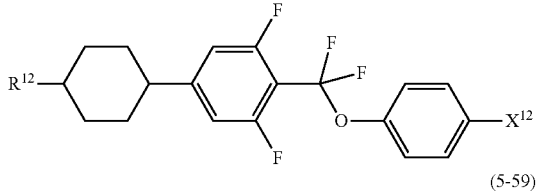

(5-60)
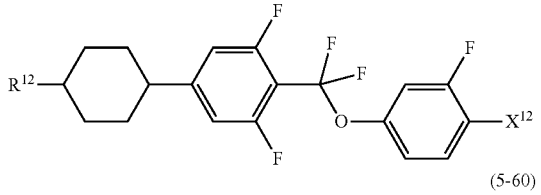

(5-61)
(5-62)
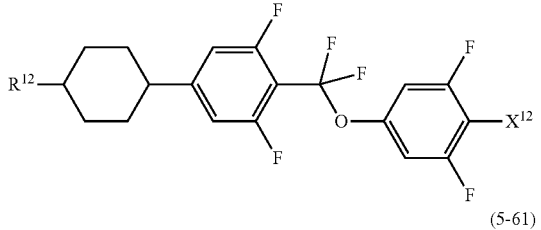

(5-63)
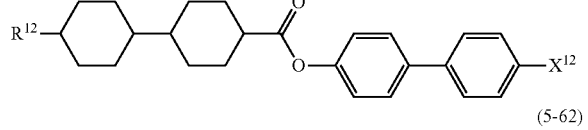

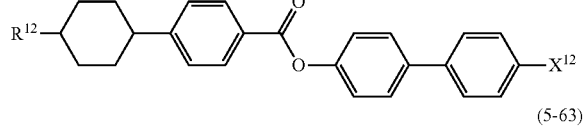

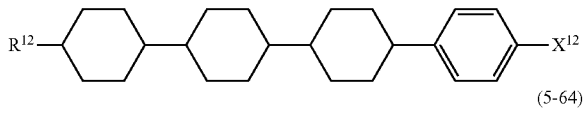

(5-64)
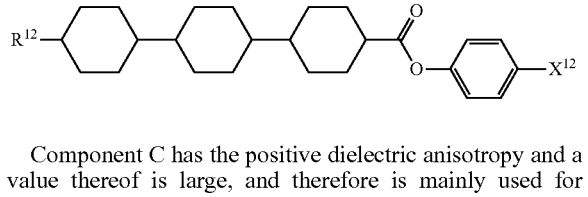

Component C has the positive dielectric anisotropy and a value thereof is large, and therefore is mainly used for preparing a composition for the STN mode, the TN mode or the PSA mode. The dielectric anisotropy of the composition can be increased by adding component C. Component C is effective in extending the temperature range of the liquid crystal phase, adjusting the viscosity or adjusting the optical anisotropy. Component C is also useful for adjusting the voltage-transmittance curve of the device.

When a composition for the STN mode or the TN mode is prepared, a content of component C is suitably in the range of 1 to 99% by weight, preferably in the range of 10 to 97% by weight, and further preferably in the range of 40 to 95% by weight, based on the weight of the composition. In the composition, the temperature range of the liquid crystal phase, the viscosity, the optical anisotropy, the dielectric anisotropy and so forth can be adjusted by adding component E.

Component D includes compounds (6) to (12). The compounds have a benzene ring in which hydrogen in lateral positions are replaced by two of halogen, such as 2,3-difluoro-1,4-phenylene. Specific preferred examples of component D include compounds (6-1) to (6-8), compounds (7-1) to (7-17), compound (8-1), compounds (9-1) to (9-3), compounds (10-1) to (10-11), compounds (11-1) to (11-3) and compounds (12-1) to (12-3). In the compounds (component D), $R^{13}$, $R^{14}$ and $R^{15}$ are defined in a manner identical with the definition in item 11 described above.

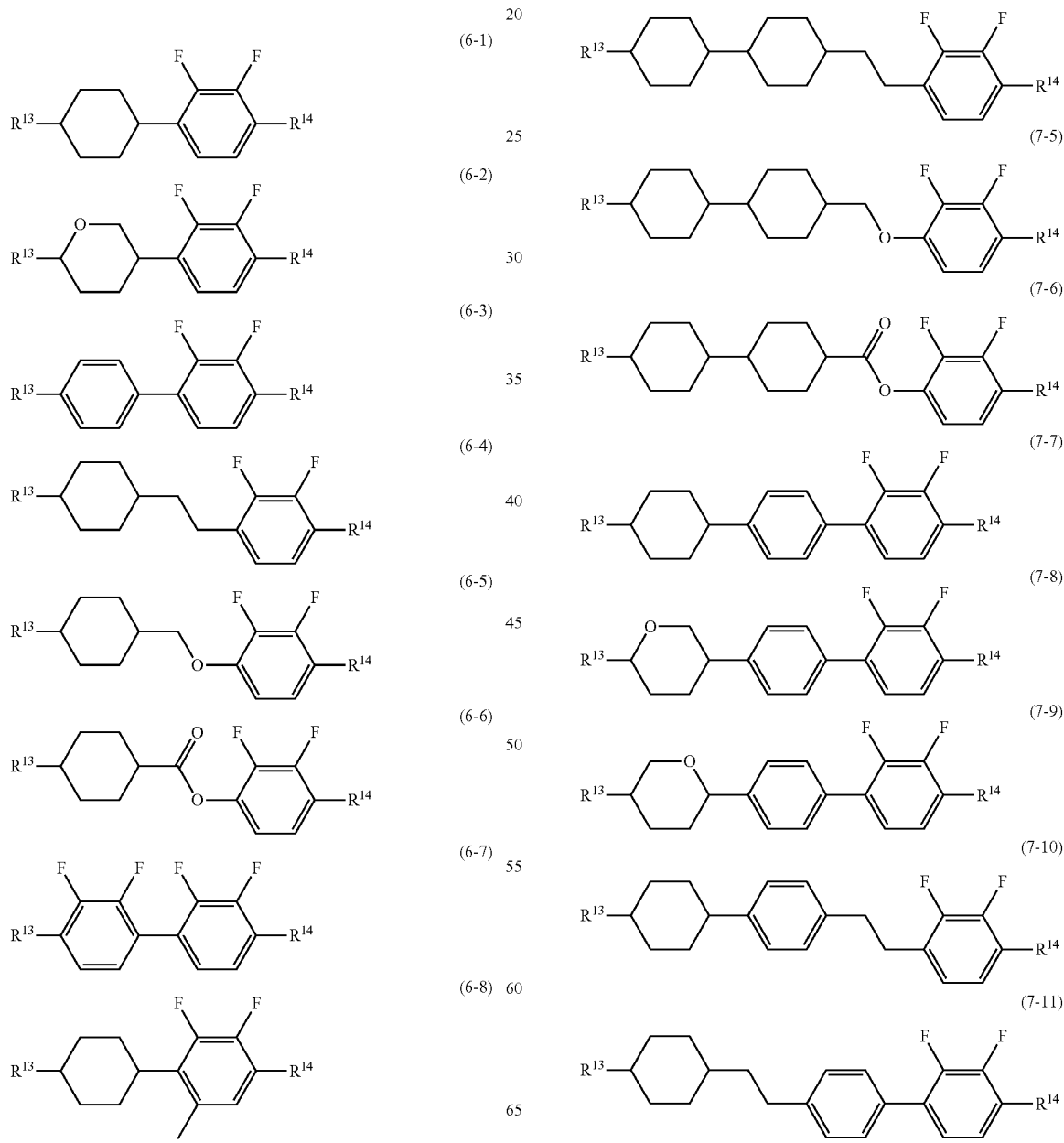

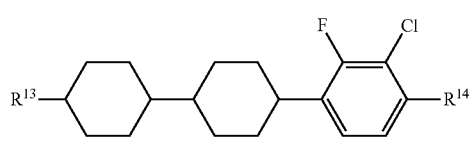
(7-12)
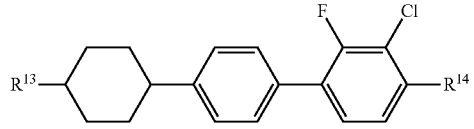
(7-13)
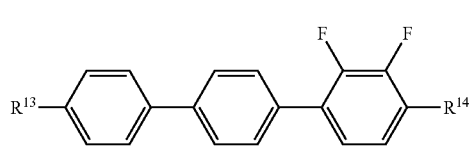
(7-14)
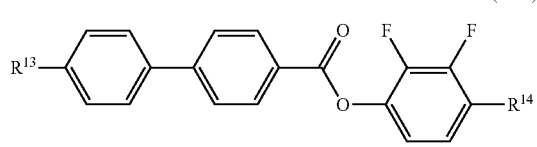
(7-15)
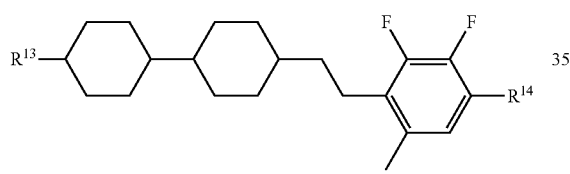
(7-16)
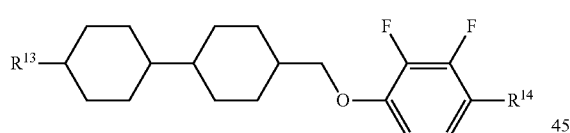
(7-17)
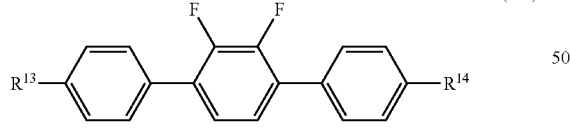
(8-1)
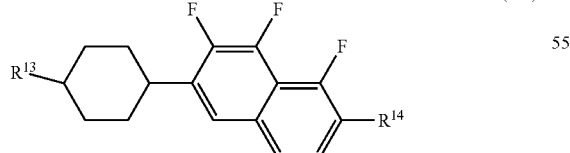
(9-1)
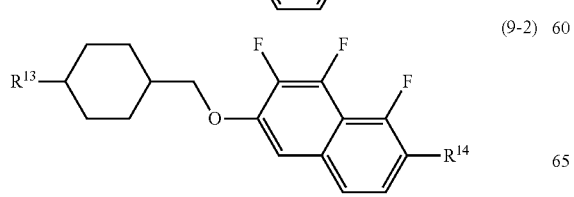
(9-2)
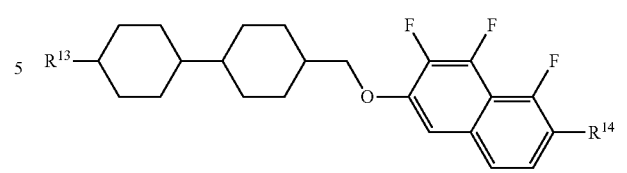
(9-3)
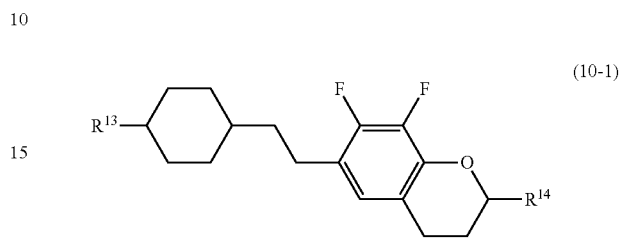
(10-1)
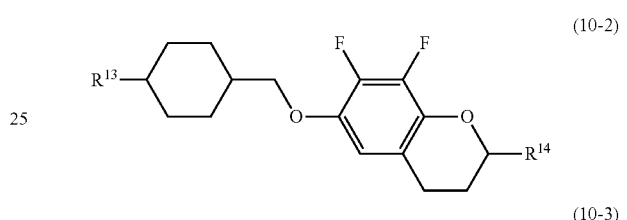
(10-2)
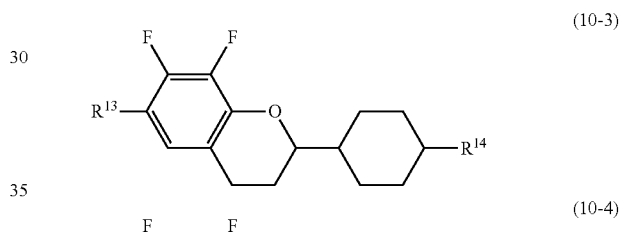
(10-3)
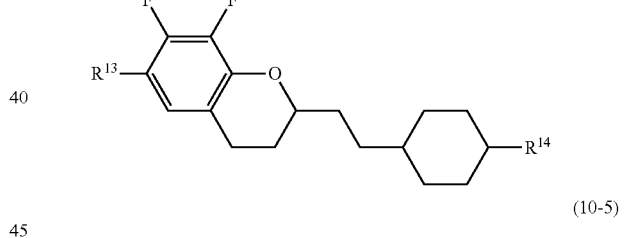
(10-4)
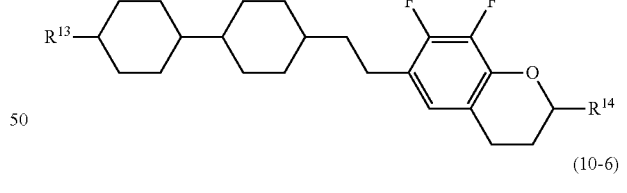
(10-5)
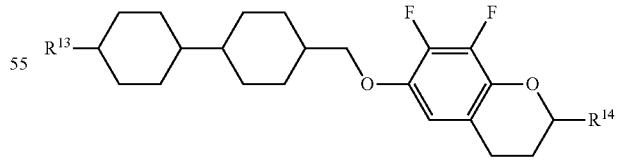
(10-6)
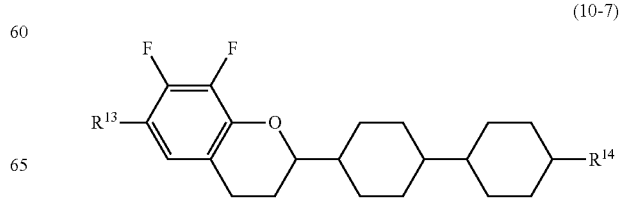
(10-7)

-continued

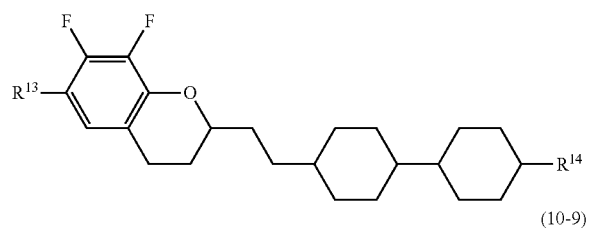
(10-8)

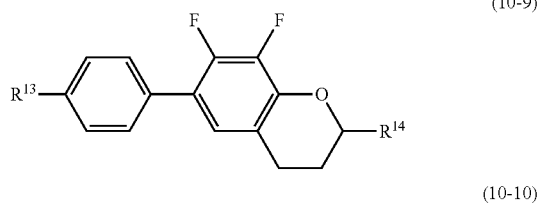
(10-9)

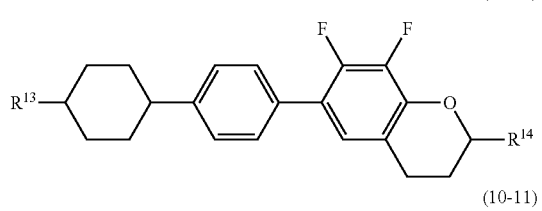
(10-10)

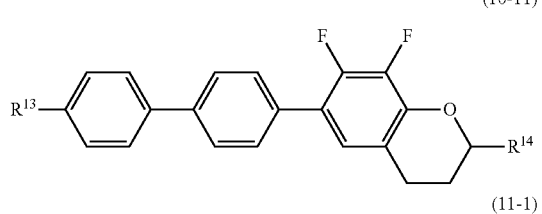
(10-11)

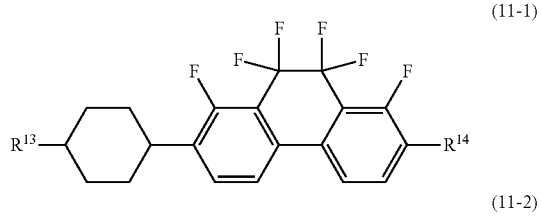
(11-1)

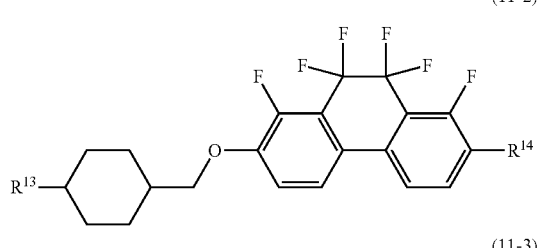
(11-2)

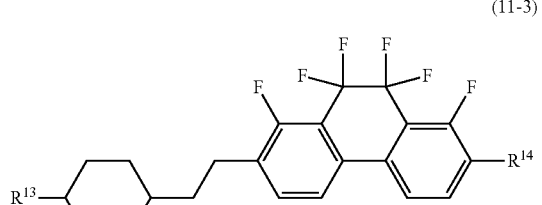
(11-3)

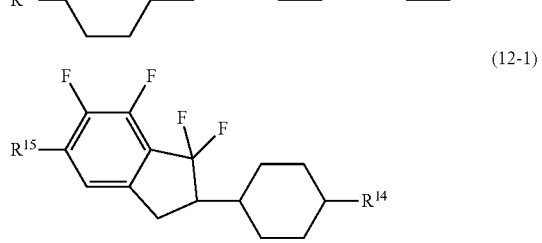
(12-1)

-continued

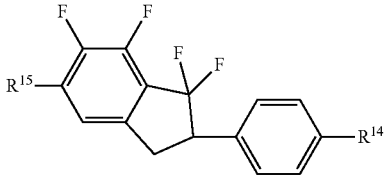
(12-2)

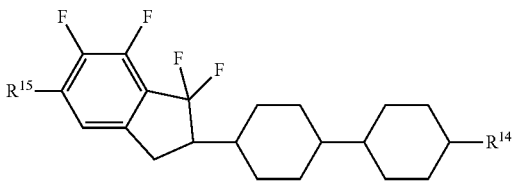
(12-3)

Component D is a compound having the negative dielectric anisotropy. Component D is mainly used for preparing a composition for the VA mode or the PSA mode. Among types of component D, compound (6) is a bicyclic compound, and therefore is effective mainly in adjusting the viscosity, the optical anisotropy or the dielectric anisotropy. Compounds (7) and (8) are a tricyclic compound, and therefore are effective in increasing the maximum temperature, the optical anisotropy or the dielectric anisotropy. Compounds (9) to (12) are effective in increasing the dielectric anisotropy.

When a composition for the VA mode or the PSA mode is prepared, a content of component D is preferably 40% by weight or more, and further preferably in the range of 50 to 95% by weight, based on the weight of the composition. When component D is added to a composition having the positive dielectric anisotropy, a content of component D is preferably 30% by weight or less based on the weight of the composition. The voltage-transmittance curve of the device of the composition can be adjusted by adding component D.

Component E is a compound in which two terminal groups are alkyl or the like. Preferred examples of component E include compounds (13-1) to (13-11), compounds (14-1) to (14-19) and compounds (15-1) to (15-7). In the compounds (component E), $R^{16}$ and $R^{17}$ are defined in a manner identical with the definitions in item 12 described above.

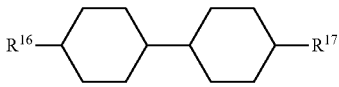
(13-1)

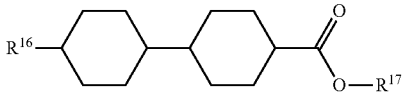
(13-2)

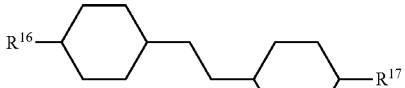
(13-3)

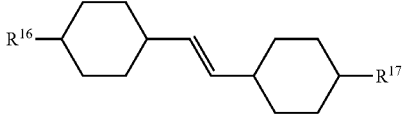
(13-4)

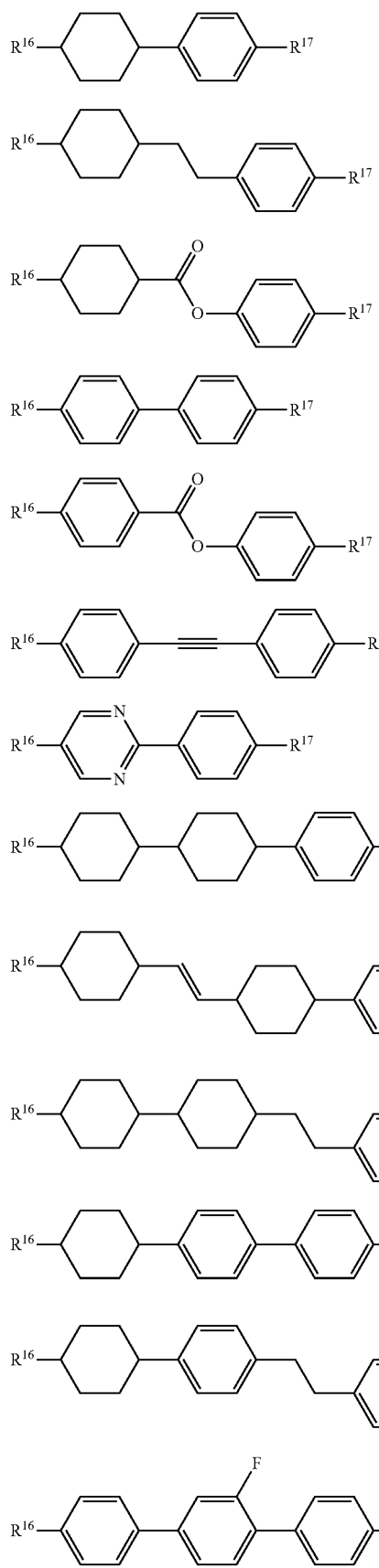
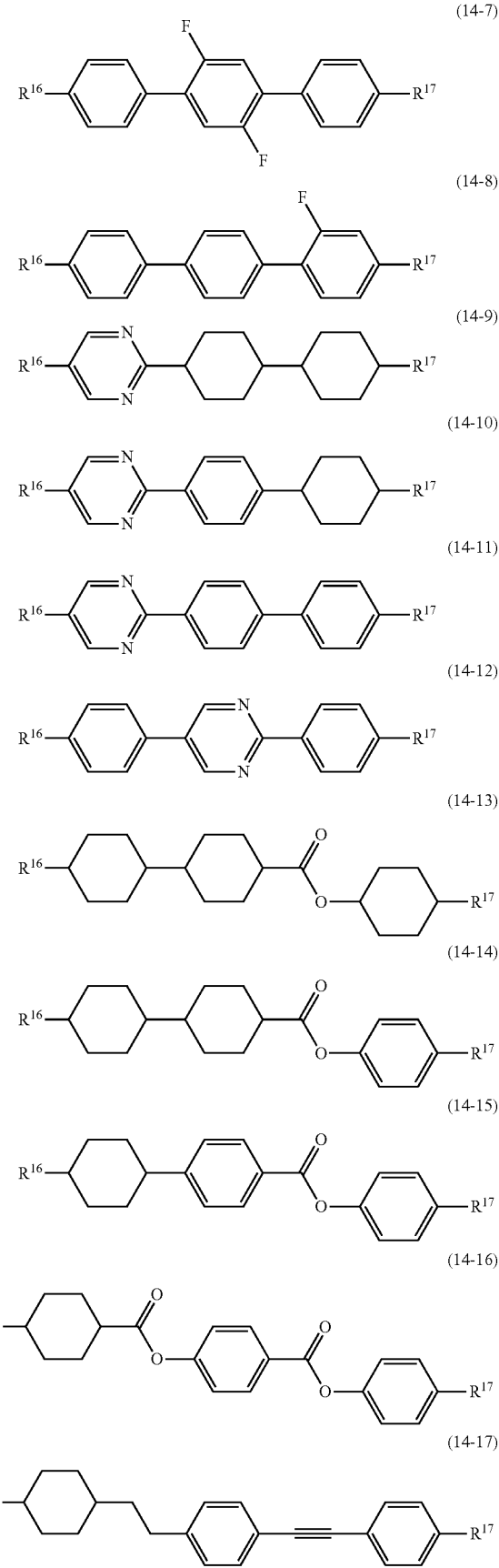

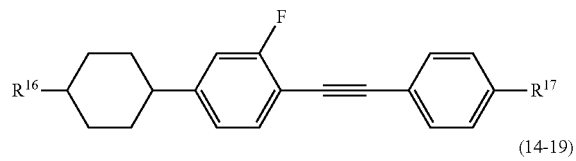
(14-18)

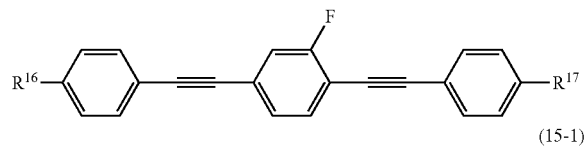
(14-19)

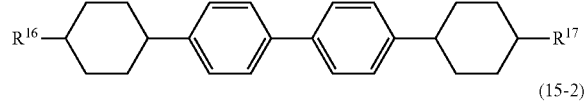
(15-1)

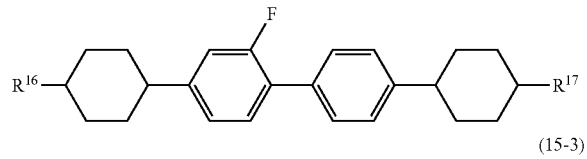
(15-2)

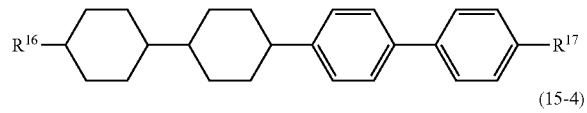
(15-3)

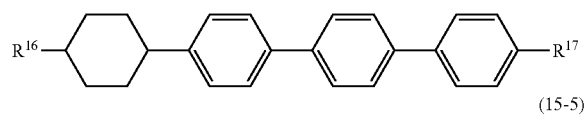
(15-4)

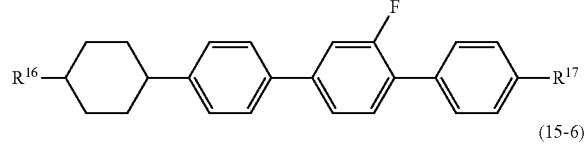
(15-5)

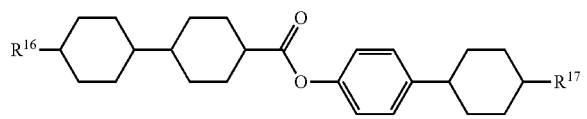
(15-6)

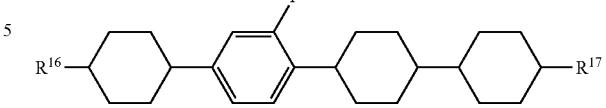
(15-7)

Component E has a small absolute value of dielectric anisotropy, and therefore is a compound close to neutrality. Compound (13) is effective mainly in adjusting the viscosity or the optical anisotropy. Compounds (14) and (15) are effective in extending the temperature range of the nematic phase by increasing the maximum temperature, or effective in adjusting the optical anisotropy.

If a content of component E is increased, the dielectric anisotropy of the composition decreases, but the viscosity also decreases. Thus, as long as a desired value of threshold voltage of the device is met, the content is desirably as large as possible. Accordingly, when the composition is prepared, the content of component E is preferably 30% by weight or more, and further preferably 40% by weight or more, based on the weight of the composition.

Preparation of composition (1) is performed by a method for dissolving required components at a high temperature, or the like. According to an application, an additive may be added to the composition. Examples of the additive include the optically active compound, the polymerizable compound, the polymerization initiator, the antioxidant, the ultraviolet light absorber, the light stabilizer, the heat stabilizer, the defoaming agent and the dye. Such additives are well known to those skilled in the art, and described in literature.

Composition (1) may further contain at least one optically active compound. The optically active compound is effective in inducing helical structure in liquid crystal molecules to give a required twist angle, thereby being effective in preventing a reverse twist. Specific preferred examples of the optically active compound include compounds (Op-1) to (Op-18) described below.

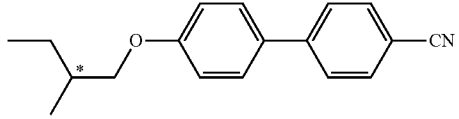
(Op-1)

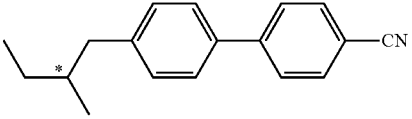
(Op-2)

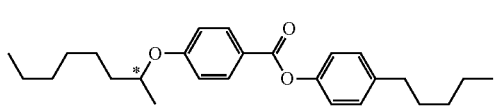
(Op-3)

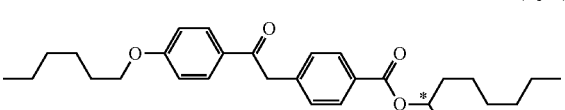
(Op-4)

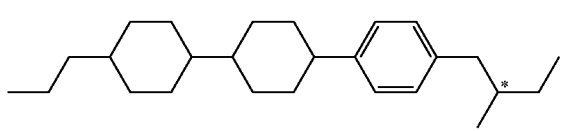
(Op-5)

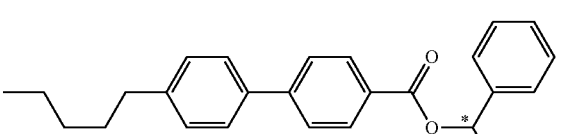
(Op-6)

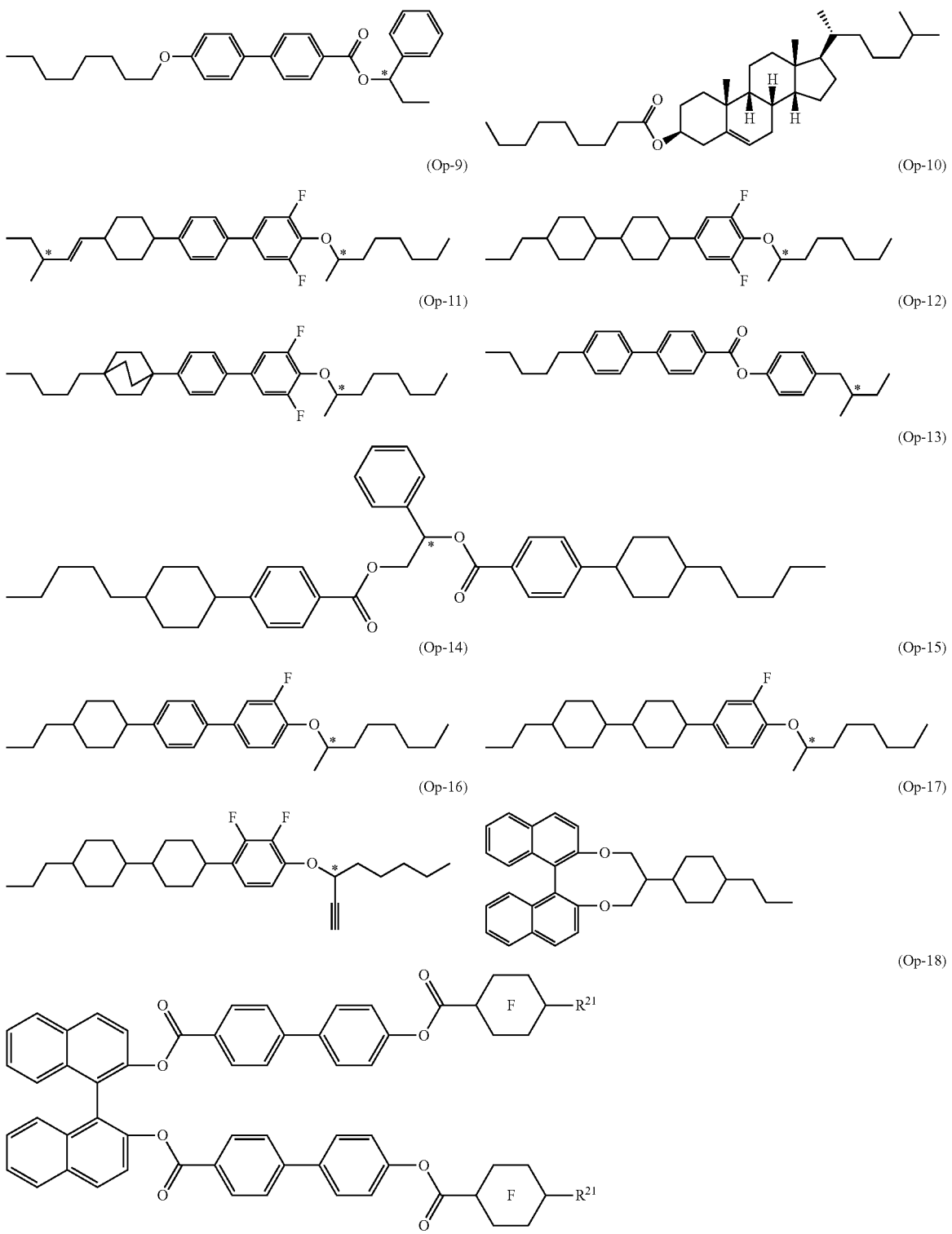

wherein, in compound (Op-18), ring F is 1,4-cyclohexylene or 1,4-phenylene, and $R^{21}$ is alkyl having 1 to 10 carbons.

In composition (1), a helical pitch is adjusted by adding such an optically active compound. The helical pitch is preferably adjusted in the range of 40 to 200 micrometers in a composition for the TFT mode and the TN mode. In a composition for the STN mode, the helical pitch is preferably adjusted in the range of 6 to 20 micrometers. In the case of a composition for a BTN mode, the helical pitch is preferably adjusted in the range of 1.5 to 4 micrometers. For the purpose of adjusting temperature dependence of the helical pitch, two or more optically active compounds may be added.

Composition (1) can also be used for the PSA mode by adding the polymerizable compound. Examples of the polymerizable compound include acrylate, methacrylate, a vinyl compound, a vinyloxy compound, propenyl ether, an epoxy compound (oxirane, oxetane) and vinyl ketone. The polymerizable compound is polymerized by irradiation with ultraviolet light or the like. An initiator such as a photopolymerization initiator may be added. Suitable conditions for polymerization, suitable types of the initiator and suitable amounts thereof are known to those skilled in the art and are described in literature. Preferred examples of the polymerizable compound include compounds (M-1) to (M-12).

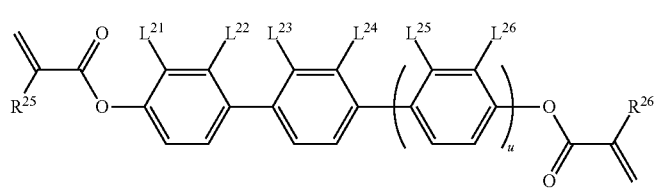
(M-1)

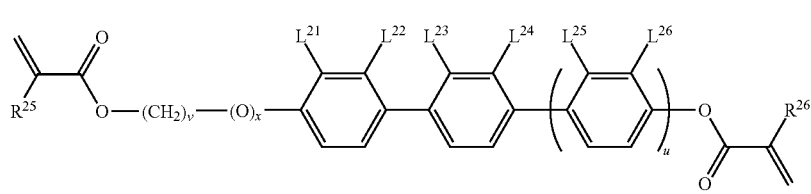
(M-2)

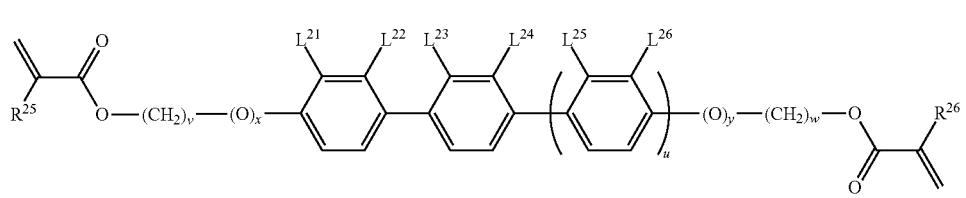
(M-3)

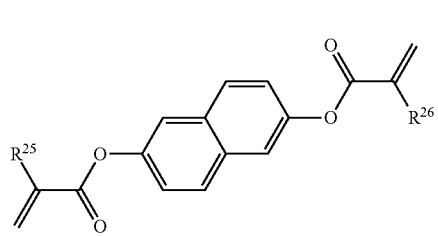
(M-4)

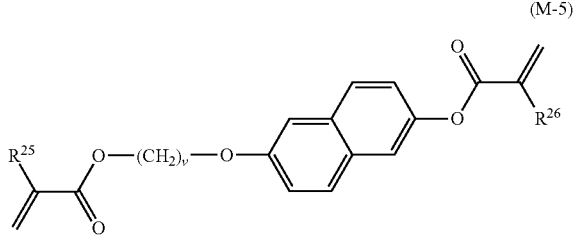
(M-5)

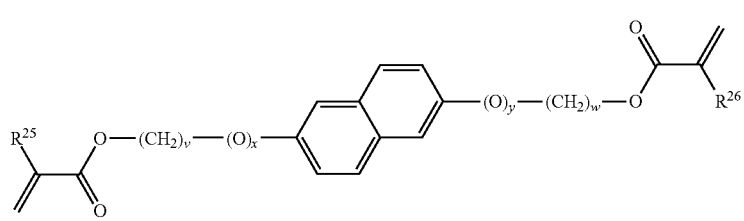
(M-6)

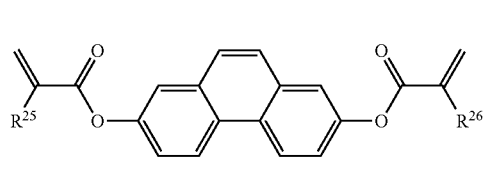
(M-7)

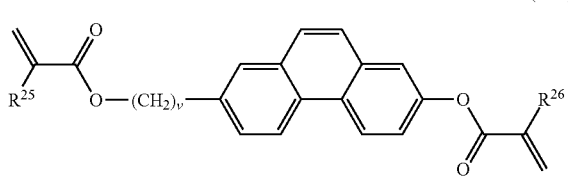
(M-8)

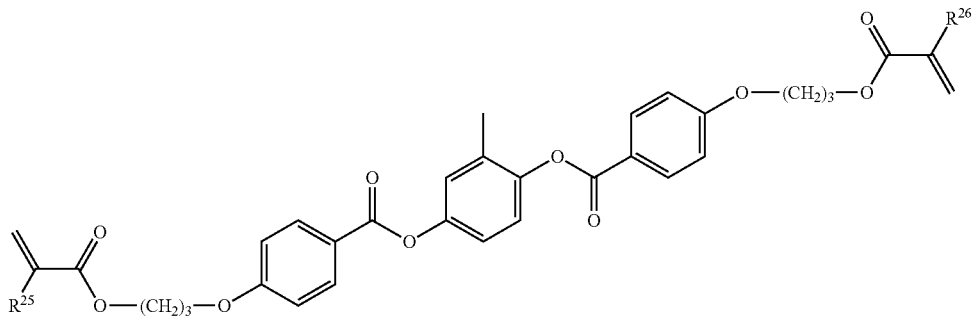
(M-9)

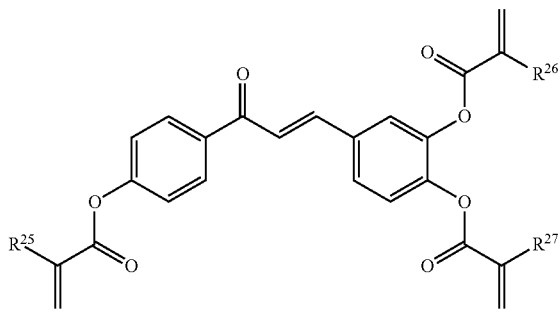
(M-10)

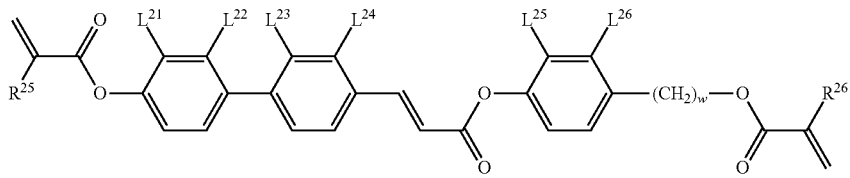
(M-11)

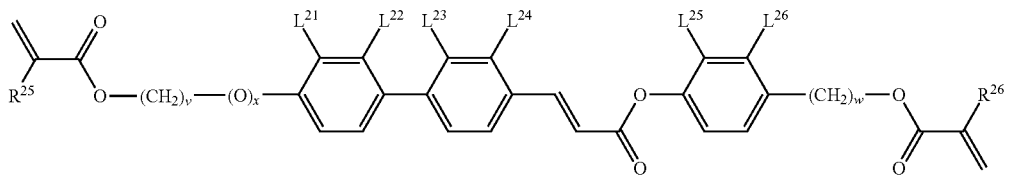
(M-12)

In compounds (M-1) to (M-12), $R^{25}$, $R^{26}$ and $R^{27}$ are independently hydrogen or methyl; u, x and y are independently 0 or 1; v and w are independently an integer from 1 to 10; and $L^{21}$, $L^{22}$, $L^{23}$, $L^{24}$, $L^{25}$ and $L^{26}$ are independently hydrogen or fluorine.

The antioxidant is effective for maintaining a large voltage holding ratio. Preferred examples of the antioxidant include compounds (AO-1) and (AO-2) described below, IRGANOX 415, IRGANOX 565, IRGANOX 1010, IRGANOX 1035, IRGANOX 3114 and IRGANOX 1098 (trade names: BASF SE). The ultraviolet light absorber is effective for preventing a decrease in the maximum temperature. Preferred examples of the ultraviolet light absorber include a benzophenone derivative, a benzoate derivative and a triazole derivative. Specific examples include compounds (AO-3) and (AO-4) described below, TINUVIN329, TINUVIN P, TINUVIN 326, TINUVIN 234, TINUVIN 213, TINUVIN 400, TINUVIN 328, TINUVIN 99-2 (trade names: BASF SE); and 1,4-diazabicyclo[2.2.2]octane (DABCO). The light stabilizer such as an amine having steric hindrance is preferred for maintaining the large voltage holding ratio. Preferred examples of the light stabilizer include compounds (AO-5) and (AO-6) described below, TINUVIN 144, TINUVIN 765 and TINUVIN 770DF (trade names: BASF SE). The heat stabilizer is also effective for maintaining the large voltage holding ratio, and preferred examples include IRGAFOS 168 (trade name: BASF SE). The defoaming agent is effective in preventing foam formation. Preferred examples of the defoaming agent include dimethyl silicone oil and methylphenyl silicone oil.

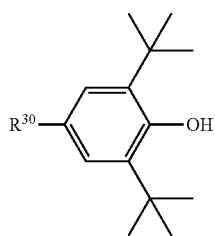
(AO-1)

83

-continued

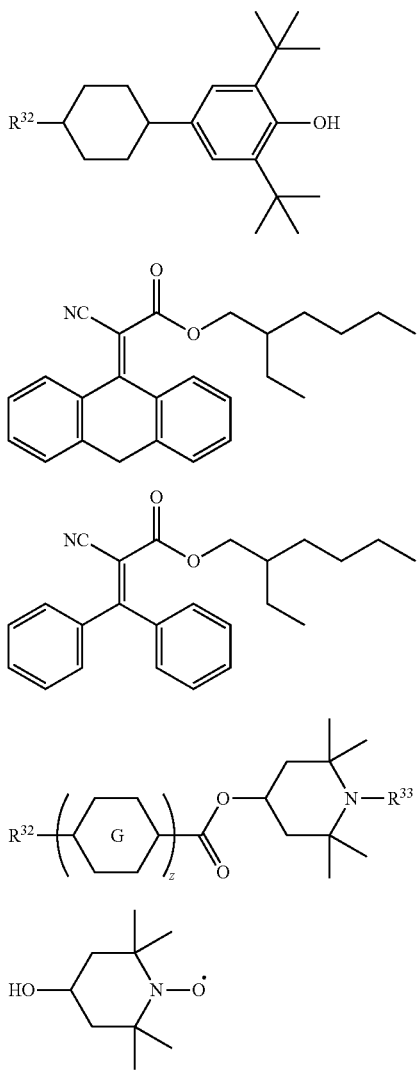

(AO-2)

(AO-3)

(AO-4)

(AO-5)

(AO-6)

In compound (AO-1), $R^{30}$ is alkyl having 1 to 20 carbons, alkoxy having 1 to 20 carbons, —COOR$^{31}$ or —CH$_2$CH$_2$COOR$^{31}$, and $R^{31}$ is alkyl having 1 to 20 carbons. In compound (AO-2), $R^{32}$ is alkyl having 1 to 20 carbons. In compound (AO-5), $R^{32}$ is alkyl having 1 to 20 carbons; $R^{33}$ is hydrogen, methyl or O. (oxygen radical); ring G is 1,4-cyclohexylene or 1,4-phenylene; and z is 1, 2 or 3.

Composition (1) can also be used for a guest host (GH) mode by addition of a dichroic dye such as a merocyanine type, a stylyl type, an azo type, an azomethine type, an azoxy type, a quinophthalone type, an anthraquinone type and a tetrazine type.

3. Liquid Crystal Display Device

Composition (1) can be used for a liquid crystal display device having an operating mode such as the PC mode, the TN mode, the STN mode, the OCB mode and the PSA mode, and driven by an active matrix (AM mode). Composition (1) can also be used for a liquid crystal display device having the operating mode such as the PC mode, the TN mode, the STN mode, the OCB mode, the VA mode and the IPS mode, and driven by a passive matrix (PM) mode. The AM mode device and the PM mode device can be applied to any of a reflective type, a transmissive type and transflective type.

Composition (1) can also be used for a nematic curvilinear aligned phase (NCAP) device prepared by microencapsulating a nematic liquid crystal, a polymer dispersed liquid crystal display (PDLCD) device and a polymer network liquid crystal display (PNLCD) device, in which a three-dimensional network polymer is formed in the liquid crystal.

EXAMPLES

The invention is described in greater detail by way of Examples. The invention is not limited by the Examples.

1-1. Example of Compound (1)

Compound (1) was prepared according to procedures described below. The thus prepared compound was identified by methods such as an NMR analysis. Physical properties of the compound were measured by the methods described below.

NMR Analysis

As a measuring apparatus, DRX-500 made by Bruker BioSpin Corporation was used. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. Then, $^{19}$F-NMR measurement was carried out using CFCl$_3$ as an internal standard and under conditions of 24 times of accumulation. In the explanation of a nuclear magnetic resonance spectrum, s, d, t, q, quin, sex, m and br stand for a singlet, a doublet, a triplet, a quartet, a quintet, a sextet, a multiplet and being broad, respectively.

Sample for Measurement

When phase structure and transition temperature were measured, a liquid crystal compound itself was used as a sample. When physical properties such as a maximum temperature of a nematic phase, viscosity, optical anisotropy and dielectric anisotropy were measured, a composition prepared by mixing the compound with a base liquid crystal was used as the sample.

When the sample in which the compound was mixed with the base liquid crystal was used, measurement was carried out as described below. The sample was prepared by mixing 15% by weight of the compound and 85% by weight of the base liquid crystal. Then, extrapolated values were calculated from measured values of the sample, according to an extrapolation method, expressed by an equation below, and the extrapolated values were described: (extrapolated value)={100×(measured value of a sample)−(% by weight of a base liquid crystal)×(measured value of the base liquid crystal)}/(% by weight of compound).

When crystals (or a smectic phase) precipitated at 25° C. even at the ratio of the compound to the base liquid crystal, a ratio of the compound to the base liquid crystal was changed in the order of (10% by weight:90% by weight), (5% by weight:95% by weight) and (1% by weight:99% by weight), and physical properties of the sample were measured at a ratio at which the crystals (or the smectic phase) did not precipitate at 25° C. In addition, unless otherwise noted, the ratio of the compound to the base liquid crystal was 15% by weight:85% by weight.

As the base liquid crystal, base liquid crystal (i) described below was used. Ratios of components of base liquid crystal (i) are expressed in terms of % by weight.

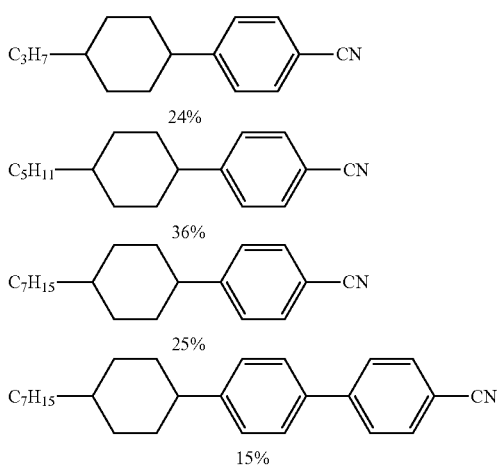

Measurement Method

Physical properties were measured according to methods described below. Most of the methods are applied as described in the Standard of the Japan Electronics and Information Technology Industries Association (hereinafter, abbreviated as JEITA) (JEITA ED-2521B) discussed and established by JEITA, or as modified thereon. No TFT was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

A differential scanning calorimeter, Diamond DSC System, made by PerkinElmer, Inc., or a high-sensitivity differential scanning calorimeter, X-DSC7000, made by SII NanoTechnology Inc. was used for measurement. A sample was heated and then cooled at a rate of 3° C. per minute, and a starting point of an endothermic peak or an exothermic peak caused by a phase change of the sample was determined by extrapolation, and thus a transition temperature was determined. Temperature at which a compound undergoes transition from a solid to a liquid crystal phase such as a smectic phase and a nematic phase may be occasionally abbreviated as a "minimum temperature of the liquid crystal phase." Temperature at which a compound undergoes transition from the liquid crystal phase to an isotropic liquid may be occasionally abbreviated as a "clearing point."

Crystals were expressed as C. When kinds of the crystals were distinguishable, each of the crystals was expressed as $C_1$ or $C_2$. The smectic phase was expressed as S, and the nematic phase was expressed as N. When smectic A phase, smectic B phase, smectic C phase or smectic F phase was distinguishable among the smectic phases, the phases were expressed as $S_A$, $S_B$, $S_C$ or $S_F$, respectively. The liquid (isotropic) was expressed as I. The transition temperature was expressed as "C 50.0 N 100.0 I", for example. The expression indicates that the transition temperature from the crystal to the nematic phase is 50.0° C., and the transition temperature from the nematic phase to the liquid is 100.0° C.

(3) Compatibility at a Low Temperature

Samples in which the base liquid crystal and the compound were mixed such that a ratio of the compound was 20% by weight, 15% by weight, 10% by weight, 5% by weight, 3% by weight or 1% by weight were prepared, and placed in glass vials. After the glass vials were kept in freezers at −10° C. or −20° C. for a predetermined period of time, whether or not crystals or a smectic phase precipitated was observed.

(4) Maximum Temperature of a Nematic Phase ($T_{NI}$ or NI; ° C.)

A sample was placed on a hot plate in a melting point apparatus equipped with a polarizing microscope and was heated at the rate of 1° C. per minute. Temperature was measured when a part of the sample began to change from a nematic phase to an isotropic liquid. A higher limit of a temperature range of the nematic phase may be occasionally abbreviated as "maximum temperature". When the sample was a mixture of a compound and the base liquid crystal, the maximum temperature was expressed using a symbol $T_{NI}$. When the sample was a mixture of a compound and component B, the maximum temperature was expressed using a symbol NI.

(5) Minimum Temperature of a Nematic Phase ($T_C$; ° C.)

Samples each having a nematic phase were kept in freezers at temperatures of 0° C., −10° C., −20° C., −30° C. and −40° C. for 10 days, and then the liquid crystal phases were observed. For example, when the sample maintained the nematic phase at −20° C. and changed to crystals or a smectic phase at −30° C., $T_c$ was expressed as $T_c \leq -20°$ C. A lower limit of the temperature range of the nematic phase may be occasionally abbreviated as "minimum temperature."

(6) Viscosity (Bulk Viscosity; η; Measured at 20° C.; mPa·s)

A cone-plate (E type) rotational viscometer, made by Tokyo Keiki Inc. was used for measurement.

(7) Viscosity (Rotational Viscosity; γ1; Measured at 25° C.; mPa·s)

Measurement was carried out according to a method described in M. Imai et al., Molecular Crystals and Liquid Crystals, Vol. 259, 37 (1995). A sample was put in a TN device in which a twist angle was 0 degrees and a distance (cell gap) between two glass substrates was 5 micrometers. Voltage was stepwise applied to the device in the range from 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. A value of dielectric anisotropy required for the calculation was determined using the device with which the rotational viscosity was measured and by a method described below.

(8) Optical Anisotropy (Refractive Index Anisotropy; Measured at 25° C.; Δn)

Measurement was carried out using an Abbe refractometer with a polarizing plate mounted on an ocular by using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy (Δn) was calculated from an equation: Δn=n∥−n⊥.

87

(9) Dielectric Constant in a Minor Axis Direction ($\varepsilon\perp$) and Dielectric Anisotropy ($\Delta\varepsilon$; Measured at 25° C.)

A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant in a major axis direction ($\varepsilon\|$) of liquid crystal molecules was measured. Sine waves (0.5 V, 1 kHz) were applied to the device, and after 2 seconds, a dielectric constant in a minor axis direction ($\varepsilon\perp$) of the liquid crystal molecules was measured. A value of dielectric anisotropy was calculated from an equation: $\Delta\varepsilon=\varepsilon\|-\varepsilon\perp$.

(10) Elastic Constant (K; Measured at 25° C.; pN)

HP4284A LCR Meter made by Yokogawa-Hewlett-Packard Co. was used for measurement. A sample was put in a horizontal alignment device in which a distance (cell gap) between two glass substrates was 20 micrometers. An electric charge from 0 V to 20 V was applied to the device, and electrostatic capacity and applied voltage were measured. Measured values of the electrostatic capacity (C) and the applied voltage (V) were fitted to equation (2.98) and equation (2.101) on page 75 of "Liquid Crystal Device Handbook" (Ekisho Debaisu Handobukku in Japanese) (The Nikkan Kogyo Shimbun, Ltd.), and values of $K_{11}$ and $K_{33}$ were obtained from equation (2.99). Next, $K_{22}$ was calculated using the previously determined values of $K_{11}$ and $K_{33}$ in equation (3.18) on page 171 of the same Handbook. An elastic constant K was represented by a mean value of the thus determined $K_{11}$, $K_{22}$ and $K_{33}$.

(11) Threshold Voltage (Vth; Measured at 25° C.; V)

An LCD-5100 luminance meter made by Otsuka Electronics Co., Ltd. was used for measurement. A light source was a halogen lamp. A sample was put in a normally white mode TN device in which a distance (cell gap) between two glass substrates was approximately 0.45/$\Delta$n ($\mu$m) and a twist angle was 80 degrees. Voltage (32 Hz, rectangular waves) to be applied to the device was stepwise increased from 0 V to 10 V at an increment of 0.02 V. On the occasion, the device was irradiated with light from a perpendicular direction, and an amount of light transmitted through the device was measured. A voltage-transmittance curve was prepared, in which the maximum value of the amount of light corresponded to 100% transmittance and the minimum value of the amount of light corresponded to 0% transmittance. A threshold voltage was a voltage at 90% transmittance.

(12) Voltage Holding Ratio (VHR-1; Measured at 25° C.; %)

A TN device used for measurement had a polyimide alignment film, and a distance (cell gap) between two glass substrates was 5 micrometers. A sample was put in the device, and then the device was sealed with an ultraviolet-curable adhesive. A pulse voltage (60 microseconds at 5 V) was applied to the device at 25° C. and the device was charged. A decaying voltage was measured for 16.7 milliseconds with a high-speed voltmeter, and area A between a voltage curve and a horizontal axis in a unit cycle was obtained. Area B was an area without decay. A voltage holding ratio was a percentage of area A to area B.

(13) Voltage Holding Ratio (VHR-2; Measured at 80° C.; %)

A voltage holding ratio (VHR-2) was determined in a manner similar to VHR-1 except that measurement was carried out at 80° C.

Raw Material

Solmix A-11 (trade name) was a mixture of ethanol (85.5%), methanol (13.4%) and isopropanol (1.1%), and was purchased from Japan Alcohol Trading Company, Ltd.

88

Example 1

Synthesis of Compound (No. 1-2-2)

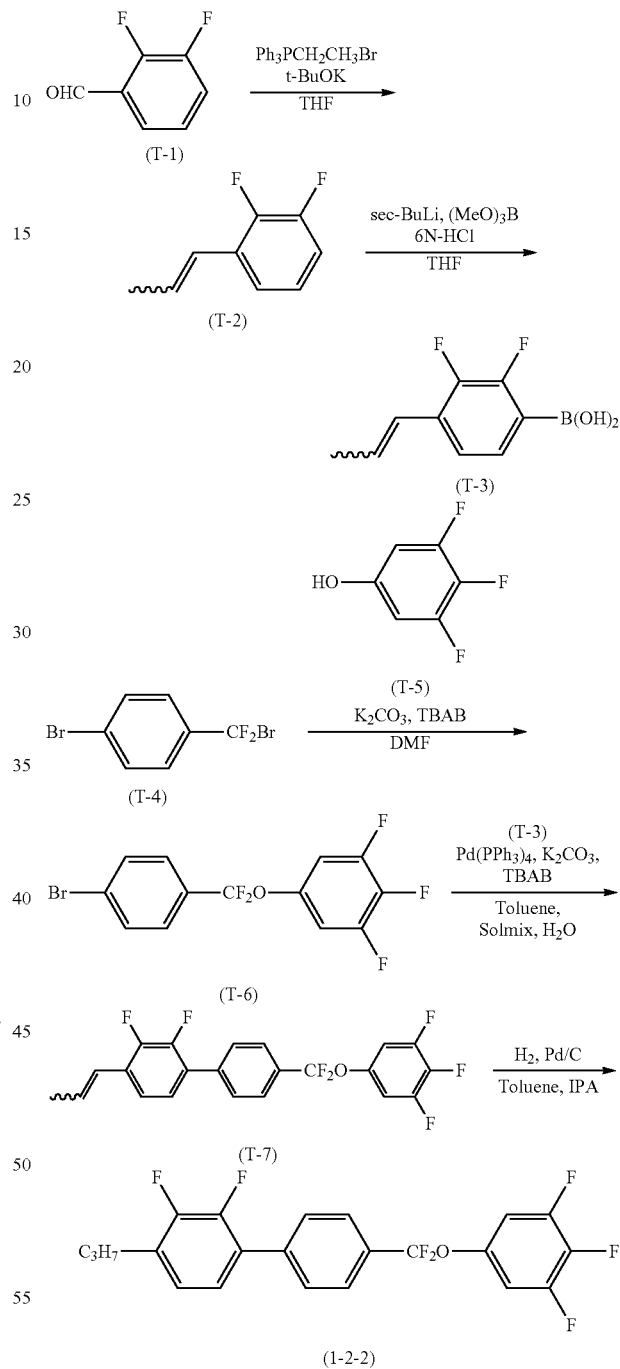

First Step

Under a nitrogen atmosphere, ethyltriphenylphosphonium bromide (61.8 g) and THF (600 mL) were put in a reaction vessel, and the resulting mixture was cooled to −30° C. Potassium t-butoxide (17.9 g) was slowly added thereto, and the resulting mixture was stirred for 30 minutes. Next, a THF (100 mL) solution of compound (T-1) (18.9 g) was slowly added thereto, and the resulting mixture was stirred for 3 hours while the mixture was returned to room temperature. The resulting reaction mixture was poured into ice water, and the resulting aqueous layer was subjected to extraction with diethyl ether. Organic layers combined were washed with brine, and dried over anhydrous magnesium sulfate. The resulting solution was concentrated under reduced pressure, and the residue was purified by silica gel chromatography (hexane) to give compound (T-2) (16.4 g; 80%).

Second Step

Under a nitrogen atmosphere, compound (T-2) (10.0 g) and THF (100 mL) were put in a reaction vessel, and the resulting mixture was cooled to −70° C. Then, sec-butyllithium (1.07 M; cyclohexane, n-hexane solution; 66.7 mL) was slowly added thereto, and the resulting mixture was stirred for 2 hours. Next, a THF (20.0 mL) solution of trimethyl borate (9.73 g) was slowly added thereto, and the resulting mixture was stirred for 12 hours while the mixture was returned to room temperature. Next, the resulting mixture was cooled to −30° C., 6 N hydrochloric acid (65.0 mL) was slowly added thereto, and the resulting mixture was stirred for 3 hours while the mixture was returned to room temperature. The resulting reaction mixture was poured into water, and the resulting aqueous layer was subjected to extraction with ethyl acetate. Organic layers combined were washed with brine, and dried over anhydrous magnesium sulfate. The resulting solution was concentrated under reduced pressure and purified by recrystallization from heptane to give compound (T-3) (11.0 g; 86%).

Third Step

Under a nitrogen atmosphere, compound (T-4) (50.0 g) prepared according to the method described in JP 2011-98942 A, compound (T-5) (31.1 g), potassium carbonate (72.5 g), TBAB (tetrabutylammonium bromide) (11.3 g) and DMF (500 mL) were put in a reaction vessel, and the resulting mixture was stirred at 90° C. for 2 hours. The resulting reaction mixture was poured into water, and the resulting aqueous layer was subjected to extraction with toluene. Organic layers combined were washed with brine, and dried over anhydrous magnesium sulfate. The resulting solution was concentrated under reduced pressure, and the residue was purified by silica gel chromatography (heptane) to give compound (T-6) (52.1 g; 84%).

Fourth Step

Under a nitrogen atmosphere, compound (T-6) (10.0 g), compound (T-3) (6.73 g), tetrakis(triphenylphosphine)palladium (0.330 g), potassium carbonate (7.83 g), TBAB (1.83 g), toluene (50.0 mL), Solmix (registered trade name) A-11 (50.0 mL) and water (50.0 mL) were put in a reaction vessel, and the resulting mixture was heated under reflux for 3 hours. The resulting reaction mixture was poured into water, and the resulting aqueous layer was subjected to extraction with toluene. Organic layers combined were washed with water, and dried over anhydrous magnesium sulfate. The resulting solution was concentrated under reduced pressure, and the residue was purified by silica gel chromatography (heptane) to give compound (T-7) (6.79 g; 56%).

Fifth Step

Compound (T-7) (6.79 g), a palladium on carbon catalyst (5% Pd/C NX type (50% wet basis); made by N.E. CHEMCAT Corporation; 0.340 g), toluene (50.0 mL) and IPA (50.0 mL) were put in a reaction vessel, and the resulting mixture was stirred for 8 hours under a hydrogen atmosphere. The catalyst was removed by filtration, and then the resulting mixture was concentrated under reduced pressure, and the residue was purified by silica gel chromatography (heptane). The resulting product was further purified by recrystallization from Solmix (registered trade name) A-11 to give compound (No. 1-2-2) (5.08 g; 75%).

Chemical shifts δ (ppm; CDCl$_3$): 7.77 (d, J=8.4 Hz, 2H), 7.65 (d, J=7.8 Hz, 2H), 7.15-7.09 (m, 1H), 7.06-6.94 (m, 3H), 2.69 (t, J=7.3 Hz, 2H), 1.75-1.65 (m, 2H), 1.00 (t, J=7.4 Hz, 3H).

Physical properties of compound (No. 1-2-2) were as described below.

Transition temperature: C 31.1 I.

Maximum temperature ($T_{NI}$)=−0.3° C.; optical anisotropy (Δn)=0.117; dielectric anisotropy (Δε)=19.4; dielectric constant in minor axis direction (ε⊥)=9.2; and viscosity (η)=38.9 mPa·s.

Example 2

Synthesis of Compound (No. 1-2-19)

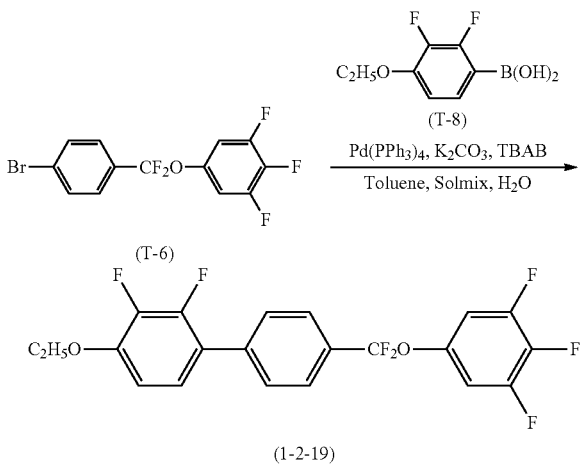

First Step

Under a nitrogen atmosphere, compound (T-6) (10.0 g), compound (T-8) (6.86 g), tetrakis(triphenylphosphine)palladium (0.330 g), potassium carbonate (7.83 g), TBAB (1.83 g), toluene (70.0 mL), Solmix (registered trade name) A-11 (70.0 mL) and water (70.0 mL) were put in a reaction vessel, and the resulting mixture was heated under reflux for 3 hours. The resulting reaction mixture was poured into water, and the resulting aqueous layer was subjected to extraction with toluene. Organic layers combined were washed with water, and dried over anhydrous magnesium sulfate. The resulting solution was concentrated under reduced pressure, and the residue was purified by silica gel chromatography (heptane:toluene=2:1 in a volume ratio). The resulting product was further purified by recrystallization from a mixed solvent of heptane and toluene (1:1 in a volume ratio) to give compound (No. 1-2-19) (8.14 g; 67%).

Chemical shifts δ (ppm; CDCl$_3$): 7.75 (d, J=8.4 Hz, 2H), 7.62 (d, J=7.6 Hz, 2H), 7.15-7.09 (m, 1H), 7.02-6.94 (m, 2H), 6.87-6.80 (m, 1H), 4.18 (q, J=7.0 Hz, 2H), 1.50 (t, J=7.1 Hz, 3H).

Physical properties of compound (No. 1-2-19) were as described below. In addition, for measurement of maximum temperature, optical anisotropy, dielectric anisotropy, a dielectric constant in a minor axis direction and viscosity, a sample in which a ratio of the compound to the base liquid crystal was (5% by weight:95% by weight) was used.

Transition temperature: C 101 I.

Maximum temperature ($T_{NI}$)=33.7° C.; optical anisotropy ($\Delta n$)=0.157; dielectric anisotropy ($\Delta \varepsilon$)=21.9; dielectric constant in minor axis direction ($\varepsilon\perp$)=8.5; and viscosity ($\eta$)=55.5 mPa·s.

Example 3

Synthesis of Compound (No. 1-2-10)

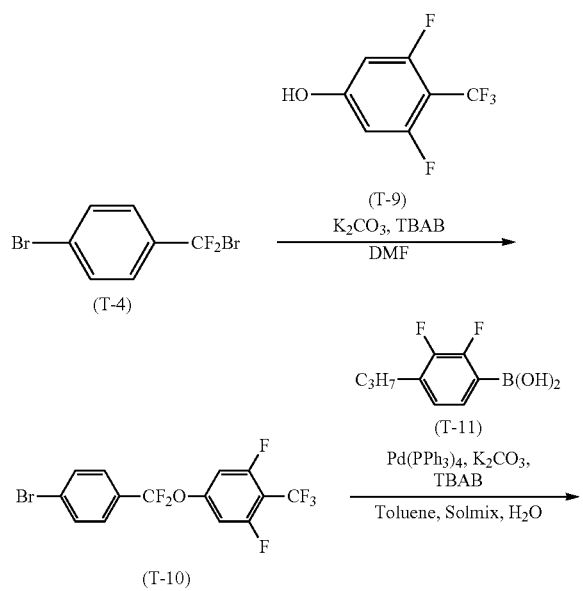

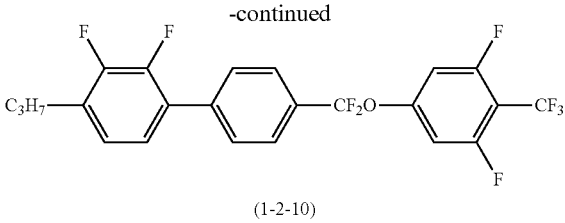

(1-2-10)

First Step

Compound (T-10) (9.45 g; 67%) was obtained by using compound (T-4) (10.0 g) and compound (T-9) (7.63 g) as raw materials in a manner similar to the procedures in the third step in Example 1.

Second Step

Compound (1-2-10) (3.70 g; 52%) was obtained by using compound (T-10) (6.00 g) and compound (T-11) (3.16 g) as raw materials in a manner similar to the operation in the first step in Example 2.

Chemical shifts δ (ppm; CDCl$_3$): 7.77 (d, J=8.4 Hz, 2H), 7.67 (d, J=7.7 Hz, 2H), 7.15-7.10 (m, 1H), 7.06-6.96 (m, 3H), 2.69 (t, J=7.6 Hz, 2H), 1.74-1.64 (m, 2H), 1.00 (t, J=7.4 Hz, 3H).

Physical properties of compound (No. 1-2-10) were as described below.

Transition temperature: C 44.8 I.

Maximum temperature ($T_{NI}$)=−0.3° C.; optical anisotropy ($\Delta n$)=0.117; dielectric anisotropy ($\Delta \varepsilon$)=27.2; dielectric constant in minor axis direction ($\varepsilon\perp$)=8.5; and viscosity ($\eta$)=51.5 mPa·s.

Example 4

Synthesis of Compound (No. 1-3-16)

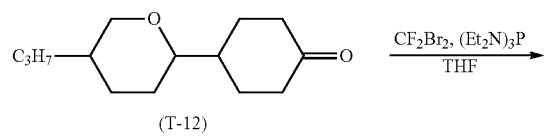

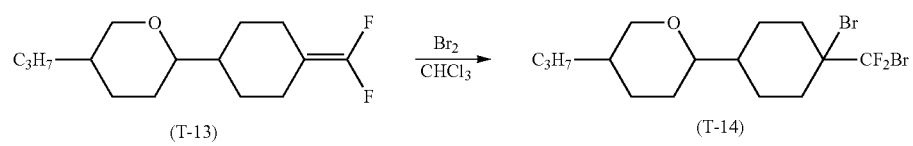

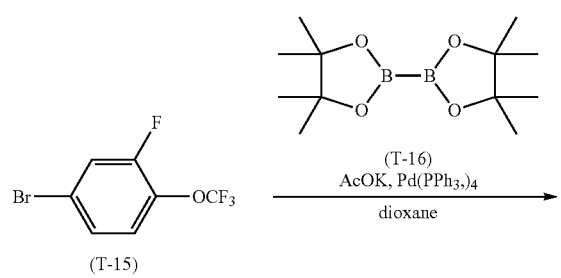

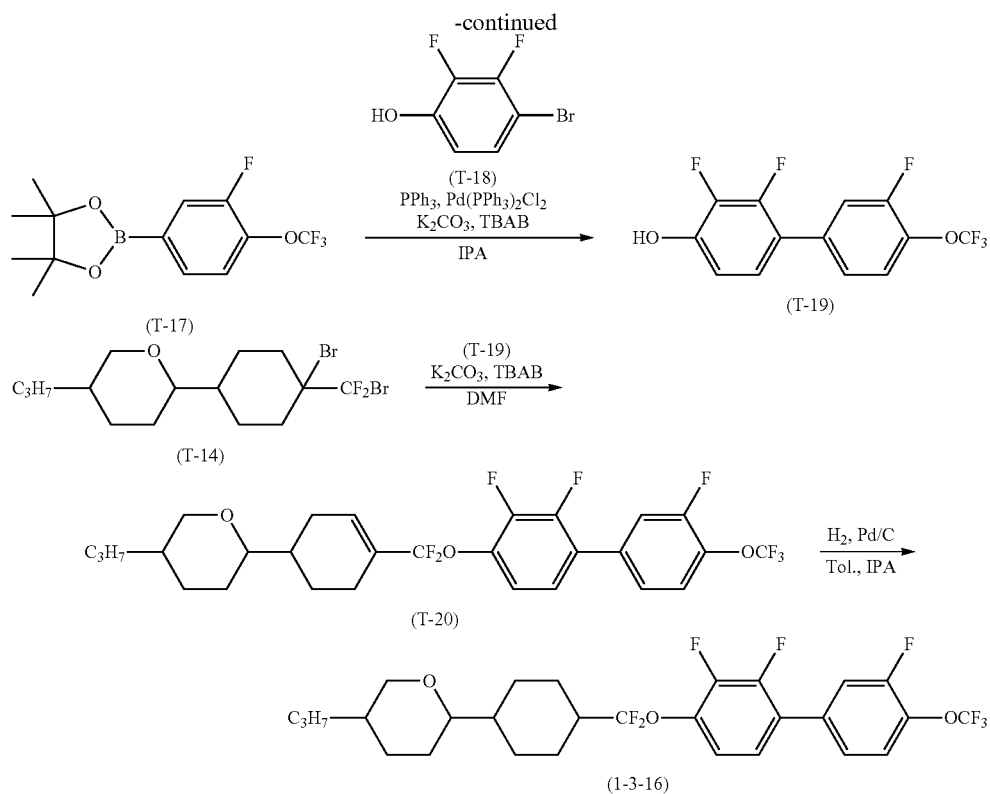

First Step

Under a nitrogen atmosphere, dibromodifluoromethane (18.7 g) and THF (55.0 mL) were put in a reaction vessel, and the resulting mixture was cooled to −10° C. A THF (100 mL) solution of trisdiethylaminophosphine (44.1 g) was slowly added thereto, and the resulting mixture was stirred for 1 hour while the mixture was returned to room temperature. Next, a THF (45.0 mL) solution of compound (T-12) (10.0 g) prepared according to the technique described in P. Kirsch et al., European Journal of Organic Chemistry. 2008, 20, 3479 was slowly added thereto, and the resulting mixture was stirred for 5 hours. The resulting reaction mixture was poured into ice water, and the resulting aqueous layer was subjected to extraction with heptane. Organic layers combined were washed with 3 N hydrochloric acid and brine in the order, and dried over anhydrous magnesium sulfate. The resulting solution was concentrated under reduced pressure, and the residue was purified by silica gel chromatography (heptane) to give compound (T-13) (10.0 g; 87%).

Second Step

Under a nitrogen atmosphere, compound (T-13) (10.0 g) and chloroform (130 mL) were put in a reaction vessel, and the resulting mixture was cooled to −10° C. A chloroform (20.0 mL) solution of bromine (2.09 mL) was slowly added thereto, and the resulting mixture was stirred for 30 minutes while the mixture was returned to room temperature. The resulting reaction mixture was poured into water, and the resulting aqueous layer was subjected to extraction with dichloromethane. Organic layers combined were washed with a saturated aqueous solution of sodium thiosulfate and water in the order, and dried over anhydrous magnesium sulfate. The resulting solution was concentrated under reduced pressure, and the residue was purified by silica gel chromatography (heptane:ethyl acetate=20:1 in a volume ratio) to give compound (T-14) (15.7 g; 97%).

Third Step

Under a nitrogen atmosphere, compound (T-15) (20.0 g), compound (T-16) (21.6 g), tetrakis(triphenylphosphine)palladium (1.34 g), potassium acetate (21.6 g), and 1,4-dioxane (100 mL) were put in a reaction vessel, and the resulting mixture was stirred at 100° C. for 3 hours. The resulting reaction mixture was poured into water, and the resulting aqueous layer was subjected to extraction with toluene. Organic layers combined were washed with brine, and dried over anhydrous magnesium sulfate. The resulting solution was concentrated under reduced pressure, and the residue was purified by silica gel chromatography (toluene). The resulting product was further purified by recrystallization from heptane to give compound (T-17) (13.0 g; 55%).

Fourth Step

Under a nitrogen atmosphere, dichlorobis(triphenylphosphine)palladium (0.430 g), triphenylphosphine (0.322 g) and IPA (30.0 mL) were put in a reaction vessel, and the resulting mixture was heated under reflux for 1 hour. Next, compound (T-17) (6.88 g), compound (T-18) (4.27 g), potassium carbonate (5.65 g), TBAB (1.32 g) and IPA (70.0 mL) were added thereto, and the resulting mixture was heated under reflux for 5 hours. The resulting reaction mixture was poured into 3 N hydrochloric acid (100 mL), and the resulting aqueous layer was subjected to extraction with toluene. Organic layers combined were washed with brine, and dried over anhydrous magnesium sulfate. The resulting solution was concentrated under reduced pressure, and the residue was purified by silica gel chromatography (toluene:ethyl acetate=10:1 in a volume ratio) to give compound (T-19) (6.72 g; 99%).

Fifth Step

Compound (T-20) (5.20 g; 53%) was obtained by using compound (T-14) (7.33 g) and compound (T-19) (6.48 g) as raw materials in a manner similar to the procedures in the third step in Example 1.

Sixth Step

Compound (T-20) (5.20 g), a palladium on carbon catalyst (5% Pd/C E type (50% wet basis); made by N.E. CHEMCAT Corporation; 0.520 g), toluene (26.0 mL) and IPA (26.0 mL) were put in a reaction vessel, and the resulting mixture was stirred at 50° C. for 48 hours under a hydrogen atmosphere. The catalyst was removed by filtration, and then the resulting mixture was concentrated under reduced pressure, and the residue was purified by silica gel chromatography (heptane:ethyl acetate=10:1 in a volume ratio). The resulting product was further purified by recrystallization from a mixed solvent of IPA and ethyl acetate (1:1 in a volume ratio) to give compound (No. 1-3-16) (1.74 g; 33%).

Chemical shifts δ (ppm; $CDCl_3$): 7.42-7.35 (m, 2H), 7.34-7.29 (m, 1H), 7.21-7.15 (m, 1H), 7.15-7.08 (m, 1H), 3.94 (ddd, J=11.1 Hz, J=4.1 Hz, J=2.1 Hz, 1H), 3.04-2.93 (m, 2H), 2.16-2.06 (m, 4H), 1.95-1.81 (m, 2H), 1.70-1.62 (m, 1H), 1.57-1.48 (m, 1H), 1.48-1.22 (m, 6H), 1.19-1.00 (m, 5H), 0.89 (t, J=7.3 Hz, 3H).

Physical properties of compound (No. 1-3-16) were as described below.

Transition temperature: C 55.6 $S_A$ 130 N 222 I.

Maximum temperature ($T_{NI}$)=145° C.; optical anisotropy (Δn)=0.130; dielectric anisotropy (Δε)=12.8; dielectric constant in minor axis direction (ε⊥)=5.8; and viscosity (η)=74.2 mPa·s.

Example 5

Synthesis of Compound (No. 1-4-1)

First Step

Compound (1-4-1) (2.87 g; 50%) was obtained by using compound (T-6) (4.00 g) and compound (T-21) (3.13 g) as raw materials in a manner similar to the procedures in the first step in Example 2.

Chemical shifts δ (ppm; $CDCl_3$): 7.85 (d, J=8.4 Hz, 2H), 7.62 (d, J=7.7 Hz, 2H), 7.52 (dd, J=8.1 Hz, J=1.1 Hz, 2H), 7.34-7.24 (m, 4H), 7.03-6.95 (m, 2H), 2.66 (t, J=7.9 Hz, 2H), 1.76-1.66 (m, 2H), 0.99 (t, J=7.4 Hz, 3H).

Physical properties of compound (No. 1-4-1) were as described below. In addition, for measurement of maximum temperature, optical anisotropy, dielectric anisotropy, a dielectric constant in a minor axis direction and viscosity, a sample in which a ratio of the compound to the base liquid crystal was (5% by weight:95% by weight) was used.

Transition temperature: C 117 $S_A$ 136 N 169 I.

Maximum temperature ($T_{NI}$)=116° C.; optical anisotropy (Δn)=0.179; dielectric anisotropy (Δε)=21.9; dielectric constant in minor axis direction (ε⊥)=4.5; and viscosity (η)=54.3 mPa·s.

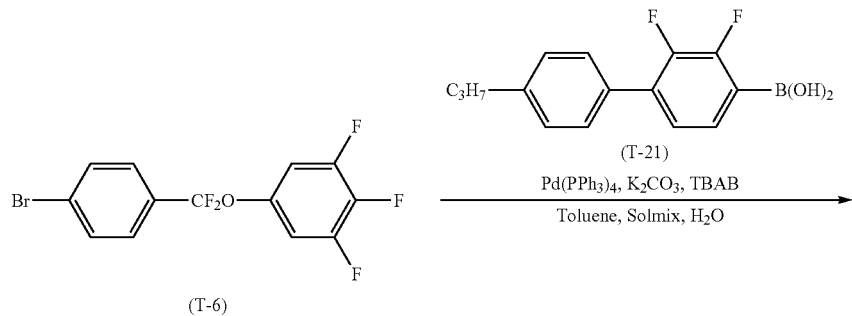

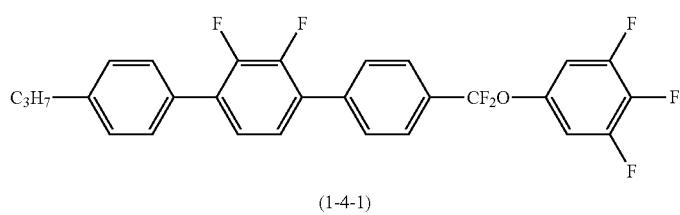

Example 6

Synthesis of Compound (No. 1-4-21)

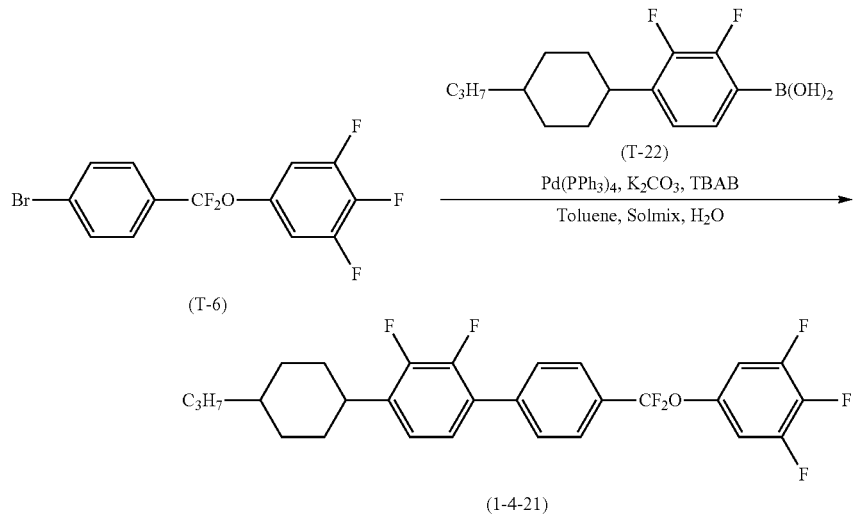

First Step

Compound (1-4-21) (4.97 g; 86%) was obtained by using compound (T-6) (4.00 g) and compound (T-22) (3.20 g) as raw materials in a manner similar to the procedures in the first step in Example 2.

Chemical shifts δ (ppm; CDCl$_3$): 7.76 (d, J=8.4 Hz, 2H), 7.65 (d, J=8.2 Hz, 2H), 7.17-7.12 (m, 1H), 7.10-7.04 (m, 1H), 7.02-6.94 (m, 2H), 2.89 (tt, J=12.2 Hz, J=3.1 Hz, 1H), 1.96-1.86 (m, 4H), 1.58-1.46 (m, 2H), 1.42-1.29 (m, 3H), 1.28-1.20 (m, 2H), 1.17-1.06 (m, 2H), 0.91 (t, J=7.4 Hz, 3H).

Physical properties of compound (No. 1-4-21) were as described below.

Transition temperature: C 72.0 N 158 I.

Maximum temperature (T$_{NI}$)=113° C.; optical anisotropy (Δn)=0.150; dielectric anisotropy (Δε)=16.8; dielectric constant in minor axis direction (ε⊥)=5.8; and viscosity (η)=63.8 mPa·s.

Example 7

Synthesis of Compound (No. 1-4-38)

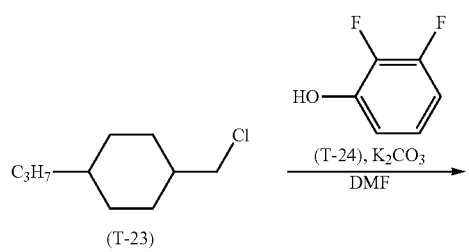

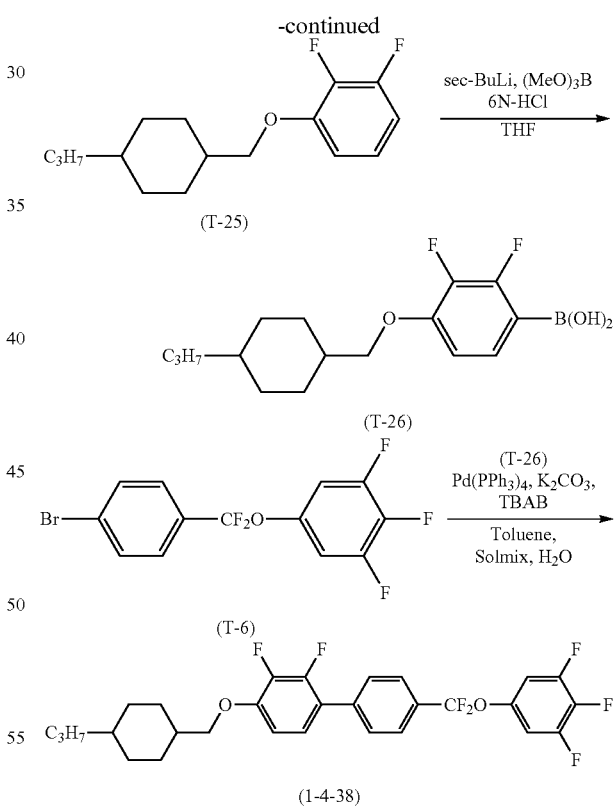

First Step

Under a nitrogen atmosphere, compound (T-23) (15.0 g), compound (T-24) (11.7 g), potassium carbonate (12.5 g) and DMF (100 mL) were put in a reaction vessel, and the resulting mixture was stirred at 120° C. for 7 hours. The resulting reaction mixture was poured into water, and the resulting aqueous layer was subjected to extraction with toluene. Organic layers combined were washed with brine, and dried over anhydrous magnesium sulfate. The resulting solution was concentrated under reduced pressure, and the residue was purified by silica gel chromatography (heptane) to give compound (T-25) (15.9 g; 69%).

Second Step

Compound (T-26) (12.5 g; 68%) was obtained by using compound (T-25) (15.9 g) as a raw material in a manner similar to the procedures in the second step in Example 1.

Third Step

Compound (1-4-38) (4.24 g; 59%) was obtained by using compound (T-6) (4.71 g) and compound (T-26) (5.00 g) as raw materials in a manner similar to the procedures in the first step in Example 2.

Chemical shifts δ (ppm; CDCl$_3$): 7.75 (d, J=8.3 Hz, 2H), 7.62 (d, J=7.6 Hz, 2H), 7.13-7.08 (m, 1H), 7.01-6.94 (m, 2H), 6.84-6.78 (m, 1H), 3.88 (d, J=6.5 Hz, 2H), 1.98-1.89 (m, 2H), 1.88-1.77 (m, 3H), 1.38-1.29 (m, 2H), 1.29-1.15 (m, 3H), 1.13-1.03 (m, 2H), 1.01-0.85 (m, 5H).

Physical properties of compound (No. 1-4-38) were as described below. In addition, for measurement of maximum temperature, optical anisotropy, dielectric anisotropy, a dielectric constant in a minor axis direction and viscosity, a sample in which a ratio of the compound to the base liquid crystal was (10% by weight:90% by weight) was used.

Transition temperature: C 103 N 144 I.

Maximum temperature (T$_{NI}$)=111° C.; optical anisotropy (Δn)=0.157; dielectric anisotropy (Δε)=11.8; dielectric constant in minor axis direction (ε⊥)=8.5; and viscosity (η)=80.6 mPa·s.

Example 8

Synthesis of Compound (No. 1-4-54)

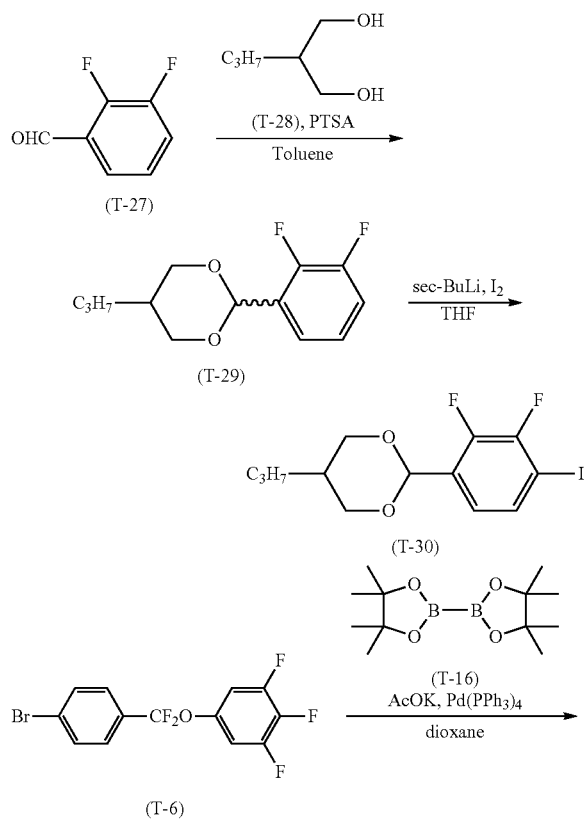

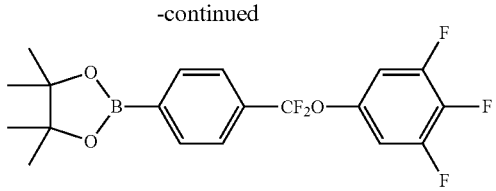

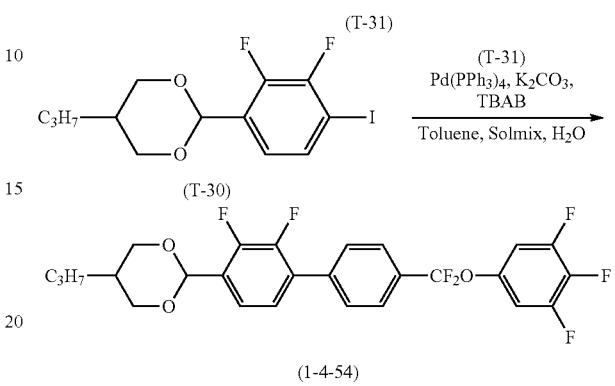

First Step

Under a nitrogen atmosphere, compound (T-27) (50.0 g), compound (T-28) (62.4 g), PTSA (p-toluenesulfonic acid monohydrate) (6.69 g) and toluene (250 mL) were put in a reaction vessel, and the resulting mixture was heated under reflux for 2 hours while water distilled therefrom was removed. The resulting reaction mixture was washed with water, and dried over anhydrous magnesium sulfate. The resulting solution was concentrated under reduced pressure, and the residue was purified by silica gel chromatography (heptane:toluene=1:1 in a volume ratio) to give compound (T-29) (71.6 g; 84%).

Second Step

Under a nitrogen atmosphere, compound (T-29) (35.0 g) and THF (450 mL) were put in a reaction vessel, and the resulting mixture was cooled to −70° C. Then, sec-butyl-lithium (1.01 M; cyclohexane, n-hexane solution; 172 mL) was slowly added thereto, and the resulting mixture was stirred for 1 hour. Next, a THF (270 mL) solution of iodine (47.7 g) was slowly added thereto, and the resulting mixture was stirred for 8 hours while the mixture was returned to room temperature. The resulting reaction mixture was poured into water, and the resulting aqueous layer was subjected to extraction with toluene. Organic layers combined were washed with a saturated aqueous solution of sodium thiosulfate and brine in the order, and dried over anhydrous magnesium sulfate. The resulting solution was concentrated under reduced pressure, and the residue was purified by silica gel chromatography (heptane:toluene=1:1 in a volume ratio). The resulting product was further purified by recrystallization from heptane to give compound (T-30) (37.6 g; 71%).

Third Step

Compound (T-31) (26.9 g; 79%) was obtained by using compound (T-6) (30.0 g) as a raw material in a manner similar to the procedures in the third step in Example 4.

Fourth Step

Compound (1-4-54) (27.2 g; 83%) was obtained by using compound (T-30) (23.6 g) and compound (T-31) (26.9 g) as raw materials in a manner similar to the procedures in the first step in Example 2.

Chemical shifts δ (ppm; CDCl$_3$): 7.77 (d, J=8.3 Hz, 2H), 7.64 (d, J=7.9 Hz, 2H), 7.51-7.45 (m, 1H), 7.26-7.20 (m, 1H), 7.02-6.94 (m, 2H), 5.76 (s, 1H), 4.25 (dd, J=11.8 Hz, J=4.6 Hz, 2H), 3.59 (t, J=11.5 Hz, 2H), 2.25-2.15 (m, 1H), 1.41-1.31 (m, 2H), 1.15-1.08 (m, 2H), 0.94 (t, J=7.5 Hz, 3H).

Physical properties of compound (No. 1-4-54) were as described below. In addition, for measurement of maximum temperature, optical anisotropy, dielectric anisotropy, a dielectric constant in a minor axis direction and viscosity, a sample in which a ratio of the compound to the base liquid crystal was (5% by weight:95% by weight) was used.

Transition temperature: C 117 N 138 I.

Maximum temperature $(T_{NI})$=114° C.; optical anisotropy ($\Delta$n)=0.157; dielectric anisotropy ($\Delta\epsilon$)=29.9; dielectric constant in minor axis direction ($\epsilon\perp$)=4.5; and viscosity ($\eta$)=73.5 mPa·s.

Example 9

Synthesis of Compound (No. 1-2-15)

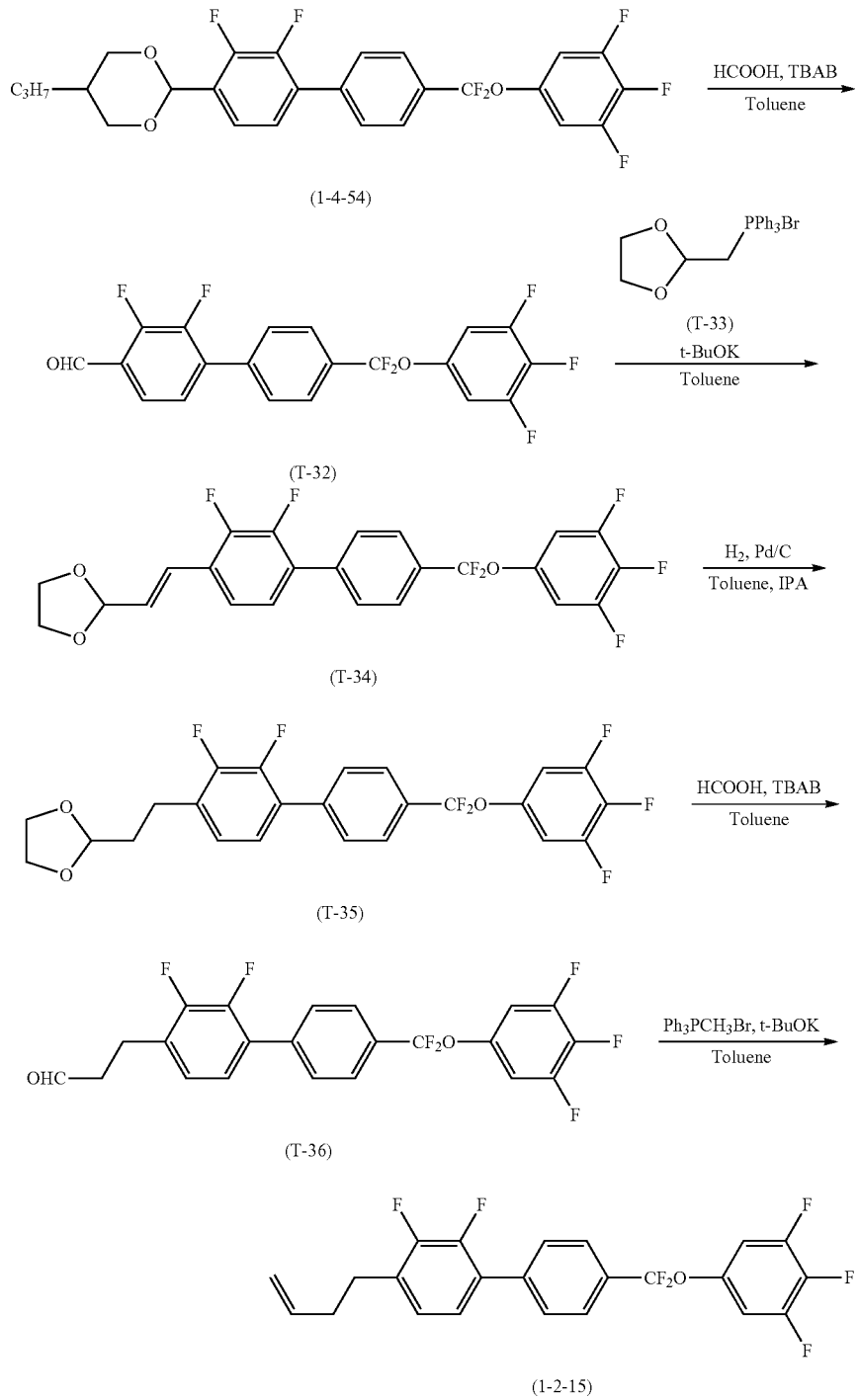

First Step

Under a nitrogen atmosphere, compound (1-4-54) (24.2 g), formic acid (121 mL), TBAB (4.55 g) and toluene (240 mL) were put in a reaction vessel, and the resulting mixture was stirred for 72 hours. The resulting reaction mixture was poured into water, and the resulting aqueous layer was subjected to extraction with toluene. Organic layers combined were washed with a saturated aqueous solution of sodium hydrogencarbonate and brine in the order, and dried over anhydrous magnesium sulfate. The resulting solution was concentrated under reduced pressure, and the residue was purified by silica gel chromatography (heptane:toluene=1:2 in a volume ratio) to give compound (T-32) (17.0 g; 87%).

Second Step

Compound (T-34) (19.7 g; 99%) was obtained by using compound (T-32) (17.0 g) and compound (T-33) (22.0 g) as raw materials in a manner similar to the procedures in the first step in Example 1.

Third Step

Compound (T-35) (17.7 g; 88%) was obtained by using compound (T-34) (19.7 g) as a raw material in a manner similar to the procedures in the fifth step in Example 1.

Fourth Step

Compound (T-36) (14.4 g; 89%) was obtained by using compound (T-35) (17.7 g) as a raw material in a manner similar to the procedures in the first step in Example 9.

Fifth Step

Compound (1-2-15) (2.01 g; 67%) was obtained by using compound (T-36) (3.00 g) and methyltriphenylphosphonium bromide (2.91 g) as raw materials in a manner similar to the procedures in the first step in Example 1.

Chemical shifts δ (ppm; CDCl$_3$): 7.77 (d, J=8.3 Hz, 2H), 7.65 (d, J=7.8 Hz, 2H), 7.16-7.10 (m, 1H), 7.06-6.94 (m, 3H), 5.92-5.81 (m, 1H), 5.12-5.00 (m, 2H), 2.82 (t, J=7.7 Hz, 2H), 2.46-2.38 (m, 2H).

Physical properties of compound (No. 1-2-15) were as described below.

Transition temperature: C 37.5 I.

Maximum temperature ($T_{NI}$)=9.0° C.; optical anisotropy (Δn)=0.130; dielectric anisotropy (Δε)=18.9; dielectric constant in minor axis direction (ε⊥)=8.5; and viscosity (η)=29.7 mPa·s.

Example 10

Synthesis of Compound (No. 1-5-21)

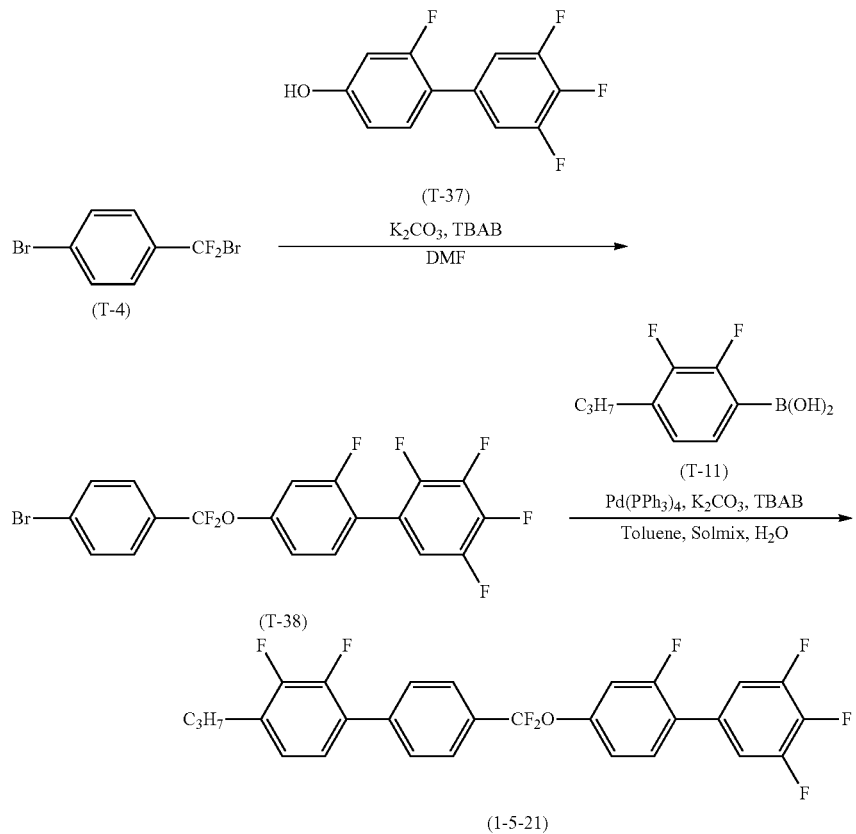

First Step

Compound (T-38) (13.9 g; 89%) was obtained by using compound (T-4) (10.0 g) and compound (T-37) (9.31 g) as raw materials in a manner similar to the procedures in the third step in Example 1.

Second Step

Compound (1-5-21) (2.44 g; 50%) was obtained by using compound (T-38) (4.15 g) as a raw material in a manner similar to the procedures in the first step in Example 2.

Chemical shifts δ (ppm; CDCl₃): 7.81 (d, J=8.3 Hz, 2H), 7.66 (d, J=7.7 Hz, 2H), 7.41-7.35 (m, 1H), 7.22-7.10 (m, 5H), 7.06-7.00 (m, 1H), 2.70 (t, J=7.5 Hz, 2H), 1.74-1.65 (m, 2H), 1.00 (t, J=7.4 Hz, 3H).

Physical properties of compound (No. 1-5-21) were as described below.

Transition temperature: C 74.4 N 122 I.

Maximum temperature ($T_{NI}$)=85.0° C.; optical anisotropy (Δn)=0.184; dielectric anisotropy (Δε)=23.9; dielectric constant in minor axis direction (ε⊥)=7.8; and viscosity (η)=78.8 mPa·s.

Example 11

Synthesis of Compound (No. 1-7-2)

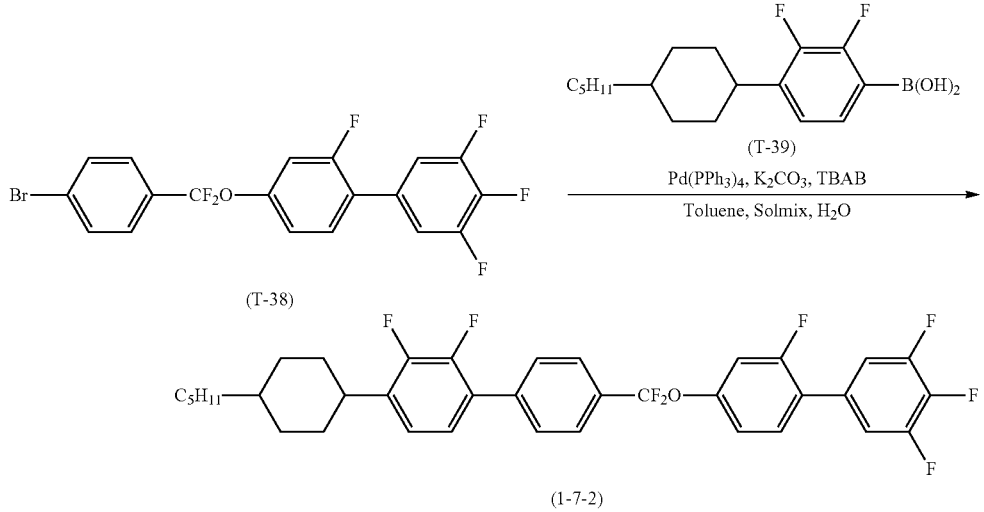

First Step

Compound (1-7-2) (3.92 g; 55%) was obtained by using compound (T-38) (5.00 g) and compound (T-39) (3.82 g) prepared according to the technique described in WO 2009/150966 A¹ as raw materials in a manner similar to the procedures in the first step in Example 2.

Chemical shifts δ (ppm; CDCl₃): 7.81 (d, J=8.3 Hz, 2H), 7.66 (d, J=8.2 Hz, 2H), 7.41-7.36 (m, 1H), 7.22-7.13 (m, 5H), 7.09-7.04 (m, 1H), 2.89 (tt, J=12.3 Hz, J=3.0 Hz, 1H), 1.95-1.87 (m, 4H), 1.58-1.46 (m, 2H), 1.38-1.21 (m, 9H), 1.16-1.06 (m, 2H), 0.90 (t, J=7.3 Hz, 3H).

Physical properties of compound (No. 1-7-2) were as described below.

Transition temperature: C 94.5 N 256 I.

Maximum temperature ($T_{NI}$)=174° C.; optical anisotropy (Δn)=0.190; dielectric anisotropy (Δε)=17.9; dielectric constant in minor axis direction (ε⊥)=5.2; and viscosity (η)=94.8 mPa·s.

Compounds (No. 1-1-1) to (No. 1-1-20), compounds (No. 1-2-1) to (No. 1-2-53), compounds (No. 1-3-1) to (No. 1-3-35), compounds (No. 1-4-1) to (No. 1-4-75), compounds (No. 1-5-1) to (No. 1-5-33), compounds (No. 1-6-1) to (No. 1-6-4) and compounds (No. 1-7-1) to (No. 1-7-3) shown below can be prepared according to the synthetic method of compound (1) as already described and the synthetic procedures described in Examples 1 to 11.

| No. | |
|---|---|
| 1-1-1 | 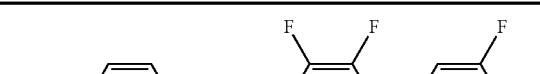 |
| 1-1-2 | 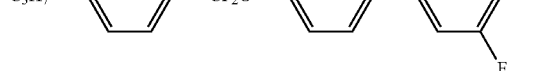 |

-continued
| No. |  |
|---|---|
| 1-1-3 | 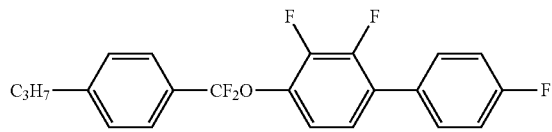 |
| 1-1-4 | 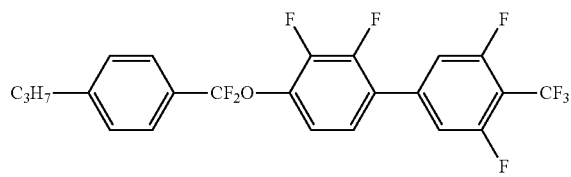 |
| 1-1-5 | 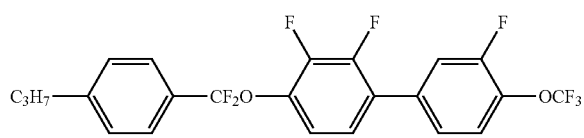 |
| 1-1-6 | 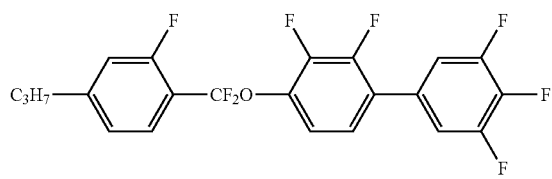 |
| 1-1-7 | 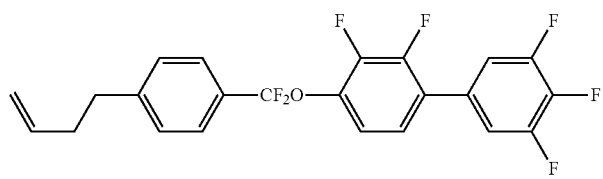 |
| 1-1-8 | 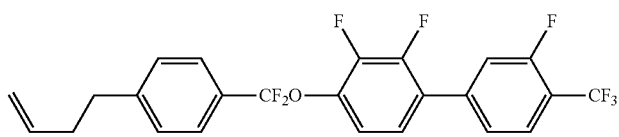 |
| 1-1-9 | 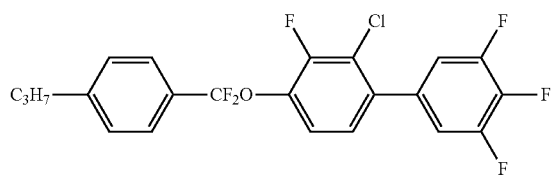 |
| 1-1-10 | 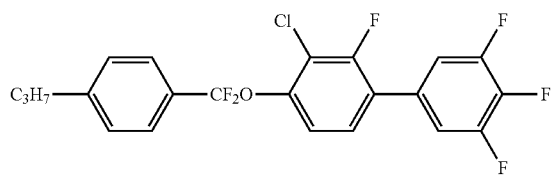 |
| 1-1-11 | 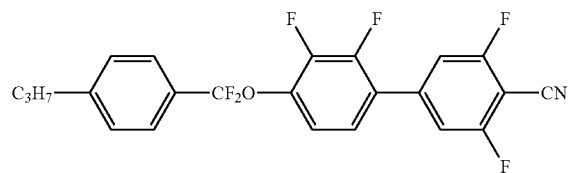 |

| No. | |
|---|---|
| 1-1-12 | 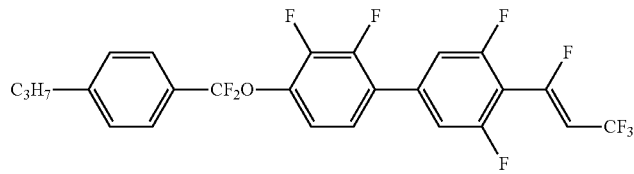 |
| 1-1-13 | 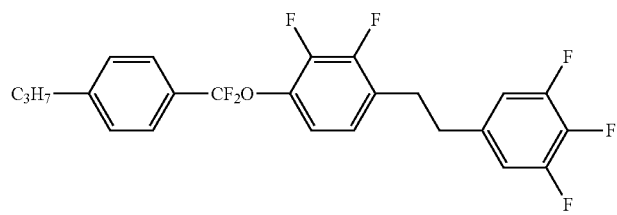 |
| 1-1-14 | 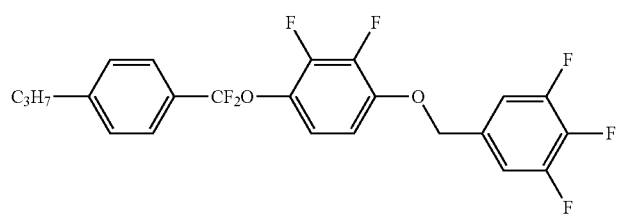 |
| 1-1-15 | 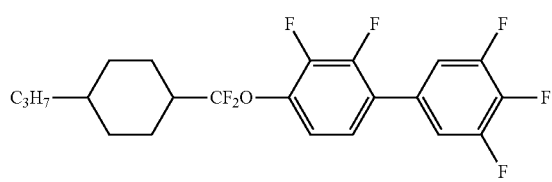 |
| 1-1-16 | 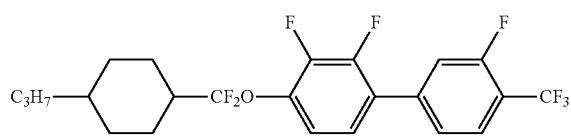 |
| 1-1-17 | 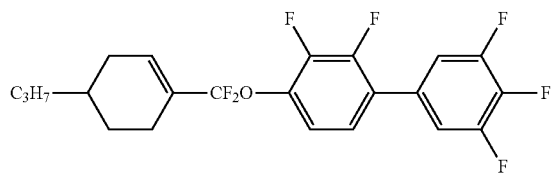 |
| 1-1-18 | 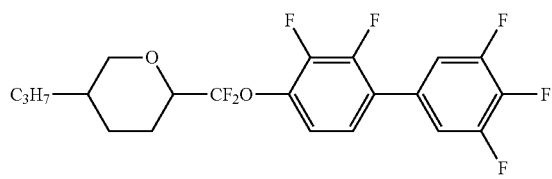 |
| 1-1-19 | 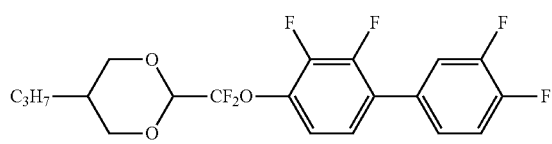 |

-continued
| No. | |
|---|---|
| 1-1-20 | 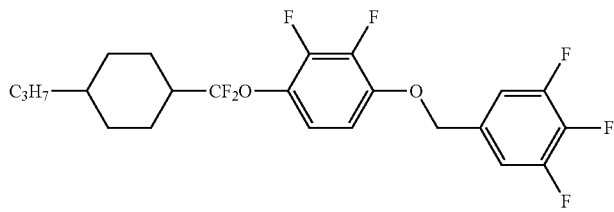 |
| 1-2-1 | 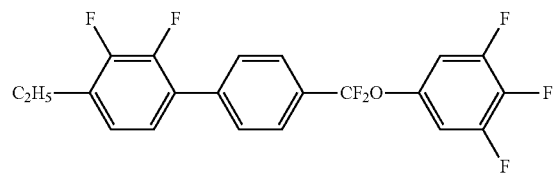 |
| 1-2-2 | 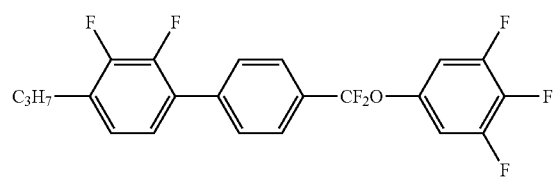 |
C 31.1 I
$T_{NI} = -0.3°$ C., $\Delta n = 0.117$, $\Delta \varepsilon = 19.4$, $\varepsilon (\perp) = 9.2$
| | |
|---|---|
| 1-2-3 | 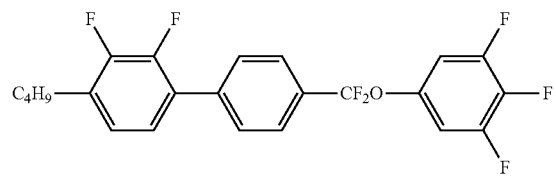 |
| 1-2-4 | 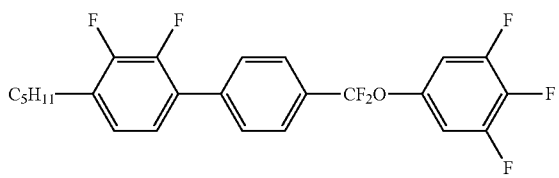 |
| 1-2-5 | 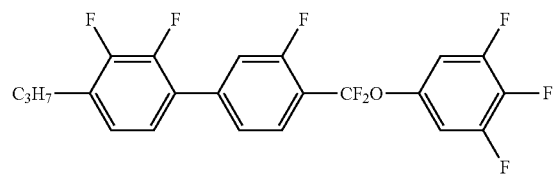 |
| 1-2-6 | 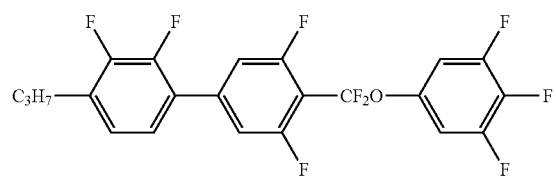 |
| 1-2-7 | 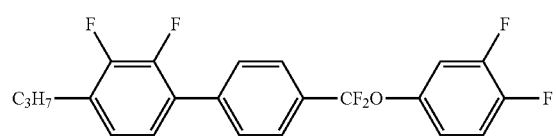 |

-continued
| No. | |
|---|---|
| 1-2-8 | 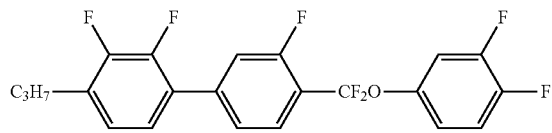 |
| 1-2-9 | 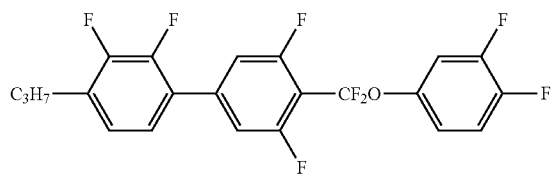 |
| 1-2-10 | 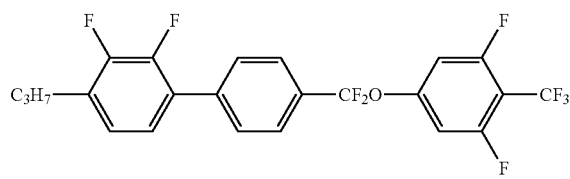<br>C 44.8 I<br>$T_{NI}$ = -0.3° C., $\Delta n$ = 0.117, $\Delta\varepsilon$ = 27.2, $\varepsilon$ ($\perp$) = 8.5 |
| 1-2-11 | 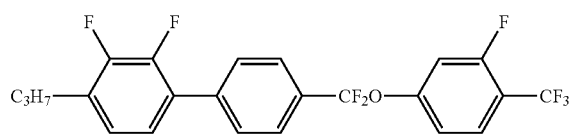 |
| 1-2-12 | 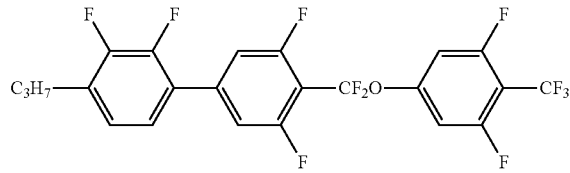 |
| 1-2-13 | 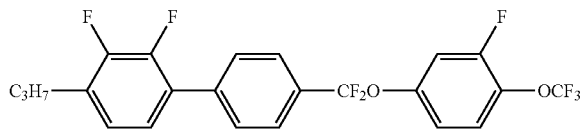 |
| 1-2-14 | 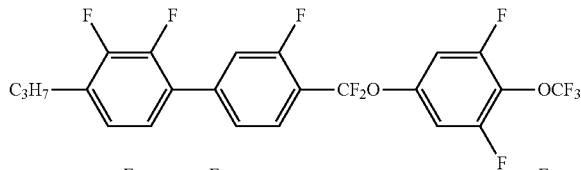 |
| 1-2-15 | 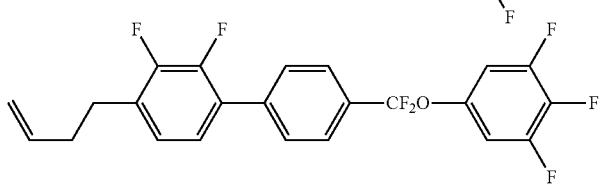<br>C 37.5 I<br>$T_{NI}$ = 9.0° C., $\Delta n$ = 0.130, $\Delta\varepsilon$ = 18.9, $\varepsilon$ ($\perp$) = 8.5 |
| 1-2-16 | 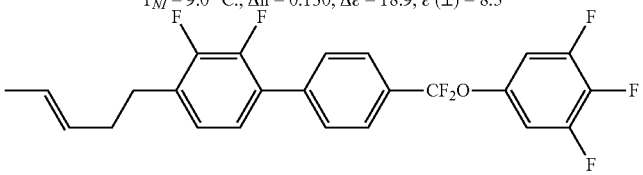 |

-continued
| No. | |
|---|---|
| 1-2-17 | 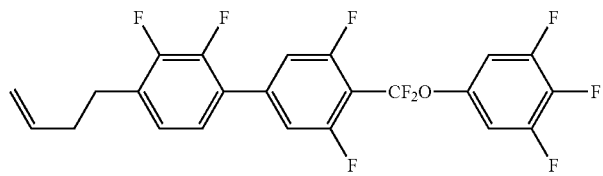 |
| 1-2-18 | 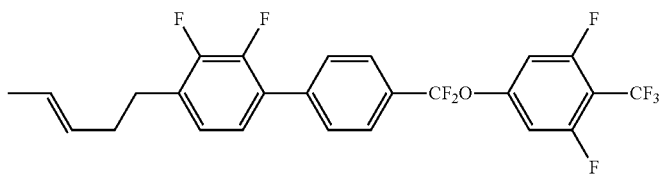 |
| 1-2-19 | 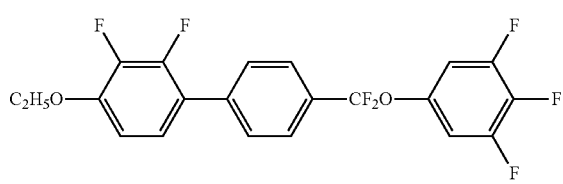 C 101 I $T_{NI} = 33.7°$ C., $\Delta n = 0.157$, $\Delta \varepsilon = 21.9$, $\varepsilon (\perp) = 8.5$ |
| 1-2-20 | 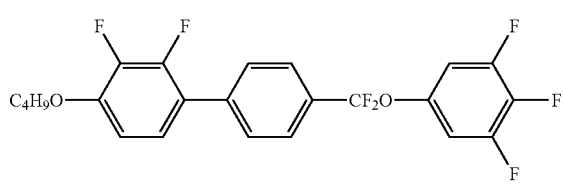 |
| 1-2-21 | 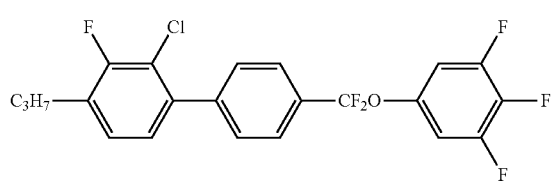 |
| 1-2-22 | 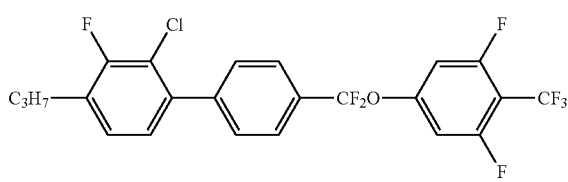 |
| 1-2-23 | 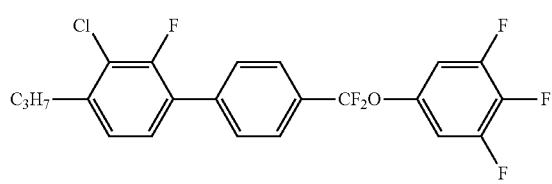 |
| 1-2-24 | 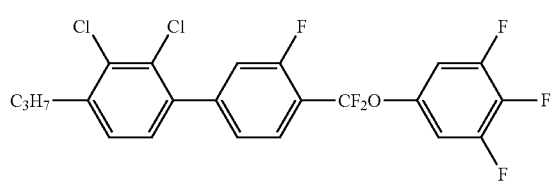 |

-continued
| No. | |
|---|---|
| 1-2-25 | 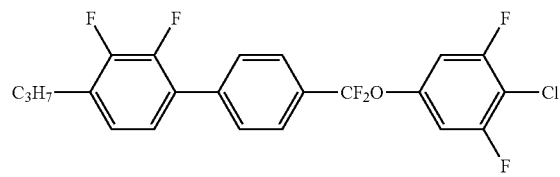 |
| 1-2-26 | 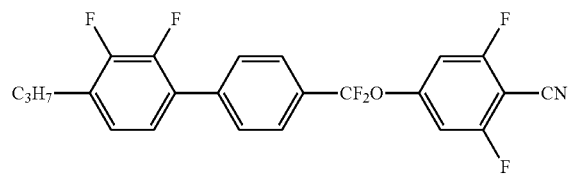 |
| 1-2-27 | 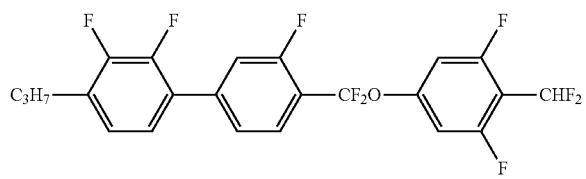 |
| 1-2-28 | 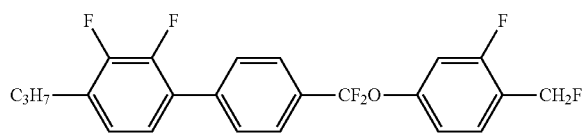 |
| 1-2-29 | 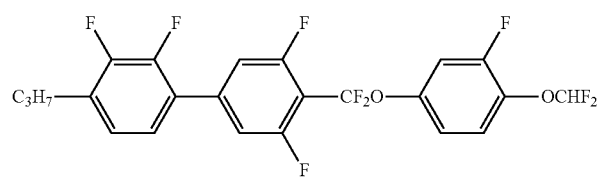 |
| 1-2-30 | 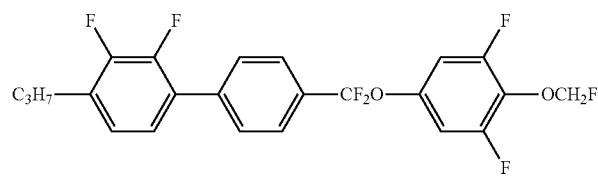 |
| 1-2-31 | 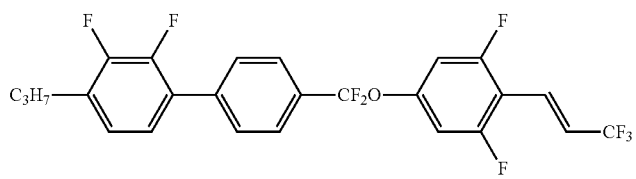 |
| 1-2-32 | 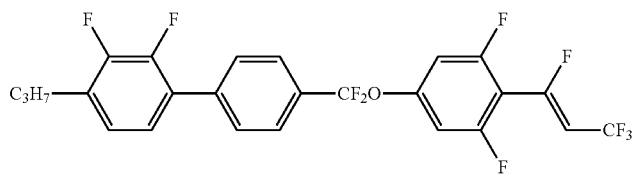 |
| 1-2-33 | 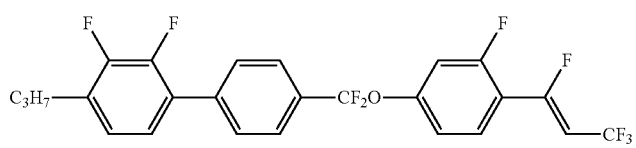 |

| No. | |
|---|---|
| 1-2-34 | 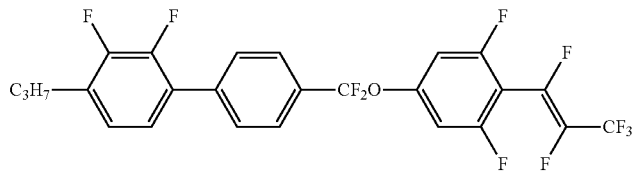 |
| 1-2-35 | 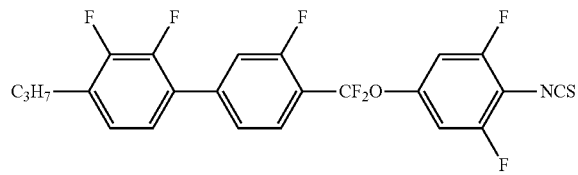 |
| 1-2-36 | 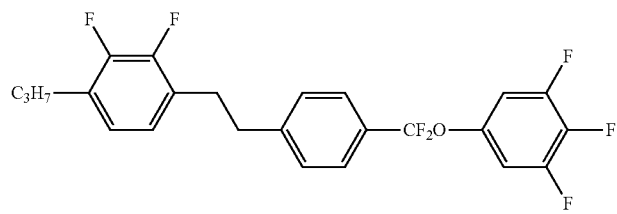 |
| 1-2-37 | 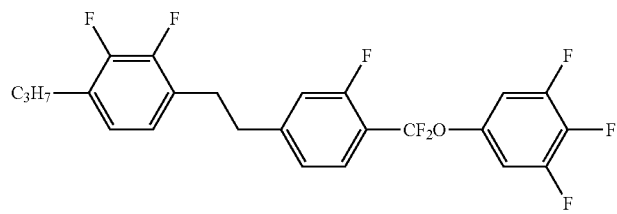 |
| 1-2-38 | 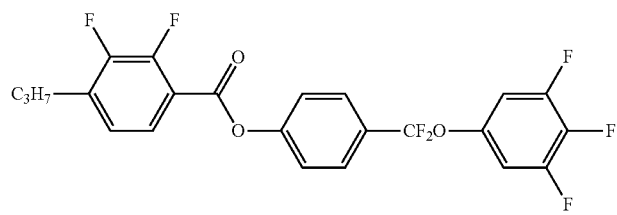 |
| 1-2-39 | 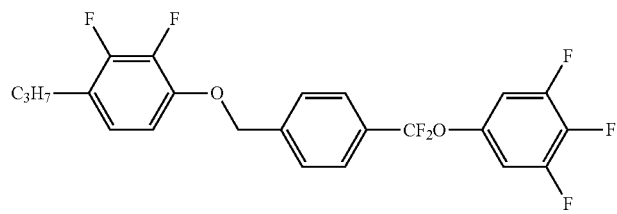 |
| 1-2-40 | 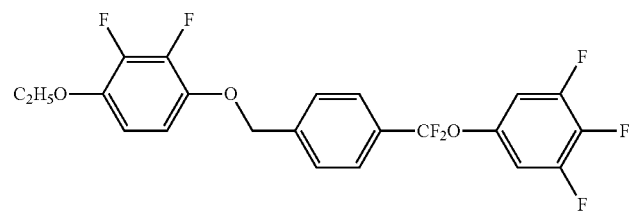 |

| No. | |
|---|---|
| 1-2-41 | 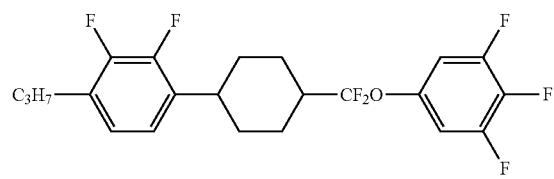 |
| 1-2-42 | 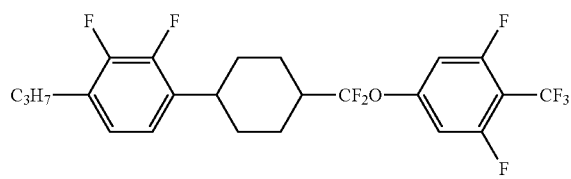 |
| 1-2-43 | 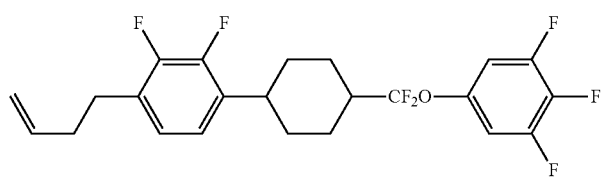 |
| 1-2-44 | 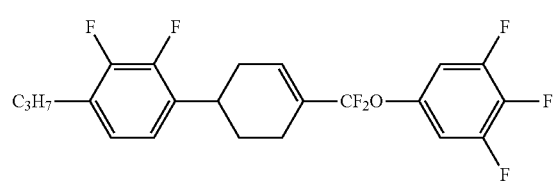 |
| 1-2-45 | 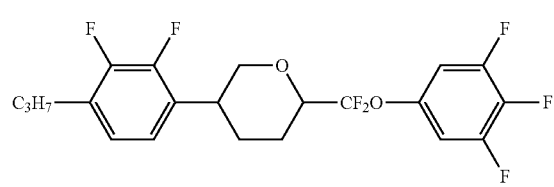 |
| 1-2-46 | 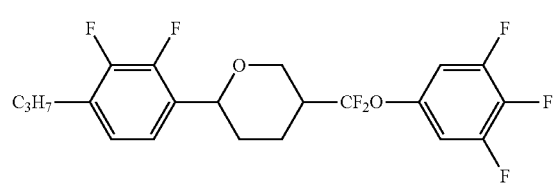 |
| 1-2-47 | 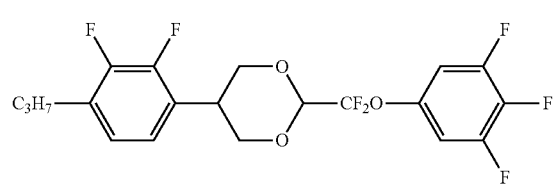 |
| 1-2-48 | 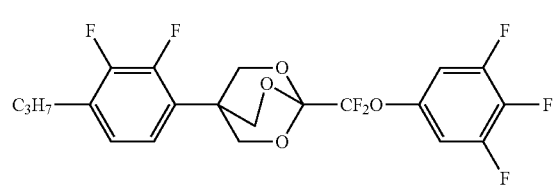 |

-continued
| No. | |
|---|---|
| 1-2-49 | 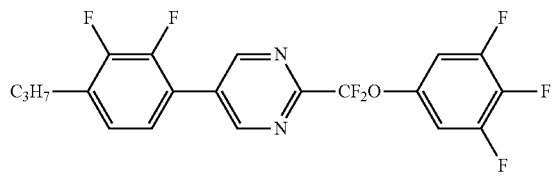 |
| 1-2-50 | 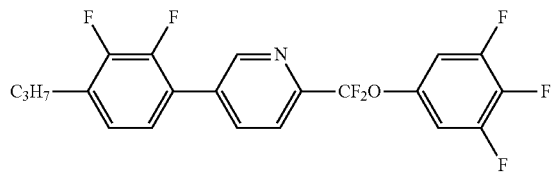 |
| 1-2-51 | 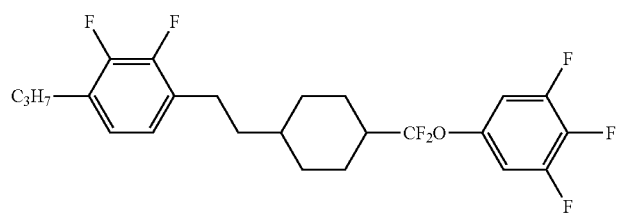 |
| 1-2-52 | 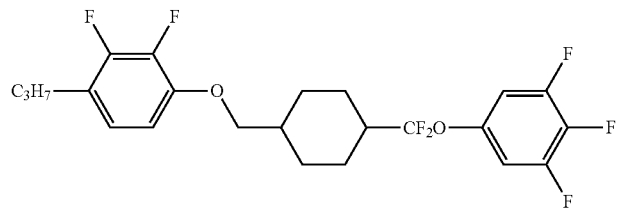 |
| 1-2-53 | 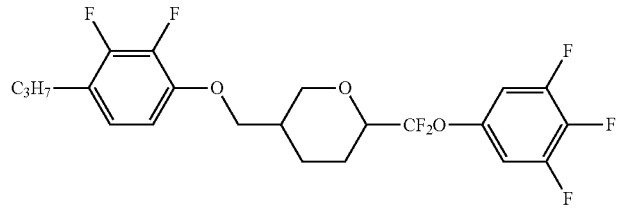 |
| 1-3-1 | 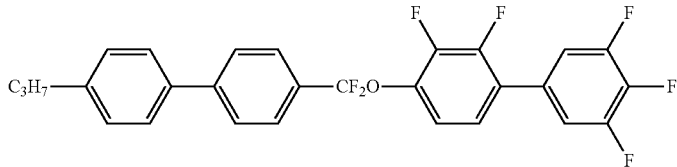 |
| 1-3-2 | 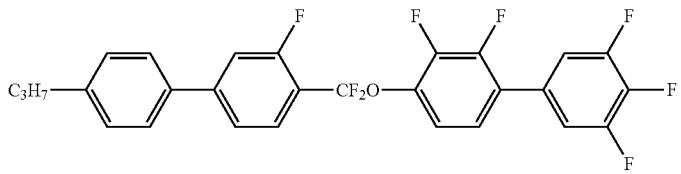 |
| 1-3-3 | 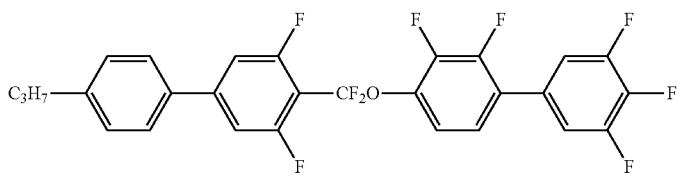 |

-continued
| No. |
|---|
| 1-3-4 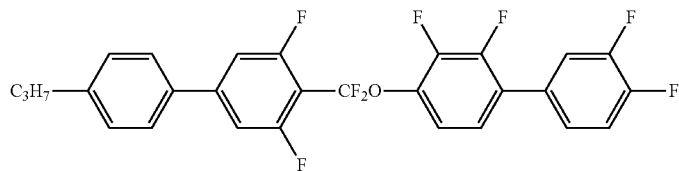 |
| 1-3-5 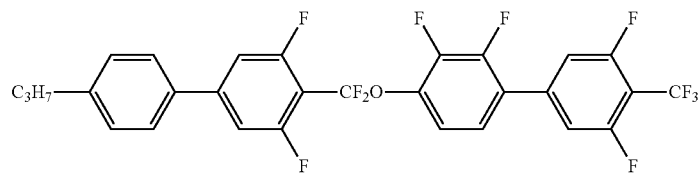 |
| 1-3-6 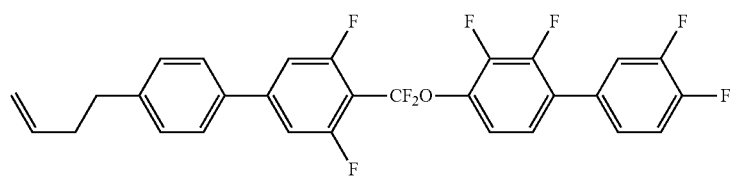 |
| 1-3-7 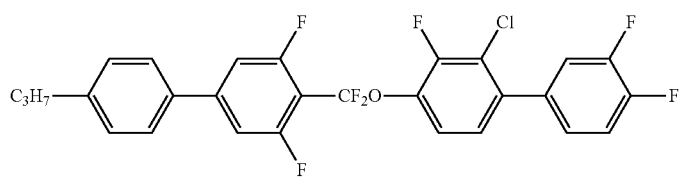 |
| 1-3-8 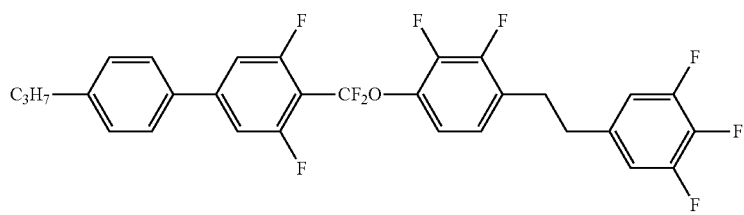 |
| 1-3-9 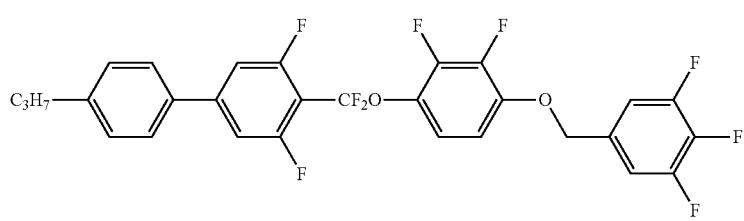 |
| 1-3-10 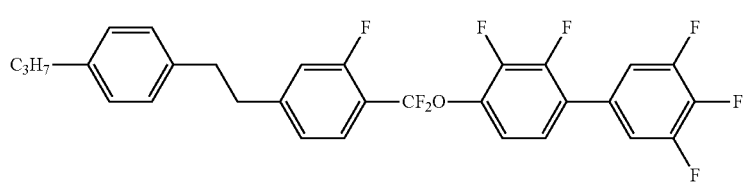 |
| 1-3-11 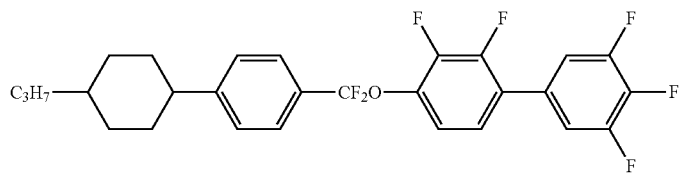 |

-continued
| No. |
|---|
| 1-3-12 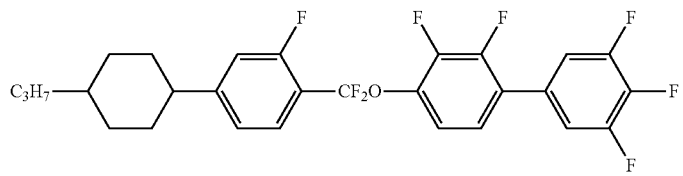 |
| 1-3-13 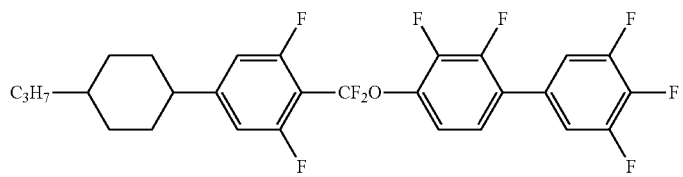 |
| 1-3-14 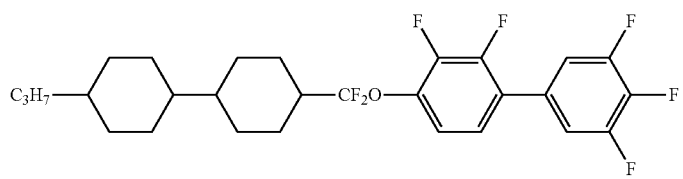 |
| 1-3-15 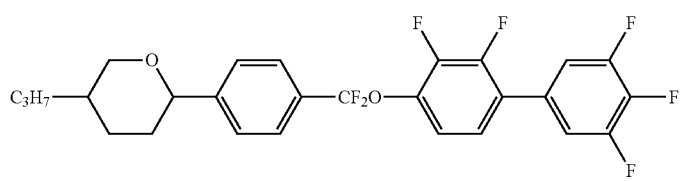 |
| 1-3-16 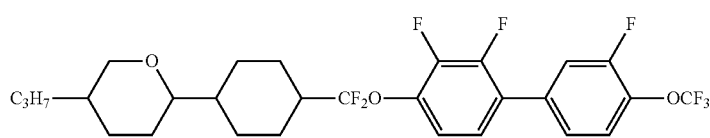 C 55.6 $S_A$ 130 N 222 I<br>$T_{NI}$ = 145° C., Δn = 0.130, Δε = 12.8, ε (⊥) = 5.8 |
| 1-3-17 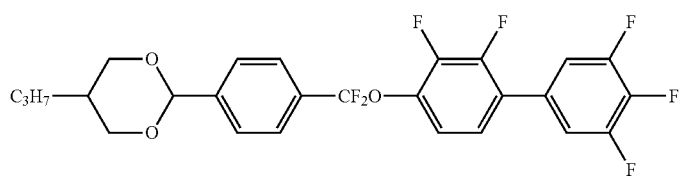 |
| 1-3-18 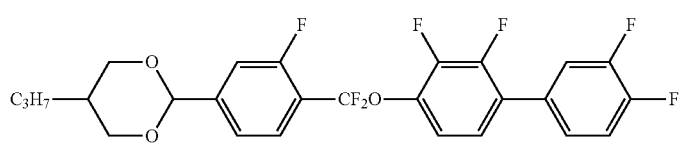 |
| 1-3-19 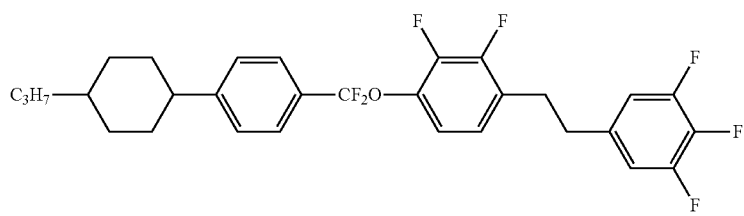 |

| No. | |
|---|---|
| 1-3-20 | 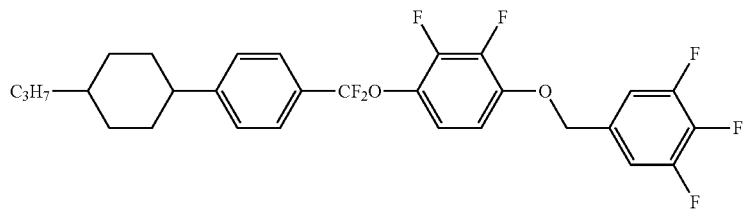 |
| 1-3-21 | 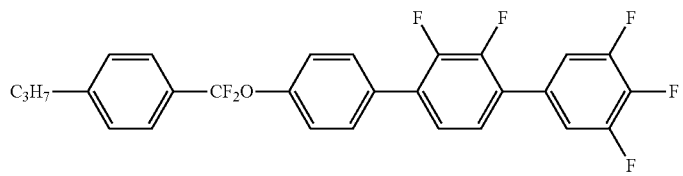 |
| 1-3-22 | 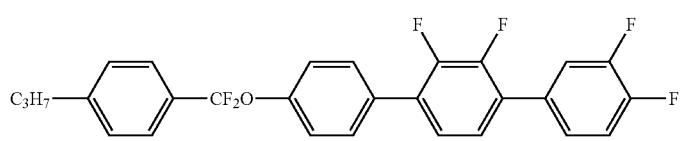 |
| 1-3-23 | 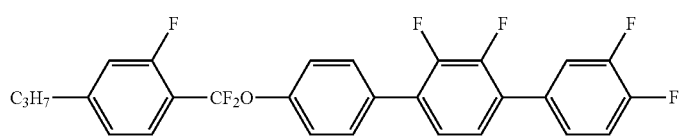 |
| 1-3-24 | 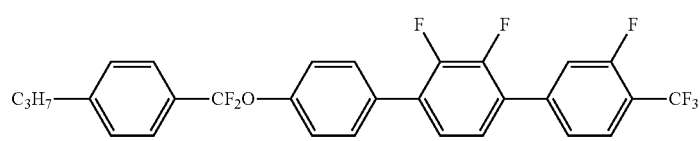 |
| 1-3-25 | 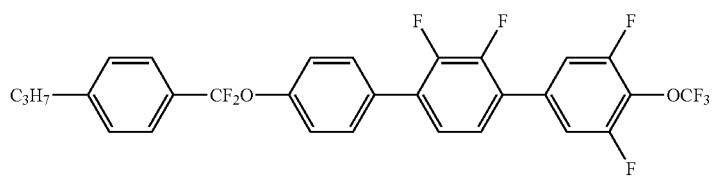 |
| 1-3-26 | 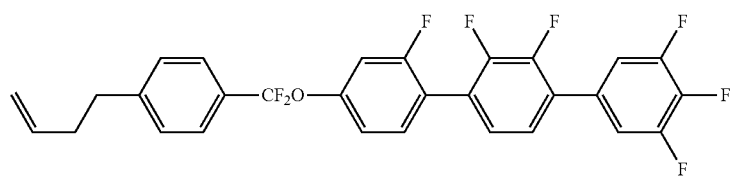 |
| 1-3-27 | 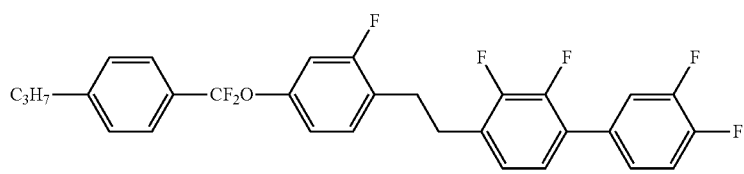 |
| 1-3-28 | 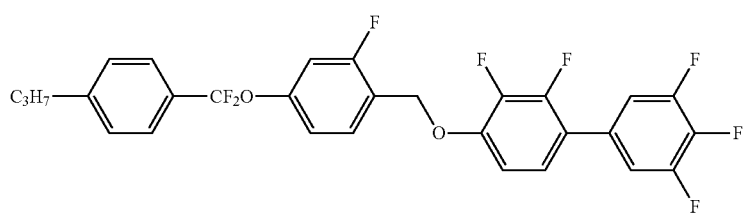 |

-continued
| No. | |
|---|---|
| 1-3-29 | 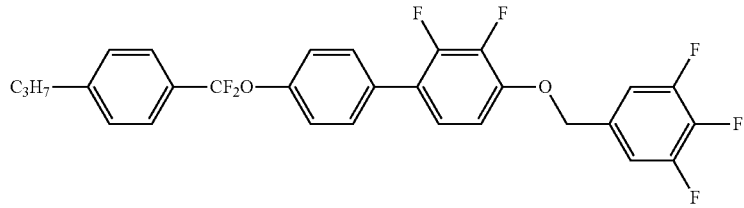 |
| 1-3-30 | 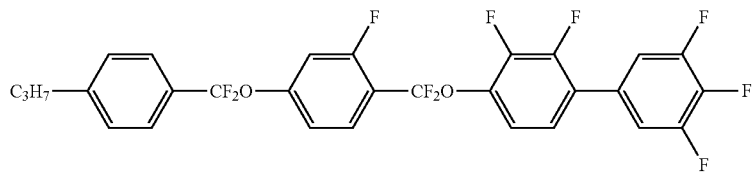 |
| 1-3-31 | 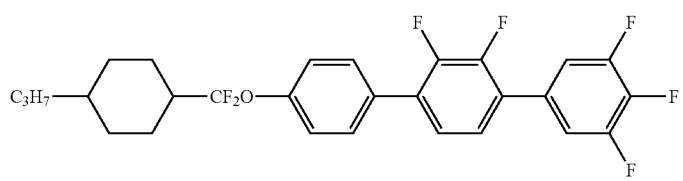 |
| 1-3-32 | 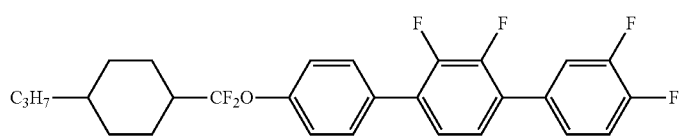 |
| 1-3-33 | 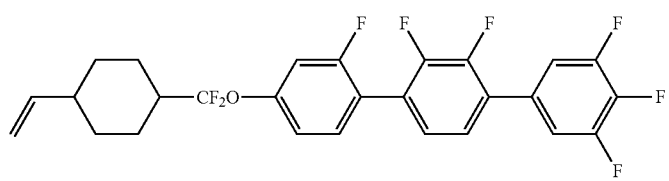 |
| 1-3-34 | 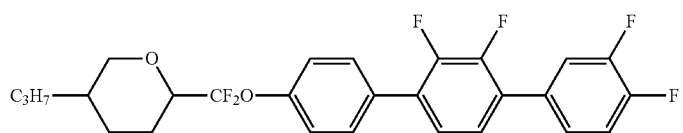 |
| 1-3-35 | 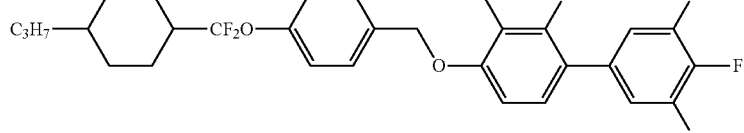 |
| 1-4-1 | 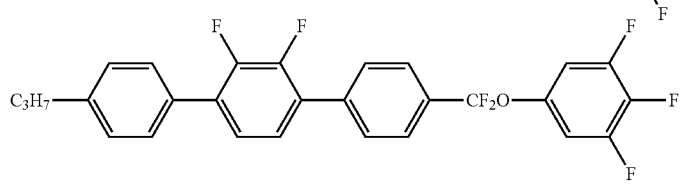 |
| | C 117 $S_A$ 136 N 169 I |
| | $T_{NI}$ = 116° C., Δn = 0.179, Δε = 21.9, ε (⊥) = 4.5 |
| 1-4-2 | 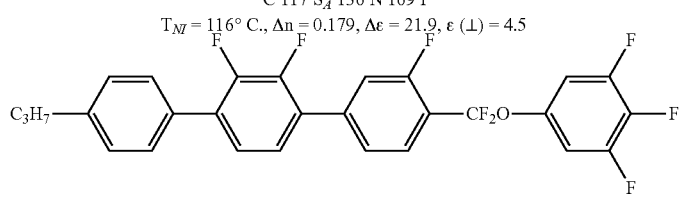 |

-continued
| No. | |
|---|---|
| 1-4-3 | 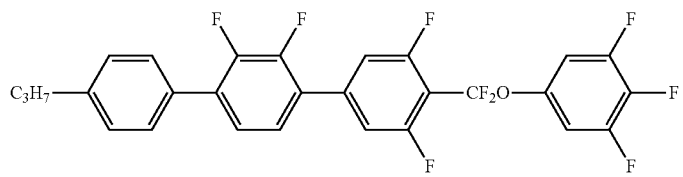 |
| 1-4-4 | 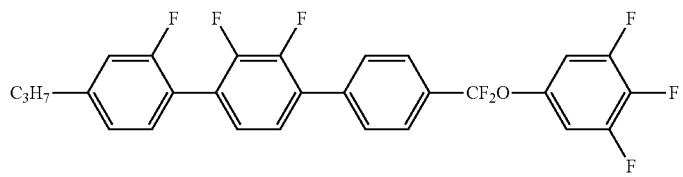 |
| 1-4-5 | 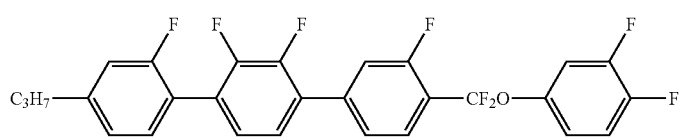 |
| 1-4-6 | 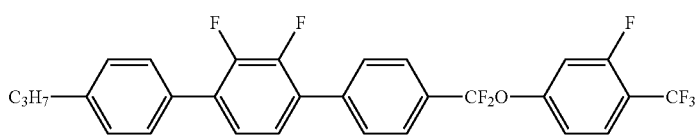 |
| 1-4-7 | 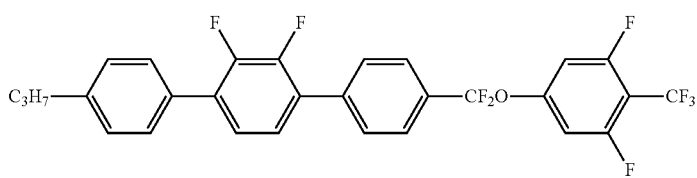 |
| 1-4-8 | 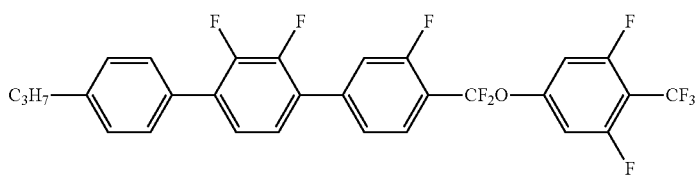 |
| 1-4-9 | 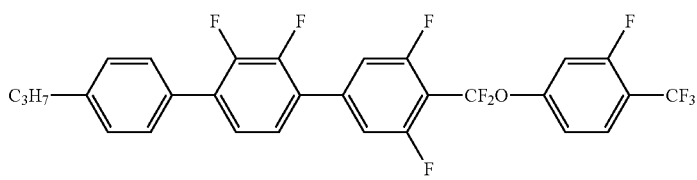 |
| 1-4-10 | 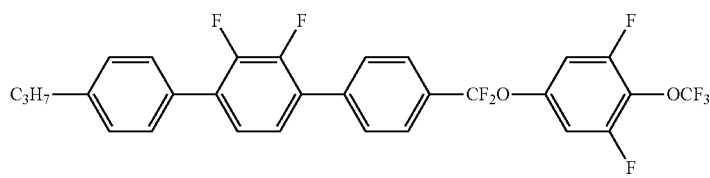 |
| 1-4-11 | 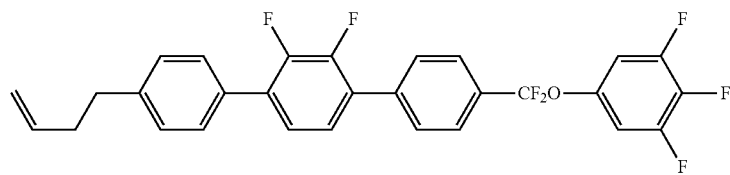 |

-continued
| No. |
|---|
1-4-12 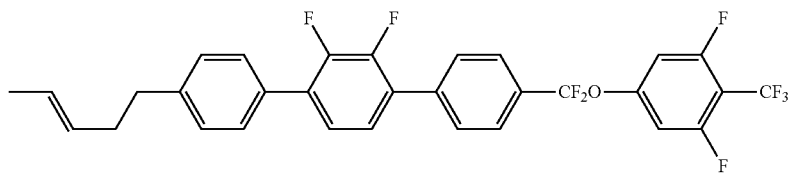
1-4-13 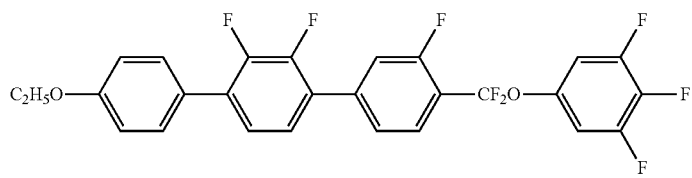
1-4-14 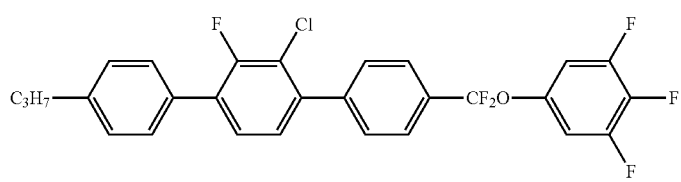
1-4-15 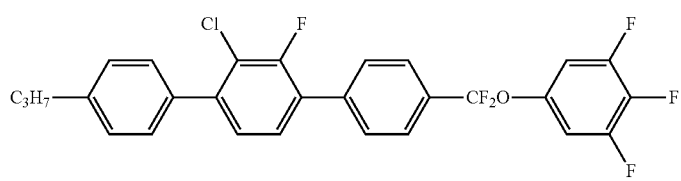
1-4-16 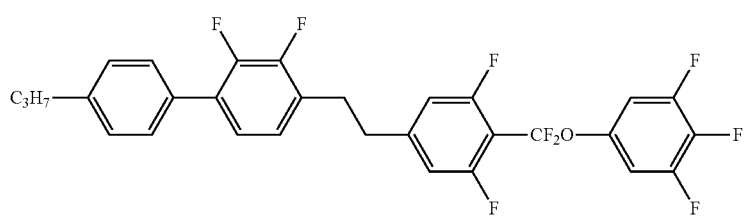
1-4-17 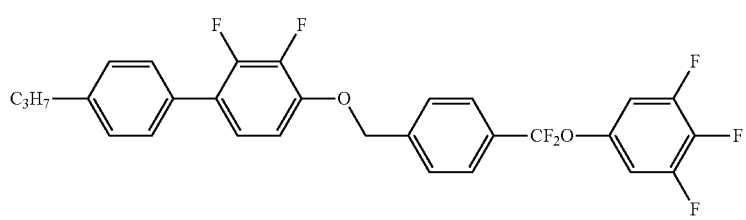
1-4-18 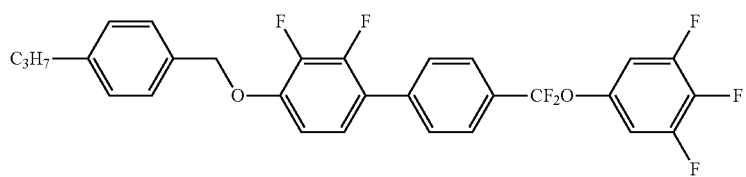
1-4-19 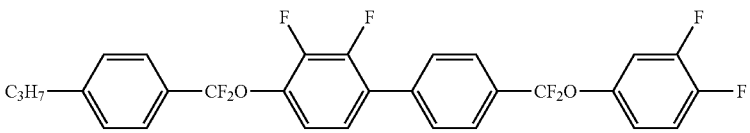

-continued
| No. | |
|---|---|
| 1-4-20 | 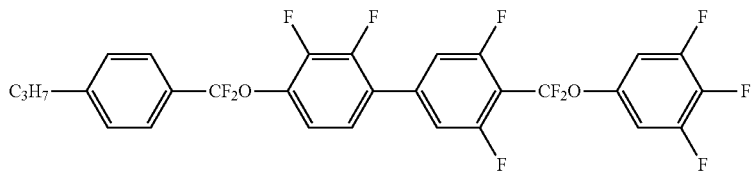 |
| 1-4-21 | 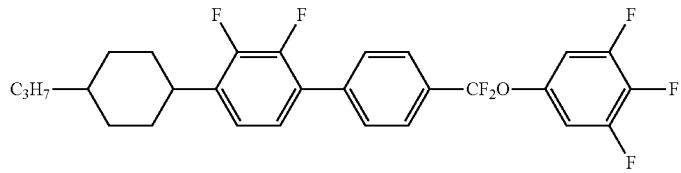<br>C 72.0 N 158 I<br>$T_{NI} = 113°$ C., $\Delta n = 0.150$, $\Delta\varepsilon = 16.8$, $\varepsilon (\perp) = 5.8$ |
| 1-4-22 | 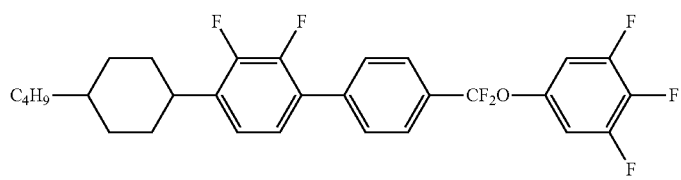 |
| 1-4-23 | 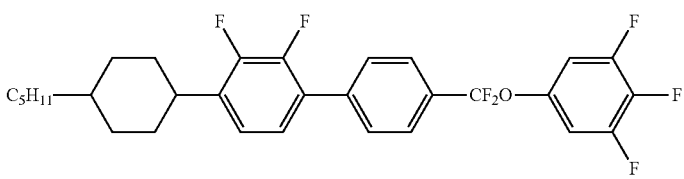 |
| 1-4-24 | 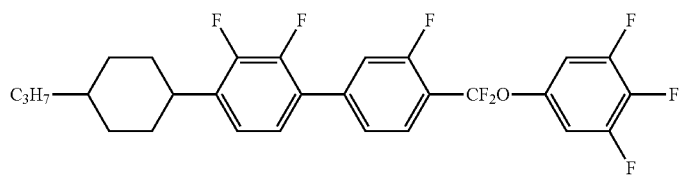 |
| 1-4-25 | 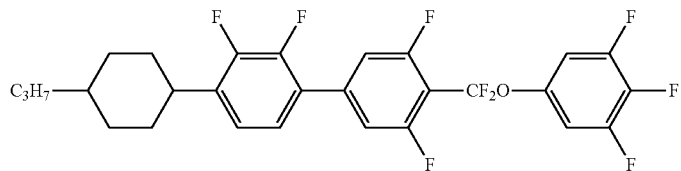 |
| 1-4-26 | 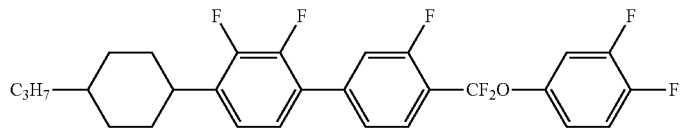 |
| 1-4-27 | 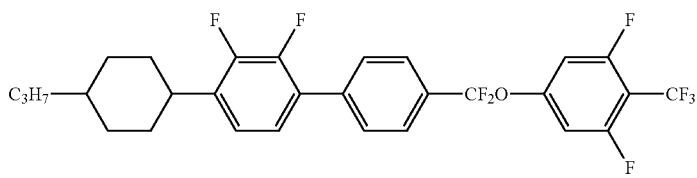 |

-continued
| No. | |
|---|---|
| 1-4-28 | 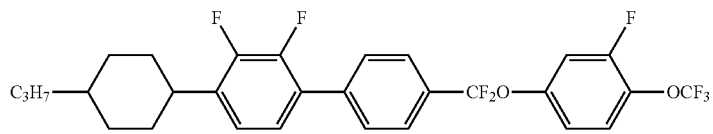 |
| 1-4-29 | 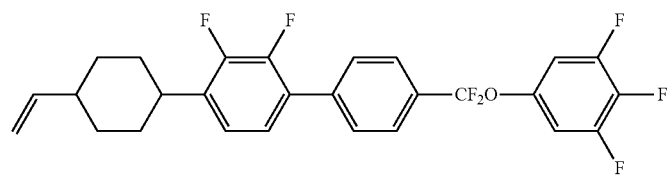 |
| 1-4-30 | 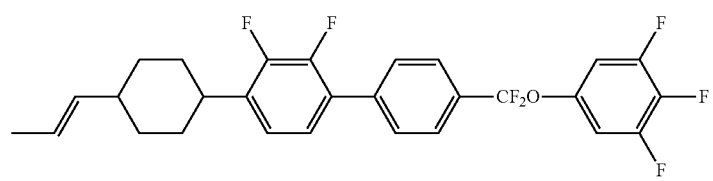 |
| 1-4-31 | 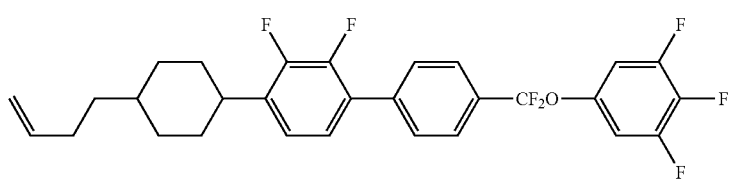 |
| 1-4-32 | 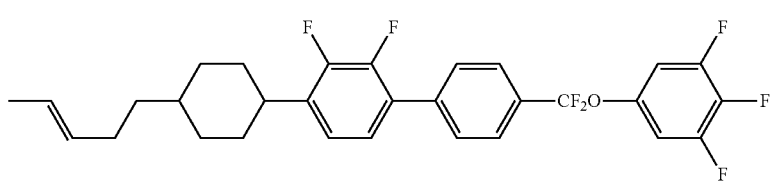 |
| 1-4-33 | 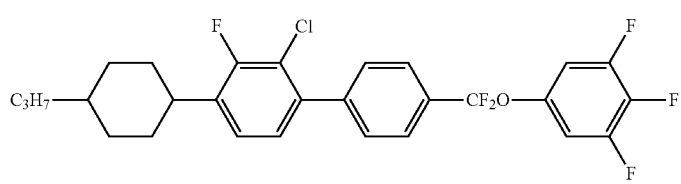 |
| 1-4-34 | 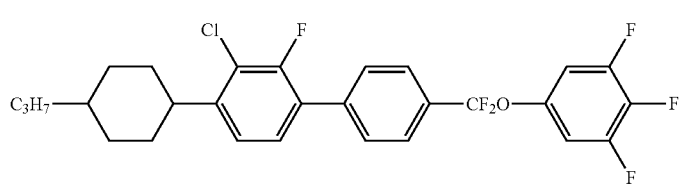 |
| 1-4-35 | 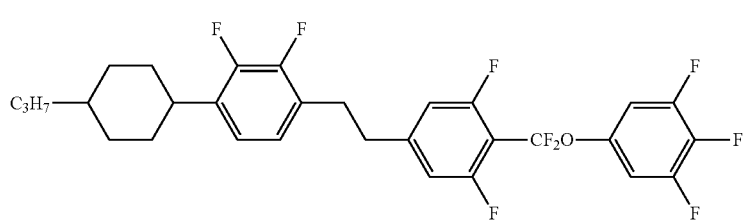 |

-continued
| No. | |
|---|---|
| 1-4-36 | 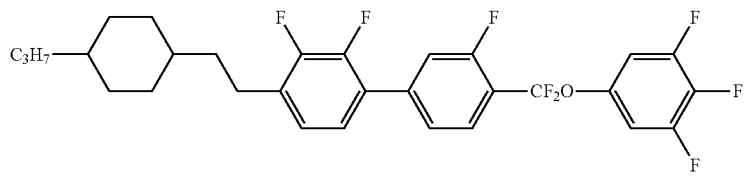 |
| 1-4-37 | 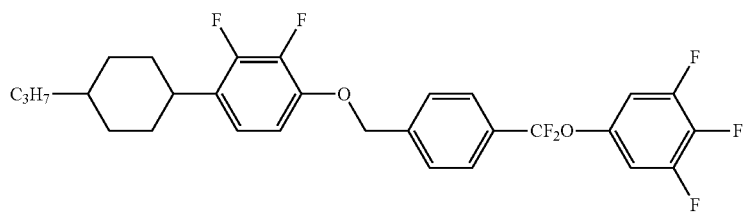 |
| 1-4-38 | 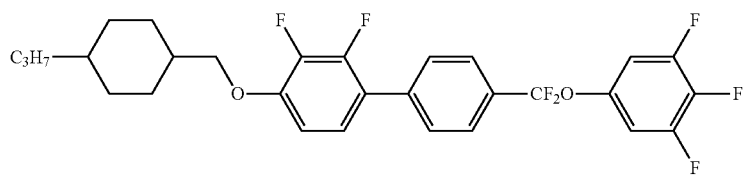<br>C 103 N 144 I<br>$T_{NI}$ = 111° C., $\Delta n$ = 0.157, $\Delta\varepsilon$ = 11.8, $\varepsilon$ ($\perp$) = 8.5 |
| 1-4-39 | 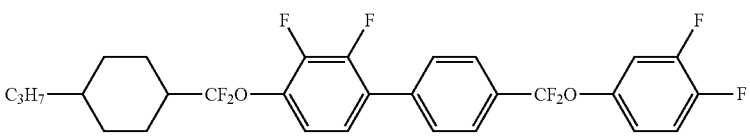 |
| 1-4-40 | 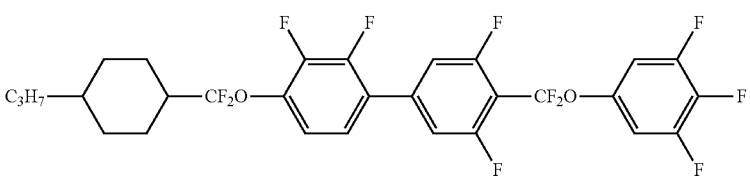 |
| 1-4-41 | 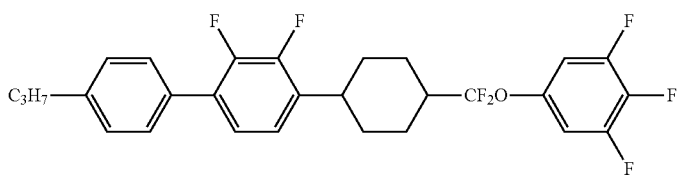 |
| 1-4-42 | 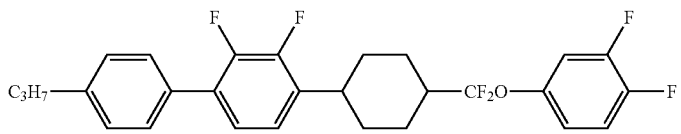 |
| 1-4-43 | 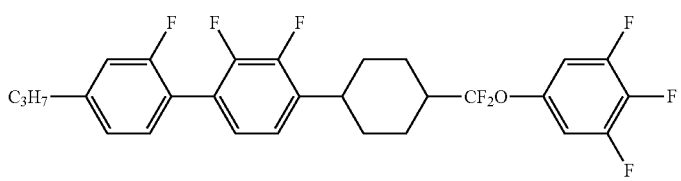 |

| No. | |
|---|---|
| 1-4-44 | 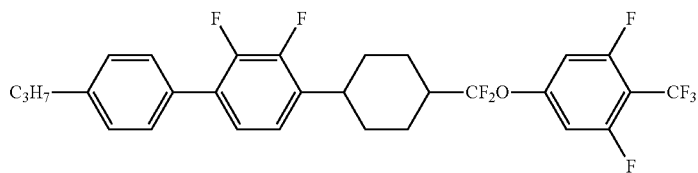 |
| 1-4-45 | 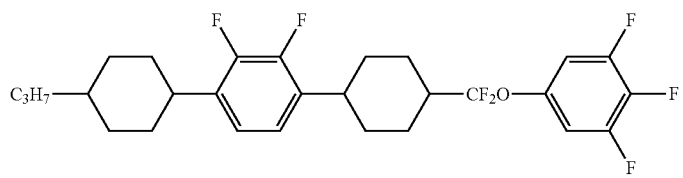 |
| 1-4-46 | 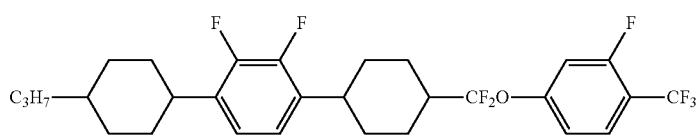 |
| 1-4-47 | 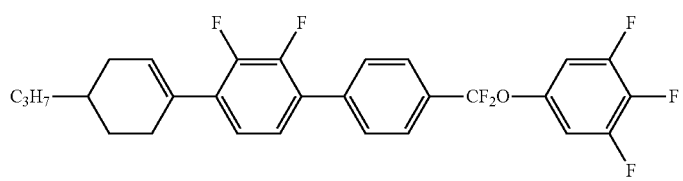 |
| 1-4-48 | 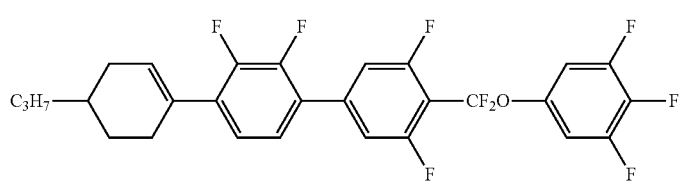 |
| 1-4-49 | 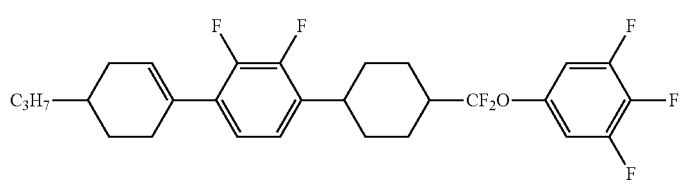 |
| 1-4-50 | 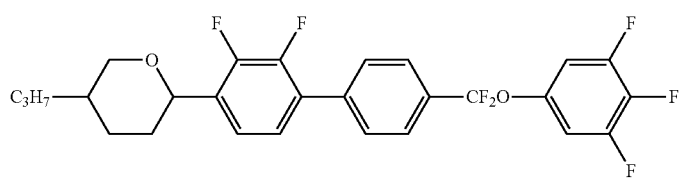 |
| 1-4-51 | 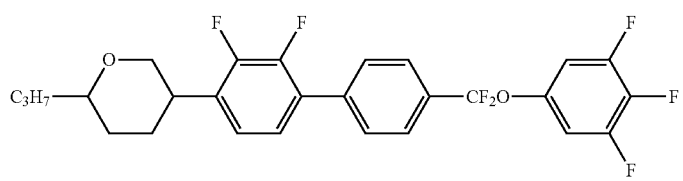 |
| 1-4-52 | 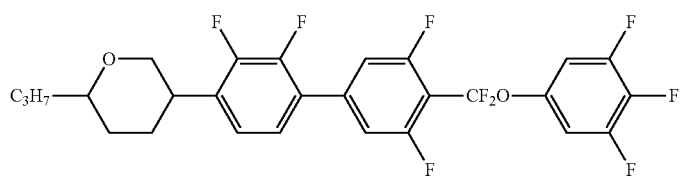 |

| No. | |
|---|---|
| 1-4-53 | 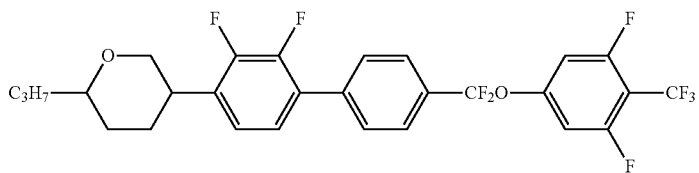 |
| 1-4-54 | 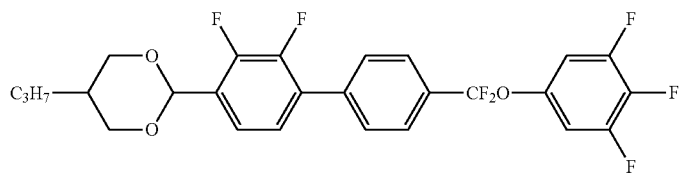<br>C 117 N 138 I<br>$T_{NI}$ = 114° C., Δn = 0.157, Δε = 29.9, ε (⊥) = 4.5 |
| 1-4-55 | 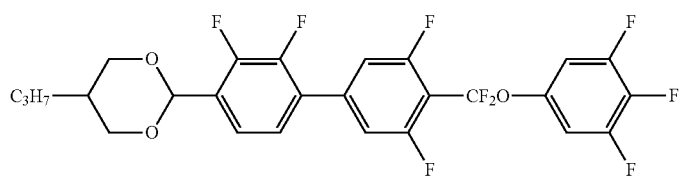 |
| 1-4-56 | 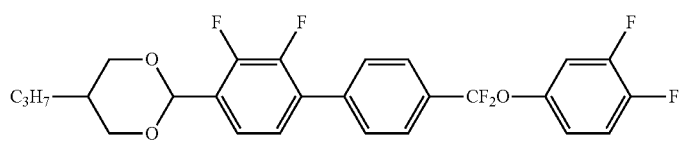 |
| 1-4-57 | 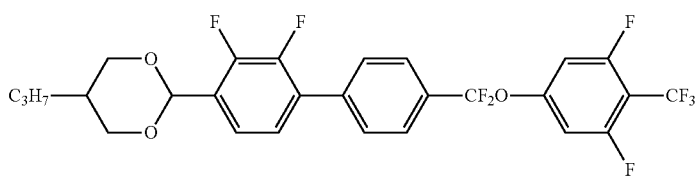 |
| 1-4-58 | 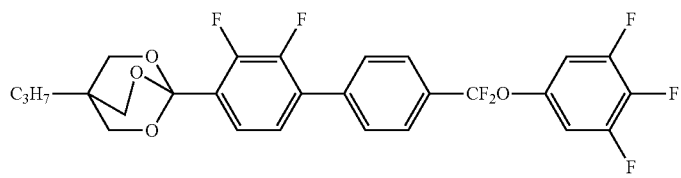 |
| 1-4-59 | 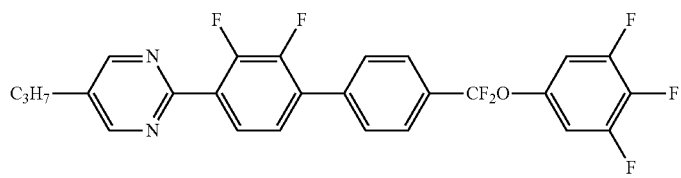 |
| 1-4-60 | 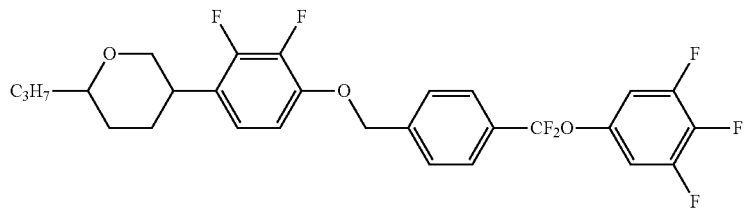 |

-continued
| No. |
|---|
| 1-4-61 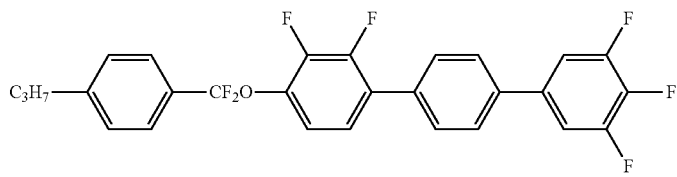 |
| 1-4-62 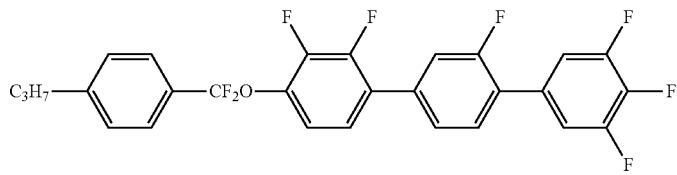 |
| 1-4-63 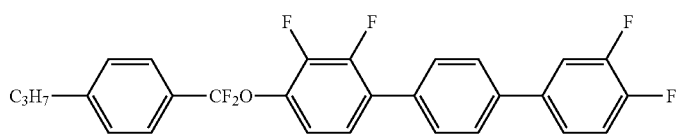 |
| 1-4-64 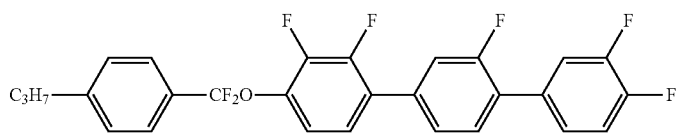 |
| 1-4-65 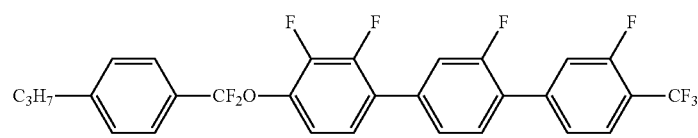 |
| 1-4-66 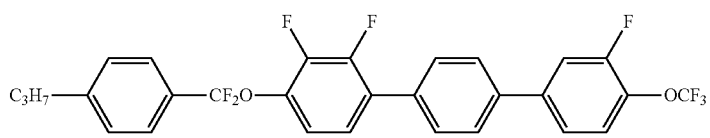 |
| 1-4-67 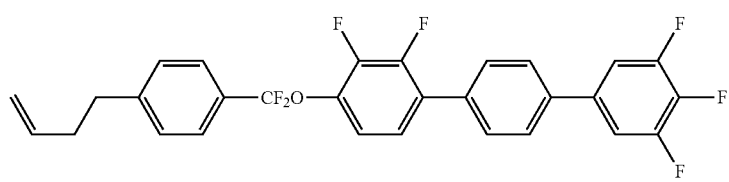 |
| 1-4-68 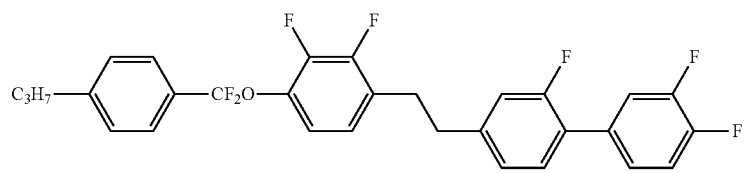 |
| 1-4-69 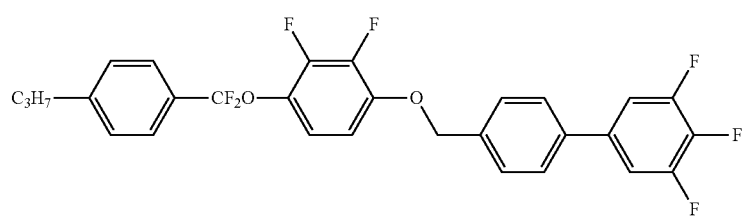 |

| No. |
|---|
| 1-4-70 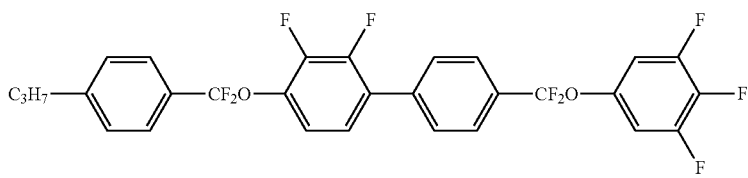 |
| 1-4-71 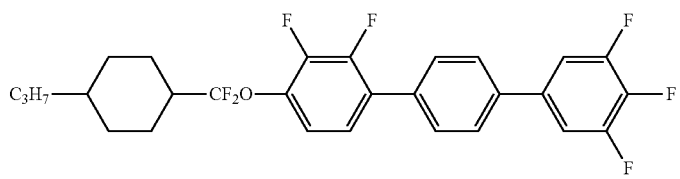 |
| 1-4-72 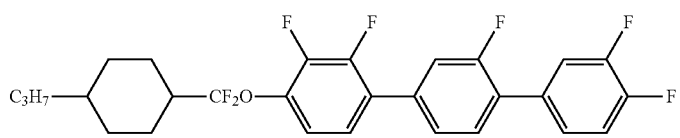 |
| 1-4-73 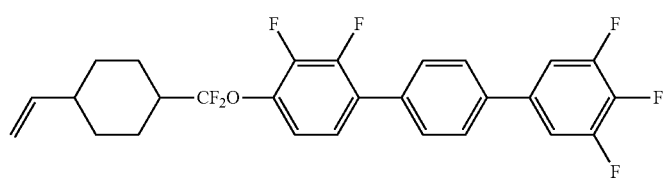 |
| 1-4-74 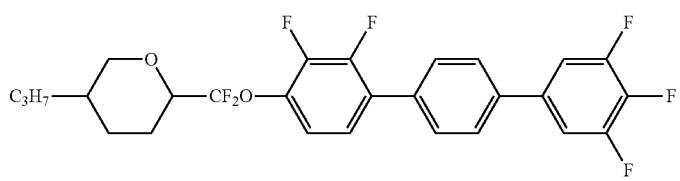 |
| 1-4-75 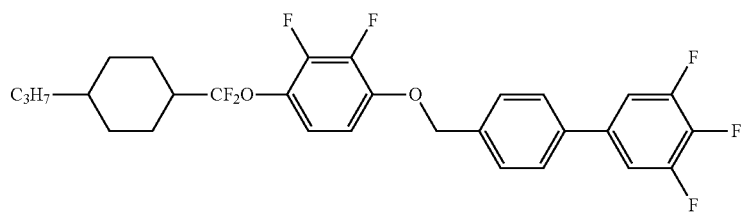 |
| 1-5-1 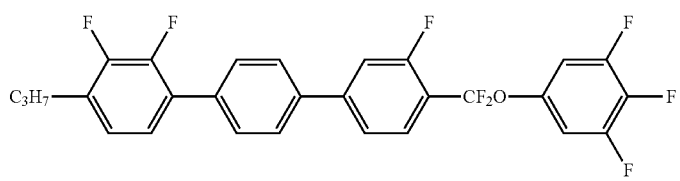 |
| 1-5-2 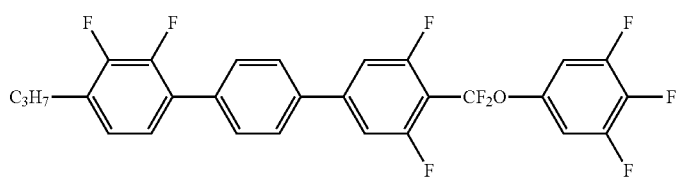 |

| No. | |
|---|---|
| 1-5-3 | 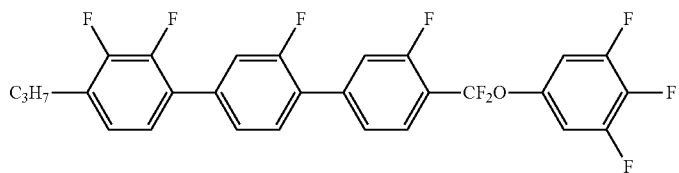 |
| 1-5-4 | 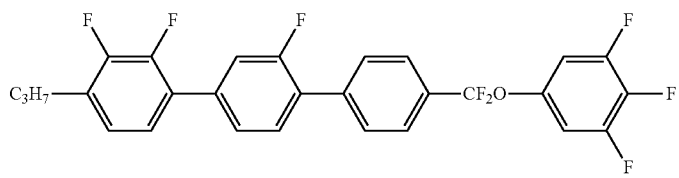 |
| 1-5-5 | 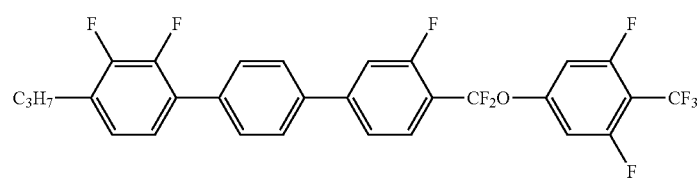 |
| 1-5-6 | 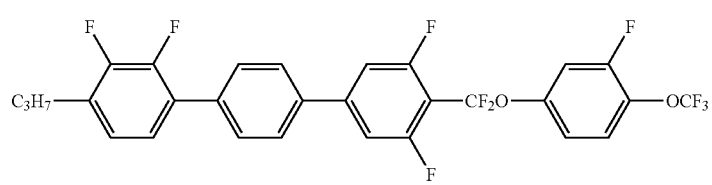 |
| 1-5-7 | 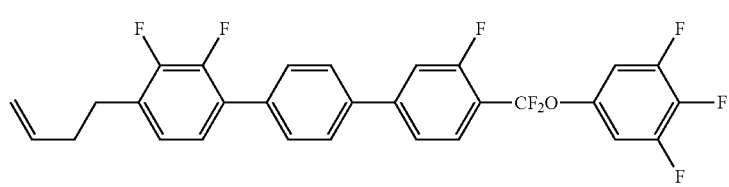 |
| 1-5-8 | 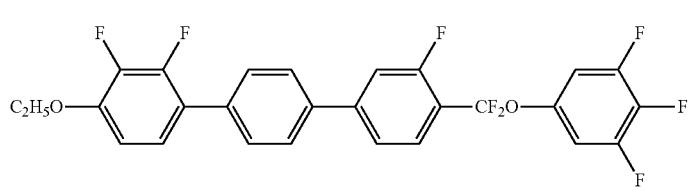 |
| 1-5-9 | 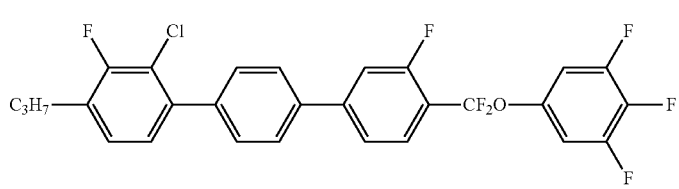 |
| 1-5-10 | 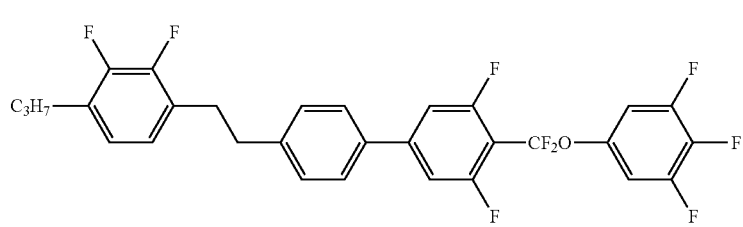 |

-continued
| No. | |
|---|---|
| 1-5-11 | 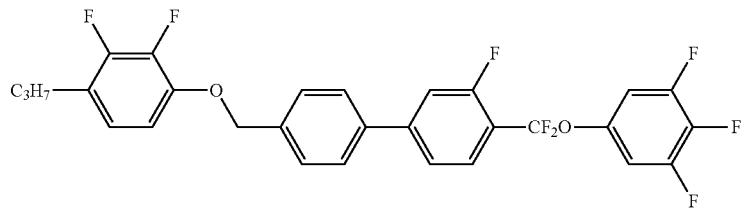 |
| 1-5-12 | 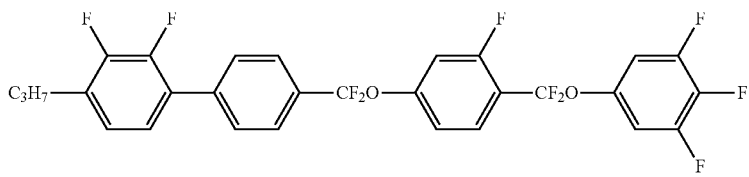 |
| 1-5-13 | 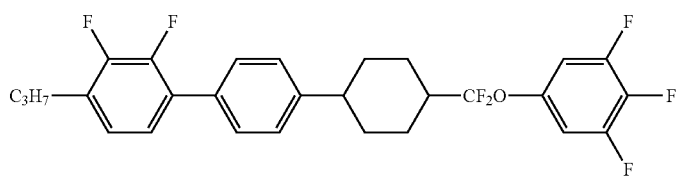 |
| 1-5-14 | 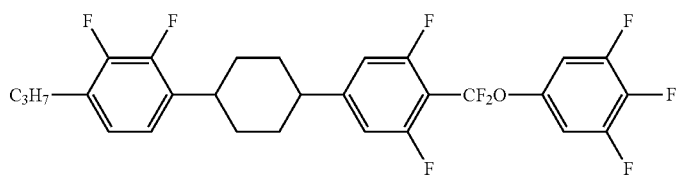 |
| 1-5-15 | 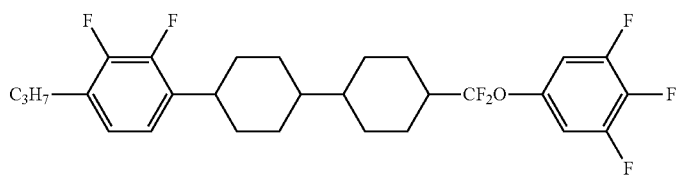 |
| 1-5-16 | 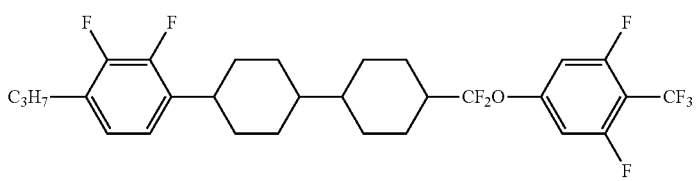 |
| 1-5-17 | 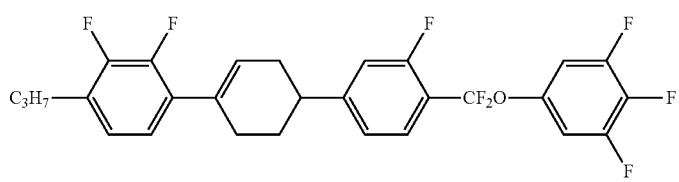 |
| 1-5-18 | 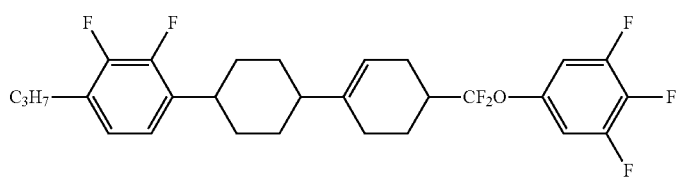 |

-continued
| No. | |
|---|---|
| 1-5-19 | 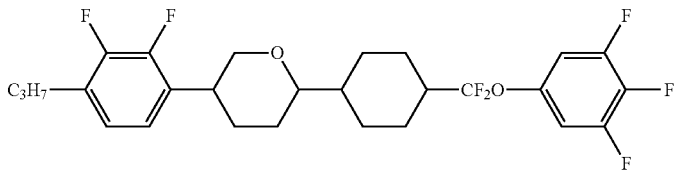 |
| 1-5-20 | 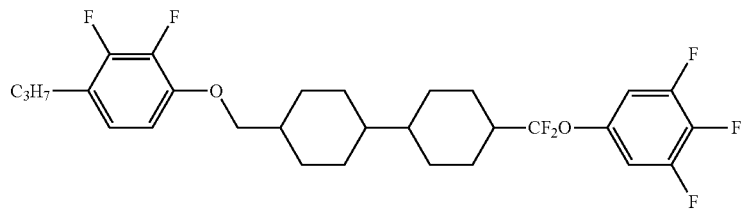 |
| 1-5-21 | 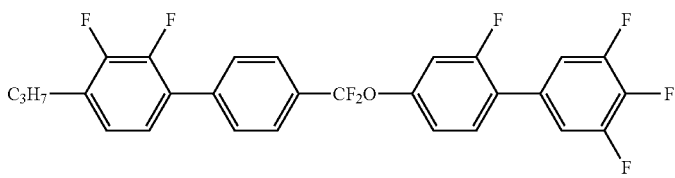<br>C 74.4 N 122 I<br>$T_{NI}$ = 85.0° C., Δn = 0.184, Δε = 23.9, ε (⊥) = 7.8 |
| 1-5-22 | 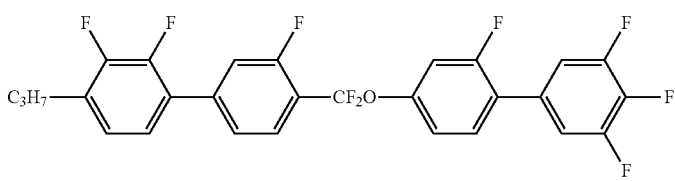 |
| 1-5-23 | 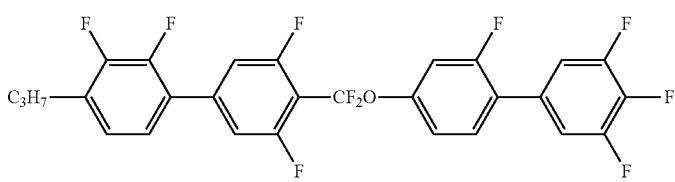 |
| 1-5-24 | 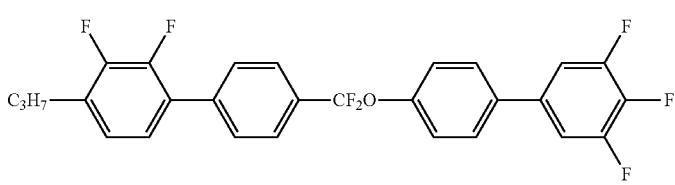 |
| 1-5-25 | 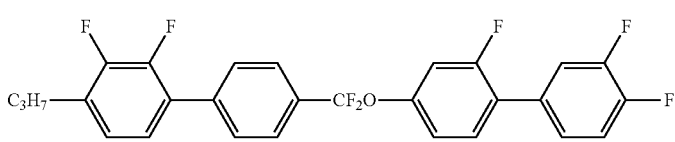 |
| 1-5-26 | 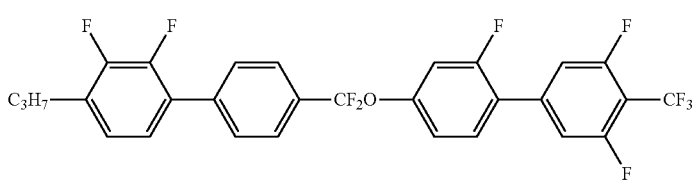 |

| No. | |
|---|---|
| 1-5-27 | 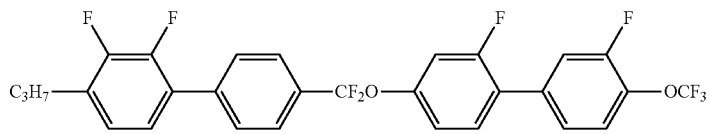 |
| 1-5-28 | 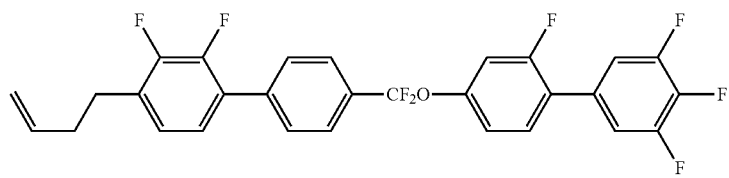 |
| 1-5-29 | 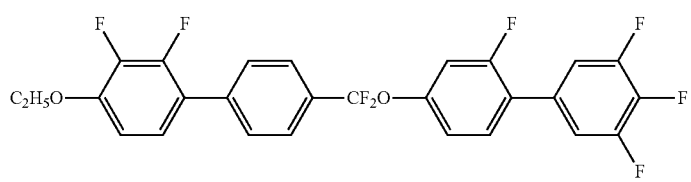 |
| 1-5-30 | 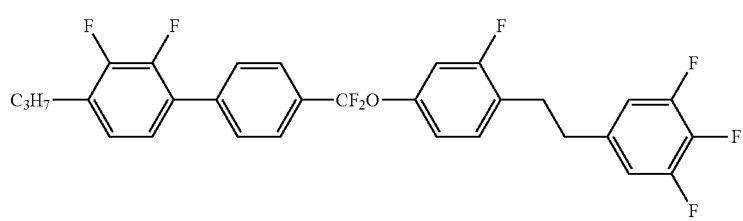 |
| 1-5-31 | 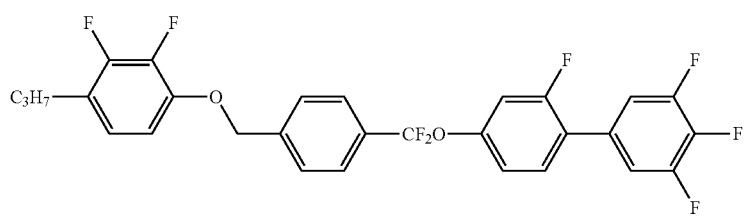 |
| 1-5-32 | 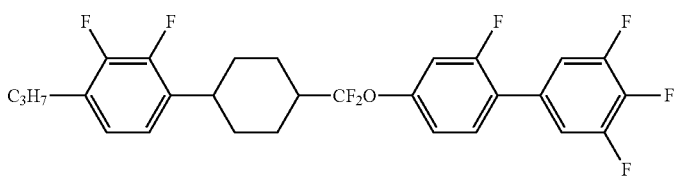 |
| 1-5-33 | 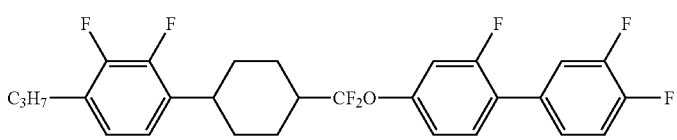 |
| 1-6-1 | 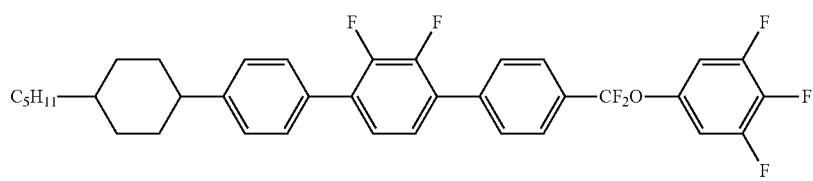 |

-continued

| No. | |
|---|---|
| 1-6-2 | 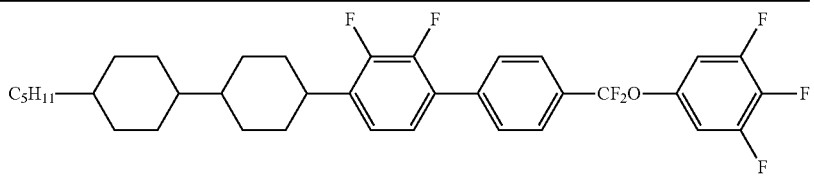 |
| 1-6-3 | 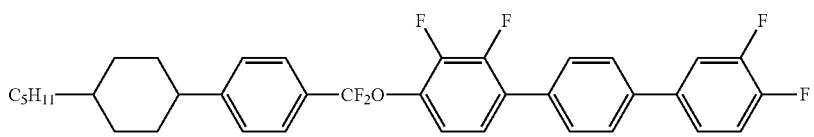 |
| 1-6-4 | 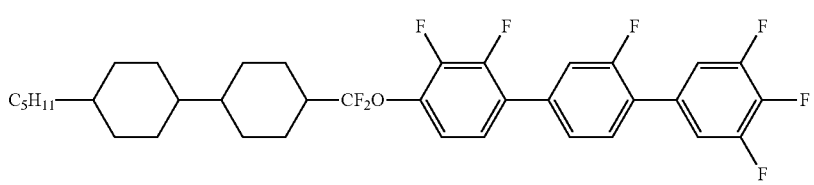 |
| 1-7-1 | 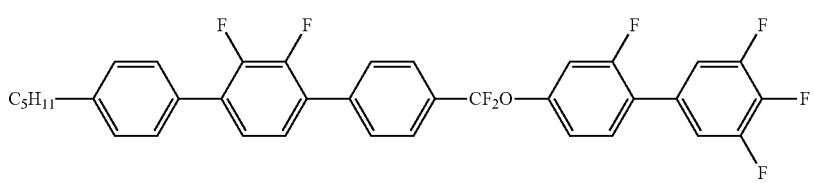 |
| 1-7-2 | 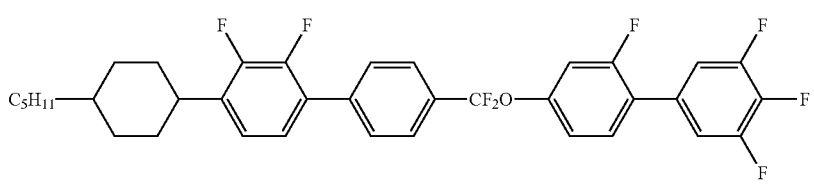 |
| | C 94.5 N 256 I<br>$T_{NI} = 174°$ C., $\Delta n = 0.190$, $\Delta\varepsilon = 17.9$, $\varepsilon\,(\bot) = 5.2$ |
| 1-7-3 | 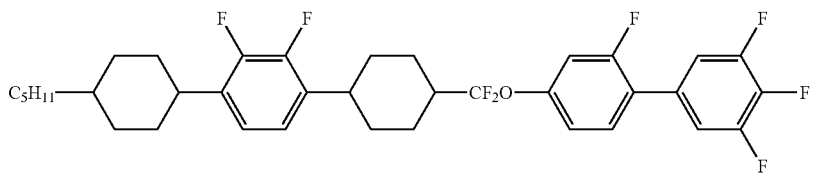 |

Comparative Example 1

As a comparative compound, compound (S-1) was prepared. The reason is that the compound is described in JP 2002-327175 A, and similar to the compound of the invention.

(S-1)

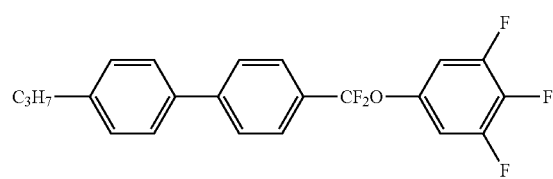

Chemical shifts δ (ppm; CDCl$_3$): 7.75 (d, J=8.4 Hz, 2H), 7.68 (d, J=8.4 Hz, 2H), 7.53 (d, J=8.1 Hz, 2H), 7.29 (d, J=8.1 Hz, 2H), 7.02-6.94 (m, 2H), 2.65 (t, J=7.9 Hz, 2H), 1.75-1.65 (m, 2H), 0.98 (t, J=7.5 Hz, 3H).

Physical properties of comparative compound (S-1) were as described below.

Transition temperature: C 80.3 I.

Maximum temperature ($T_{NI}$)=35.0° C.; optical anisotropy (Δn)=0.144; dielectric anisotropy (Δε)=19.6; dielectric constant in minor axis direction (ε⊥)=5.2; and viscosity (η)=19.6 mPa·s.

TABLE 1

Physical properties of compound (No. 1-2-2) and comparative compound (S-1)

| | Compound (No. 1-2-2) | Comparative compound (S-1) |
|---|---|---|
| Structure | $C_3H_7$–[2,3-diF-phenyl]–[phenyl]–$CF_2O$–[2,3,5-triF-phenyl]–F | $C_3H_7$–[phenyl]–[phenyl]–$CF_2O$–[2,3,5-triF-phenyl]–F |
| Transition temperature ($T_{NI}$) | C 31.1 I | C 80.3 I |
| Maximum temperature ($T_{NI}$) | −0.3° C. | 35.0° C. |
| Optical anisotropy (Δn) | 0.117 | 0.144 |
| Dielectric anisotropy (Δε) | 19.4 | 19.6 |
| Dielectric constant in a minor axis direction (ε⊥) | 9.2 | 5.2 |
| Viscosity (η) | 38.9 mPa·s | 19.6 mPa·s |

Physical properties of compound (No. 1-2-2) obtained in Example 1 and comparative compound (S-1) are summarized in Table 1. Table 1 shows that compound (No. 1-2-2) is superior in that the dielectric constant in the minor axis direction is larger, although the dielectric anisotropy is almost equivalent, in comparison with comparative compound (S-1).

Moreover, all of tricyclic compounds (No. 1-2-19), (No. 1-2-10) and (No. 1-2-15) shown in Example 2, Example 3 and Example 9 have a larger dielectric constant in the minor axis direction in comparison with comparative compound (S-1). Therefore, the compound of the invention is found to be a superior compound that can improve a transmittance of the liquid crystal composition used for the FFS mode liquid crystal display device.

Comparative Example 2

As a comparative compound, compound (S-2) was prepared. The reason is that the compound is described in JP H10-251186 A (1998), and similar to the compound of the invention.

(S-2)

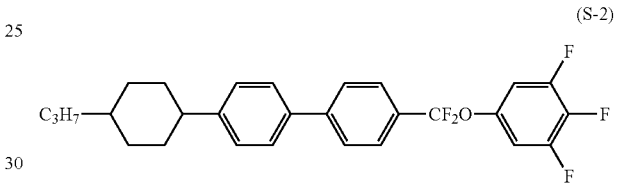

Chemical shifts δ (ppm; $CDCl_3$): 7.73 (d, J=8.3 Hz, 2H), 7.68 (d, J=8.4 Hz, 2H), 7.54 (d, J=8.2 Hz, 2H), 7.32 (d, J=8.2 Hz, 2H), 7.02-6.93 (m, 2H), 2.52 (tt, J=12.0 Hz, J=3.2 Hz, 1H), 1.97-1.84 (m, 4H), 1.55-1.43 (m, 2H), 1.41-1.27 (m, 3H), 1.27-1.20 (m, 2H), 1.14-1.02 (m, 2H), 0.91 (t, J=7.3 Hz, 3H).

Physical properties of comparative compound (S-2) were as described below.

Transition temperature: C 67.1 $S_A$ 93.8 N 188 I.

Maximum temperature ($T_{NI}$)=156° C.; optical anisotropy (Δn)=0.170; dielectric anisotropy (Δε)=19.2; dielectric constant in minor axis direction (ε⊥)=3.8; and viscosity (η)=55.2 mPa·s.

TABLE 2

Physical properties of compound (No. 1-4-21) and comparative compound (S-2)

| | Compound (No. 1-4-21) | Comparative compound (S-2) |
|---|---|---|
| Structure | $C_3H_7$–[cyclohexyl]–[2,3-diF-phenyl]–[phenyl]–$CF_2O$–[2,3,5-triF-phenyl]–F | $C_3H_7$–[cyclohexyl]–[phenyl]–[phenyl]–$CF_2O$–[2,3,5-triF-phenyl]–F |
| Transition temperature ($T_{NI}$) | C 72.0 N 158 I | C 67.1 $S_A$ 93.8 N 188 I |
| Maximum temperature ($T_{NI}$) | 113° C. | 156° C. |
| Optical anisotropy (Δn) | 0.150 | 0.170 |
| Dielectric anisotropy (Δε) | 16.8 | 19.2 |

TABLE 2-continued

Physical properties of compound (No. 1-4-21) and comparative compound (S-2)

| Compound (No. 1-4-21) | Comparative compound (S-2) |
|---|---|
| 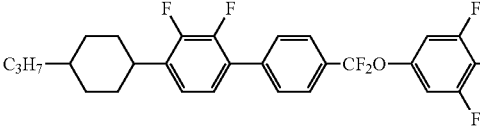 | 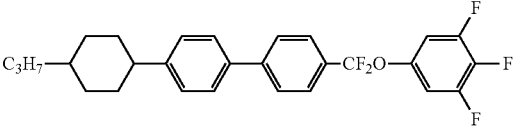 |
| Dielectric constant in a minor axis direction ($\epsilon\perp$): 5.8 | 3.8 |
| Viscosity ($\eta$): 63.8 mPa·s | 55.2 mPa·s |

Physical properties of compound (No. 1-4-21) obtained in Example 6 and comparative compound (S-2) are summarized in Table 2. Table 2 shows that compound (No. 1-4-21) is superior in that the dielectric constant in the minor axis direction is larger, although the dielectric anisotropy is almost equivalent, in comparison with comparative compound (S-2).

Moreover, all of tetracyclic compounds (No. 1-3-16), (No. 1-4-1), (No. 1-4-38), (No. 1-4-54) and (No. 1-5-21) shown in Example 4, Example 5, Example 7, Example 8 and Example 10 have a larger dielectric constant in the minor axis direction in comparison with comparative compound (S-2). Therefore, the compound of the invention is found to be a superior compound that can improve a transmittance of the liquid crystal composition used for the FFS mode liquid crystal display device.

Comparative Example 3

As a comparative compound, compound (S-3) was prepared. The reason is that the compound is described in JP 2002-80452 A, and similar to the compound of the invention.

(S-3)

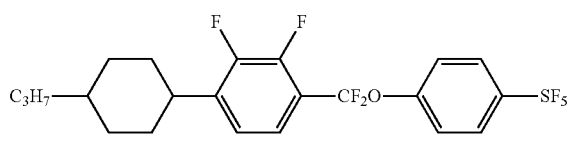

Chemical shifts δ (ppm; CDCl$_3$): 7.81-7.75 (m, 2H), 7.42-7.33 (m, 3H), 7.11-7.04 (m, 1H), 2.89 (tt, J=12.4 Hz, J=2.9 Hz, 1H), 1.93-1.84 (m, 4H), 1.55-1.43 (m, 2H), 1.41-1.27 (m, 3H), 1.27-1.19 (m, 2H), 1.16-1.03 (m, 2H), 0.91 (t, J=7.4 Hz, 3H).

Physical properties of comparative compound (S-3) were as described below.

Transition temperature: C 53.8 I.

Maximum temperature (T$_{NI}$)=3.7° C.; optical anisotropy (Δn)=0.0703; dielectric anisotropy (Δε)=16.4; dielectric constant in minor axis direction (ε⊥)=7.2; and viscosity (η))=71.8 mPa·s.

TABLE 3

Physical properties of compound (No. 1-2-2) and comparative compound (S-3)

| Compound (No. 1-2-2) | Comparative compound (S-3) |
|---|---|
| 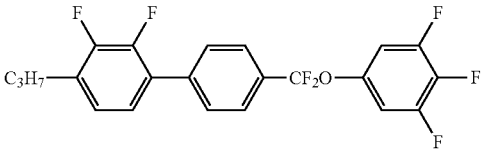 | 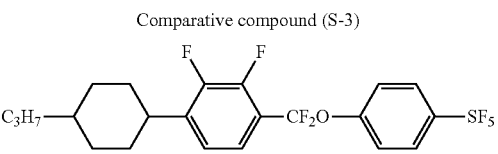 |
| Transition temperature (T$_{NI}$): C 31.1 I | C 53.8 I |
| Maximum temperature (T$_{NI}$): −0.3° C. | 3.7° C. |
| Optical anisotropy (Δn): 0.117 | 0.0703 |
| Dielectric anisotropy (Δε): 19.4 | 16.4 |
| Dielectric constant in a minor axis direction (ε⊥): 9.2 | 7.2 |
| Viscosity (η): 38.9 mPa·s | 71.8 mPa·s |

Physical properties of compound (No. 1-2-2) obtained in Example 1 and comparative compound (S-3) are summarized in Table 3. Table 3 shows that compound (No. 1-2-2) is superior in that the dielectric anisotropy is larger, the dielectric constant in the minor axis direction is larger, and the viscosity is smaller, although the maximum temperature is almost equivalent, in comparison with comparative compound (S-3).

Moreover, all of tricyclic compounds (No. 1-2-19), (No. 1-2-10) and (No. 1-2-15) shown in Example 2, Example 3 and Example 9 have a larger dielectric anisotropy, a larger dielectric constant in the minor axis direction and a smaller viscosity in comparison with comparative compound (S-3). Therefore, the compound of the invention is found to be a superior compound that can shorten a response time of the device, while the compound improves a transmittance of the liquid crystal composition used for the FFS mode liquid crystal display device.

1-2. Example of Composition (1)

Liquid crystal composition (1) of the invention is described in detail by way of Examples. Compounds in Examples were expressed using symbols according to definitions in Table 2 described below. In Table 2, a configuration of 1,4-cyclohexylene is trans. A parenthesized number next to a symbolized compound in Examples corresponds to the number of the compound. A symbol (-) means any other liquid crystal compound. A ratio (percentage) of a liquid crystal compound is expressed in terms of weight percentage (% by weight) based on the weight of the liquid crystal composition. Values of physical properties of the composition were summarized in a last part. Physical properties were measured according to the methods described above, and measured values were directly described (without extrapolation).

TABLE 4

| Method for Description of Compounds using Symbols R—(A$_1$)—Z$_1$— ... —Z$_n$—(A$_n$)—R' | |
|---|---|
| 1) Left-terminal Group R— | Symbol |
| C$_n$H$_{2n+1}$— | n- |
| C$_n$H$_{2n+1}$O— | nO— |
| C$_m$H$_{2m+1}$OC$_n$H$_{2n}$— | mOn- |
| CH$_2$=CH— | V— |
| C$_n$H$_{2n+1}$—CH=CH— | nV— |
| CH$_2$=CH—C$_n$H$_{2n}$— | Vn- |
| C$_m$H$_{2m+1}$—CH=CH—C$_n$H$_{2n}$— | mVn- |
| CF$_2$=CH— | VFF— |
| CF$_2$=CH—C$_n$H$_{2n}$— | VFFn- |
| 2) Right-terminal Group —R' | Symbol |
| —C$_n$H$_{2n+1}$ | -n |
| —OC$_n$H$_{2n+1}$ | —On |
| —COOCH$_3$ | —EMe |
| —CH=CH$_2$ | —V |
| —CH=CH—C$_n$H$_{2n+1}$ | —Vn |
| —C$_n$H$_{2n}$—CH=CH$_2$ | -nV |
| —C$_m$H$_{2m}$—CH=CH—C$_n$H$_{2n+1}$ | -mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —OCH=CH—CF$_3$ | —OVCF3 |
| —C≡N | —C |

TABLE 4-continued

| 3) Bonding Group —Z$_n$— | Symbol |
|---|---|
| —C$_n$H$_{2n}$— | n |
| —COO— | E |
| —CH=CH— | V |
| —CH$_2$O— | 1O |
| —OCH$_2$— | O1 |
| —CF$_2$O— | X |
| —C≡C— | T |
| 4) Ring Structure —A$_n$— | Symbol |
| 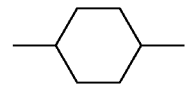 | H |
| 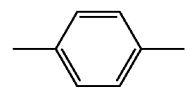 | B |
| 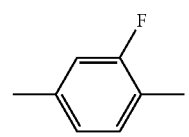 | B(F) |
| 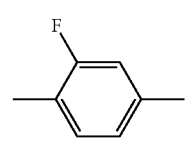 | B(2F) |
| 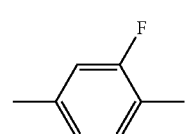 | B(F,F) |
| 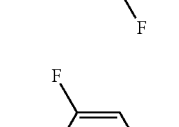 | B(2F,5F) |
| 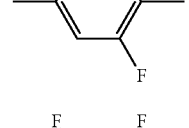 | B(2F,3F) |
| 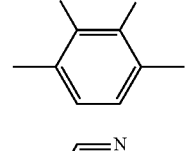 | Py |
| 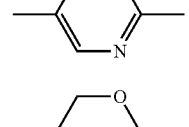 | G |
| 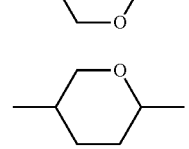 | dh |

TABLE 4-continued

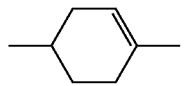

5) Examples of Description

Example 1 3-B(2F,3F)BXB(F,F)—F

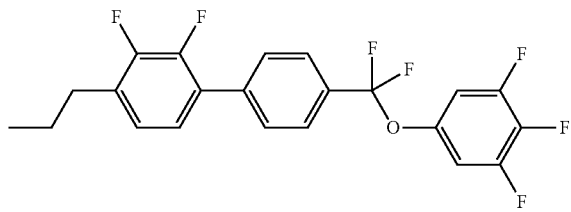 [SMILES: CCCc1ccc(-c2ccc(C(F)(F)Oc3cc(F)c(F)c(F)c3)cc2)c(F)c1F]

Example 2 3-HB(2F,3F)BXB(F,F)—F

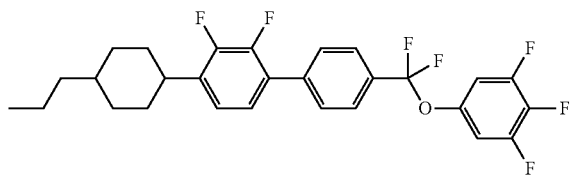 [SMILES: CCCC1CCC(c2ccc(-c3ccc(C(F)(F)Oc4cc(F)c(F)c(F)c4)cc3)c(F)c2F)CC1]

Example 3 3-HH-4

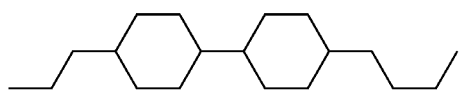 [SMILES: CCCCC1CCC(C2CCC(CCC)CC2)CC1]

Example 4 3-HBB(F,F)—F

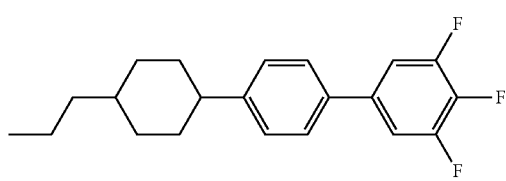 [SMILES: CCCC1CCC(c2ccc(-c3cc(F)c(F)c(F)c3)cc2)CC1]

Example 12

| | | |
|---|---|---|
| 3-B(2F,3F)BXB(F,F)-F | (1-2-2) | 17% |
| 3-H2HB(F,F)-F | (3-15) | 8% |
| 5-H2HB(F,F)-F | (3-15) | 8% |
| 3-HBB(F,F)-F | (3-24) | 21% |
| 5-HBB(F,F)-F | (3-24) | 20% |
| 3-H2BB(F,F)-F | (3-27) | 10% |
| 5-HHBB(F,F)-F | (4-6) | 3% |
| 5-HHEBB-F | (4-17) | 2% |
| 3-HH2BB(F,F)-F | (4-15) | 3% |
| 1O1-HBBH-4 | (15-1) | 4% |
| 1O1-HBBH-5 | (15-1) | 4% |

NI=83.2° C.; Δn=0.123; Δε=11.0; η=36.9 mPa·s.

A pitch when 0.25 part of compound (Op-5) was added to 100 parts of the composition described above was 61.7 micrometers.

Example 13

| | | |
|---|---|---|
| 2O-B(2F,3F)BXB(F,F)-F | (1-2-19) | 5% |
| 2-HB-C | (5-1) | 5% |
| 3-HB-C | (5-1) | 12% |
| 3-HB-O2 | (13-5) | 15% |
| 2-BTB-1 | (13-10) | 3% |
| 3-HHB-F | (3-1) | 4% |
| 3-HHB-1 | (14-1) | 8% |
| 3-HHB-O1 | (14-1) | 5% |
| 3-HHB-3 | (14-1) | 14% |
| 3-HHEB-F | (3-10) | 4% |
| 5-HHEB-F | (3-10) | 4% |
| 2-HHB(F)-F | (3-2) | 7% |
| 3-HHB(F)-F | (3-2) | 7% |
| 5-HHB(F)-F | (3-2) | 7% |

NI=98.4° C.; Δn=0.104; Δε=5.1; η=19.2 mPa·s.

Example 14

| | | |
|---|---|---|
| 3-HB(2F,3F)BXB(F,F)-F | (1-4-21) | 4% |
| 5-HB-CL | (2-2) | 16% |
| 3-HH-4 | (13-1) | 12% |
| 3-HH-5 | (13-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 8% |
| 5-HBB(F)-F | (3-23) | 4% |
| 1O1-HBBH-5 | (15-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI=114.0° C.; Δn=0.093; Δε=4.3; η=21.1 mPa·s.

Example 15

| | | |
|---|---|---|
| 3-HB(2F,3F)BXB(F,F)-F | (1-4-21) | 4% |
| 3-B(2F,3F)BXB(F,F)-F | (1-2-2) | 5% |
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 7% |
| 4-HHB-OCF3 | (3-1) | 7% |
| 5-HHB-OCF3 | (3-1) | 5% |
| 3-HH2B-OCF3 | (3-4) | 4% |
| 5-HH2B-OCF3 | (3-4) | 4% |
| 3-HH2B(F)-F | (3-5) | 3% |
| 3-HBB(F)-F | (3-23) | 10% |
| 5-HBB(F)-F | (3-23) | 10% |
| 5-HBBH-3 | (15-1) | 3% |
| 3-HB(F)BH-3 | (15-2) | 3% |

NI=82.6° C.; Δn=0.096; Δε=5.0; η=15.2 mPa·s.

Example 16

| | | |
|---|---|---|
| 3-HB(2F,3F)BXB(F,F)-F | (1-4-21) | 3% |
| 5-HB-CL | (2-2) | 11% |
| 3-HH-4 | (13-1) | 8% |

-continued

| | | |
|---|---|---|
| 3-HHB-1 | (14-1) | 5% |
| 3-HHB(F,F)-F | (3-3) | 8% |
| 3-HBB(F,F)-F | (3-24) | 20% |
| 5-HBB(F,F)-F | (3-24) | 15% |
| 3-HHEB(F,F)-F | (3-12) | 10% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 6% |

NI=80.8° C.; Δn=0.105; Δε=8.9; η=23.1 mPa·s.

Example 17

| | | |
|---|---|---|
| 3-B(2F,3F)BXB(F,F)-CF3 | (1-2-10) | 9% |
| 2-HB-C | (5-1) | 5% |
| 3-HB-C | (5-1) | 9% |
| 3-HB-O2 | (13-5) | 12% |
| 2-BTB-1 | (13-10) | 3% |
| 3-HHB-F | (3-1) | 4% |
| 3-HHB-1 | (14-1) | 8% |
| 3-HHB-O1 | (14-1) | 5% |
| 3-HHB-3 | (14-1) | 11% |
| 3-HHEB-F | (3-10) | 4% |
| 5-HHEB-F | (3-10) | 4% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 5% |

NI=94.2° C.; Δn=0.101; Δε=6.6; η=21.7 mPa·s.

Example 18

| | | |
|---|---|---|
| 3-dhHXB(2F,3F)B(F)-OCF3 | (1-3-16) | 3% |
| 5-HB-CL | (2-2) | 14% |
| 3-HH-4 | (13-1) | 11% |
| 3-HH-5 | (13-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 9% |
| 5-HHB(F)-F | (3-2) | 9% |
| 7-HHB(F)-F | (3-2) | 8% |
| 5-HBB(F)-F | (3-23) | 4% |
| 1O1-HBBH-5 | (15-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI=118.7° C.; Δn=0.093; Δε=4.1; η=21.9 mPa·s.

Example 19

| | | |
|---|---|---|
| 3-BB(2F,3F)BXB(F,F)-F | (1-4-1) | 3% |
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 19% |
| 5-HBB(F,F)-F | (3-24) | 19% |
| 3-H2BB(F,F)-F | (3-27) | 10% |
| 5-HHBB(F,F)-F | (4-6) | 3% |

-continued

| | | |
|---|---|---|
| 5-HHEBB-F | (4-17) | 2% |
| 3-HH2BB(F,F)-F | (4-15) | 3% |
| 1O1-HBBH-4 | (15-1) | 4% |
| 1O1-HBBH-5 | (15-1) | 4% |

NI=99.7° C.; Δn=0.118; Δε=9.3; η=35.5 mPa·s.

Example 20

| | | |
|---|---|---|
| V2-B(2F,3F)BXB(F,F)-F | (1-2-15) | 8% |
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 7% |
| 4-HHB-OCF3 | (3-1) | 7% |
| 5-HHB-OCF3 | (3-1) | 5% |
| 3-HH2B-OCF3 | (3-4) | 4% |
| 5-HH2B-OCF3 | (3-4) | 4% |
| 3-HHB(F,F)-OCF2H | (3-3) | 4% |
| 3-HHB(F,F)-OCF3 | (3-3) | 5% |
| 3-HH2B(F)-F | (3-5) | 3% |
| 3-HBB(F)-F | (3-23) | 6% |
| 5-HBB(F)-F | (3-23) | 6% |
| 5-HBBH-3 | (15-1) | 3% |
| 3-HB(F)BH-3 | (15-2) | 3% |

NI=79.1° C.; Δn=0.092; Δε=5.3; η=14.7 mPa·s.

Example 21

| | | |
|---|---|---|
| 3-B(2F,3F)BXB(F)B(F,F)-F | (1-5-21) | 9% |
| 5-HB-CL | (2-2) | 10% |
| 3-HH-4 | (13-1) | 8% |
| 3-HHB-1 | (14-1) | 5% |
| 3-HHB(F,F)-F | (3-3) | 8% |
| 3-HBB(F,F)-F | (3-24) | 16% |
| 5-HBB(F,F)-F | (3-24) | 11% |
| 3-HHEB(F,F)-F | (3-12) | 10% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 6% |

NI=83.6° C.; Δn=0.109; Δε=9.9; η=26.4 mPa·s.

Example 22

| | | |
|---|---|---|
| 3-B(2F,3F)BXB(F)-F | (1-2-7) | 3% |
| 3-HH-4 | (13-1) | 4% |
| 3-HBB(F,F)-F | (3-24) | 31% |
| 5-HBB(F,F)-F | (3-24) | 31% |
| 3-H2HB(F,F)-F | (3-15) | 10% |
| 4-H2HB(F,F)-F | (3-15) | 10% |
| 5-H2HB(F,F)-F | (3-15) | 8% |
| 3-HHBB(F,F)-F | (4-6) | 3% |

Example 23

| | | |
|---|---|---|
| 3-HB(2F,3F)BXB(F)-OCF3 | (1-4-28) | 3% |
| 5-HB-CL | (2-2) | 15% |
| 7-HB(F,F)-F | (2-4) | 3% |
| 3-HH-4 | (13-1) | 10% |
| 3-HH-5 | (13-1) | 5% |
| 3-HB-O2 | (13-5) | 14% |
| 3-HHB-1 | (14-1) | 8% |
| 3-HHB-O1 | (14-1) | 5% |
| 2-HHB(F)-F | (3-2) | 7% |
| 3-HHB(F)-F | (3-2) | 7% |
| 5-HHB(F)-F | (3-2) | 7% |
| 3-HHB(F,F)-F | (3-3) | 6% |
| 3-H2HB(F,F)-F | (3-15) | 5% |
| 4-H2HB(F,F)-F | (3-15) | 5% |

Example 24

| | | |
|---|---|---|
| 3-chB(2F,3F)BXB(F,F)-F | (1-4-47) | 3% |
| 5-HB-CL | (2-2) | 3% |
| 7-HB(F)-F | (2-3) | 7% |
| 3-HH-4 | (13-1) | 9% |
| 3-HH-EMe | (13-2) | 20% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 5% |
| 5-GHB(F,F)-F | (3-109) | 7% |

Example 25

| | | |
|---|---|---|
| 1V2-B(2F,3F)BXB(F,F)-CF3 | (1-2-18) | 3% |
| 3-HH-4 | (13-1) | 4% |
| 3-HBB(F,F)-F | (3-24) | 31% |
| 5-HBB(F,F)-F | (3-24) | 31% |
| 3-H2HB(F,F)-F | (3-15) | 10% |
| 4-H2HB(F,F)-F | (3-15) | 10% |
| 5-H2HB(F,F)-F | (3-15) | 8% |
| 3-HHBB(F,F)-F | (4-6) | 3% |

INDUSTRIAL APPLICABILITY

A liquid crystal compound of the invention satisfies at least one of physical properties such as a high stability to heat, light and so forth, a high clearing point, a low minimum temperature of a liquid crystal phase, a small viscosity, a suitable optical anisotropy, a large dielectric anisotropy, a large dielectric constant in a minor axis direction, a suitable elastic constant and an excellent compatibility with other liquid crystal compounds. A liquid crystal composition of the invention contains the compound and satisfies at least one of physical properties such as a high maximum temperature, a low minimum temperature, a small viscosity, a suitable optical anisotropy, a large dielectric anisotropy, a large dielectric constant in a minor axis direction and a suitable elastic constant. The composition has a suitable balance regarding at least two of the physical properties. A liquid crystal display device of the invention includes the composition, and has a wide temperature range in which the device can be used, a short response time, a large voltage holding ratio, a low threshold voltage, a large contrast ratio and a long service life. Therefore, the device can be widely applied to a liquid crystal display device used for a personal computer, a television and so forth.

What is claimed is:

1. A compound represented by formula (1):

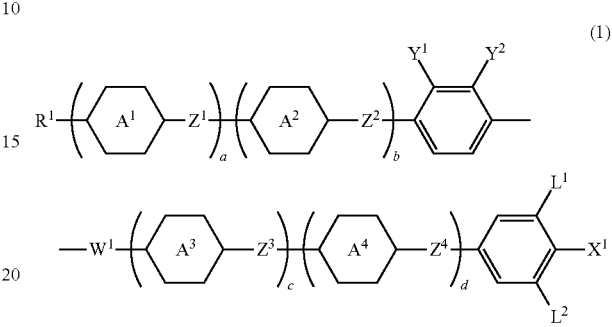

wherein, in formula (1),
$R^1$ is alkyl having 1 to 15 carbons, in the alkyl, at least one of —$CH_2$— may be replaced by —O— or —S—, at least one of —$(CH_2)_2$— may be replaced by —CH=CH—, and in the groups, at least one of hydrogen may be replaced by halogen;
ring $A^1$, ring $A^2$, ring $A^3$ and ring $A^4$ are independently 1,4-cyclohexylene, 1,4-cyclohexenylene, 1,4-phenylene, 2-fluoro-1,4-phenylene, 2,6-difluoro-1,4-phenylene, 2-chloro-1,4-phenylene, 2,6-dichloro-1,4-phenylene, 2-chloro-6-fluoro-1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl or pyridine-2,5-diyl;
$X^1$ is fluorine, chlorine, —C≡N, —$CF_3$, —$CHF_2$, —$OCF_3$, —$OCHF_2$, —CH=$CHCF_3$, —CF=$CHCF_3$ or —CF=$CFCF_3$;
$L^1$ and $L^2$ are independently hydrogen or fluorine;
$Y^1$ and $Y^2$ are independently fluorine or chlorine;
$W^1$ is a single bond, —$(CH_2)_2$—, —CH=CH—, —C≡C—, —COO—, —OCO—, —$CH_2O$—, —$OCH_2$— or —CF=CF—;
$Z^1$, $Z^2$, $Z^3$ and $Z^4$ are independently a single bond, —$(CH_2)_2$—, —CH=CH—, —C≡C—, —COO—, —OCO—, —$CF_2O$—, —$CH_2O$—, —$OCH_2$— or —CF=CF—;
a, b, c and d are independently 0 or 1, a sum of a, b, c and d is 1, 2 or 3; and
at least one of $Z^1$ when a is 1, $Z^2$ when b is 1, $Z^3$ when c is 1, and $Z^4$ when d is 1 is —$CF_2O$—.

2. The compound according to claim 1, wherein, in formula (1) described in claim 1, $R^1$ is alkyl having 1 to 15 carbons, alkenyl having 2 to 15 carbons, alkoxy having 1 to 14 carbons or alkenyloxy having 2 to 14 carbons; and $X^1$ is fluorine, chlorine, —C≡N, —$CF_3$, —$CHF_2$, —$OCF_3$, —$OCHF_2$, —CH=$CHCF_3$, —CF=$CHCF_3$ or —CF=$CFCF_3$.

3. The compound according to claim 1, wherein, in formula (1) described in claim 1, $R^1$ is alkyl having 1 to 10 carbons, alkenyl having 2 to 10 carbons, alkoxy having 1 to 9 carbons or alkenyloxy having 2 to 9 carbons; and $X^1$ is fluorine, chlorine, —C≡N, —$CF_3$, —$CHF_2$, —$OCF_3$, —$OCHF_2$, —CH=$CHCF_3$, —CF=$CHCF_3$ or —CF=$CFCF_3$.

4. The compound according to claim 1, represented by any one of formulas (1-1) to (1-7):

5. The compound according to claim 1, represented by any one of formulas (1-8) to (1-12):

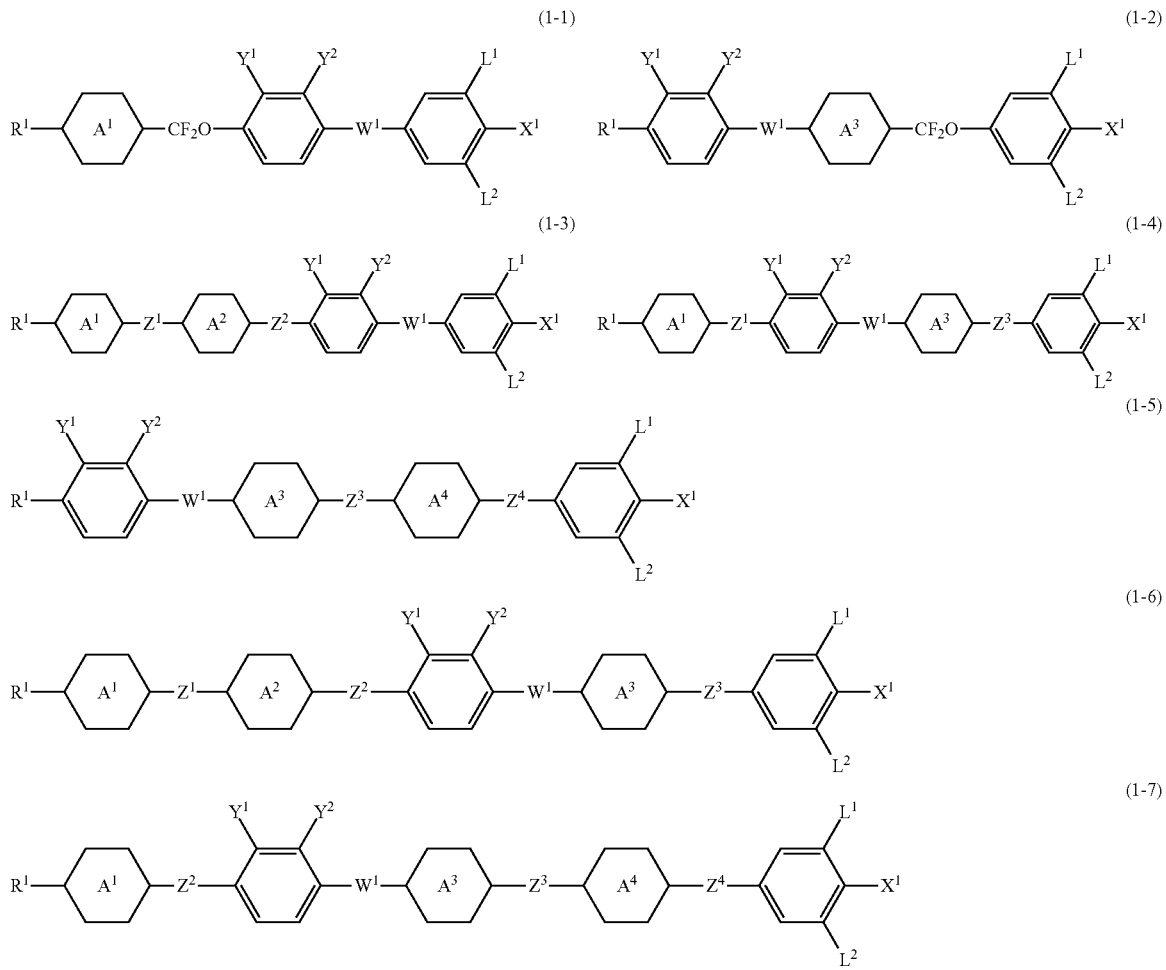

wherein, in formulas (1-1) to (1-7),

R¹ is alkyl having 1 to 10 carbons, alkenyl having 2 to 10 carbons or alkoxy having 1 to 9 carbons;

ring A¹, ring A², ring A³ and ring A⁴ are independently 1,4-cyclohexylene, 1,4-cyclohexenylene, 1,4-phenylene, 2-fluoro-1,4-phenylene, 2,6-difluoro-1,4-phenylene, tetrahydropyran-2,5-diyl or 1,3-dioxane-2,5-diyl;

Z¹, Z², Z³ and Z⁴ are independently a single bond, —(CH₂)₂—, —COO—, —CF₂O—, —CH₂O— or —OCH₂—;

W¹ is a single bond, —(CH₂)₂— or —OCH₂—;

X¹ is fluorine, —CF₃ or —OCF₃;

L¹ and L² are independently hydrogen or fluorine;

Y¹ and Y² are independently fluorine or chlorine;

in formula (1-3), any one of Z¹ and Z² is —CF₂O—;

in formula (1-4), any one of Z¹ and Z³ is —CF₂O—;

in formula (1-5), any one of Z³ and Z⁴ is —CF₂O—;

in formula (1-6), any one of Z¹, Z² and Z³ is —CF₂O—; and in formula (1-7), any one of Z¹, Z³ and Z⁴ is —CF₂O—.

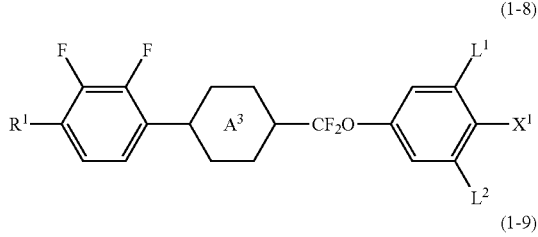

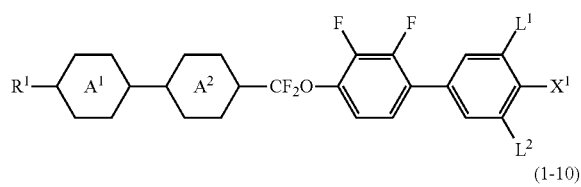

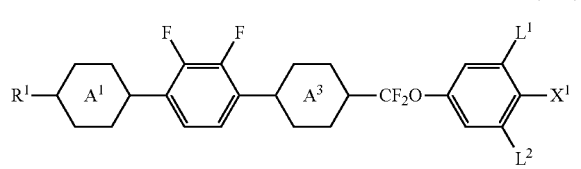

(1-11)
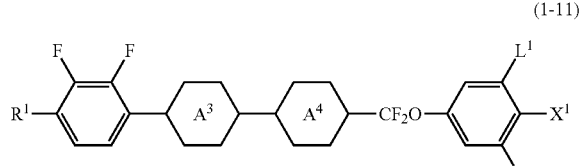

(1-12)
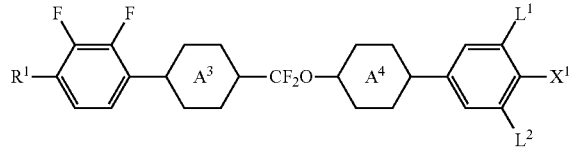

wherein, in formulas (1-8) to (1-12),

R¹ is alkyl having 1 to 10 carbons, alkenyl having 2 to 10 carbons or alkoxy having 1 to 9 carbons;

ring A¹, ring A², ring A³ and ring A⁴ are independently 1,4-cyclohexylene, 1,4-cyclohexenylene, 1,4-phenylene, 2-fluoro-1,4-phenylene, 2,6-difluoro-1,4-phenylene, tetrahydropyran-2,5-diyl or 1,3-dioxane-2,5-diyl;

X¹ is fluorine, —CF₃ or —OCF₃; and

L¹ and L² are independently hydrogen or fluorine.

6. The compound according to claim 1, represented by any one of formulas (1-13) to (1-22):

(1-13)
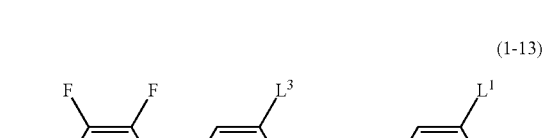

(1-14)
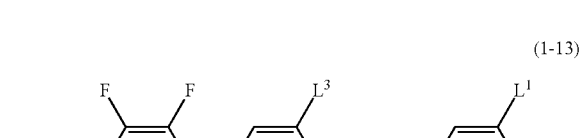

(1-15)
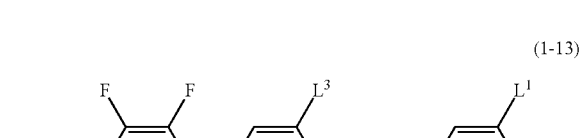

(1-16)
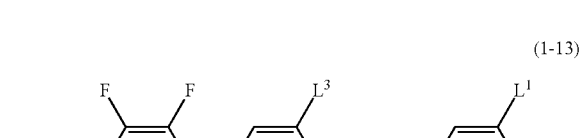

(1-17)
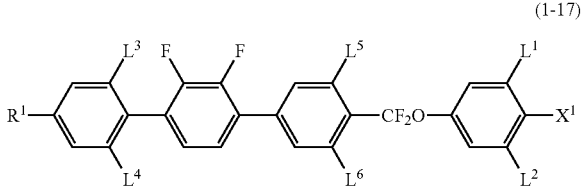

(1-18)
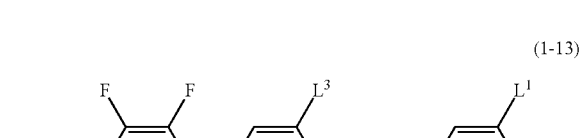

(1-19)
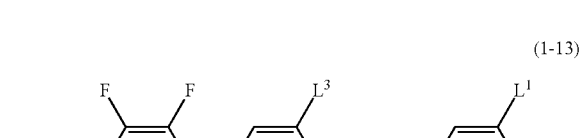

(1-20)
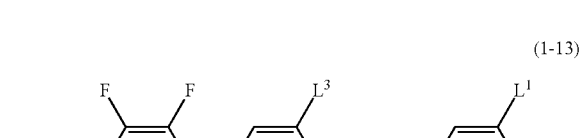

(1-21)
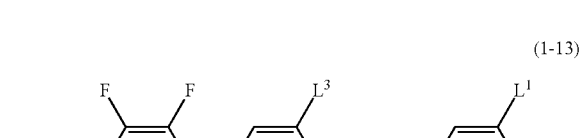

(1-22)
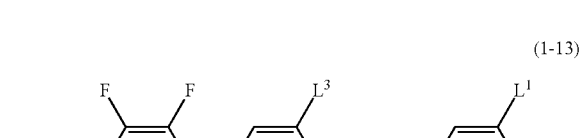

wherein, in formulas (1-13) to (1-22), R¹ is alkyl having 1 to 10 carbons, alkenyl having 2 to 10 carbons or alkoxy having 1 to 9 carbons; X¹ is fluorine, —CF₃ or —OCF₃; and L¹, L², L³, L⁴, L⁵ and L⁶ are independently hydrogen or fluorine.

7. The compound according to claim 1, represented by any one of formulas (1-23) to (1-25):

(1-23)
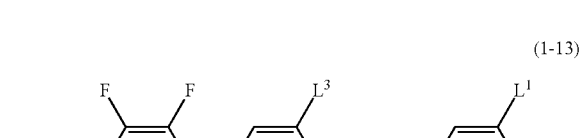

-continued (1-24)
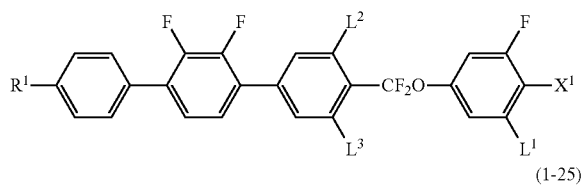

(1-25)
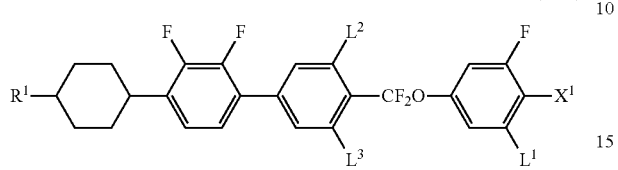

wherein, in formulas (1-23) to (1-25), $R^1$ is alkyl having 1 to 10 carbons, alkenyl having 2 to 10 carbons or alkoxy having 1 to 9 carbons; $X^1$ is fluorine, —$CF_3$ or —$OCF_3$; and $L^1$, $L^2$ and $L^3$ are independently hydrogen or fluorine.

8. A liquid crystal composition, containing at least one compound according to claim 1.

9. The liquid crystal composition according to claim 8, further containing at least one compound selected from the group of compounds represented by formulas (2) to (4):

(2)
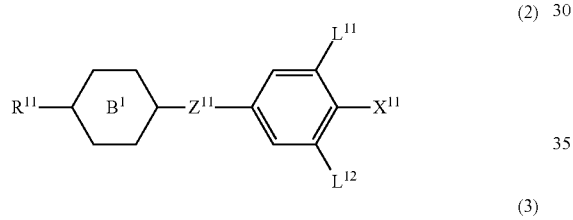

(3)
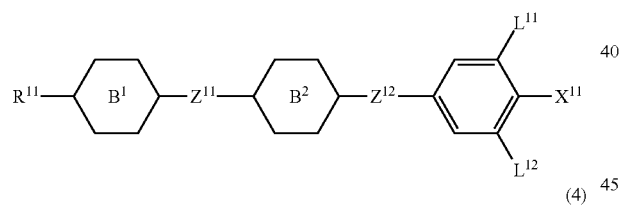

(4)
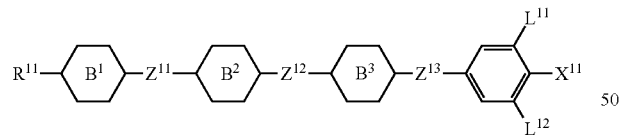

wherein, in formulas (2) to (4),
$R^{11}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;
$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;
ring $B^1$, ring $B^2$ and ring $B^3$ are independently 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl or pyrimidine-2,5-diyl;
$Z^{11}$, $Z^{12}$ and $Z^{13}$ are independently a single bond, —$CH_2CH_2$—, —CH=CH—, —C≡C—, —COO—, —$CF_2O$—, —$OCF_2$—, —$CH_2O$— or —$(CH_2)_4$—; and
$L^{11}$ and $L^{12}$ are independently hydrogen or fluorine.

10. The liquid crystal composition according to claim 8, further containing at least one compound selected from the group of compounds represented by formula (5):

(5)
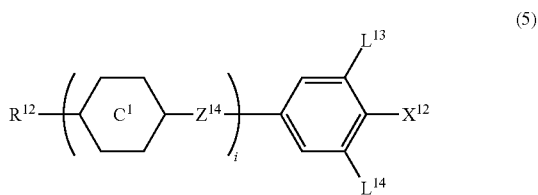

wherein, in formula (5),
$R^{12}$ is alkyl having 1 to 10 carbons or alkenyl having 2 to 10 carbons, and in the alkyl and the alkenyl, at least one of hydrogen may be replaced by fluorine, and at least one of —$CH_2$— may be replaced by —O—;
$X^{12}$ is —C≡N or —C≡C—C≡N;
ring $C^1$ is 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl or pyrimidine-2,5-diyl;
$Z^{14}$ is a single bond, —$CH_2CH_2$—, —C≡C—, —COO—, —$CF_2O$—, —$OCF_2$— or —$CH_2O$—;
$L^{13}$ and $L^{14}$ are independently hydrogen or fluorine; and
i is 1, 2, 3 or 4.

11. The liquid crystal composition according to claim 8, further containing at least one compound selected from the group of compounds represented by formulas (6) to (12):

(6)
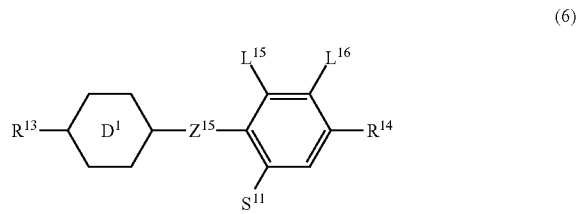

(7)
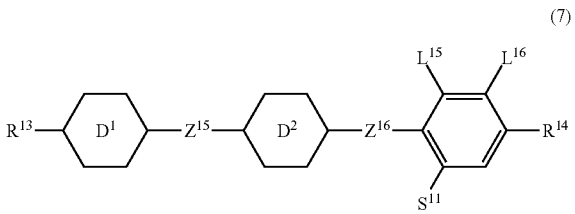

-continued

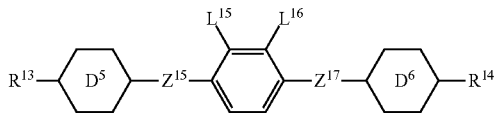 (8)

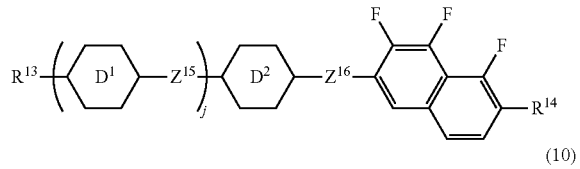 (9)

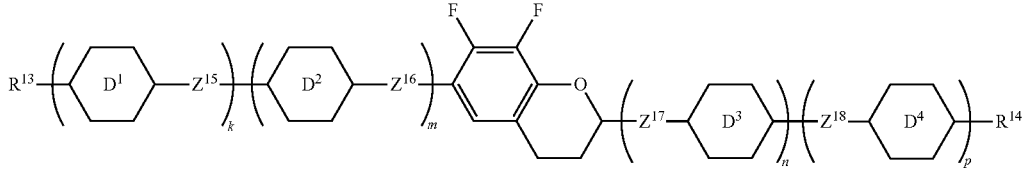 (10)

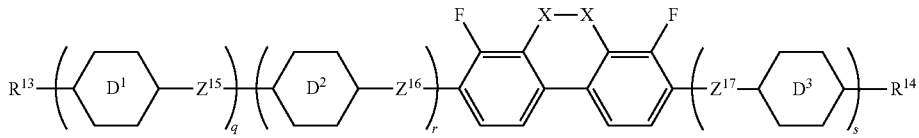 (11)

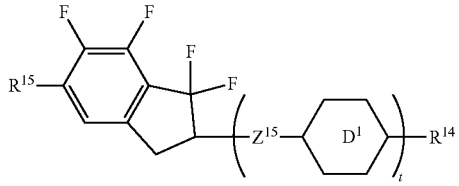 (12)

wherein, in formulas (6) to (12), $R^{13}$ and $R^{14}$ are independently alkyl having 1 to 10 carbons or alkenyl having 2 to 10 carbons, and in the alkyl and the alkenyl, at least one of —CH$_2$— may be replaced by —O—;

$R^{15}$ is hydrogen, fluorine, alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;

$S^{11}$ is hydrogen or methyl;

X is —CF$_2$—, —O— or —CHF—;

ring $D^1$, ring $D^2$, ring $D^3$ and ring $D^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring $D^5$ and ring $D^6$ are independently 1,4-cyclohexylene, 1,4-cyclohexenylene, 1,4-phenylene, tetrahydropyran-2,5-diyl or decahydronaphthalene-2,6-diyl;

$Z^{15}$, $Z^{16}$, $Z^{17}$ and $Z^{18}$ are independently a single bond, —CH$_2$CH$_2$—, —COO—, —CH$_2$O—, —OCF$_2$— or —OCF$_2$CH$_2$CH$_2$—;

$L^{15}$ and $L^{16}$ are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

12. The liquid crystal composition according to claim 8, further containing at least one compound selected from the group of compounds represented by formulas (13) to (15):

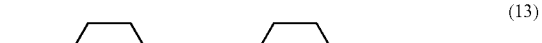 (13)

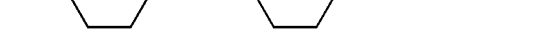 (14)

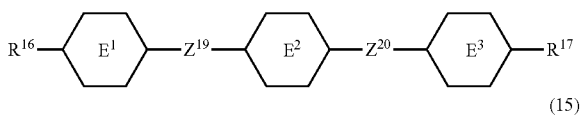 (15)

wherein, in formulas (13) to (15), $R^{16}$ and $R^{17}$ are independently alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, —CH$_2$CH$_2$—, —CH=CH—, —C≡C— or —COO—.

13. The liquid crystal composition according to claim 8, further containing at least one of a polymerizable compound, an optically active compound, an antioxidant, an ultraviolet light absorbent, a light stabilizer, a heat stabilizer and a defoaming agent.

14. A liquid crystal display device, including the liquid crystal composition according to claim 8.

* * * * *